US007947650B2

(12) United States Patent
Chen et al.

(10) Patent No.: US 7,947,650 B2
(45) Date of Patent: May 24, 2011

(54) ARTICLE OF MANUFACTURE

(75) Inventors: Yvonne Man-Yee Chen, San Mateo, CA (US); Ross G. Clark, Auckland (NZ); Andrea G. Cochran, San Francisco, CA (US); Yves Dubaquie, Lawrenceville, NJ (US); Paul J. Fielder, Redwood City, CA (US); Ellen Filvaroff, San Francisco, CA (US); Henry B. Lowman, El Granda, CA (US); Deborah L. Mortensen, Pacifica, CA (US); Iain C. A. F. Robinson, St. Albans (GB); Nicholas J. Skelton, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 238 days.

(21) Appl. No.: 11/929,468

(22) Filed: Oct. 30, 2007

(65) Prior Publication Data
US 2009/0011988 A1 Jan. 8, 2009

Related U.S. Application Data

(60) Division of application No. 10/271,869, filed on Oct. 16, 2002, now Pat. No. 7,423,017, which is a continuation of application No. 09/858,935, filed on May 16, 2001, now abandoned, and a continuation-in-part of application No. 09/477,923, filed on Jan. 5, 2000, now abandoned, and a continuation-in-part of application No. 09/477,924, filed on Jan. 5, 2000, now Pat. No. 6,403,764, and a continuation-in-part of application No. 09/337,227, filed on Jun. 22, 1999, now Pat. No. 6,420,518, and a continuation-in-part of application No. 09/052,888, filed on Mar. 31, 1998, now Pat. No. 6,251,865.

(60) Provisional application No. 60/248,985, filed on Nov. 15, 2000, provisional application No. 60/204,490, filed on May 16, 2000, provisional application No. 60/115,010, filed on Jan. 6, 1999, provisional application No. 60/170,261, filed on Dec. 9, 1999.

(51) Int. Cl.
*A61K 38/30* (2006.01)
(52) U.S. Cl. .................. 514/12; 514/2; 530/350
(58) Field of Classification Search .................. None
See application file for complete search history.

(56) References Cited

U.S. PATENT DOCUMENTS

| 3,721,252 A | 3/1973 | Ayella |
| 4,411,890 A | 10/1983 | Momany |
| 4,511,503 A | 4/1985 | Olson et al. |
| 4,876,242 A | 10/1989 | Applebaum et al. |
| 4,988,675 A | 1/1991 | Froesch et al. |
| 5,068,224 A | 11/1991 | Fryklund et al. |
| 5,077,276 A | 12/1991 | Ballard et al. |
| 5,093,317 A | 3/1992 | Lewis et al. |
| 5,106,832 A | 4/1992 | Froesch et al. |
| 5,126,324 A | 6/1992 | Clark et al. |
| 5,164,370 A | 11/1992 | Ballard et al. |
| 5,187,151 A | 2/1993 | Clark et al. |
| 5,202,119 A | 4/1993 | Clark et al. |
| 5,206,235 A | 4/1993 | Fisher et al. |
| 5,210,017 A | 5/1993 | Carlsson et al. |
| 5,223,409 A | 6/1993 | Ladner et al. |
| 5,273,961 A | 12/1993 | Clark |
| 5,342,763 A | 8/1994 | Swartz |
| 5,374,620 A | 12/1994 | Clark et al. |
| 5,444,047 A | 8/1995 | DiPasquale |
| 5,466,670 A | 11/1995 | Dunger et al. |
| 5,470,828 A | 11/1995 | Ballard et al. |
| 5,514,646 A | 5/1996 | Chance et al. |
| 5,534,617 A | 7/1996 | Cunningham et al. |
| 5,565,428 A | 10/1996 | Clark et al. |
| 5,569,648 A | 10/1996 | Lewis et al. |
| 5,593,844 A | 1/1997 | Carlsson et al. |
| 5,597,797 A | 1/1997 | Clark |
| 5,622,932 A | 4/1997 | DiMarchi et al. |
| 5,652,214 A | 7/1997 | Lewis et al. |
| 5,703,045 A | 12/1997 | Lewis et al. |
| 5,714,460 A | 2/1998 | Gluckman et al. |
| 5,741,776 A | 4/1998 | Clark et al. |
| 5,750,373 A | 5/1998 | Garrard et al. |
| 5,776,897 A | 7/1998 | Lewis et al. |
| 5,821,047 A | 10/1998 | Garrard et al. |
| 5,834,250 A | 11/1998 | Wells et al. |
| 5,843,899 A | 12/1998 | Halloran |
| 5,891,722 A | 4/1999 | Fuks et al. |
| 5,985,830 A | 11/1999 | Acott et al. |
| 5,994,303 A | 11/1999 | Arrhenius-Nyberg et al. |

FOREIGN PATENT DOCUMENTS

| EP | 128733 | 12/1984 |
| EP | 135094 | 3/1985 |
| EP | 214826 | 3/1987 |
| EP | 230869 | 8/1987 |
| EP | 288451 | 10/1988 |
| EP | 294021 | 12/1988 |
| EP | 369943 | 5/1990 |
| EP | 375438 | 6/1990 |
| EP | 379338 | 7/1990 |
| EP | 560723 | 9/1993 |

(Continued)

OTHER PUBLICATIONS

Amin, A. R., et al., "The role of nitric oxide in articular cartilage breakdown in osteoarthritis" *Current Opinion in Rheumatology* 10(3):263-268 (1998).

(Continued)

*Primary Examiner* — Hope A Robinson
(74) *Attorney, Agent, or Firm* — Craig Svoboda; Ginger R. Dreger; Arnold & Porter LLP

(57) ABSTRACT

The present invention relates to a method for the treatment of a cartilage disorder, including cartilage damaged by injury or degenerative cartilagenous disorders. The method involves contacting the cartilage with an IGF-1 analog with altered affinity for IGF-binding proteins (IGFBPs) or an IGFBP displacer peptide that prevents the interaction of an IGF with an IGFBP and does not bind to a human IGF receptor.

7 Claims, 35 Drawing Sheets

FOREIGN PATENT DOCUMENTS

| | | |
|---|---|---|
| EP | 434652 | 11/1994 |
| EP | 436469 | 2/1995 |
| EP | 434625 | 4/1995 |
| EP | 681842 | 11/1995 |
| EP | 742228 | 11/1996 |
| EP | 965596 | 12/1999 |
| WO | WO 89/05822 | 6/1989 |
| WO | WO 89/08667 | 9/1989 |
| WO | WO 89/09268 | 10/1989 |
| WO | WO 89/09792 | 10/1989 |
| WO | WO 91/03253 | 3/1991 |
| WO | WO 91/19510 | 12/1991 |
| WO | WO 92/11865 | 7/1992 |
| WO | WO 92/13565 | 8/1992 |
| WO | WO 92/15679 | 9/1992 |
| WO | WO 93/08826 | 5/1993 |
| WO | WO 93/20836 | 10/1993 |
| WO | WO 93/23071 | 11/1993 |
| WO | WO 93/25219 | 12/1993 |
| WO | WO 94/04569 | 3/1994 |
| WO | WO 94/16722 | 8/1994 |
| WO | WO 94/16723 | 8/1994 |
| WO | WO 95/07697 | 3/1995 |
| WO | WO 95/17422 | 6/1995 |
| WO | WO 95/17423 | 6/1995 |
| WO | WO 96/01124 | 1/1996 |
| WO | WO 96/15148 | 5/1996 |
| WO | WO 96/33216 | 10/1996 |
| WO | WO 96/37514 | 11/1996 |
| WO | WO 96/40189 | 12/1996 |
| WO | WO 96/40750 | 12/1996 |
| WO | WO 97/37010 | 10/1997 |
| WO | WO 97/39032 | 10/1997 |
| WO | WO 98/20036 | 5/1998 |
| WO | WO 98/45427 | 10/1998 |
| WO | WO 98/56406 | 12/1998 |
| WO | WO 99/32620 | 7/1999 |
| WO | 99/51262 | 10/1999 |
| WO | WO 99/51262 | 10/1999 |
| WO | WO 00/20023 | 4/2000 |
| WO | WO 00/23469 | 4/2000 |
| WO | WO 00/40612 | 7/2000 |
| WO | WO 00/69901 | 11/2000 |
| WO | WO 01/72771 | 10/2001 |

OTHER PUBLICATIONS

Arend W. P. et al., "Interleukin-1 Receptor Antagonist: Role in Biology" *Ann. Rev. Immunol.* 16:27-55 (1998).

Bach and Rechler, "Insulin-like Growth Factor Binding Proteins" *Diabetes Reviews* 3:38-61 (1995).

Bagley et al., "A key functional role for the insulin-like growth-factor 1 N-terminal pentapeptide" *Biochemical Journal* 259(3):665-671 (May 1, 1989).

Baragi et al., "Transplantation of adenovirally transduced allogenic chondrocytes into articular cartilage defects in vivo" *Osteoarthritis & Cartilage* 5(4):275-282 (1997).

Baragi et al., "Transplantation of transduced chondrocytes protects articular cartilage from interleukin 1-induced extracellular matrix degradation" *J. of Clin. Invest.* 96(5):2454-2460 (1995).

Bass et al., "Hormone Phage: An Enrichment Method for Variant Proteins with Altered Binding Properties" *Proteins: Structure, Function, and Genetics* 8(4):309-314 (1990).

Baxter et al., "High Molecular Weight Insulin-like Growth Factor Binding Protein Complex" *Journal of Biological Chemistry* 264(20):11843-11848 (1989).

Baxter et al., "Structural determinants for binary and ternary complex formation between insulin-like growth factor-I (IGF-I) and IGF binding protein-3" *Journal of Biological Chemistry* 267(1):60-65 (Jan. 5, 1992).

Bayne et al., "Structural analogs of human insulin-like growth factor I with reduced affinity for serum binding proteins and the type 2 insulin-like growth factor receptor" *Journal of Biological Chemistry* 263:6233-6239 (1988).

Bayne et al., "The C region of human insulin-like growth factor (IGF) I is required for high affinity binding to the type 1 IGF receptor" *Journal of Biological Chemistry* 264(19):11004-11008 (1988).

Bayne et al., "The roles of tyrosines 24, 31, and 60 in the high affinity binding of insulin-like growth factor-I to the type I insulin-like growth factor receptor" *Journal of Biological Chemistry* 265(26):15648-15652 (Sep. 15, 1990).

Bhakta et al., "The insulin-like growth factors (IGFs) I and II bind to articular cartilage via teh IGF-binding proteins" *J. of Biol. Chem.* 275(8):5860-5866 (2000).

Castellanos-Serra ete al., "Expression and folding of an interleukin-2-proinsulin fusion protein and its conversion into insulin by a single step enzymatic removal of the C-peptide and the N-terminal fused sequence" FEBS Letters 378:171-176 (1996).

Chang et al., "Single-Step Solubilization and Folding of IGF-1 Aggregates from *Escherichia coli*" Protein Folding: in Vivo and in Vitro, American Chemical Society, Chapter 14, pp. 178-188 (1993).

Chen et al., "Chondrocyte transplantation and experimental treatment options for articular cartilage defects" *American Journal of Orthopedics* 26(6):396-406 (1997).

Chevalier, X and Tyler, J.A., "Production of Binding Proteins and Role of the Insulin-Like Growth Factor I Binding Protein 3 in Human Articular Cartilage Explants" *Brit. J. Rheum.* 35:515-522 (1996).

Chin et al., "Interactions between interleukin-1 and basic fibroblast growth factor on articular chondrocytes. Effects on cell growth, prostanoid production, and receptor modulation" *Arthritis and Rheumatism* 34(3):314-324 (1991).

Clarkson and Wells, "A Hot Spot of Binding Energy in a Hormone-Receptor Interface" *Science* 267:383-386 (1995).

Clemmons et al., "Competition for binding to insulin-like growth factor (IGF) binding protein-2, 3, 4, and 5 by the IGFs and IGF analogs" *Endocrinology* 131(2):890-895 (Aug. 1992).

Clemmons et al., "Discrete Alterations of the Insulin-like Growth Factor I Molecule Which Alter Its Affinity for Insulin-like Growth Factor-binding Proteins Result in Changes in Bioactivity" *Journal of Biological Chemistry* 265(21):12210-12216 (1990).

Clemmons, D., "Insulin-like growth factor binding proteins and their role in controlling IGF actions" *Cytokine & Growth Factor Reviews* 8(1):45-62 (Mar. 1997).

Collett-Solberg and Cohen, "The Role of the Insulin-Like Growth Factor Binding Proteins and the IGFBP Proteases in Modulating IGF Action" *Endocrinology and Metabolism Clinics of North America* 25(3):591-614 (Sep. 1996).

Cooke et al., "Solution Structure of Human Insulin-Like Growth Factor 1: A Nuclear Magnetic Resonance and Restrained Molecular Dynamics Study" *Biochemistry* 30:5484-5491 (1991).

Coutts et al., "Effect of Growth Factors on Cartilage Repair" *Amer. Acad. Orthop. Surg.* (Instructional Course Lect.), Chapter 47, 47:487-494 (1997).

Cunningham and Wells, "Comparison of a structural and a functional epitope" *Journal of Molecular Biology* 234(3):554-563 (Dec. 5, 1993).

Cunningham and Wells, "High-Resolution Epitope Mapping of hGH-Receptor Interactions by Alanine-Scanning Mutagenesis" *Science* 244:1081-1085 (1989).

Cunningham et al., "Production of an Atrial Natriuretic Peptide Variant that is Specific for Type A Receptor" *EMBO Journal* 13(11):2508-2515 (1994).

Cwirla et al., "Peptides on phage: a vast library of peptides for identifying ligands" *Proc. Natl. Acad. Sci. USA* 87(16):6378-6382 (1990).

Davidson, M., "Effect of growth hormone on carbohydrate and lipid metabolism" *Endocrine Reviews* 8(2):115-131 (May 1987).

Devlin et al., "Random peptide libraries: a source of specific protein binding molecules" *Science* 249:404-406 (1990).

Di Cera, E., "Site-specific thermodynamics: understanding cooperativity in molecular recognition" *Chem. Rev.* 98:1563-1591 (1998).

Dubaquie and Lowman, "Total Alanine-Scanning Mutagenesis of Insulin-Like Growth Factor I (IGF-I) Identifies Differential Binding Epitopes for IGFBP-1 and IGFBP-3" *Biochemistry* 38(20):6386-6396 (1999).

Evans and Robbins, "Getting genes into human synovium" *Journal of Rheumatology* 24(11):2061-2063 (1997).

Evans et al., "Blocking cytokines with genes" *Journal of Leukocyte Biology* 64:55-61 (1998).

Farndale et al., "Improved quantitation and discrimination of sulphated glycosaminoglycans by use of dimethylmethylene blue" *Biochem. Biophys. Acta* 883:173-177 (1986).

Fernihough et al., "Local disruption of the insulin-like growth factor system in the arthritic joint" *Arth. & Rheum.* 39(9):1556-1565 (Sep. 1996).

Ferry R. J., Jr. et al., "Cellular Actions of Insulin-Like Growth Factor Binding Proteins" *Horm. Metab. Res.* 31:192-202 (1999).

Firth, S. M. et al., "Structural Determinants of Ligand and Cell Surface Binding of Insulin-like Growth Factor-binding Protein-3" *Journal of Biological Chemistry* 273(5):2631-2638 (Jan. 30, 1998).

Florini and Roberts, "Effect of rat age on blood levels of somatomedin-like growth factors" *Journal of Gerontology* 35(1):23-30 (1980).

Geysen et al., "A priori delineation of a peptide which mimics a discontinuous antigenic determinant" *Molecular Immunology* 23(7):709-715 (1986).

Giebel et al., "Screening of cyclic peptide phage libraries identifies ligands that bind streptavidin with high affinities" *Biochemistry* 34:15430-15435 (1995).

Guerne et al., "Growth factor responsiveness of human articular chondrocytes: distinct profiles in primary chondrocytes, subcultured chondrocytes, and fibroblasts" *Journal of Cellular Physiology* 158(3):476-484 (1994).

Hawkins et al., "Selection of Phage Antibodies by Binding Affinity Mimicking Affinity Maturation" *J. Mol. Biol.* 226:889-896 (1992).

Heding et al., "Biosensor measurement of the binding of insulin-like growth factors I and II and their analogues to the insulin-like growth factor-binding protein-3" *Journal of Biological Chemistry* 271(24):13948-13952 (Jun. 14, 1996).

Hill and Logan, "Peptide growth factors and their interactions during chondrogenesis" *Progress in Growth Factor Research* 4(1):45-86 (1992).

Hober et al., "Disulfide Exchange Folding of Insulin-Like Growth Factor I" *Biochemistry* 31:1749-1756 (1992).

Janosi, J. B. M. et al., "N-Linked Glycosylation and Sialylation of the Acid-labile Subunit" *Journal of Biological Chemistry* 274(9):5292-5298 (Feb. 1999).

Jansson et al., "Structural Changes in Insulin-Like Growth Factor (IGF) I Mutant Proteins Affecting Binding Kinetic Rates to IGF Binding Protein 1 and IGF-I Receptor" *Biochemistry* 36:4108-4117 (1997).

Jansson et al., "The Insulin-like Growth Factor (IGF) Binding Protein 1 Binding Epitope on IGF-I Probed by Heteronuclear NMR Spectroscopy and Mutational Analysis" *The Journal of Biological Chemistry* 273(38):24701-24707 (Sep. 18, 1998).

Joly et al., "Overexpression of *Escherichia coli* oxidoreductases increases recombinant insulin-like growth factor-I accumulation" *Proc. Natl. Acad. Sci. USA* 95:2773-2777 (Mar. 1998).

Jones et al., "Insulin-Like Growth Factors and Their Binding Proteins: Biological Actions" *Endocrine Reviews* 16(1):3-34 (1995).

Kanety, H. et al., "Insulin-Like Growth Factor I and Its Binding Proteins 3 and 4 are Increased in Human Inflammatory Synovial Fluid" *J. Rheumatol.* 23(5):815-818 (1996).

Kang et al., "Ex vivo gene transfer to chondrocytes in full-thickness articular cartilage defects: a feasibility study" *Osteoarthritis & Cartilage* 5(2):139-143 (1997).

Kang et al., "Gene therapy for arthritis: principles and clinical practice" *Biochemical Society Transactions* 25(2):533-537 (1997).

Kay et al., "An M13 phage library displaying random 38-amino-acid peptides as a source of novel sequences with affinity to selected targets" *Gene* 128:59-65 (1993).

Kelley et al., "Analysis of the Factor VIIa Binding Site on Human Tissue Factor: Effects of Tissue Factor Mutations on the Kinetics and Thermodynamics of Binding" *Biochemistry* 34(33):10383-10392 (1995).

Kunkel et al., "Efficient site-directed mutagenesis using uracil-containing DNA" *Methods in Enzymology* 204:125-139 (1991).

Leong S. R. et al., "Structure and Functional Expression of the Acid-Labile Subunit of the Insulin-Like Growth Factor-Binding Protein Complex" *Mol. Endocrinol.* 6(6):870-876 (1992).

Livnah et al., "Functional mimicry of a protein hormone by a peptide agonist: the EPO receptor complex at 2.8 A" *Science* 273(5274):464-471 (Jul. 26, 1996).

Loddick et al., "Displacement of insulin-like growth factors from their binding proteins as a potential treatment for stroke" *Proc. Natl. Acad. Sci. USA* 95(4):1894-1898 (Feb. 17, 1998).

Lowman and Wells, "Affinity Maturation of Human Growth Hormone by Monovalent Phage Display" *J. Mol. Biol.* 234:564-578 (1993).

Lowman et al., "Molecular mimics of insulin-like growth factor 1 (IGF-1) for inhibiting IGF-1: IGF-binding protein interactions" *Biochemistry* 37(25):8870-8878 (1998).

Lowman et al., "Selecting High-Affinity Binding Proteins by Monovalent Phage Display" *Biochemistry* 30(45):10832-10838 (1991).

Lowman, H., "Phage display of peptide libraries on protein scaffolds" *Methods in Molecular Biology*, Chapter 24, 87:249-264 (1998).

Manes et al., "Functional epitope mapping of insulin-like growth I (IGF-I) by Anti-IGF-I monoclonal antibodies" *Endocrinology* 138(3):905-915 (1997).

Martel-Pelletier et al., "IGF/IGFBP axis in cartilage and bone in osteoarthritis pathogenesis" *Inflamm. res.* 47:90-100 (1998).

Martin & Baxter, "Insulin-like Growth Factor-binding Protein from Human Plasma. Purification and Characterization" *Journal of Biological Chemistry* 261(19):8754-8760 (1986).

Martin et al., "Age-Related Decline in Chondrocyte Response to Insulin-Like Growth Factor-I: The Role of Growth Factor Binding Proteins" *J. Orthop. Res.* 15:491-498 (1997).

McLafferty et al., "M13 bacteriophage displaying disulfide-constrained microproteins" *Gene* 128:29-36 (1993).

Miller et al., "Oxidative refolding of insulin-like growth factor 1 yields two products of similar thermodynamic stability: a bifurcating protein-folding pathway" *Biochemistry* 32:5203-5213 (1993).

Morales, T. I., "The Role and Content of Endogenous Insulin-Like Growth Factor-Binding Proteins in Bovine Articular Cartilage" *Arch Biochem. Biophys.* 343(2):164-172 (Jul. 1997).

Mortensen, D. L. et al., "Insulin-Like Growth Factor Binding Protein-1 Induces Insulin Release in the Rat" *Endocrinology* 138(5):2073-2080 (1997).

Moses, A., "Recombinant insulinlike growth factor-I as therapy in states of altered carbohydrate homeostasis" *Current Opinion in Endocrinology and Diabetes* 4:16-25 (1997).

Nilsson et al., "A synthetic IgG-binding domain based on staphylococcal protein A" *Protein Eng.* 1:107-113 (1987).

Nilsson et al., "Integrated production of human insulin and its C-peptide" *Journal of Biotechnology* 48:241-250 (1996).

O'Neil et al., "Identification of novel peptide antagonists for GPIIb/IIIa from a conformationally constrained phage peptide library" *Proteins: Structure, Function, and Genetics* 14:509-515 (1992).

Oldenburg et al., "Peptide ligands for a sugar-binding protein isolated from a random peptide library" *Proc. Natl. Acad. Sci.* 89:5393-5397 (1992).

Olney, R.C. et al., "Chondrocytes from Osteoarthritic Cartilage Have Increased Expression of Insulin-Like Growth Factor I (IGF-I) and IGF-Binding Protein-3 (IGFBP-3) and -5, but not IGF-II or IGFBP-4" *J. Clin. Endo. and Metab.* 81(3):1096-1103 (1996).

Osborn et al., "Growth factor stimulation of adult articular cartilage" *Journal of Orthopedic Research* 7(1):35-42 (1989).

Pelletier, J. et al., "Reduced Progression of Experimental Osteoarthritis in Vivo by Selective Inhibition of Inducible Nitric Oxide Synthase" *Arthritis and Rheumatism* 41(7):1275-1286 (Jul. 1998).

Phelan et al., "A General Method for Constraining Short Peptides to an α-Helical Conformation" *J. Am. Chem. Soc.* 119(3):455-460 (Jan. 22, 1997).

Rogachefsky et al., "Treatment of canine osteoarthrtis with sodium pentosan polysulfate and insulin-like growth factor-1" *Annals of the New York Academy of Sciences* 732:392-394 (1994).

Rogachefsky, R.A., et al., "Treatment of canine osteoarthritis with insulin-like growth factor-1 (IGF-1) and sodium pentosan polysulfate" *Osteoarthritis and Cartilage* 1:105-114 (1993).

Rosenfield et al., "IGF-1 treatment of syndromes of growth hormone insensitivity" *The Insulin-ike growth factors and their regulatory proteins*, Baxter RC, Gluckman PD, Rosenfield RG, Excerpta Medica edition, Amsterdam pp. 457-464 (1994).

Sadick, M. D. et al., "Kinase receptor activation (KIRA): a rapid and accurate alternative to end-point bioassays" *J. Pharm. Biomed. Analysis* 19(6):883-891 (1999).

Sah et al., "Differential Effects of bFGF and IGF-1 on Matrix Metabolism in Calf and Adult Bovin Cartilage Explants" *Arch. of Biochem. and Biophys.*, Academic Press, Inc. vol. 308(1):137-147 (1994).

Sato and Urist, "Bone morphogenic protein-induced cartilage development in tissue culture" *Clinical Orthopaedics and Related Research* 183:180-187 (1984).

Scharf et al., "Insulin-like growth factor-I serum concentrations and patterns of insulin-like growth factor binding proteins in patients with chronic liver disease" *Journal of Hepatology* 25(5):689-699 (Nov. 1996).

Schumacher, T. N. M., et al., "Identification of D-Peptide Ligands Through Mirror-Image Phage Display" *Science* 271:1854-1857 (Mar. 1996).

Scott and Smith, "Searching for peptide ligands with an epitope library" *Science* 249:386-390 (1990).

Simpson et al., "Insulin-like growth factor-I and diabetes. A review" *Growth Hormone and IGF Research* 8:83-95 (1998).

Smith, "Filamentous fusion phage: novel expression vectors that display cloned antigens on the virion surface" *Science* 228(4705):1315-1317 (1985).

Smith, B.J., "Enzymatic Methods for Cleaving Proteins" *Methods in Molecular Biology*, J.M. Walker, Totowa, NJ:Humana Press Inc. vol. 32:289-296 (1994).

Stichtenoth and Frolich, "Nitric oxide and inflammatory joint diseases" *British Journal of Rheumatology* 37(3):246-257 (1998).

Toolan et al., "Development of novel osteochondral graft for cartilage repair" *Journal of Biomedical Materials Research* 41(2):244-250 (1998).

Twigg, S. M. and Baxter, R. C., "Insulin-like Growth Factor (IGF)-binding Protein 5 Forms an Alternative Ternary Complex with IGFs and the Acid-labile Subunit" *Journal of Biological Chemistry* 273(11):6074-6079 (Mar. 1998).

van de Loo et al., "Reduced cartilage proteoglycan loss during zymosan-induced gonarthritis in NOS2-deficient mice and in anti-interleukin-1-treated wild-type mice with unabated joint inflammation" *Arthritis and Rheumatism* 41(4):634-646 (1998).

van der Kraan et al., "Inhibition of proteoglycan synthesis by transforming growth factor beta in anatomically intact articular cartilage of murine patellae" *Annals of Rheumatic Diseases* 51(5):643-647 (1992).

Varadarajan et al., "Cloning, expression in *Escherichia coli*, and reconstitution of human myoglobin" *Proc. Natl. Acad. Sci. USA* 82:5681-5684 (1985).

Vieira et al., "Production of Single-stranded Plasmid DNA" *Methods in Enzymology* 153:3-11 (1987).

Wells and Lowman, "Rapid Evolution of Peptide and Protein Binding Properties in Vitro" *Curr. Opin. Struct. Biol.* 2:597-604 (1992).

Wells, J. A., "Additivity of Mutational Effects in Proteins" *Biochemistry* 29(37):8509-8517 (Sep. 18, 1990).

Wood et al., "Cloning and expression of the growth hormone-dependent insulin-like growth factor-binding protein" *Molecular Endocrinology* 2:1176-1185 (1988).

Wood et al., "Crystal structure analysis of deamino-oxytocin: conformational flexibility and receptor binding" *Science* 232:633-636 (1986).

Wrighton et al., "Small peptides as potent mimetics of the protein hormone erythropoietin" *Science* 273:458-463 (1996).

Dubaquie et al., "Binding Protein-3-Selective Insulin-Like Growth Factor I Variants: Engineering, Biodistributions, and Clearance." *Endocrinology*, 142(1):165-173 (Jan. 2001).

Alberts et al. *Molecular Biology of the Cell*, 3rd edition, New York:Gardland Publishing, Inc. pp. 119 (1994).

Amin and Abramson., "The Role of Nitric Oxide in Articular Cartilage Breakdown in Osteoarthritis." *Curr. Opin. Rheum.* 10(3):263-268 (1998).

Arend W. P. et al., "Interleukin-1 Receptor Antagonist: Role in Biology" *Ann. Rev. Immunol.* 16:27-55 (1998).

Bach and Rechler., "Insulin-Like Growth Factor Binding Proteins." *Diabetes Reviews.* 3(1):38-61 (1995).

Bagley et al., "A key functional role for the insulin-like growth factor 1 N-terminal pentapeptide" *Biochemical Journal* 259(3):665-671 (May 1, 1989).

Ballard et al., "Does IGF-I Ever Act Through the Insulin Receptor?" *The Insulin-Like Growth Factors and Their Regulatory Proteins.*, Baxter, eds., Amsterdam: Elsevier pp. 131-138 (1994).

Bar et al., "Tissue Localization of Perfused Endothelial Cell IGF Binding Protein is Markedly Altered by Association with IGF-I." *Endocrinology.* 127(6):3243-3245 (1990).

Baragi et al., "Transplantation of Adenovirally Transduced Allogeneic Chondrocytes into Articular Cartilage Defects in Vivo." *Osteoarthritis and Cartilage.* 5(4):275-282 (1997).

Baragi et al., "Transplantation of Transduced Chondrocytes Protects Articular Cartilage from Interleukin 1-Induced Extracellular Matrix Degradation" *J. Clin. Invest.* 96(5):2454-2460 (Nov. 1995).

Barinaga, M., "Neurotrophic Factors Enter the Clinic [News]." *Science.* 264:772-774 (1994).

Barnett and Owens, "Insulin analogues" *Lancet* 349(9044):47-51 (Jan. 4, 1997).

Baron et al., "Dexamethasone acts locally to inhibit longitudinal bone growth in rabbits" *American Journal of Physiology* 263(3 Pt 1):E489-E492 (Sep. 1992).

Barreca et al., "Short stature associated with high circulating insulin-like growth factor (IGF)-binding protein-1 and low circulating IGF-II: effect of growth hormone therapy" *Journal of Clinical Endocrinology & Metabolism* 83(10):3534-3541 (Oct. 1998).

Batch et al., "Abnormal regulation of insulin-like growth factor binding proteins in adolescents with insulin-dependent diabetes" *Journal of Clinical Endocrinology & Metabolism* 73(5):964-968 (Nov. 1991).

Baxter & Martin, "Binding Proteins for Insulin-Like Growth Factors in Adult Rat Serum. Comparison With Other Human and Rat Binding Proteins" *Biochem. & Biophys. Res. Comm.* 147(1):408-415 (1987).

Baxter et al., "Recommendations for nomenclature of the insulin-like growth factor binding protein superfamily" *Endocrinology* 139(10):4036 (Oct. 1998).

Baxter, "Physiological Roles of IGF Binding Proteins" *Modern Concepts of Insulin-like Growth Factors*, Spencer, eds., Elsevier, New York pp. 371-380 (1991).

Baxter, R., "The Insulin-Like Growth Factors and Their Binding Proteins" *Comp. Biochem. Physiol.* 91B(2):229-235 (1988).

Baxter., "The Somatomedins: Insulin-Like Growth Factors." *Advances in Clinical Chemistry.* 25:49-115 (1986).

Bayne et al., "Structural Analogs of Human Insulin-Like Growth Factor I with Reduced Affinity for Serum Binding Proteins and the Type 2 Insulin-Like Growth Factor Receptor." *J. Bio. Chem.* 263:6233-6239 (1988).

Bayne et al., "The C Region of Human Insulin-Like Growth Factor (IGF) I is Required for High Affinity Binding to the Type 1 IGF Receptor." *J. Bio. Chem.* 264(19):11004-11008 (1988).

Bayne et al., "The Roles of Tyrosines 24, 31, and 60 in the High Affinity Binding of Insulin-Like Growth Factor-I to the Type I Insulin-Like Growth Factor Receptor." *J. Bio. Chem.* 265(26):15648-15652 (Sep. 15, 1990).

Bereket et al., "Insulin treatment normalizes reduced free insulin-like growth factor-I concentrations in diabetic children" *Clinical Endocrinology* 45(3):321-326 (Sep. 1996).

Bereket et al., "Regulation of the insulin-like growth factor system by acute acidosis" *Endocrinology* 137(6):2238-2245 (Jun. 1996).

Bhakta et al., "The Insulin-Like Growth Factors (IGFs) and I and II Bind to Articular Cartilage via the IGF-binding Proteins" *Journal of Biological Chemistry* 275(8):5860-5866 (Feb. 25, 2000).

Binkert et al., "Cloning, sequence analysis and expression of a cDNA encoding a novel insulin-like growth factor binding protein (IGFBP-2)" *EMBO Journal* 8:2497-2502 (1989).

Binoux, M., "Recent Data on Somatomedins (Insulin-Like Growth Factors)." *Annales d'Endocrinologie* (English Abstract Included) 41:157-192 (1980).

Blum et al., "Growth hormone resistance and inhibition of somatomedin activity by excess of insulin-like growth factor binding protein in uraemia" *Pediatric Nephrology* 5(4):539-544 (Jul. 1991).

Blum, W., "Insulin-like growth factors (IGFs) and IGF binding proteins in chronic renal failure: evidence for reduced secretion of IGFs" *Acta Paediatr. Scand.* 379(Suppl):24-31 (1991).

Bogan and Thorn, "Anatomy of hot spots in protein interfaces" *Journal of Molecular Biology* 280(1):1-9 (Jul. 3, 1998).

Bondy, C., "Clinical Uses of Insulin-Like Growth Factor I." *Annals of Internal Medicine.* 120:593-601 (1994).

Bornfeldt et al., "Binding and biological effects of insulin, insulin analogues and insulin-like growth factors in rat aortic smooth muscle cells. Comparison of maximal growth promoting activities" *Diabetologia* 34(5):307-313 (May 1991).

Bowers, C. Y., "GH Releasing Peptides—Structure and Kinetics" *J. Pediatr. Endocrinology* 6(1):21-31 (1993).

Bowie et al., "Deciphering the Message in Protein Sequences: Tolerance to Amino Acid Substitutions" *Science* 247:1306-1310 (1990).

Brandt et al., "Role of natriuretic peptide clearance receptor in in vivo control of C-type natriuretic peptide" *American Journal of Physiology* 269(1 Pt 2):H326-H331 (Jul. 1995).

Brange et al., "Designing insulin for diabetes therapy by protein engineering" *Curr. Opin. Struct. Biol.* 1:934-940 (1991).

Brange et al., "Monomeric insulins obtained by protein engineering and their medical implications" *Nature* 333(6174):679-682 (Jun. 16, 1988).

Brange, J., "Insulin Preparations" *Galenics of Insulin, The Physicochemical and Pharmaceutical Aspects of Insulin and Insulin Preparations*, New York:Springer-Verlag pp. 17-40 (1987).

Brems et al., "Altering the association properties of insulin by amino acid replacement" *Protein Engineering* 5(6):527-533 (1992).

Brenner, S.E., "Errors in genome annotation" *Trends in Genetics* 15:132-133 (1999).

Brewer et al., "Cloning, Characterization, and Expression of a Human Insulin-Like Growth Factor Binding Protein" *Biochem. & Biophys. Res. Comm.* 152(3):1289-1297 (1988).

Brinkman et al., "Isolation and characterization of a cDNA encoding the low molecular weight insulin-like growth factor binding protein (IBP-1)" *The EMBO J.* 7:2417-2423 (1988).

Cara et al., "An insulin-like growth factor I/insulin hybrid exhibiting high potency for interaction with the type I insulin-like growth factor and insulin receptors of placental plasma membranes" *Journal of Biological Chemistry* 265(29):17820-17825 (Oct. 15, 1990).

Carlsson et al., "Growth Hormone and Growth in Diabetic Rats: Effects of Insulin and Insulin-Like Growth Factor-I Infusions" *J. Endocrinol.* 122:661-670 (1989).

Cascieri et al., "Analysis of the interaction of IGF-I analogs with the IGF-I receptor and IGF binding proteins" *Advances in Experimental Medicine & Biology* 343:33-40 (1993).

Cascieri et al., "Mutants of Human Insulin-Like Growth Factor I with Reduced Affinity for the Type 1 Insulin-Like Growth Factor Receptor." *Biochemistry* 27(9):3229-3233 (May 3, 1988).

Cascieri et al., "Structural Analogs of Human Insulin-Like Growth Factor (IGF) I with Altered Affinity for Type 2 IGF Receptors." *J. Bio. Chem.* 264:2199-2202 (1989).

Castellanos-Serra ete al., "Expression and folding of an interreukin-2-proinsulin fusion protein and its conversion into insulin by a single step enzymatic removal of the C-peptide and the N-terminal fused sequence" *FEBS Letters* 378:171-176 (1996).

Charlton et al., "Growth hormone-deficient dwarfism in the rat: a new mutation" *J. of Endocrinology* 119:51-58 (1988).

Cheetham et al., "The Effects of Recombinant Human Insulin-like Growth Factor I on Growth Hormone Secretion in Adolescents With Insulin Dependent Diabetes Mellitus" *Clin. Endocrinol.* 40:515-522 (1994).

Cheetham et al., "The Effects of Recombinant Insulin-like Growth Factor I Administration on Growth Hormone Levels and Insulin Requirements in Adolescents With Type 1 (Insulin-dependent) Diabetes Mellitus" *Diabetologia* 36:678-681 (1993).

Chen et al., "Chondrocyte Transplantation and Experimental Treatment Options for Articular Cartilage Defects" *Amer. J. Orthop.* 26(6):396-406 (1997).

Chen et al., "Recombinant human IGF-I infusion results in transient improvement in nitrogen balance: evidence for IGF-I autoregulation" *US Endocrine Meeting* (Abstract 1596) pp. 449 (1993).

Chernausek et al., "Proteolytic cleavage of insulin-like growth factor binding protein 4 (IGFBP-4). Localization of cleavage site to nonhomologous region of native IGFBP-4" *Journal of Biological Chemistry* 270(19):11377-11382 (May 12, 1995).

Chin et al., "Interactions Between Interleukin-1 and Basic Fibroblast Growth Factor on Articular Chondrocytes. Effects on Cell Growth, Prostanoid Production, and Receptor Modulation" *Arthritis Rheum.* 34(3):314-324 (Mar. 1991).

Clark and Robinson, "Up and down the growth hormone cascade" *Cytokine & Growth Factor Reviews* 7(1):65-80 (Jun. 1996).

Clark et al., "Growth-Responses to Patterned GH Delivery" *Endocrine* 3:717-723 (1995).

Clark et al., "Insulin-Like Growth Factor-1 and Growth Hormone (GH) Have Distinct and Overlapping anabolic Effects in GH-Deficient Rats" *Endocrine* 3:297-304 (1995).

Clemmons and Van Wyk., "Somatomedin: Physiological Control and Effects on Cell Proliferation." *Handbook Exp. Pharmacol.* 57:161-208 (1981).

Clemmons et al., "Discrete Alterations of the Insulin-Like Growth Factor I Molecule Which Alter Its Affinity for Insulin-Like Growth Factor-Binding Proteins Result in Changes in Bioactivity." *J. Bio. Chem.* 265(21):12210-12216 (1990).

Cohick and Clemmons, "The insulin-like growth factors" *Annu. Rev. Physiol.* 55:131-153 (1993).

Collett-Solberg and Cohen, "The Role of the Insulin-Like Growth Factor Binding Proteins and the IGFBP Proteases in Modulating IgF Action" *Endocrin. Metab. Clin. N. Amer.* 25(3):591-614 (Sep. 1996).

Conover, "Potentiation of insulin-like growth factor (IGF) action by IGF-binding protein-3: studies of underlying mechanism" *Endocrinology* 130(6):3191-3199 (Apr. 1992).

Conover, C., "Insulin-like growth factor binding protein proteolysis in bone cell models" *Progress in Growth Factor Research* 6(2-4):301-309 (1995).

Coutts et al., "Effect of Growth Factors on Cartilage Repair" *Amer. Acad. Orthop. Surg.* (Instructional Course Lect.), Chapter 47, pp. 487-494 (1997).

Cox et al., "Recombinant human insulin-like growth factor (IGF)-binding protein-1 inhibits somatic growth stimulated by IGF-I and growth hormone in hypophysectomized rats" *Endocrinology* 135(5):1913-1920 (1994).

Crown and Holly, "The insulin-like growth factor system in critical illness: pathophysiology and therapeutic potential" *Clinical Nutrition* 14:321-328 (1995).

Cunningham et al., "Engineering human prolactin to bind to the human growth hormone receptor" *Science* 247:1461-1465 (1990).

Davidson, M.B., "Effect of growth hormone on carbohydrate and lipid metabolism" *Endocrin Rev.* 8(2):115-131 (May 1987).

DeWolf et al., "Solution structure of a mini IGF-1" *Protein Science* 5(11):2193-2202 (Nov. 1996).

DiMarchi et al., "Synthesis of a fast-acting insulin analog based on structural homology with insulin-like growth factor-I" *Peptides: Chemistry and Biology* (Proceedings of the Twelfth American Peptide Symposium), J.A. Smith and J.E. Rivier, eds., Leiden:ESCOM pp. 26-28 (1992).

Dodd et al., "Reversible adsorption of soluble hexameric insulin onto the surface of insulin crystals cocrystallized with protamine: an electrostatic interaction" *Pharmaceutical Research* 12(1):60-68 (Jan. 1995).

Drejer, K., "The bioactivity of insulin analogues from in vitro receptor binding to in vivo glucose uptake" *Diabetes-Metabolism Reviews* 8(3):259-285 (Oct. 1992).

Dubaquie et al., "Binding Protein-3-Selective Insulin-Like Growth Factor I Variants: Engineering, Biodistributions, and Clearance." *Endocrinology.* 142(1):165-173 (Jan. 2001).

Duerr et al., "Insulin-Like Growth Factor-1 Enhances Ventricular Hypertrophy and Function During the Onset of Experimental Cardiac Failure." *J. Clin. Invest.* 95:619-627 (1995).

Elahi et al., "Hemodynamic and Metabolic Responses to Human Insulin-Like Growth Factor I (IGF-I) in Men." *Modern Concepts of*

*Insulin-Like Growth Factors.*, Spencer, EM, ed., New York:Elsevier Science Publ. Co. pp. 219-224 (1991).

Evans and Robbins, "Getting Genes Into Human Synovium" *J. Rheumatol.* 24(11):2061-2063 (1997).

Evans et al., "Blocking Cytokines with Genes" *J. Leukocyte Biol.* 64:55-61 (Jul. 1998).

Fielder et al., "Differential long-term effects of insulin-like growth factor-I (IGF-I) growth hormone (GH), and IGF-I plus GH on body growth and IGF binding proteins in hypophysectomized rats" *Endocrinology* 137:1913-1920 (1996).

Florini and Roberts, "Effect of Rat Age on Blood Levels of Somatomedin-like Growth Factors" *J. Gerontol.* 35(1):23-30 (1980).

Franklin et al., "Insulin-Like Growth Factor I Preserves Renal Function Postoperatively" *Am. J. Physiol.* 272:F257-F259 (1997).

Froesch et al., "Metabolic and Therapeutic Effects of Insulin-Like Growth Factor I" *Horm. Res.* 42:66-71 (1994).

Fuller et al., "Stimulation of Cardiac Protein Synthesis by Insulin-like Growth Factors" *Biochemical Society Transactions* 19:277S (1991).

Furnsinn et al., "Insulin-Like Growth Factor-I Inhibits Insulin and Amylin Secretion in Conscious Rats" *Endocrinology* 135(5):2144-2149 (1994).

Garrett et al., "Crystal Structure of the First Three Domains of the Type-1 Insulin-Like Growth Factor Receptor." *Nature.* 394(6691):395-399 (Jul. 23, 1998).

Ghazzi et al., "Cardiac and glycemic benefits of troglitazone treatment in NIDDM" *Diabetes* 46:433-439 (1997).

Guerne et al., "Growth Factor Responsiveness of Human Articular Chondrocytes: District Profiles in Primary Chondrocytes, Subcultured Chondrocytes, and Fibroblasts." *J. Cellular Physiology* 158(3):476-484 (1994).

Guler et al., "Effects of Insulin-like Growth Factor I in Man" *Acta Paediatr. Scand.* 367:52-54 (Suppl. 1990).

Guler et al., "Effects of recombinant insulin-like growth factor I on insulin secretion and renal function in normal human subjects" *Proc. Natl. Acad. Sci. USA* 86:2868-2872 (Apr. 1989).

Guler et al., "Insulin-like growth factor I increases glomerular filtration rate and renal plasma flow in man" *Acta Endocrinologica* 121:101-106 (1989).

Guler et al., "Recombinant Human Insulin-Like Growth Factor 1 Stimulates Growth and has Distinct Effects on Organ Size in Hypophysectomized Rats." *Proc. Natl. Acad. Sci. USA* 85:4889-4893 (1988).

Guler et al., "Short-term metabolic effects of recombinant human insulin-like growth factor I in healthy adults" *New England J. of Medicine* 317(3):137-140 (1987).

Hall et al., "Serum levels of the low molecular weight form of insulin-like growth factor binding protein in healthy subjects and patients with growth hormone deficiency, acromegaly and anorexia nervosa" *Acta Endocrinologica* 118(3):321-326 (Jul. 1988).

Hammerman and Miller., "The Growth Hormone Insulin-Like Factor Axis in Kidney Revisited." *Am. J. Physiol.* 265:F1-F14 (1993).

Hammerman and Miller., "Therapeutic Use of Growth Factors in Renal Failure." *J. Am. Soc. Nephrol.* 5:1-11 (1994).

Hampton et al., "Purification and Characterization of an Insulin-like Growth Factor II Variant from Human Plasma" *Journal of Biological Chemistry* 264(32):19155-19160 (Nov. 15, 1989).

Hartman et al., "A low dose euglycemic infusion of recombinant human insulin-like growth factor I rapidly suppresses fasting-enhanced pulsatile growth hormone secretion in humans" *J. Clin. Invest.* 91:2453-2462 (1993).

Hasegawa et al., "The Free Form of Insulin-Like Growth Factor I Increases in Circulation During Normal Human Pregnancy." *J. Clin. Endocrinol. Metabol.* 80:3284-3286 (1995).

Hirschberg et al., "Effects of insulin-like growth factor I on renal function in normal men" *Kidney International* 43:387-397 (1993).

Hise et al., "Influence of circulating insulin-like growth factor-I compared with that of intrarenal insulin-like growth factor-I on proximal nephron receptor density in rats" *Clinical Science* 83:233-239 (1992).

Hizuka et al., "Measurement of Free Form of Insulin-Like Growth Factor I in Human Plasma." *Growth Regulation.* 1:51-55 (1991).

Hoogenberg et al., "Effect of growth hormone and insulin-like growth factor I on urinary albumin excretion: studies in acromegaly and growth hormone deficiency" *Acta Endocrinologica* 129:151-157 (1993).

Horber et al., "Differential effects of prednisone and growth hormone on fuel metabolism and insulin antagonism in humans" *Diabetes* 40(1):141-149 (Jan. 1991).

Howey et al., "[Lys(B28), Pro(B29)]-Human Insulin: an Equipotent Analog of Human Insulin with Rapid Onset and Short Duration of Action" *Diabetes* (Abstract #1688) 40(Suppl 1):423A (1991).

Hua et al., "Native and non-native structure in a protein-folding intermediate: spectroscopic studies of partially reduced IGF-I and an engineered alanine model" *Journal of Molecular Biology* 259(2):297-313 (Jun. 7, 1996).

Hua, Qing-Hua et al., "Mini-proinsulin and Mini-IGF-I: Homogogous Protein Sequences Encoding Non-homologous Structures" *JMB* 277:103-118 (1998).

Humbel., "Insulin-Like Growth Factors I and II." *European Journal of Biochemistry.* 190:445-462 (1990).

Ikkos et al., "Glomerular filtration rate and renal plasma flow in acromegaly" *Acta Endocrinologica* 21:226-236 (1956).

Jabri et al., "Adverse Effects of Recombinant Human Insulin-Like Growth Factor I in Obese Insulin-Resistant Type II Diabetic Patients." *Diabetes* 43:369-374 (1994).

Jansson et al., "The Insulin-Like Growth Factor (IGF) Binding Protein 1 Binding Epitope on IGF-I Probed by Heteronuclear NMR Spectroscopy and Mutational Analysis." *J. Bio. Chem.* 273(38):24701-24707 (Sep. 18, 1998).

Johnson et al., "Underexpression of β cell high $K_m$ glucose transporters in noninsulin-dependent diabetes" *Science* 250:546-549 (1990).

Joly et al., "Overexpression of *Escherichia coli* Oxidoreductases Increases Recombinant Insulin-Like Growth Gactor-I Accumulation." *Proc. Natl. Acad. Sci. USA* 95:2773-2777 (Mar. 1998).

Jones and Clemmons., "Insulin-Like Growth Factors and Their Binding Proteins: Biological Actions." *Endocrine Rev.* 16(1):3-34 (1995).

Juul et al., "Serum Concentrations of Free and Total Insulin-Like Growth Factor-I, IGF Binding Proteins-1 and -3 and IGFBP-3 Protease Activity in Boys with Normal or Precocious Puberty." *Clin. Endocrin.* 44:515-523 (1996).

Kalus et al., "Structure of the IGF-binding domain of the insulin-like growth factor-binding protein-5 (IGFBP-5): implications for IGF and IGF-I receptor interactions" *EMBO Journal* 17(22):6558-6572 (Nov. 16, 1998).

Kanety et al., "Long-term treatment of Laron type dwarfs with insulin-like growth factor-1 increases serum insulin-like growth factor-binding protein-3 in the absence of growth hormone activity" *Acta Endocrinologica* 128(2):144-149 (Feb. 1993).

Kang et al., "Comparison of subcutaneous soluble human insulin and insulin analogues ($Asp^{B9}$, $Glu^{B27}$; $Asp^{B10}$; $Asp^{B28}$) on meal-related plasma glucose excursions in type I diabetic subjects" *Diabetes Care* 14(7):571-577 (Jul. 1991).

Kang et al., "Ex Vivo Gene Transfer to Chondrocytes in Full-Thickness Articular Cartilage Defects: A Feasibility Study." *Osteoarthritis and Cartilage.* 5(2):139-143 (1997).

Kang et al., "Gene Therapy for Arthritis: Principles and Clinical Practice." *Biochemical Society Transactions.* 25(2):533-537 (1997).

Kerr et al., "Effect of Insulin-like Growth Factor 1 on the Responses to and Recognition of Hypoglycemia" *Diabetes: American Diabetes Association (ADA)*, San Antonio, Texas, Jun. 20-23, 1992 (abstract #225), 52nd Annual Meeting edition 41(supp 1):60A (Jun. 1992).

Kerr et al., "Effect of Insulin-like Growth Factor-1 on the Responses to and Recognition of Hypoglycemia in Humans: A Comparison with Insulin." *J. Clin. Invest.* 91:141-147 (1993).

King et al., "Production and characterization of recombinant insulin-like growth factor-I (IGF-I) and potent analogues of IGF-I, with Gly or Arg substituted for $Glu^3$, following their expression in *Escherichia coli* as fusion proteins" *Journal of Molecular Endocrinology* 8(1):29-41 (Feb. 1992).

Kletzien et al., "Enhancement of adipocyte differentiation by an insulin-sensitizing agent" *Molecular Pharmacology* 41(2):393-398 (Feb. 1992).

Kristensen, C. et al., "Alanine Scanning Mutagenesis of Insulin" *The Journal of Biological Chemistry* 272(20):12978-12983 (May 16, 1997).

Kupfer et al., "Enhancement of the anabolic effects of growth-hormone and insulin-like growth factor I by use of both agents simultaneously" *J. Clin Invest.* 91:391-396 (1993).

Kuzuya et al., "Trial of Insulinlike Growth Factor I Therapy for Patients with Extreme Insulin Resistance Syndromes." *Diabetes.* 42:696-705 (1993).

Lassalle et al., "ESM-1 is a novel human endothelial cell-specific molecule expressed in lung and regulated by cytokines" *Journal of Biological Chemistry* 271:20458-20464 (1996).

Leahy et al., "Insulin-Like Growth Factor-I at Physiological Concentrations is a Potent Inhibitor of Insulin Secretion" *Endocrinology* 126(3):1593-1598 (1990).

Lee et al., "IGF binding proteins in growth-retarded children with chronic renal failure" *Pediatric Research* 26(4):308-315 (Oct. 1989).

Lee et al., "Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-I and IGF-II Receptors" *Mol. Endocrinol.* 2(5):404-411 (1988).

Lee et al., "Insulin-like growth factor-binding protein-1: recent findings and new directions" *Proceedings of the Society for Experimental Biology & Medicine* 216(3):319-357 (Dec. 1997).

Lee et al., "Regulation and Function of Insulin-Like Growth Factor-Binding Protein-1." *Proc. Soc. Exp. Biol. & Med.* 204:4-29 (1993).

Leong S. R. et al., "Structure and Functional Expression of Acid-Labial Subunit of the Insulin-Like Growth Factor-Binding Protein Complex" *Mol. Endocrinol.* 6(6):870-876 (1992).

Leung et al., "Growth hormone receptor and serum binding protein: purification, cloning and expression" *Nature* 330:537-543 (1987).

Lewitt and Baxter, "Insulin-Like Growth Factor-Binding Protein-1: A Role in Glucose Counterregulation?" *Mol. Cell. Endocrin.* 79(1-3):C147-C152 (1991).

Lewitt et al., "Bioavailability of insulin-lake growth factors (IGFs) in rats determined by the molecular distribution of human IGF-binding protein-3" *Endocrinology* 133:1797-1802 (1993).

Lewitt et al., "Insulin-like Growth Factor-binding Protein-1 Modulates Blood Glucose Levels" *Endocrinology* 129(4):2254-2256 (1991).

Lieberman et al., "Anabolic effects of recombinant insulin-like growth factor I in AIDS-associated cachexia" *US Endocrine Meeting* (Abstract 1664) pp. 466 (1993).

Lieberman et al., "Anabolic effects of recombinant insulin like growth factor-I in cachectic patients with the acquired immunodeficiency syndrome" *J. Clin. Endocrinol. and Metab.* 78(2):404-410 (1994).

Lieberman et al., "Effects of Recombinant Human Insulin-Like Growth Factor-I (rhIGF-I) on Total and Free IGF-I Concentrations, IGF-Binding Proteins, and Glycemic Response in Humans." *J. Clin. Endocrinol. & Metab.* 75(1):30-36 (1992).

Liu et al., "Characterization of insulin-like growth factor-binding proteins in human serum from patients with chronic renal failure" *Journal of Clinical Endocrinology & Metabolism* 70(3):620-628 serum from (Mar. 1990).

Livnah et al., "Functional mimicry of a protein hormone by a peptide agonist: the EPO receptor complex at 2.8 Å" *Science* 273(5274):464-471 (Jul. 26, 1996).

Loddick et al., "Displacement of insulin-like growth factors from their binding proteins as a potential treatment for stroke" *Proc. Natl. Acad. Sci. USA* 95(4):1894-1898 (Feb. 17, 1998).

Lowman et al., "Molecular Mimics of Insulin-Like Growth Factor 1 (IGF-1) for Inhibiting IGF-1: IGF-Binding Protein Interactions." *Biochemistry* 37(25):8870-8878 (1998).

Lowman et al., "Peptides that displace IGFs from their BPS as potential novel treatment modalities of growth orders-basic aspects" (Abstract presented at the Intl. Pediatric Nephrology Assn.'s 6th Symposium on Growth and Development in Children with Chronic Renal Failure held in NY on Mar. 11-13, 1999).

Lowman, H., "Bacteriophage display and discovery of peptide leads for drug development" *Annual Review of Biophysics and Biomolecular Structure* 26:401-424 (1997).

Lowman, Henry et al., "Exchanging Interleukin-8 and Melanoma Growth-stimulating Activity Receptor Binding Specificities" *Journal of Biological Chemistry* 271(24):14344-14352 (1996).

Lowman, Henry et al., "Mutational Analysis and Protein Engineering of Receptor-binding Determinants in Human Placental Lactogen" *Journal of Biological Chemistry* 266(17):10982-10988 (Jun. 15, 1991).

Maack et al., "Physiological Role of Silent Receptors of Atrial Natriuretic Factor" *Science* 238:675-678 (Oct. 30, 1987).

Magee et al., "Insulin-like growth factor I and its binding proteins: a study of the binding interface using B-domain analogues" *Biochemistry* 38(48):15863-15870 (Nov. 30, 1999).

Martin and Baxter, "Regulation and actions of the insulin-like growth factor binding proteins" *Current Opinion in Endocrinology and Diabetes* pp. 16-21 (1994).

McCarthy et al., "Cortisol inhibits the synthesis of insulin-like growth factor-I in skeletal cells" *Endocrinology* 126(3):1569-1575 (Mar. 1990).

McInnes and Sykes, "Growth factor receptors: structure, mechanism, and drug discovery" *Biopolymers* 43(5):339-366 (1997).

Miller et al., "Effects of IGF-I on renal function in end-stage chronic renal failure" *Kidney International* 46:201-207 (1994).

Morrow et al., "Recombinant Human (rh) IGF-1 Reverses Hyperglycemia and Improves Insulin Sensitivity in Severe Insulin Resistance" *Diabetes-53rd Annual Meeting*, Jun. 12-15, 1993 (Suppl. 1, abstract No. 269) 42:83A (1993).

Moses, A.C., "Recombinant insulinlike growth factor-I as therapy in states of altered carbohydrate homeostasis" *Curr. Opin. Endocrin. Diab.* 4:16-25 (1997).

Murphy et al., "Phenotypic manifestations of insulin-like growth factor binding protein-1 (IGFBP-1) and IGFBP-3 overexpression in transgenic mice" *Progress in Growth Factor Research* 6(2-4):425-432 (s 1995).

Nakagawa, S. et al., "Role of the Phenylalanine B25 Side Chain in Directing Insulin Interaction with Its Receptor" *The Journal of Biological Chemistry* 261(16):7332-7341 (Jun. 5, 1986).

Ngo et al., "Computational Complexity, Protein Structure Prediction, and the Levinthal Paradox" *The Protein Folding Problem and Tertiary Structure Prediction*, Merz & Le Grand, Boston:Birkhauser pp. 491-495 (1994).

O'Shea and Layish, "Growth hormone and the kidney: a case presentation and review of the literature" *J. Am. Soc. Nephrol.* 3:157-161 (1992).

O'Shea et al., "Effects of IGF-I on renal function in patients with chronic renal failure" *Am. J. Physiol.* 264:F917-F922 (1993).

Oh et al., "Characterization of the Affinities of Insulin-Like Growth Factor (IGF)-Binding Proteins 1-4 for IGF-I, IGF-II, IGF-I/Insulin Hybrid, and IGF-I Analogs." *Endocrinology.* 132:1337-1344 (1993).

Oh et al., "Synthesis and characterization of insulin-like growth factor-binding protein (IGFBP)-7. Recombinant human mac25 protein specifically binds IGF-I and -II" *Journal of Biological Chemistry* 271:30322-30325 (1996).

Olney et al., "Chondrocytes from Osteoarthritic Cartilage Have Increased Expression of Insulin-Like Growth Factor I (IGF-I) and IGF-Binding Protein-3 (IGFBP-3) and -5, but not IGF-II or IGFBP-4" *J. Clin. Endo. and Metab.* 81(3):1096-1103 (1996).

Osborn et al., "Growth Factor Stimulation of Adult Articular Cartilage" *J. Orthoped. Res.* 7(1):35-42 (1989).

Peterkofsky et al., "Elevated Activity of Low Molecular Weight Insulin-Like Growth Factor-Binding Proteins in Sera of Vitamin C-Deficient and Fasted Guinea Pigs" *Endocrinology* 128(4):1769-1779 (1991).

Powell et al., "Characterization of insulin-like growth factor binding protein-3 in chronic renal failure serum" *Pediatric Research* 33(2):136-143 (Feb. 1993).

Powell et al., "Modulation of growth factors by growth hormone in children with chronic renal failure." *Kidney International* 51(6):1970-1979 (Jun. 1997).

Powell et al., "Serum concentrations of insulin-like growth factor (IGF)-1, IGF-2 and unsaturated somatomedin carrier proteins in children with chronic renal failure" *American Journal of Kidney Diseases* 10(4):287-292 (Oct. 1987).

Quigley and Baum, "Effects of growth hormone and insulin-like growth factor I on rabbit proximal convoluted tubule transport" *J. Clin. Invest.* 88:368-374 (1991).
Quin et al., "Acute Response to Recombinant Insulin-like Growth Factor I in a Patient with Mendenhall's Syndrome" *New England J. of Medicine* 323:1425-1426 (1990).
Rajkumar et al., "Growth retardation and hyperglycemia in insulin-like growth factor binding protein-1 transgenic mice" *Endocrinology* 136(9):4029-4034 (Sep. 1995).
Rinderknecht and Humbel, "Polypeptides with Nonsuppressible Insulin-Like and Cell-Growth Promoting Activities in Human Serum: Isolation, Chemical Characterization, and Some Biological Properties of Forms I and II." *Proc. Natl. Acad. Sci USA*. 73(7):2365-2369 (1976).
Rinderknecht and Humbel., "The Amino Acid Sequence of Human Insulin-Like Growth Factor I and Its Structural Homology with Proinsulin." *Journal of Biological Chemistry* 253(8) :2769-2776 (1978).
Rogachefsky et al., "Treatment of canine osteoarthritis with insulin-like growth factor-1 (IGF-1) and sodium pentosan polysulfate" *Osteoarthritis and Cartilage* 1:105-114 (1993).
Rogachefsky et al., "Treatment of Canine Osteoarthritis with Sodium Pentosan Polysulfate and Insulin-Like Growth Factor-1" *Annals NY Acad. Sci*. 732:392-394 (1994).
Rosenfeld et al., "IGF-1 treatment of syndromes of growth hormone insensitivity" *The insulin-like growth factors and their regulatory proteins*, Baxter et al. eds., Amsterdam:Excerpta Medica pp. 457-463 (1994).
Ross et al., "Critically ill patients have high basal growth hormone levels with attenuated oscillatory activity associated with low levels of insulin-like growth factor-I" *Clinical Endocrinology* 35(1):47-54 (Jul. 1991).
Ross et al., "The Role of Insulin, Growth Hormone and IGF-I as Anabolic Agents in the Critically Ill" *Intensive Care Med*. 19(2):S54-S57 (Suppl. 1993).
Rudinger, J., "Characteristics of the Amino Acids as Components of a Peptide Hormone Sequence" *Peptide Hormones*, J.A. Parsons, Baltimore:University Park Press pp. 6 (1976).
Saad et al., "Low-Doses of Insulin-Like Growth Factor-I Improve Insulin Sensitivity." *Diabetologia*. (Abstract 152) 37:A40 (Supp. 1 1994).
Sapir et al., "The role of alanine and glutamine in steroid-induced nitrogen wasting in man" *Clinical Science & Molecular Medicine* 53(3):215-220 (Sep. 1977).
Sato and Urist, "Bone Morphogenetic Protein-Induced Cartilage Development in Tissue Culture." *Clin. Ortho. Rel. Res*. (Sect. II, Basic Science and Pathology) 183:180-187 (Mar. 1984).
Schalch et al., "Short-Term Effects of Recombinant-Human Insulin-Like Growth Factor I on Metabolic Control of Patients with Type II Diabetes Mellitus" *J. of Clinical Endocrinology & Metabolism* 77(6):1563-1568 (1993).
Schalch et al., "Short-Term Metabolic Effects of Recombinant Human Insulin-Like Growth Factor I (rhIGF-I) in Type II Diabetes Mellitus." *Modern Concepts of Insulin-Like Growth Factors*., Spencer, ed., New York:Elsevier Science Publ. Co. pp. 705-713 (1991).
Schoen et al., "Growth Hormone Secretagogues" *Annual Reports in Medicinal Chemistry: Section IV-Immunology, Endocrinology & Metabolic Diseases*, William K. Hagmann, Chapter 19, vol. 28:177-186 (1993).
Schoenle et al., "Recombinant Human Insulin-Like Growth Factor I (rhIGF I) Reduces Hyperglycaemia in Patients with Extreme Insulin Resistance." *Diabetologia*. 34:675-679 (1991).
Sherwin et al., "Metabolic Effects of Insulin-like Growth-Factor I in Normal Humans" *Horm. Res*. 41:97-101 (Suppl. 2 1994).
Shmueli et al., "High insulin-like growth factor binding protein 1 levels in cirrhosis: link with insulin resistance" *Hepatology* 24(1):127-133 (Jul. 1996).
Simmons et al., "Increased proteolysis. An effect of increases in plasma cortisol within the physiologic range" *Journal of Clinical Investigation* 73(2):412-420 (Feb. 1984).
Skottner et al., "Growth responses in a mutant dwarf rat to human growth hormone and recombinant human insulin-like growth factor I" *Endocrinology* 124(5):2519-2526 (1989).

Slieker and Sundell, "Modifications in the 28-29 position of the insulin B-chain alter binding to the IGF-I receptor with minimal effect on insulin receptor binding" *Diabetes* (Abstract #670) 40(Suppl. 1):168A (1991).
Slieker et al., "Insulin and IGF-I Analogs: Novel Approaches to Improved Insulin Pharmacokinetics" *Adv. Experimental Med. Biol*. 343:25-32 (1994).
Stern et al., "Insulin resistance and pancreatic insulin release in the genetically obese Zucker rat" *Proc. Soc. Exp. Biol. Med*. 139:66-69 (1972).
Suikkari et al., "Insulin Regulates the Serum Levels of Low Molecular Weight Insulin-Like Growth Factor-Binding Protein." *J. Clin. Endocrin. Metabol*. 66:266-272 (1988).
Swisshelm et. al., "Enhanced expression of an insulin growth factor-like binding protein (mac25) in senescent human mammary epithelial cells and induced expression with retinoic acid" *Proc. Natl. Acad. Sci*. 92:4472-4476 (1995).
Takano et al., "Effects of sc Administration of Recombinant Human Insulin-like Growth Factor I (IGF-I) on Normal Human Subjects" *Endocrinol. Japan* 37(2):309-317 (1990).
Tanner et al., "Comparative rapidity of response of height, limb muscle and limb fat to treatment with human growth hormone in patients with and without growth hormone deficiency" *Acta Endocrinologica* 84:681-696 (1977).
Terasawa et al., "Solution structure of human insulin-like growth factor II; recognition sites for receptors and binding proteins" *EMBO Journal* 13(23):5590-5597 (Dec. 1, 1994).
Thrailkill et al., "Dual hormonal replacement therapy with insulin and recombinant human insulin-like growth factor (IGF)-I in insulin-dependent diabetes mellitus: effects on the growth hormone/IGF/IGF-binding protein system" *Journal of Clin. Endocrinol. & Metab*. 82(4):1181-1187 (Apr. 1997).
Tomas et al., "Insulin-like growth factor-I (IGF-I) and especially IGF-I variants are anabolic in dexamethasone-treated rats" *Biochemical Journal* 282(Pt 1):91-97 (Feb. 15, 1992).
Tonshoff at al., "Decreased hepatic insulin-like growth factor (IGF)-I and increased IGF binding protein-1 and -2 gene expression in experimental uremia" *Endocrinology* 138(3):938-946 (Mar. 1997).
Tonshoff et al., "Insulin-like growth factors (IGF) and IGF binding proteins in children with chronic renal failure" *Progress in Growth Factor Research* 6(2-4):481-491 (1995).
Tonshoff at al., "Serum insulin-like growth factors (IGPs) and IGF binding proteins 1, 2, and 3 in children with chronic renal failure: relationship to height and glomerular filtration rate" *Journal of Clinical Endocrinology & Metabolism* 80(9):2684-2691 (Sep. 1995).
Tonshoff et al., "Serum insulin-like growth factors and their binding proteins in children with end-stage renal disease" *Pediatric Nephrology* 10(3):269-274 (Jun. 1996).
Toolan et al., "Development of Novel Osteochondral Graft for Cartilage Repair." *J. Biomed. Mater. Res*. 41(2):244-250 (1998).
Torres et al., "Solution Structure of Human Insulin-Like Growth Factor II: Relationship to Receptor and Binding Protein Interactions." *J. Mol. Bio*. 248(2):385-401 (Apr. 28, 1995).
Trainer et al., "Pyridostigmine partially reverses dexamethasone-induced inhibition of the growth hormone response to growth hormone-releasing hormone" *Journal of Endocrinology* 134(3):513-517 (Sep. 1992).
Ullrich et al., "Insulin-like growth factor I receptor primary structure: comparison with insulin receptor suggests structural determinants that define functional specificity" *EMBO Journal* 5(10):2503-2512 (1986).
Umpleby et al., "Effects of Insulin-like Growth Factor-I (IGF-I), Insulin and Combined IGF-I-insulin Infusions on Protein Metabolism in Dogs" *Eur. J. Clin. Invest*. 24:337-344 (1994).
Underwood et al., "IGFs: Function and Clinical Importance 6 Therapy With Recombinant Human Insulin-like Growth Factor I in Children With Insensitivity to Growth Hormone and in catabolic conditions" *J. Internal Med*. 234:571-577 (1993).
Underwood et al., "Regulation of somatomedin-c/insulin-like growth factor I by nutrients" *Hormone Res*. 24:166-176 (1986).

Usala et al., "Brief Report: Treatment of Insulin-Resistant Diabetic Ketoacidosis with Insulin-Like Growth Factor I in an Adolescent with Insulin-Dependent Diabetes." *New Engl. J. Med.* 327(12):853-857 (1992).

Uthne et al., "Effects of human somatomedin preparations on membrane transport and protein synthesis in the isolated rat diaphragm" *J. Clin. Endocrinol. Metab.* 39(3):548-554 (1974).

van de Loo et al., "Reduced cartilage proteoglycan loss during zymosan-induced gonarthritis in NOS2-deficient mice and in anti-interleukin-1-treated wild-type mice with unabated joint inflammation" *Arthritis Rheum.* 41(4):634-646 (1998).

van der Kraan et al., "Inhibition of Proteoglycan Synthesis by Transforming Growth Factor β in Anatomically Intact Articular Cartilage of Murine Patellae" *Annals Rheum. Dis.* 51(5):643-647 (1992).

Van-Wyk et al., "The Somatomedins: A Family of Insulinlike Hormones Under Growth Hormone Control." *Recent Prog. Horm. Res.* 30:259-318 (1974).

Vlachopapadopoulou et al., "Metabolic and Clinical Response to Recombinant Human Insulin-like Growth Factor I in Myotonic Dystrophy—A Clinical Research Center Study" *J. Clin. Endo. Metab.* 80(12):3715-3723 (1995).

Walker et al., "Stimulation of statural growth by recombinant insulin-like growth factor I in a child with growth hormone insensitivity syndrome (Laron type)" *J. Pediatr.* 121:641-646 (1992).

Weiss et al., "Heteronuclear 2D NMR studies of an engineered insulin monomer: assignment and characterization of the receptor-binding surface by selective $^2$H and $^{13}$C labeling with application to protein design" *Biochemistry* 30(30):7373-7389 (Jul. 30, 1991).

Wilton et al., "Treatment with recombinant human insulin-like growth factor I of children with growth hormone receptor deficiency (Laron syndrome)" *Acta Paediatr Suppl* 383:137-142 (1992).

Wolpert et al., "Identification of an insulin analog with enhanced growth effect in aortic smooth muscle cells" *Diabetes* 39(Suppl. 1):140A (1990).

Woolfson et al., "Insulin to inhibit protein catabolism after injury" *New England J. of Medicine* 300(1):14-17 (Jan. 4, 1979).

Yamauchi et al., "Purification and molecular cloning of prostacyclin-stimulating factor from serum-free conditioned medium of human diploid fibroblast cells" *Biochemical Journal* 303(Part 2):591-598 (1994).

Zenobi et al., "Effects of Insulin-Like Growth Factor-I on Glucose Tolerance, Insulin Levels, and Insulin Secretion." *J. Clin. Invest.* 89:1908-1913 (1992).

Zenobi et al., "Insulin-Like Growth Factor-I Improves Glucose and Lipid Metabolism in Type 2 Diabetes Mellitus." *J. Clin. Invest.* 90:2234-2241 (1992).

plasmid t4.g8
length: 5140 (circular)

```
   1  GAATTCAACT TCTCCATACT TTGGATAAGG AAATACAGAC ATGAAAAATC TCATTGCTGA GTTGTTATTT AAGCTTGCCC AAAAGAAGAA AGAGTCGAAT
      CTTAAGTTGA AGAGGTATGA AACCTATTCC TTTATGTCTG TACTTTTTAG AGTAACGACT CAACAATAAA TTCGAACGGG TTTTCTTCTT TCTCAGCTTA

101  GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
      CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201  GGGCGCTGTA CGAGGTAAAG CCCGATGCCA GCATTCCTGA CGACGATACG GAGCTGCTGC CGATTACGTT AAAGAAGTTA TTGAAGCATC CTCGTCAGTA
      CCCGCGACAT GCTCCATTTC GGGCTACGGT CGTAAGGACT GCTGCTATGC CTCGACGACG GCTAATGCAA TTTCTTCAAT AACTTCGTAG GAGCAGTCAT

301  AAAAGTTAAT CTTTTCAACA GCTGTCATAA AGTTGTCACG GCCGAGACTT ATAGTCGCTT TGTTTTTATT TTTGTAACTA GTACGCAAGT
      TTTTCAATTA GAAAAGTTGT CGACAGTATT TCAACAGTGC CGGCTCTGAA TATCAGCGAA ACAAAAATAA AAACATTGAT CATGCGTTCA

401  TCACGTAAAA AGGGTATCTA GAGGTTGAGG TGATTTTATG AAAAAGAATA TCGGATTCT AGCGTAAAGA TCTTGCATCT ATGTTCGTTT TACAAATGCC
      AGTGCATTTT TCCCATAGAT CTCCAACTCC ACTAAAATAC TTTTTCTTAT AGCCTAAAGA TCGCATTTCT AGAACGTAGA TACAAGCAAA ATGTTTACGG

501  TATGCATCTG GTACCGCCAT GTACGGGGTA GGCTGATCCG AACCGTTCCC AAGCCCTCAG TCTGGCAGGT TCACCAGGTG GAGGATCCGG AGGAGGGGCC
           SerG lyThrAlaMe tValArgGly ArgLeuSerA rgProPheP roSerProGl nSerGlyArg SerProGlyG lyGlySerGl yGlyGlyAla

601  ATCCCCGAAA AGCGGCCTTT AACTCCCTGC AAGCCCTCGC ATCGGTTATG GACCGAATAT CAATTAAAGG CTCCCTTTGG AGCCTTTTTT TTCAACGTGA
           ProAlaLy sAlaAlaPhe AsnSerLeuL euAlaSerAr gSerGlyTyr AspArgIleL euIleLysGl yLeuProLeu GluProPheP hePheArgAsp

701  TATCAAGCTG TTTAAGAAAT CCACCTCGAA AGCAAGCTGA TAAACCGATA AGCAAGCTAT TTCCTTTGAA TATGAAAAGA CCCATACAG AAAATTCATT
           IleLysLeu PheLysLysS erThrSerLy sAlaSerLy sLysProIle SerLysLeuP heProLeuAs nMetLysArg ProIleGln LysIleHis

801  AAAAATTATT ATTCGCAATT CCTTAGTTG TTCCTTTCTA TTCTCACTCC GCTGAAACTG TTGAAAGTTG ACCTTGGAAC CCCATACAG AAAATTCATT
      TTTTTAATAA TAAGCGTTAA GGAATCAAC AAGGAAAGAT AAGAGTGAGG CGACTTTGAC AACTTTCAAC TGGAAGTT GGGTAGTC TTTTAAGTAA

901  TACTAACGTC TGGAAGACG ACAAAACTTT AGATCGTTAC GCTAACTATG AGGGTGTCT ACAGGCGTTG TAGTTTGTAC TGGTGACGAA
      ATGATTGCAG ACCTTTCTGC TGTTTTGAAA TCTAGCAATG CGATTGATAC TCCCACAGA TGTCCGCAAC ATCAAACATG ACCACTGCTT

1001  ACTCAGTGTC TAGCTAGAGT GGGGTGGCT CTGGTTCCCGG TGATTTGAT TATGAAAAGA TGGCAAACGC TAATAAGGGG GCTATGACCG AAAATGCCGA
      TGAGTCACAG ATCGATCTCA CCCCACCGA GACCAAGGCC ACTAAACTA ATACTTTTCT ACCGTTTGCG ATTATTCCCC CGATACTGGC TTTACGGCT
```

FIG. 1A

```
1101  TGAAAACGCG CTACAGTCTG ACGCTAAAGG CAAACTTGAT TCTGTCGCTA CTGATTACGG TGCTGCTATC GATGGTTTCA TTGGTGACGT TTCCGGCCTT
      ACTTTTGCGC GATGTCAGAC TGCGATTTCC GTTTGAACTA AGACAGCGAT GACTAATGCC ACGACGATAG CTACCAAAGT AACCACTGCA AAGGCCGGAA

1201  GCTAATGGTA ATGGTGCTAC TGGTGATTTT GCTGGCTCTA ATTCCCAAAT GGCTCAAGTC GGTGACGGTG ATAATTCACC TTTAATGAAT AATTCCGTC
      CGATTACCAT TACCACGATG ACCACTAAAA CGACCGAGAT TAAGGGTTTA CCGAGTTCAG CCACTGCCAC TATTAAGTGG AAATTACTTA TTAAGGCAG

1301  AATATTATTAC TTCCCCTCCCT CAATCGGTTG AAGGAGGGA GTTAGCCAAC TTACGCGGG TTTTGTCTTT AGCGCTGGTA AACCATATGA ATTTCTATT GATTGTGACA AATAACTT
      TTATAAATGG AAGGGAGGGA GTTAGCCAAC TTACGCGGG AAAACAGAAA TCGCGACCAT TGGTATACT TAAAGATAA CTAACACTGT TTTATTGAA

1401  ATTCCGTGGT GTCTTTGCGT TTCTTTTATA TGTTGCCACC TTTATGTATG GTTTGCTAAC ATACTGCGTA ATAAGGAGTC TTAATCATGC
      TAAGGCACCA CAGAAACGCA AAGAAAATAT ACAACGGTGG AAATACATAC CAAACGATTG TATGACGCAT TATTCCTCAG AATTAGTACG

3201  ACTCAAAGGC GGTAATACGG TTATCCACAG AATCAGGGGA TAACGCAGGA AAGAACATGT GAGCAAAAGG CCAGCAAAAG GCCAGGAACC GTAAAAAGGC
      TGAGTTTCCG CCATTATGCC AATAGGTGTC TTAGTCCCCT ATTGCGTCCT TTCTTGTACA CTCGTTTTCC GGTCGTTTTC CGGTCCTTGG CATTTTTCCG

3301  CGCGTTGCTG GCGTTTTTCC ATAGGCTCCG CCCCCCTGAC GAGCATCACA AAAATCGACG CTCAAGTCAG AGGTGGCGAA ACCCGACAGG ACTATAAAGA
      GCGCAACGAC CGCAAAAAGG TATCCGAGGC GGGGGGACTG CTCGTAGTGT TTTTAGCTGC GAGTTCAGTC TCCACCGCTT TGGGCTGTCC TGATATTTCT

3401  TACCAGGCGT TTCCCCCTGG AAGCTCCCTC GTGCGCTCTC CTGTTCCGAC CCTGCCGCTT ACCGGATACC TGTCCGCCTT TCTCCCTTCG GGAAGCGTGG
      ATGGTCCGCA AAGGGGGACC TTCGAGGGAG CACGCGAGAG GACACGGCTG GGACCGGCTG TGGCCTATGG ACAGGCGGAA AGAGGGAGC CCTTCGCACC

3501  CGCTTTCTCA TAGCTCACGC TGTAGGTATC TCAGTTCGGT GTAGGTCGTT CGCTCCAAGC TGGGCTGTGT GCACGAACCC CCCGTTCAGC CCGACCGCTG
      GCGAAAGAGT ATCGAGTGCG ACATCCATAG AGTCAAGCCA CATCCAGCAA GCGAGGTTCG ACCCGACACA CGTGCTTGGG GGGCAAGTCG GGCTGGCGAC

3601  CGCCTTATCC GGTAACTATC GTCTTGAGTC CAACCCGGTA TATCGCCACT GGCAGCAGCC ACTGGTAACA GGATTAGCAG AGCGAGGTAT
      GCGGAATAGG CCATTGATAG CAGAACTCAG GTTGGGCCAT TCTGTGCTGA ATAGCGGTGA CCGTCGTCGG CCTAATGCT CGCTCCATA

3701  GTAGGCGGTG CTACAGAGTT CTTGAAGTGG TGGCCTAACT ACGGCTACAC TAGAAGGACA GTATTTGGTA TCTGCGCTCT GCTGAAGCCA GTTACCTTCG
      CATCCGCCAC GATGTCTCAA GAACTTCACC ACCGGATTGA TGCCGATGTG ATCTTCCTGT CATAAACCAT AGACGCGAGA CGACTTCGGT CAATGGAAGC

3801  GAAAAAGAGT TGGTAGCTCT TGATCCGGCA AACAAACCAC CGCTGGTAGC GGTGGTTTTT TTGTTTGCAA GCAGCAGATT ACGGCGCAGAA AAAAAGGATC
      CTTTTTCTCA ACCATCGAGA ACTAGGCCGT TTGTTTGGTG GCGACCATCG CCACCAAAAA AACAAACGTT CGTCGTCTAA TGCCGCGTCTT TTTTTCCTAG

3901  TCAAGAAGAT CCTTTGATCT TTTCTACGGG GTCTGACGCT CAGTGGAACG AAAACTCACG TTAAGGGATT TGGTCATGA GATTATCAAA AAGGATCTTC
      AGTTCTTCTA GGAAACTAGA AAAGATGCCC CAGACTGCGA GTCACCTTGC TTTTGAGTGC AATTCCCTAA AACCAGTACT CTAATAGTTT TTCCTAGAAG

4001  ACCTAGATCC TTTAAATTA AAAATGAAGT TTTAAATCAA TCTAAAGTAT ATATGAGTAA ACTTGGTCTG ACAGTTACCA ATGCTTAATC AGTGAGGCAC
      TGGATCTAGG AAATTTAAT TTTTACTTCA AGATTTAGTT AGATTTCATA TATACTCATT TGAACCAGAC TGTCAATGGT TACGAATTAG TCACTCCGTG
```

FIG. 1B

```
4101  CTATCTCAGC GATCTGTCTA TTTCGTTCAT CCATAGTTGC CTGACTCCCC GTCGTGTAGA TAACTACGAT ACGGGAGGGC TTACCATCTG GCCCCAGTGC
      GATAGAGTCG CTAGACAGAT AAAGCAAGTA GGTATCAACG GACTGAGGGG CAGCACATCT ATTGATGCTA TGCCCTCCCG AATGGTAGAC CGGGGTCACG

4201  TGCAATGATA CGGCGAGACC CACGCTCACC GGCTCCAGAT TTATCAGCAA TAAACCAGCC AGCCGGAAGG GCCGAGCGCA GAAGTGGTCC TGCAACTTTA
      ACGTTACTAT GCCGCTCTGG GTGCGAGTGG CCGAGGTCTA AATAGTCGTT ATTTGGTCGG TCGGCCTTCC CGGCTCGCGT CTTCACCAGG ACGTTGAAAT

4301  TCCGCCTCCA TCCAGTCTAT TAATTGTTGC CGGGAAGCTA GAGTAAGTAG TTCGCCCAGT AATAGTTTGC GCAACGTTGT TGCCCATTGCT GCAGGCATCG
      AGGCGGAGGT AGTCAGATA ATTAACAACG GCCCTTCGAT CTCATTCATC AAGCGGTCAA TTATCAAACG CGTTGCAACA ACGGTAACGA CGTCCGTAGC

4401  TGGTGTCACG CTCGTCGTTT GGTATGGCTT CATTCAGCTC CGGTTCCCAA CGATCAAGGC GAGTTACATG ATCCCCCATG TTGTGCAAAA AAGCGGTTAG
      ACCACAGTGC GAGCAGCAAA CCATACCGAA GTAAGTCGAG GCCAAGGGTT GCTAGTTCCG CTCAATGTAC TAGGGGGTAC AACACGTTTT TTCGCCAATC

4501  CTCCTTCGGT CCTCCGATCG TTGTCAGAAG TAAGTTGGCC GCAGTGTTAT CACTCATGGT TATGGCAGCA CTGCATAATT CTCTTACTGT CATGCCATCC
      GAGGAAGCCA GGAGGCTAGC AACAGTCTTC ATTCAACCGG CGTCACAATA GTGAGTACCA ATACCGTCGT GACGTATTAA GAGAATGACA GTACGGTAGG

4601  GTAAGATGCT TTTCTGTGAC TGGTGAGTAC TCAACCAAGT CATTCTGAGA ATAGTGTATG CGGCGACCGA GTTGCTCTTG CCCGGCGTCA ACACGGGATA
      CATTCTACGA AAAGACACTG ACCACTCATG AGTTGGTTCA GTAAGACTCT TATCACATAC GCCGCTGGCT CAACGAGAAC GGGCCGCAGT TGTGCCCTAT

4701  ATACCGCGCC ACATAGCAGA ACTTTAAAAG TGCTCATCAT TTCAGCATCT TGGAAAACGT TCTTCGGGGC GAAACTCTC AAGGATCTTA CCGCTGTTGA GATCCAGTTC
      TATGGCGCGG TGTATCGTCT TGAAATTTTC ACGAGTAGTA AAGTCGTAGA ACCTTTTGCA AGAAGCCCCG CTTTTGAGAG TTCCTAGAAT GGCGACAACT CTAGTCAAG

4801  GATGTAACCC ACTCGTGCAC CCAACTGATC TTTACTTTCA CCAGCGTTTC TGGGTGAGCA AAAACAGGAA GGCAAAATGC CGCAAAAAAG
      CTACATTGGG TGAGCACGTG GGTTGACTAG AAGTCGTAGA GGTCGCAAAG ACCCACTCGT TTTTGTCCTT CCGTTTTACG GCGTTTTTC

4901  GGAATAAGGG CGACACGGAA ATGTTGAATA CTCATACTCT TCCTTTTTCA ATATTATTGA AGCATTTATC AGGGTTATTG TCTCATGAGC GGATACATAT
      CCTTATTCCC GCTGTGCCTT TACAACTTAT GAGTATGAGA AGGAAAAAGT TATAATAACT TCGTAAATAG TCCCAATAAC AGAGTACTCG CCTATGTATA

5001  TTGAATGTAT TTAGAAAAAT AAACAAATAG GGGTTCCGCG CACATTTCCC CGAAAAGTGC CACCTGACGT CTAAGAAACC ATTATTATCA TGACATTAAC
      AACTTACATA AATCTTTTTA TTTGTTTATC CCCAAGGCGC GTGTAAAGGG GCTTTTCACG GTGGACTGCA GATTCTTTGG TAATAATAGT ACTGTAATTG

5101  CTATAAAAAT AGGCGTATCA CGAGGCCCTT TCGTCTTCAA
      GATATTTTTA TCCGCATAGT GCTCCGGGAA AGCAGAAGTT
```

*FIG. 1C*

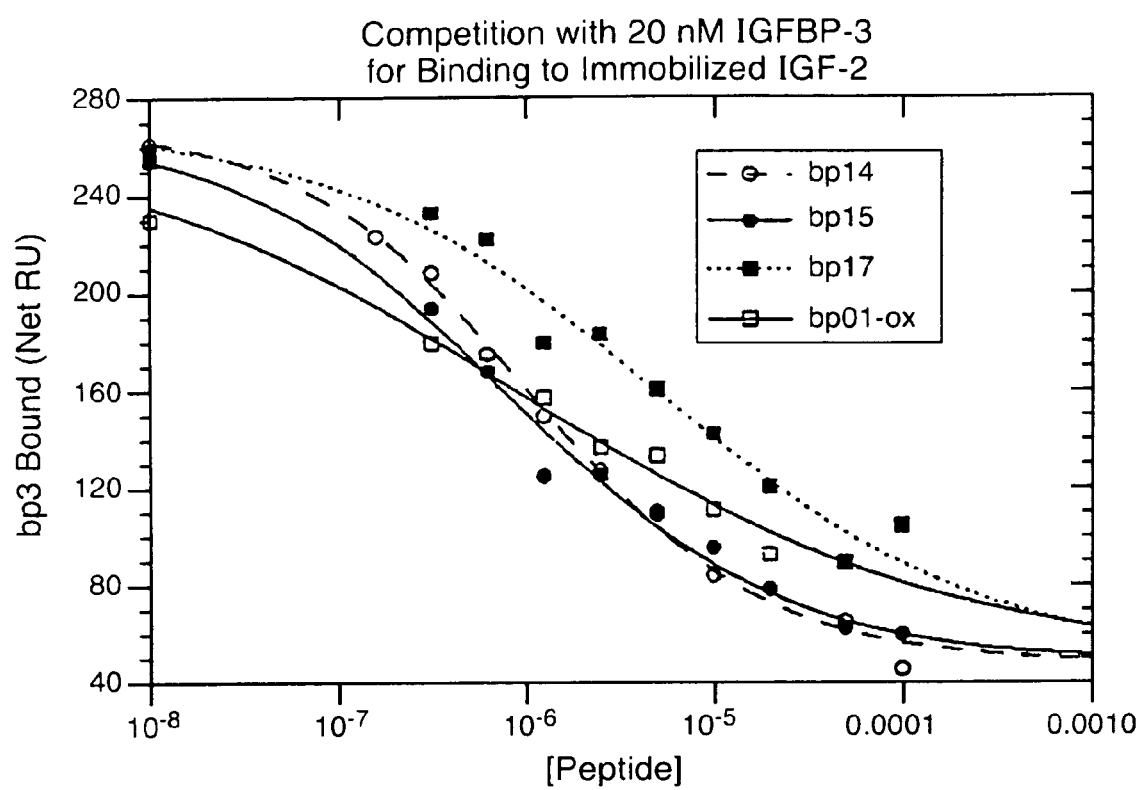
FIG._12

```
              10             20                        30
wtIGF      GPETLCGAELVDALQFVCGDRGFYFNKPT---------------GYGS
              ***  ** **  *** ***    *                * *
proin-     FVNQHLCGSHLVEALYLVCGERGFFYTPKTRREAEDLQVGQVELGGGPGA
sulin         10         20         30         40         50
              ***  ** **  *** ***    *
insulin    FVNQHLCGSHLVEALYLVCGERGFFYTPKT
(B chain)     10         20         30

40             50            60           70
wtIGF      SSRRA-------PQTGIVDECCFRSCDLRRLEMYCAPLKPAKSA
               *          ***  **    *  *    ** **
proin-     GSLQPLALEGSLQKRGIVEQCCTSICSLYQLENYCN
sulin              60         70         80
                             ***  **    *  *    ** **
insulin                   GIVEQCCTSICSLYQLENYCN
(A chain)                 31         40        50
```

ARTICLE OF MANUFACTURE

RELATED APPLICATIONS

This application is a divisional of U.S. patent application Ser. No. 10/271,869 filed Oct. 16, 2002 (now U.S. Pat. No. 7,423,017), which is a continuation of U.S. patent application Ser. No. 09/858,935 filed May 16, 2001, which claims priority to U.S. Provisional Patent Application Ser. Nos. 60/248,985, filed Nov. 15, 2000 and 60/204,490, filed May 16, 2000, and is a continuation-in-part of U.S. patent application Ser. No. 09/337,227, filed Jun. 22, 1999 (now U.S. Pat. No. 6,420,518), which claims priority to U.S. patent application Ser. No. 08/825,852, filed Apr. 4, 1997 (now U.S. Pat. No. 6,121,416) and 09/052,888, filed Mar. 31, 1998 (now U.S. Pat. No. 6,251,865), and a continuation-in-part of U.S. application Ser. No. 09/052,888, filed Mar. 31, 1998 (now U.S. Pat. No. 6,251,865), which claims priority to U.S. patent application Ser. No. 08/825,852, filed Apr. 4, 1997 (now U.S. Pat. No. 6,121,416), and is a continuation-in-part of U.S. patent application Ser. No. 09/477,923, filed Jan. 5, 2000 (now abandoned), which claims priority to U.S. Provisional Patent Application Ser. No. 60/115,010, filed Jan. 6, 1999, and is a continuation-in-part of U.S. patent application Ser. No. 09/477,924, filed Jan. 5, 2000 (now U.S. Pat. No. 6,403,764), which claims priority to U.S. Provisional Patent Application Ser. Nos. 60/115,010, filed Jan. 6, 1999 and 60/170,261, filed Dec. 9, 1999, the contents of which are incorporated herein by reference.

FIELD OF THE INVENTION

The present invention relates generally to the treatment of cartilage disorders, including stimulation of cartilage repair and treatment of degenerative cartilagenous disorders.

BACKGROUND OF THE INVENTION

Degenerative cartilagenous disorders broadly describe a collection of diseases characterized by degeneration or metabolic abnormalities of the connective tissues that are manifested by pain, stiffness and limitation of motion of the affected body parts. The origin of these disorders can be pathological or as a result of trauma or injury.

Osteoarthritis (OA), also known as osteoarthrosis or degenerative joint disease, is the result of a series of localized degenerative processes that affect the articular structure and result in pain and diminished function. The incidence of OA increases with age, and evidence of OA involvement can be detected in some joints in the majority of the population by age 65. OA is often also accompanied by a local inflammatory component that may accelerate joint destruction.

OA is characterized by disruption of the smooth articulating surface of cartilage, followed by formation of clefts and fibrillation, and ultimately by the full-thickness loss of the cartilage. Coincident with the cartilaginous changes are alterations of the periarticular bone. These include the development of palpable bone enlargements at the joint margins and deformity resulting from assymetric cartilage destruction. OA symptoms include local pain at the affected joints, especially after use. With disease progression, symptoms may develop into a continuous aching sensation, local discomfort, and cosmetic alterations of the affected joint.

In contrast to the localized disorder OA, rheumatoid arthritis (RA) is a systematic destructive and debilitating disease that is believed to begin in the synovium, the tissues surrounding the joint. The prevalence of RA is about ⅙ that of OA in the general population of the United States. It is a chronic autoimmune disorder characterized by symmetrical synovitis of the joint and typically affects small and large diarthrodial joints, leading to their progressive destruction. As the disease progresses, the symptoms of RA may also include fever, weight loss, thinning of the skin, multi-organ involvement, scleritis, corneal ulcers, the formation of subcutaneous or subperiosteal nodules, and premature death.

The response of normal patients (e.g., preinjury or predisease) to injury or arthritic degeneration is often sub-optimal. The biochemical and mechanical properties of this damaged cartilage differ from those of normal cartilage, resulting in inadequate or altered function. This damaged cartilage, termed herein "fibrocartilage," does not approximate the durability and function of normal cartilage.

Since cartilage is avascular and mature chondrocytes have little intrinsic potential for replication, mature cartilage has limited ability for repair. Thus, damage to the cartilage layer that does not penetrate to the subchondral bone does not undergo efficient repair. In contrast, when the subchondral bone is penetrated, its vascular supply allows a triphasic repair to take place. The resulting tissue is usually mechanically sub-optimal fibrocartilage.

The degradation associated with osteoarthritis usually initially appears as fraying and fibrillation of the surface. Loss of proteoglycan from the matrix also occurs. As the surface fibrillation progresses, the defects penetrate deeper into the cartilage, resulting in loss of cartilage cells and matrix. The subchondral bone thickens, is slowly exposed, and may appear polished. Bony nodules or osteophytes also often form at the periphery of the cartilage surface and occasionally grow over the adjacent eroded areas. If the surface of these bony outgrowths is permeated, vascular outgrowth may occur and cause the formation of tissue plugs containing fibrocartilage.

The transplantation of chondrocytes is known as a means of stimulating cartilage repair. However, the possibility of the host's immunogenic response as well as the possible transmission of viral and other infectious diseases makes this method less desirable. These risks can be minimized to some extent with allograft and autogenous transplants; however, the culturing and growth of patient-specific cells is cost prohibitive on a mass scale.

Other methods of stimulating cartilage repair include the antagonism of molecules that are associated with or aggravate cartilage destruction, for example, interleukin-1-alpha (IL-1∀) and nitric oxide (NO). The cytokine IL-1∀ has catabolic effects on cartilage, including the generation of synovial inflammation and up-regulation of matrix metalloproteinases and prostaglandin expression (Baragi et al., *J. Clin. Invest.*, 96: 2454-2460 (1995); Baragi et al., *Osteoarthritis Cartilage*, 5: 275-282 (1997); Evans et al., *J. Leukoc. Biol.*, 64: 55-61 (1998); Evans and Robbins, *J. Rheumatol.*, 24: 2061-2063 (1997); Kang et al., *Biochem. Soc. Trans.*, 25: 533-537 (1997); Kang et al., *Osteoarthritis Cartilage*, 5: 139-143 (1997)). One means of antagonizing IL-1∀ is through application of soluble IL-1 receptor antagonist (IL-1ra), a naturally-occurring protein that inhibits the effects of IL-1 by preventing IL-1 from binding to and activating its receptor on chondrocytes and synoviocytes, thereby lowering the effective concentration of IL-1.

Nitric oxide (NO) plays a substantial role in the destruction of cartilage (Amin et al., *Curr. Opin. Rheum.*, 10: 263-268 (1998)). Cartilage obtained from osteoarthritic joints endogenously produces large amounts of NO. Normal cartilage does not produce NO unless stimulated with cytokines such as IL-1, while osteoarthritic cartilage explants continue to express NO synthase for up to 3 days in culture despite the absence of added stimuli. Moreover, the inhibition of NO has been shown to prevent IL-1∀-mediated cartilage destruction and chondrocyte death as well as the progression of osteoarthritis.

The ability of peptide growth factors to promote repair of damaged cartilage has also been examined. Peptide growth factors are very significant regulators of cartilage growth and cell behavior (i.e., differentiation, migration, division, or matrix synthesis and/or breakdown) (Chen et al., *Am J. Orthop.*, 26: 396-406 (1997)). These factors are under investigation for their potential to induce host cartilage repair without transplantation of cells, and are being incorporated into engineered devices for implantation.

Because growth factors are soluble proteins of relatively small molecular mass that are rapidly absorbed and/or degraded, a great challenge exists in making them available to cells in sufficient quantity and for sufficient duration. It is likely desirable to have different factors present at the repair site during different parts of the developmental cycle, and for varying lengths of time. The ideal delivery vehicle is biocompatible and resorbable, has the appropriate mechanical properties, and results in no harmful degradation products. Growth factors that previously have been proposed to stimulate cartilage repair include insulin-like growth factor-I (IGF-1) (Osborn, *J. Orthop. Res.*, 7: 35-42 (1989); Florini and Roberts, *J. Gerontol.*, 35: 23-30 (1980); U.S. Pat. No. 5,843,899), basic fibroblast growth factor (bFGF), [Toolan et al., *J. Biomec. Mat. Res.*, 41: 244-50 (1998); Sah et al., *Arch. Biochem. Biophys.*, 308: 137-47 (1994)), bone morphogenetic protein (BMP) (Sato and Urist, *Clin. Orthop. Relat. Res.*, 183: 180-187 (1984); Chin et al., *Arthritis Rheum.* 34: 314-324 (1991)), and transforming growth factor beta (TGF-∃) (Hill and Logan, *Prog. Growth Fac. Res.*, 4: 45-68 (1992); Guerne et al., *J. Cell Physiol.*, 158: 476-484 (1994); Van der Kraan et al., *Ann. Rheum. Dis.*, 51: 643-647 (1992)).

It has been well established that the GH/IGF/IGFBP system is involved in the regulation of anabolic and metabolic homeostasis and that defects in this system may adversely affect growth, physiology, and glycemic control (Jones et al., *Endocr. Rev.*, 16: 3-34 (1995); Davidson, *Endocr. Rev.*, 8: 115-131 (1987); Moses, *Curr. Opin. Endo. Diab.*, 4: 16-25 (1997)). It has been proposed that IGF-1 could be useful for the treatment or prevention of osteoarthritis, because of its ability to stimulate both matrix synthesis and cell proliferation in culture (Osborn, *J. Orthop. Res.*, 7: 35-42 (1989)). IGF-1 has been administered with sodium pentosan polysulfate (PPS) (a chondrocyte catabolic activity inhibitor) to severely osteoarthritic canines with the effect of reducing the severity of the disease perhaps by lowering the levels of active neutral metalloproteinase in the cartilage. In the model of mildly osteoarthritic canines, therapeutic intervention with IGF-1 and PPS together appeared to successfully maintain cartilage structure and biochemistry, while IGF alone was ineffective, as described in Rogachefsky, *Osteoarthritis and Cartilage*, 1: 105-114 (1993); Rogachefsky et al., *Ann. NY Acad. Sci.*, 732: 392-394 (1994). The use of IGF-1 either alone or as an adjuvant with other growth factors to stimulate cartilage regeneration has been described in WO 91/19510, WO 92/13565, U.S. Pat. No. 5,444,047, and EP 434,652.

IGF-1 has also been found useful in the treatment of osteoporosis in mammals exhibiting decreased bone mineral density and those exposed to drugs or environmental conditions that result in bone density reduction and potentially osteoporosis, as described in EP 560,723 and EP 436,469.

IGF-1 insufficiency may have an etiologic role in the development of osteoarthritis (Coutts et al., "Effect of growth factors on cartilage repair," *Instructional Course Lect.*, 47: 487-494 (Amer. Acad. Orthop. Surg.: Rosemont, Ill. 1997)).

Some studies indicate that serum IGF-1 concentrations are lower in osteoarthritc patients than control groups, while other studies have found no difference. Nevertheless, it has been shown that both serum IGF-1 levels and chrondrocyte responsiveness to IGF-1 decrease with age, with the latter likely due to high levels of IGF binding proteins (IGFBPs) (Florini and Roberts, *J. Gerontol.*, 35: 23-30 (1980); Martin et al., *J. Orthop. Res.*, 15: 491-498 (1997); Fernihough et al., *Arthr. Rheum.* 39: 1556-1565 (1996)). Thus, both the decreased availability of IGF-1 as well as diminished chondrocyte responsiveness/disregulation of IGFBPs thereto may contribute to the impaired cartilage matrix homeostasis and tissue degeneration that occurs with advancing age and disease.

Of the IGFBPs, IGFBP-3 appears to be the most responsible for regulating the total levels of IGF-1 and IGF-2 in plasma. IGFBP-3 is a GH-dependent protein and is reduced in cases of GH-deficiency or resistance (Jones et al., supra; Rosenfield et al., "IGF-1 treatment of syndromes of growth hormone insensitivity" In: *The insulin-like growth factors and their regulatory proteins*, Eds Baxter R C, Gluckman P D, Rosenfield R G. Excerpta Medica, Amsterdam, 1994), pp 457-464; Scharf et al., *J. Hepatology*, 25: 689-699 (1996)). IGFBPs are able to enhance or inhibit IGF activity, depending largely on their post-translational modifications and tissue localization (reviewed in Jones and Clemmons, *Endocr. Rev.* 16:3-34 (1995); Collett-Solberg and Cohen, *Endocrinol. Metabol. Clin. North Am.* 25:591-614 (1996)). In addition, disregulation in IGFBPs (-3, -4 and/or -5) may play a key role in arthritic disorders (Chevalier and Tyler, *Brit. J. Rheum.* 35: 515-522 (1996); Olney et al., *J. Clin. Endocrinol. Metab.* 81: 1096-1103 (1996); Martel-Pelletier et al., *Inflamm. Res.*, 47: 90-100 (1998)). It has been reported that IGF-1 analogs with very low binding affinity for IGFBPs were more effective than wild-type IGF-1 in stimulating proteoglycan synthesis (Morales, *Arch Biochem. Biophys.* 343(2), 164-172 (1997)). More recent data, however, suggest that IGFBPs contribute to IGF binding to and transport through cartilage tissue, and IGFBPs may thus regulate bioavailability of IGF-1 within the joint (Bhakta et al., *J. Biol. Chem.*, 275: 5860-5866 (2000)).

The biodistribution of IGF-1 critically depends on (a) the formation of long-lived high molecular weight complexes and (b) the absolute IGFBP concentrations. The majority of IGF-1 in the circulation is found in complex with IGFBP-3 and a third protein termed acid-labile subunit (ALS) (Bach and Rechler, *Diabetes Reviews*, 3: 38-61 (1995); Clemmons, *Cytokine Growth Factor Rev.*, 8: 45-62 (1997); Jones and Clemmons, *Endocr. Rev.*, 16: 3-34 (1995)). This ternary complex of 150-kD molecular weight is unable to traverse the vasculature walls and acts as a circulating reservoir for IGF's. As a consequence, the serum half-life of IGF-1 in ternary complexes is reported to be 12-15 hours, as opposed to 30 minutes in binary complexes, or 10 minutes in the free form (Simpson et al., *Growth Horm IGF Res*, 8: 83-95 (1998); Twigg and Baxter, *J. Biol. Chem.*, 273: 6074-6079 (1998)).

IGFBP-3 and -5 are apparently unique in their ability to form a ternary complex with ALS. ALS association occurs only in the presence of IGF-1, and a basic motif in the carboxy-terminal domains of IGFBP-3 and -5 seems to mediate this interaction (Baxter et al., *J. Biol. Chem.*, 267: 60-65 (1992); Firth et al., *J. Biol. Chem.*, 273: 2631-2638 (1998); Twigg and Baxter, supra).

The second determinant of IGF-1 biodistribution is the total concentration of binding proteins: IGFBP-3 is the most abundant binding protein, followed by IGFBP-1 and -2 levels, whereas the serum concentrations of IGFBP-4, -5, and -6 are quite low (Clemmons, *Cytokine Growth Factor Rev.*, 8: 45-62

(1997)). IGFBP-3 therefore represents the main IGF-1 carrier in the blood. In contrast, a substantial portion of IGFBP-1 and -2 in the blood are unoccupied. Hence, they appear to be the major modulators of free IGF-1 levels (Clemmons, 1997, supra).

WO 94/04569 discloses a specific binding molecule, other than a natural IGFBP, that is capable of binding to IGF-1 and can enhance the biological activity of IGF-1. WO 98/45427 published Oct. 15, 1998; Lowman et al., *Biochemistry*, 37: 8870-8878 (1998); and Dubaquié and Lowman, Biochemistry, 38: 6386 (1999) disclose IGF-1 agonists identified by phage display. Also, WO 97/39032 discloses ligand inhibitors of IGFBP's and methods for their use. Further, U.S. Pat. No. 5,891,722 discloses antibodies having binding affinity for free IGFBP-1 and devices and methods for detecting free IGFBP-1 and a rupture in a fetal membrane based on the presence of amniotic fluid in a vaginal secretion, as indicated by the presence of free IGFBP-1 in the vaginal secretion. WO 00/23469 published Apr. 27, 2000 discloses fragments of IGFBPs and analogs of IGF-1 for use in, e.g., cancer, ischemic injury, and diabetes treatment.

There exists a continuing need for an effective therapy for the treatment and repair of cartilage, including cartilage damaged as a result of injury and/or disease.

SUMMARY OF THE INVENTION

Accordingly, the present invention concerns a method of treating a cartilage disorder as claimed, comprising contacting cartilage with an effective amount of an active agent selected from an IGF-1 analog with a binding affinity preference for IGFBP-3 over IGFBP-1, an IGF-1 analog with a binding affinity preference for IGFBP-1 over IGFBP-3, or an IGFBP displacer peptide that prevents the interaction of IGF with IGFBP-3 or IGFBP-1 and does not bind to a human IGF receptor. Preferably, the cartilage is treated in vivo in a mammal and the active agent is administered to the mammal. Also, the active agent is optionally contacted with the cartilage in an extended-release form and/or administered locally to the joint alone or, if the active agent is an IGFBP displacer peptide or IGF-1 analog with a preference for IGFBP-3 over IGFBP-1, together with IGF-1 and/or ALS, preferably human, native-sequence IGF-1 if the mammal is human.

Preferably, the active agent is an IGF-1 variant wherein the amino acid residue at position 3, 7, 10, 16, 25, or 49, or the amino acid residues at positions 3 and 49 of native-sequence human IGF-1 are replaced with an alanine, a glycine, or a serine residue, or an IGF-1 variant wherein the amino acid residue at position 9, 12, 15, or 20 is replaced with a lysine or arginine residue, or an IGFBP-3 displacer peptide designated as: Y24LY31A IGF-1; 4D3.3P; BP3-4D3.11; BP3-4D3.11DEL; BP3-4B3.3; BP3-01-ox; BP3-02-ox; BP3-06; BP3-08; BP3-15; BP3-16; BP3-17; BP3-25; BP3-27; BP3-28; BP3-30; BP3-39; BP3-40; BP3-41; BP3-107; or BP3-108; or an IGFBP-1 displacer peptide designated as: BP1-01; BP1-02; BP1-04; BP1-10; BP1-11; BP1-12; BP1-13; BP1-14; BP1-15; BP1-16; BP1-17; BP1-18; BP1-19; BP1-20; BP1-21A; BP1-21B; BP1-25; BP1-40; BP67; BP68; BP1-625; BP1-625-Z; BP1-625T; BP1027; BP1028; BP1029; BP1030; (i+7)D; (i+8)B; and (i+8)C.

The letter followed by a number followed by a letter indicates an IGF-1 analog wherein the amino acid letter to the left of the number is the original amino acid in native-sequence human IGF-1, the number is the position where the amino acid is changed, and the amino acid letter to the right of the number is the substituted amino acid. Hence, for example, F49A indicates an IGF-1 variant wherein the phenylalanine residue at position 49 of native-sequence human IGF-1 is changed to an alanine residue, and E3AF49A indicates an IGF-1 variant wherein the glutamine residue at position 3 of native-sequence human IGF-1 is changed to an alanine residue, and the phenylalanine residue at position 49 of native-sequence human IGF-1 is changed to an alanine residue.

In another embodiment, the above method is for the treatment of cartilage damaged or diseased as a result of a degenerative cartilagenous disorder. Preferably, the disorder is an articular cartilage disorder, and most preferably is OA or RA.

In a further embodiment, the above method is for the treatment of joints damaged directly or indirectly by injury, preferably microdamage or blunt trauma, a chondral fracture, an osteochondral fracture.

Optionally, the invention concerns the above treatment method wherein the cartilage is contacted with an effective amount of the IGF-1 analog or IGFBP displacer peptide as defined above in combination with an effective amount of a cartilage growth factor or cartilage catabolism antagonist.

In another embodiment, the invention concerns a method of maintaining, enhancing, or promoting the growth of chondrocytes in serum-free culture by contacting the chondrocytes with an effective amount of an IGF-1 analog or an IGFBP displacer peptide as identified above. Alternatively, the method concerns contacting the chondrocyte with an effective amount of an IGF-1 analog or an IGFBP displacer peptide in an extended-release formulation. Alternatively, the present invention concerns a method of stimulating the regeneration or preventing the degradation of cartilage resulting from injury or a degenerative cartilagenous disorder by transplantation of an effective amount of chondrocytes previously treated with an effective amount of an IGF-1 analog or an IGFBP displacer peptide as defined above.

In another embodiment, the present invention concerns an article of manufacture comprising a container holding an IGF-1 analog or an IGFBP displacer peptide as defined above in a pharmaceutically acceptable carrier with instructions for its use in treating a cartilage disorder.

BRIEF DESCRIPTION OF THE DRAWINGS

FIGS. 1A-1C depict the DNA sequence (SEQ ID NO:1) of plasmid pt4.g8 used as a template to construct a phage library. Also shown is the amino acid sequence (SEQ ID NO:2) of an antibody-recognizable (gD-tag) peptide fused to g8p of bacteriophage M13.

FIG. 11A depicts the peptides alone, FIG. 11B depicts the peptides plus IGF-1 plus IGFBP-1, FIG. 11C depicts the peptides plus IGF-1, and FIG. 11D depicts the peptides plus IGF-1 plus IGFBP-3.

FIG. 12 depicts an IGF-2 competition assay of IGFBP-3 inhibition by four peptides, designated BP3-01-ox (open squares), BP3-14 (open circles), BP3-15 (closed circles), and BP3-17 (closed squares), using a BIACORE™ surface-plasmon-resonance device to measure free binding protein. Each peptide was tested using 20 nM IGFBP-3 and approximately 1500 RU of immobilized IGF-2.

FIG. 22A shows a time course of the rate at which both molecules are cleared from the blood of the animals, where the squares represent wild-type IGF-1, the circles represent E3A/F49A IGF-1, and the diamonds represent F49A IGF-1. FIG. 22B shows the tissue-to-blood ratio for these two IGF variants in different organs, namely, kidney, liver, spleen, heart, and pancreas, at 5, 15, and 30 minutes, where the solid bars represent wild-type IGF-1, the dotted bars represent E3A/F49A IGF-1, and the striped bars represent F49A IGF-1.

DETAILED DESCRIPTION OF THE INVENTION

I. Definitions

Figure 2:
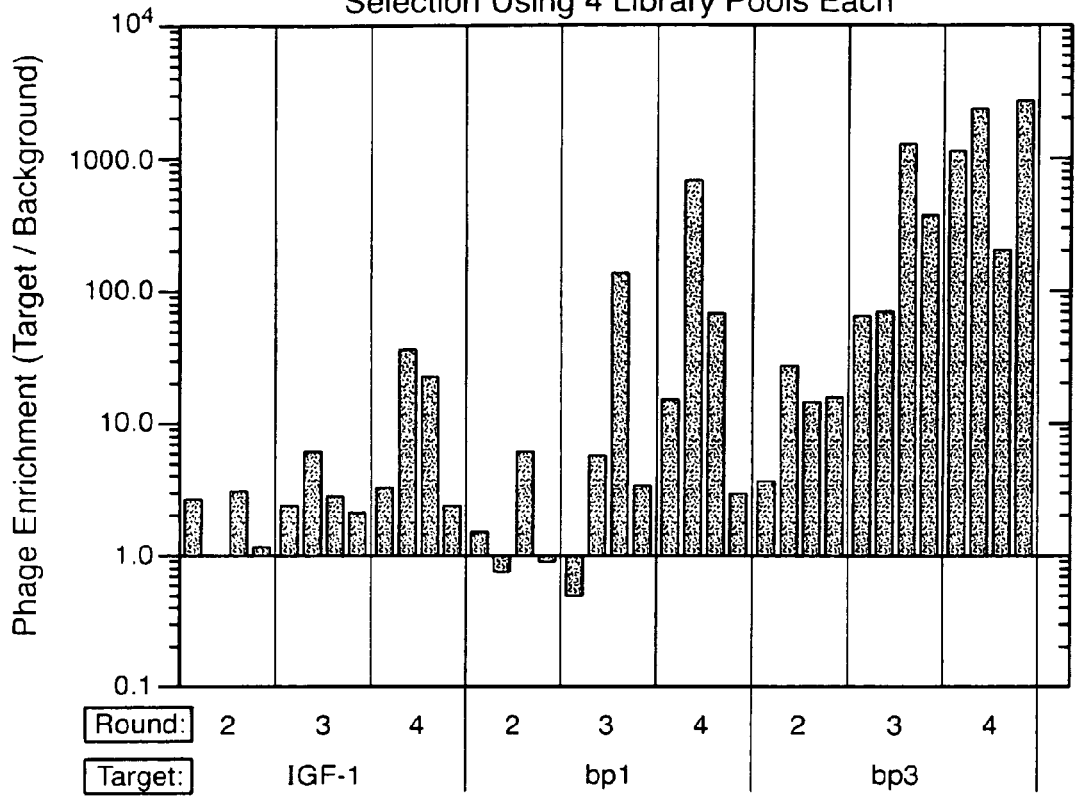
FIG. 2 shows gene-8 naive phage library enrichments with a selection using four library pools each and the targets IGF-1, IGFBP-1, and IGFBP-3.

"IGF-1 analogs" are amino acid variants of native-sequence IGF-1, preferably variants of human wild-type IGF-1. The dissociation constant ($K_D$) of wild-type IGF-1 was determined to be 13 nM for IGFBP-1 and 1.5 nM for IGFBP-3. The difference in affinity for the IGFBP's is due to a 10-fold faster association rate ($k_a$) of IGF-1 to IGFBP-3 (3.2×10 versus 3.2×10$^4$ M$^{-1}$s$^{-1}$). Such analogs may have one or more amino acid alterations as compared to native IGF-1. As used herein, the term "IGF-1 analogs" refers either to an IGF-1 analog with a binding affinity preference for IGFBP-3 over IGFBP-1 or an IGF-1 analog with a binding affinity preference for IGFBP-1 over IGFBP-3, as defined below.

An "IGF-1 analog with a binding affinity preference for IGFBP-3 over IGFBP-1" refers to an IGF-1 analog that exhibits altered binding affinity for any one or more of the IGFBPs over that of native-sequence IGF-1, such that the analog's relative binding affinity (R(3)) for IGFBP-3 [defined as R(3)=$K_D$(IGF-1:IGFBP-3)/$K_D$(analog:IGFBP-3)] is at least about 10-fold greater than its relative binding affinity (R(1)) for IGFBP-1 [defined as R(1)=$K_D$(IGF-1:IGFBP-1)/$K_D$(analog:IGFBP-1)], as shown by, for example, by kinetic analysis using a BIACORE™ surface-plasmon-resonance instrument of the expressed and purified analogs.

Conversely, an "IGF-1 analog with a binding affinity preference for IGFBP-1 over IGFBP-3" refers to an IGF-1 analog that exhibits altered binding affinity for any one or more of the IGFBPs over that of native-sequence IGF-1, such that the analog's relative binding affinity (R(1)) for IGFBP-1 [defined as R(1)=$K_D$(IGF-1:IGFBP-1)/$K_D$(analog:IGFBP-1)] is at least about 10-fold greater than its relative binding affinity (R(3)) for IGFBP-3 [defined as R(3)=$K_D$(IGF-1:IGFBP-3)/$K_D$(analog:IGFBP-3)], as shown by, for example, by kinetic analysis using a BIACORE™ surface-plasmon-resonance instrument of the expressed and purified analogs.

"Peptides" have at least two amino acids and include polypeptides having at least about 50 amino acids. The definition includes peptide derivatives, their salts, or optical isomers.

An IGFBP displacer peptide that "inhibits" or "prevents" the interaction of an IGF with an IGFBP refers to a peptide that increases serum and tissue levels of biologically active IGF, no matter how this increase occurs. For instance, the peptide may partially or completely displace active IGF from a complex in which the IGF is bound to an IGFBP. The peptide under this definition may bind to an IGFBP, and possibly thereby act to displace an endogenous IGF formerly bound to the IGFBP. Alternatively, it may bind to IGF itself at a site remote from that involved in receptor interactions so as to inhibit or prevent the interaction of the IGF with IGFBP, but not inhibit or prevent the interaction of the IGF with any of its receptors. Further, while the peptide will occupy the IGFBP-3 binding site, the effect on the ternary complex with ALS will depend on whether the binary complexes can form ternary ones. Peptides that can form complexes with the ALS of the ternary complex will replace IGFs but not affect the concentration of IGFBP-3 or of ternary complexes. Peptides that cannot form complexes with ALS will occupy IGFBP-3, and the amount of ALS/IGFBP-3/IGF complex will be reduced. Preferably, the IGFBP displacer peptide is an IGFBP-3 or IGFBP-1 displacer peptide.

A peptide that "binds to IGFBP-3" or "binds to IGFBP-1" refers to a peptide that binds IGFBP-3 or IGFBP-1 to at least some degree, whether with high affinity or not.

As used herein, "human IGF receptor" refers to any receptor for an IGF found in humans and includes the Type 1 and Type 2 IGF receptors in humans to which both human IGF-1 and IGF-2 bind, such as the placental Type 1 IGF-1 receptor, etc.

A peptide that "does not bind to a human IGF receptor" does not bind at all to any such receptor, or binds to such receptor with an affinity more than about 200-fold less than wild-type human IGF-1 (hIGF-1) or wild-type human IGF-2 (hIGF-2) binds to such receptor. Preferably, the peptide binds to such receptor with an affinity of more than about 250-fold less than wild-type hIGF-1 or hIGF-2 binds to the same receptor or does not bind at all.

The term "cartilage disorder" refers to any injury or damage to cartilage, and to a collection of diseases that are manifested by symptoms of pain, stiffness, and/or limitation of motion of the affected body parts. Included within the scope of "cartilage disorders" is "degenerative cartilagenous disorders", which is a collection of disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, the term "degenerative cartilagenous disorders" includes "articular cartilage disorders," which are characterized by disruption of the smooth articular cartilage surface and degradation of the cartilage matrix. Additional pathologies include nitric oxide production, and inhibition or reduction of matrix synthesis. Included within the scope of "articular cartilage disorder" are OA and RA. Examples of degenerative cartilagenous disorders include systemic lupus erythematosus and gout, amyloidosis or Felty's syndrome. Additionally, the term covers the cartilage degradation and destruction associated with psoriatic arthritis, kidney disorders, osteoarthrosis, acute inflammation (e.g., yersinia arthritis, pyrophosphate arthritis, gout arthritis (arthritis urica), and septic arthritis), arthritis associated with trauma, ulcerative colitis (e.g., Crohn's disease), multiple sclerosis, diabetes (e.g., insulin-dependent and non-insulin dependent), obesity, giant cell arthritis, and Sjögren's syndrome. In one preferred embodiment, the disorder is microdamage or blunt trauma, a chondral fracture, or an osteochondral fracture.

"Osteoarthritis" or "OA" defines not a single disorder, but the final common pathway of joint destruction resulting from multiple processes. OA is characterized by localized assymetric destruction of the cartilage commensurate with palpable bone enlargements at the joint margins. OA typically affects the interphalangeal joints of the hands, the first carpometacarpal joint, the hips, the knees, the spine, and some joints in the midfoot, while large joints, such as the ankles, elbows, and shoulders, tend to be spared. OA can be associated with metabolic diseases such as hemochromatosis and alkaptonuria, developmental abnormalities such as developmental dysplasia of the hips (congenital dislocation of the hips), limb-length descrepancies, including trauma and inflammatory arthritides such as gout, septic arthritis, and neuropathic arthritis. OA may also develop after extended mechanical instability, such as resulting from sports injury or obesity.

"Rheumatoid arthritis" or "RA" is a systemic, chronic, autoimmune disorder characterized by symmetrical synovitis of the joint and typically affects small and large diarthroid joints alike. As RA progresses, symptoms may include fever, weight loss, thinning of the skin, multiorgan involvement, scleritis, corneal ulcers, the formation of subcutaneous or subperiosteal nodules, and even premature death. The symptoms of RA often appear during youth and can include vasculitis, atrophy of the skin and muscle, subcutaneous nodules, lymphadenopathy, splenomegaly, leukopaenia, and chronic anaemia.

"Treatment" is an intervention performed with the intention of preventing the development or altering the pathology of a disorder. Accordingly, "treatment" refers to both therapeutic treatment and prophylactic or preventative measures, wherein the object is to prevent or slow down (lessen) the targeted pathological condition or disorder. Those in need of treatment include those already with the disorder as well as those in which the disorder is to be prevented. In treatment of a degenerative cartilagenous disorder, a therapeutic agent may directly decrease or increase the magnitude of response of a pathological component of the disorder, or render the disease more susceptible to treatment by other therapeutic agents, e.g., antibiotics, antifungals, anti-inflammatory agents, chemotherapeutics, etc. The term "treatment" includes a method for the prevention of initial or continued damage or disease of joints by degenerative cartilagenous disorders and/or injury.

The term "effective amount" is the minimum efficacious concentration of the IGF analog or IGFBP displacer peptide as set forth herein. This includes the minimum concentration of such protein or peptide that causes, induces, or results in either a detectable improvement or repair of damaged cartilage or a measurable protection from continued or induced cartilage destruction, such as the inhibition of synthesis or loss of proteoglycans from cartilage tissue.

"Cartilage growth factor" as used herein refers to agent(s) other than an IGF-1 analog or an IGFBP displacer peptide as identified herein that cause, induce, or result in an improvement in the condition of or protection from initial or continued destruction of cartilage subject to damage by either injury or a degenerative cartilagenous disorder. Such cartilage growth factors include insulin-like growth factors (e.g., IGF-1, IGF-2), platelet-derived growth factors (PDGFs), bone morphogenic proteins (BMPs), transforming growth factor-βs (1-3), members of the epidermal growth factor family (e.g., EGF, HB-EGF, TGF-α), and fibroblast growth factors (FGFs).

"Cartilage catabolism antagonists" are those agents that inhibit, attenuate or otherwise block the activity or effect of molecules that are associated with or aggravate cartilage destruction. For example, IL-1∀ and nitric oxide (NO) are agents known to be associated with cartilage destruction. Thus, direct (IL1ra) or indirect (IL-4 or IL-10) inhibitors of IL-1∀ or other inflammatory cytokines (e.g., TNF-α) and NO production would be considered "cartilage catabolism antagonists." Moreover, antagonists of chondrocyte catabolism (e.g., sodium pentosan polysulfate, glucosamine (and variants thereof, such as mannosamine) or chondroitin sulfate, tetracycline, hyaluronan) would also be considered cartilage catabolism antagonists. Also included are agents that inhibit catabolism of cartilage indirectly, for example through their effects on the underlying, subchondral bone (e.g., bisphosphonates or osteoprotegerin (OPG)).

"Chronic" administration refers to administration of the agent(s) in a continuous mode as opposed to an acute mode, so as to maintain the initial therapeutic effect (activity) for an extended period of time. "Intermittent" administration is treatment that is not consecutive without interruption, but rather is cyclic in nature.

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

Administration "in combination with" one or more further therapeutic agents includes simultaneous (concurrent) and consecutive administration in any order.

"Carriers" as used herein include pharmaceutically-acceptable carriers, excipients, or stabilizers that are non-toxic to the cell or mammal being exposed thereto at the dosages and concentrations employed. Often the physiologically-acceptable carrier is an aqueous pH-buffered solution. Examples of physiologically-acceptable carriers include buffers such as phosphate, citrate, and other organic acids; antioxidants including ascorbic acid; low-molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; hyaluronan; and/or non-ionic surfactants such as TWEEN™, polyethylene glycol (PEG), and PLURONICS™.

A "liposome" is a small vesicle composed of various types of lipids, phospholipids, and/or surfactants that is useful for delivery of a drug (such as the IGF-1 analog or IGFBP displacer peptide disclosed herein) to a mammal. The components of the liposome are commonly arranged in a bilayer formation, similar to the lipid arrangement of biological membranes.

The term "extended-release" or "sustained-release" formulations in the broadest possible sense means a formulation of active IGF-1 analog or IGFBP displacer peptide identified herein resulting in the release or activation of the active analog or peptide for a sustained or extended period of time—or at least for a period of time that is longer than if the analog or peptide were made available in vivo in the native or unformulated state. Optionally, the extended-release formulation occurs at a constant rate and/or results in sustained and/or continuous concentration of the active agent herein. Suitable extended-release formulations may comprise microencapsulation, semi-permeable matrices of solid hydrophobic polymers, biogradable polymers, biodegradable hydrogels, suspensions, or emulsions (e.g., oil-in-water or water-in-oil). Optionally, the extended-release formulation comprises poly-lactic-co-glycolic acid (PLGA) and can be prepared as described in Lewis, "Controlled Release of Bioactive Agents form Lactide/Glycolide polymer," in Biodegradable Polymers as Drug Delivery Systems, M. Chasin and R. Langeer, Ed. (Marcel Dekker, New York), pp. 1-41. Optionally, the extended-release formulation is stable and the activity of the IGF-1 analog or IGFBP displacer peptide as identified herein does not appreciably diminish with storage over time. More specifically, such stability can be enhanced through the presence of a stabilizing agent such as a water-soluble polyvalent metal salt.

Figures 16, 19:
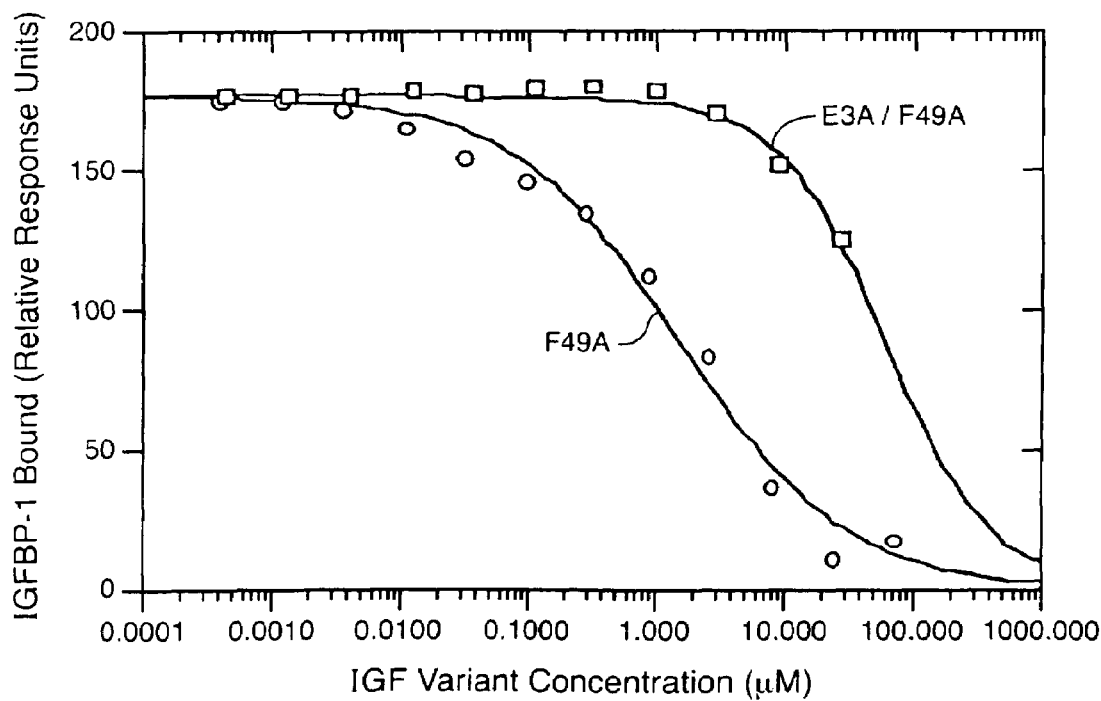
FIG. 16 discloses a sequence alignment of native-sequence human IGF-1 (designated wtIGF) (SEQ ID NO:3), native-sequence human proinsulin (designated proinsulin) (SEQ ID NO:4), and native-sequence human insulin (designated insulin (B chain) followed by insulin (A chain)) (SEQ ID NO:5). The asterisks and dots indicate sequence identity and sequence similarity, respectively, at the indicated amino acid positions among the three sequences.
FIG. 19 shows the amount of bound IGFBP-1, determined in a competitive binding experiment performed using a BIACORE™ surface-plasmon-resonance device, plotted against the IGF variant concentration for E3A/F49A (squares) and F49A (circles).

As used herein, "IGF-1" refers to insulin-like growth factor-1 from any species, including bovine, ovine, porcine, equine, and human, preferably human, and, if referring to exogenous administration, from any source, whether natural, synthetic, or recombinant. "Native-sequence" human IGF-1, the sequence of which is shown in FIG. 16 (SEQ ID NO:3), is prepared, e.g., by the process described in EP 230,869 published Aug. 5, 1987; EP 128,733 published Dec. 19, 1984; or EP 288,451 published Oct. 26, 1988. More preferably, this native-sequence IGF-1 is recombinantly produced.

As used herein, "IGF-2" refers to insulin-like growth factor-2 from any species, including bovine, ovine, porcine, equine, and human, preferably human, and, if referring to exogenous administration, from any source, whether natural, synthetic, or recombinant. It may be prepared by the method described in, e.g., EP 128,733.

An "IGFBP" or an "IGF binding protein" refers to a protein or polypeptide normally associated with or bound or complexed to IGF-1 or IGF-2, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA*, 92: 4472-4476 (1995) and Oh et al., *J. Biol. Chem.*, 271: 30322-30325 (1996). PSF is described in Yamauchi et al., *Biochemical Journal*, 303: 591-598 (1994). ESM-1 is described in Lassalle et al., *J. Biol. Chem.*, 271: 20458-20464 (1996). For other identified IGFBPs, see, e.g., EP 375,438 published 27 Jun. 1990; EP 369,943 published 23 May 1990; WO 89/09268 published 5 Oct. 1989; Wood et al., *Molecular Endocrinology*, 2: 1176-1185 (1988); Brinkman et al., *The EMBO J.*, 7: 2417-2423 (1988); Lee et al., *Mol. Endocrinol.*, 2: 404-411 (1988); Brewer et al., *BBRC*, 152: 1289-1297 (1988); EP 294,021 published 7 Dec. 1988; Baxter et al., *BBRC*, 147: 408-415 (1987); Leung et al., *Nature*, 330: 537-543 (1987); Martin et al., *J. Biol. Chem.*, 261: 8754-8760 (1986); Baxter et al., *Comp. Biochem. Physiol.*, 91B: 229-235 (1988); WO 89/08667 published 21 Sep. 1989; WO 89/09792 published 19 Oct. 1989; and Binkert et al., *EMBO J.*, 8: 2497-2502 (1989).

The term "acid-labile subunit" or "ALS" refers to an 85-kDa glycoprotein that forms a ternary complex with IGF-1 and IGFBP-3 or IGFBP-5. See, e.g., Bach and Rechler, *Diabetes Reviews*, 3: 38-61 (1995); Clemmons, *Cytokine Growth Factor Rev.*, 8: 45-62 (1997); and Jones and Clemmons, *Endocr. Rev.*, 16: 3-34 (1995).

II. Modes for Carrying Out the Invention

The invention herein relates to the use of an IGF-1 analog or an IGFBP displacer peptide as defined above to treat cartilage disorders, preferably degenerative cartilagenous disorders, including regenerating and/or preventing the degradation of cartilage.

Examples of IGF-1 analogs with a binding affinity preference for IGFBP-3 over IGFBP-1 include an IGF-1 variant wherein the amino acid(s) of wild-type human IGF-1 at position 3, 7, 10, 16, 25, or 49 or at positions 3 and 49 of native-sequence human IGF-1 are replaced with an alanine, a glycine, and/or a serine residue. Preferably, one or both of the amino acids in question are substituted by an alanine or glycine residue, most preferably alanine. The more preferred IGF-1 analog with such binding affinity preference herein is F49A, F49G, F49S, E3A, E3G, E3S, E3AF49A, E3AF49G, E3AF49S, E3GF49A, E3GF49G, E3GF49S, E3SF49A, E3SF49G, E3SF49S, F16A, F16G, F16S, F16AF49A, F16GF49A, F16SF49A, F16AF49S, F16AF49G, F16SF49S, F16SF49G, F16GF49S, or F16GF49G.

Examples of IGF-1 analogs with a binding affinity preference for IGFBP-1 over IGFBP-3 include an IGF-1 variant wherein the amino acid(s) of wild-type human IGF-1 at position 9, 12, 15, or 20 is/are replaced with a lysine or arginine residue. The more preferred IGF-1 analog with such binding affinity preference herein is D12K or D12R.

Examples of IGFBP-3 displacer peptides include a peptide selected from the group consisting of:

```
Y24LY31A (IGF-1 variant);

4D3.3P
(ASEEVCWPVAEWYLCNMWGR);      (SEQ ID NO: 6)

BP3-4D3.11
(VAWEVCWDRHDQGYICTTDS);      (SEQ ID NO: 7)

BP3-4D3.11DEL
(AWEVCWDRHQGYICTTDS);        (SEQ ID NO: 8)

BP3-4B3.3
(EESECFEGPGYVICGLVG);        (SEQ ID NO: 9)

BP3-01-OX
(SEEVCWPVAEWYLCNMWG);        (SEQ ID NO: 10)

BP3-02-OX
(DMGVCADGPWMYVCEWTE);        (SEQ ID NO: 11)

BP3-06
(TGVDCQC*GPVHC*VCMDWA);      (SEQ ID NO: 12)

BP3-08
(TVANCDC*YMPLC*LCYDSD);      (SEQ ID NO: 13)

BP3-15
(SEEVCWPVAEWYLCN);           (SEQ ID NO: 14)

BP3-16
(VCWPVAEWYLCNMWG);           (SEQ ID NO: 15)

BP3-17
(VCWPVAEWYLCN);              (SEQ ID NO: 16)

BP3-25
(CWPVAEWYLCN);               (SEQ ID NO: 17)

BP3-27
(EVCWPVAEWYLCN);             (SEQ ID NO: 18)

BP3-28
(EEVCWPVAEWYLCN);            (SEQ ID NO: 19)

BP3-30
(ASEEVCWPVAEWYLCN);          (SEQ ID NO: 20)

BP3-39
(SEEVCWPVAEWYLCN-nh2);       (SEQ ID NO: 21)

BP3-40
(ac-SEEVCWPVAEWYLCN-nh2);    (SEQ ID NO: 22)

BP3-41
(GPETCWPVAEWYLCN);           (SEQ ID NO: 23)

BP3-107
(suc-CQLVRPDLLLCQ-nh2);      (SEQ ID NO: 24)
and

BP3-108
(suc-IPVSPDWFVCQ-nh2);       (SEQ ID NO: 25)
where the C* indicates a cysteine that has been
linked to another cysteine in the peptide. The
remaining Cys pairs are also oxidized as
disulfides in each peptide. The more preferred
IGFBP-3 displacer peptide herein is BP3-15,
BP3-39, BP3-40, BP301-OX, BP3-27, BP-328, BP3-
30, BP3-41, or 4D3.3P. The most preferred
IGFBP-3 displacer peptide herein is BP3-15,
BP3-39, or BP3-40.
```

Examples of IGFBP-1 displacer peptides include a peptide selected from the group consisting of:

```
BP1-01
(CRAGPLQWLCEKYFG);           (SEQ ID NO: 26)

BP1-02
(SEVGCRAGPLQWLCEKYFG;        (SEQ ID NO: 27)

BP1-04
(CRAGPLQWLCE);               (SEQ ID NO: 28)

BP1-10
(CRKGPLQWLCELYF);            (SEQ ID NO: 29)

BP1-11
(CRKGPLQWLCEKYF);            (SEQ ID NO: 30)

BP1-12
(CKEGPLQWLCEKYF);            (SEQ ID NO: 31)

BP1-13
(CKEGPLQWLCEKYF);            (SEQ ID NO: 32)

BP1-14
(SEVGCRAGPLQWLCEKYFG-nh2);   (SEQ ID NO: 33)

BP1-15
(CAAGPLQWLCEKYF);            (SEQ ID NO: 34)

BP1-16
(CRAGPLQWLCEKYF-nh2);        (SEQ ID NO: 35)

BP1-17
(CRAGPLQWLCEK-nh2);          (SEQ ID NO: 36)

BP1-18
(CRAGPLQWLCEKAA);            (SEQ ID NO: 37)

BP1-19
(SEMVCRAGPLQWLCEIYF-nh2*);   (SEQ ID NO: 38)

BP1-20
(EARVCRAGPLQWLCEKYF-nh2);    (SEQ ID NO: 39)

BP1-21A
(SEVGCRAGPLQWLCEKYFSTY-nh2); (SEQ ID NO: 40)

BP1-21B
(CRAGPLQWLCEKYFSTY-nh2);     (SEQ ID NO: 41)

BP1-25
(EARVCRAGPLQWLCEKYFSTY);     (SEQ ID NO: 42)

BP1-40
(GQQSCRAGPLQWLCEKYFSTY);     (SEQ ID NO: 43)

BP67
(CRAGPLQWLCERYF);            (SEQ ID NO: 44)

BP68
(CRAGPLQWLCEKFF);            (SEQ ID NO: 45)

BP1-625
(GQQSCAAGPLQWLCEHYFSTYGR);   (SEQ ID NO: 46)

BP1-625-Z
(GQQSCAAGPLQWLCEHYFSTYGRGGGSGGAQHD  (SEQ ID NO: 47)

EAVDNKFNKEQQNAFYEILHLPNLNEEQRNAFIQ

SLKDDPSQSANLLAEAKKLNDAQAPNVDmn);

BP1-625T
(GQQSCAAGPLQWLCEHYFSTY);     (SEQ ID NO: 153)

BP1027
(CKAGPLLWLCERFF);            (SEQ ID NO: 48)
```

```
BP1028
(CRAGPLQWLCERFF);                    (SEQ ID NO: 49)

BP1029
(CREGPLQWLCERFF);                    (SEQ ID NO: 50)

BP1030
(CKEGPLLWLCERFF);                    (SEQ ID NO: 51)

(i + 7)D
(acRAGPLEWLAEKYEG);                  (SEQ ID NO: 52)

(i + 8)B
(acRPLEWLAEKYFE);                    (SEQ ID NO: 53)
and (i + 8)C
(acRAGPLEWLAEKYFE);                  (SEQ ID NO: 54)
where the C* indicates a cysteine that has been
linked to another cysteine in the peptide, and the
remaining Cys pairs are also oxidized as
disulfides in each peptide. The more preferred
IGFBP-1 displacer peptide herein is BP1-16,
BP1-20, BP1-21A, BP1-25, BP1-40, BP625, BP625-Z,
and BP625T; and most preferred are BP1-20,
BP1-21A, BP1-25, BP1-40, BP1-625, BP1-625-Z, and
BP1-625T.
```

The still more preferred active agents herein are F49A, E3A, F16A, E3AF49A, F16AF49A, D12K, D12R, BP3-15, BP3-40, BP3-39, BP1-16, BP1-20, BP1-21A, BP1-25, BP1-40, BP1-625, and BP1-625-Z; and the most preferred are F49A, E3AF49A, F16AF49A, D12K, D12R, BP3-15, BP3-40, BP3-39, BP1-20, BP1-21A, BP1-25, BP1-40, BP1-625, BP1-625-Z, and BP1-625T.

The IGF-1 analogs and IGFBP displacer peptides useful in accordance with this invention can be made by any means that are known in the art, including chemical synthesis or recombinant production. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer polypeptides. When recombinant procedures are selected, a synthetic gene may be constructed de novo or a natural gene may be mutated by, for example, cassette mutagenesis. Set forth below are exemplary general recombinant procedures.

From a purified IGF-1 and its amino acid sequence, for example, an IGF variant that is a peptidyl mutant of an IGF-1 parent molecule may be produced using recombinant DNA techniques. These techniques contemplate, in simplified form, taking the gene, either natural or synthetic, encoding the analog; inserting it into an appropriate vector; inserting the vector into an appropriate host cell; culturing the host cell to cause expression of the gene; and recovering or isolating the analog produced thereby. Preferably, the recovered analog is then purified to a suitable degree.

Somewhat more particularly, the DNA sequence encoding a peptidyl IGF variant is cloned and manipulated so that it may be expressed in a convenient host. DNA encoding parent polypeptides can be obtained from a genomic library, from cDNA derived from mRNA from cells expressing the parent polypeptide, or by synthetically constructing the DNA sequence (Sambrook et al., *Molecular Cloning: A Laboratory Manual* (2d ed.), Cold Spring Harbor Laboratory, N.Y., 1989).

The parent DNA is then inserted into an appropriate plasmid or vector which is used to transform a host cell. In general, plasmid vectors containing replication and control sequences that are derived from species compatible with the host cell are used in connection with those hosts. The vector ordinarily carries a replication site, as well as sequences which encode proteins or peptides that are capable of providing phenotypic selection in transformed cells.

For example, *E. coli* may be transformed using pBR322, a plasmid derived from an *E. coli* species (Mandel et al., *J. Mol. Biol.* 53: 154 (1970)). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A preferred vector is pB0475. This vector contains origins of replication for phage and *E. coli* that allow it to be shuttled between such hosts, thereby facilitating both mutagenesis and expression (Cunningham et al., *Science,* 243: 1330-1336 (1989); U.S. Pat. No. 5,580,723). Other preferred vectors are pR1T5 and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce the parent IGF-1 polypeptide, segment-substituted peptides, residue-substituted peptides, and peptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various *Pseudomonas* species. The preferred prokaryote is *E. coli* W3110 (ATCC 27325). When expressed by prokaryotes, the analogs or peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure. *Tissue Culture*, Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired analog or peptide is associated, in the vector, with a gene encoding another protein or a fragment of another protein. This results in the desired analog or peptide being produced by the host cell as a fusion with another protein or peptide. The "other" protein or peptide is often a protein or peptide that can be secreted by the cell, making it possible to isolate and purify the desired analog or peptide from the culture medium and eliminating the necessity of destroying the host cells that arises when the desired analog or peptide remains inside the cell. Alternatively, the fusion protein can be expressed intracellularly. It is useful to use fusion proteins that are highly expressed.

The use of gene fusions, though not essential, can facilitate the expression of heterologous analogs and peptides in *E. coli* as well as the subsequent purification of those gene products (Harris, in *Genetic Engineering*, Williamson, R., Ed. (Academic Press, London, Vol. 4, 1983), p. 127; Ljungquist et al., *Eur. J. Biochem.*, 186: 557-561 (1989) and Ljungquist et al., *Eur. J. Biochem.*, 186: 563-569 (1989)). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli*, but are stable when expressed as fusion proteins (Marston, *Biochem J.*, 240:1 (1986)).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired analog or peptide.

Alternatively, one can employ proteolytic cleavage of fusion protein (Carter, in *Protein Purification: From Molecular Mechanisms to Large-Scale Processes*, Ladisch et al., eds. (American Chemical Society Symposium Series No. 427, 1990), Ch 13, pages 181-193).

Proteases such as Factor Xa, thrombin, and subtilisin or its mutants, and a number of others have been successfully used to cleave fusion proteins. Typically, a peptide linker that is amenable to cleavage by the protease used is inserted between the "other" protein (e.g., the Z domain of protein A) and the desired analog or peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The analog or peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the analog or peptide is treated with a chaotrope, such a guanidine HCl. Then it is treated with a redox buffer, containing, for example, reduced and oxidized dithiothreitol or glutathione at the appropriate ratios, pH, and temperature, such that the analog or peptide is refolded to its native structure.

When analogs and peptides are not prepared using recombinant DNA technology, they are preferably prepared using solid-phase synthesis, such as that generally described by Merrifield, *J. Am. Chem. Soc.*, 85: 2149 (1963), although other equivalent chemical syntheses known in the art are employable. In vitro protein synthesis may be performed using manual techniques or by automation. Automated synthesis may be accomplished, for instance, using an Applied Biosystems peptide synthesizer (Foster City, Calif.) following the manufacturer's instructions. Various portions of the analog or peptide may be chemically synthesized separately and combined using chemical or enzymatic methods to produce the full-length analog or peptide.

Solid-phase synthesis is initiated from the C-terminus of the analog or peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London), 38: 1597-1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman and Co., San Francisco 1969), Chapter 1, pp. 1-6. BHA and MBHA resin supports are commercially available and are generally used only when the desired analog or peptide being synthesized has an unsubstituted amide at the C-terminus.

The amino acids are coupled to the analog/peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross and J. Meienhofer, *The Peptides: Analysis, Structure, Biology*, Vol. I: Major Methods of Peptide Bond Formation (Academic Press, New York, 1979).

It should be recognized that the ∀-amino group of each amino acid employed in the analog/peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides Analysis, Structure, Biology*, Vol. 3: "Protection of Functional Groups in Peptide Synthesis" (Academic Press: New York, 1981).

In the selection of a particular side-chain protecting group to be used in synthesizing the analogs/peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the analog/peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired analog/peptide under reaction conditions that will not alter the structure of the analog/peptide chain.

It will be apparent to those skilled in the art that the protecting groups known to be useful for analog/peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1-C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side-chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al., *Chemistry Letters,* 165-168 (1978) or using isopropylcarbodiimide at about 25EC for 2 hours with stirring. Following the coupling of the BOC-protected amino acid to the resin support, the ∀-amino protecting group is removed, as by using trifluoroacetic acid (TFA) in methylene chloride or TFA alone. The deprotection is carried out at a temperature between about 0EC and room temperature. Other standard cleaving reagents, such as HCl in dioxane, and conditions for removal of specific α-amino protecting groups are described in the literature.

After removal of the ∀-amino protecting group, the remaining ∀-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem,* 34: 595 (1970). The coupling reactions can be performed automatically using well known methods, for example, a BIOSEARCH 9500™ peptide synthesizer.

Upon completion of the desired analog/peptide sequence, the protected analog/peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the analog/peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the analog/peptide from the resin but also will remove all protecting groups. Hence, use of this reagent will directly afford the fully deprotected analog/peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the analog/peptide from the resin.

When it is desired to cleave the analog/peptide without removing protecting groups, the protected analog/peptide-resin can undergo methanolysis to yield the protected analog/peptide in which the C-terminal carboxyl group is methylated. The methyl ester is then hydrolyzed under mild alkaline conditions to give the free C-terminal carboxyl group. The protecting groups on the analog/peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518-521, in which the protected analog/peptide-resin is treated with methanol and potassium cyanide in the presence of crown ether.

Another method for cleaving the protected analog/peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected analog/peptide is cleaved from the support.

Purification of the analogs and peptides of the invention is typically achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

The analogs and peptides of this invention may be stabilized by polymerization. Polymerization may be accomplished by crosslinking monomer chains with polyfunctional crosslinking agents, either directly or indirectly, through multi-functional polymers. Ordinarily, two substantially identical analogs/peptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha-amino group of one analog/peptide is crosslinked to the terminal-carboxyl group of the other analog/peptide. Preferably, the analogs/peptides are substituted at their C-termini with cysteine. Under conditions well known in the art a disulfide bond can be formed between the terminal cysteines, thereby crosslinking the analog/peptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side chains of the amino acids present in the analogs/peptides. For example, disulfide crosslinking would not be preferred if cysteine were present in the analog/peptide at additional sites other than the C-terminus. Also within the scope hereof are analogs/peptides crosslinked with methylene bridges.

Suitable crosslinking sites on the analogs/peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the analogs/peptides or residues introduced into flanking sequences. Crosslinking through externally added crosslinking agents is suitably achieved, e.g., using any of a number of reagents familiar to those skilled in the art, for example, via carbodiimide treatment of the analog or peptide. Other examples of suitable multi-functional (ordinarily bifunctional) crosslinking agents are found in the literature.

The analogs and peptides of this invention also may be conformationally stabilized by cyclization. The analogs/peptides ordinarily are cyclized by covalently bonding the N- and C-terminal domains of one analog/peptide to the corresponding domain of another analog/peptide of this invention so as to form cyclo-oligomers containing two or more iterated analog/peptide sequences, each internal analog/peptide having substantially the same sequence. Further, cyclized analogs/peptides (whether cyclo-oligomers or cyclo-monomers) are crosslinked to form 1-3 cyclic structures having from 2 to 6 peptides comprised therein. The analogs/peptides preferably are not covalently bonded through α-amino and main chain carboxyl groups (head to tail), but rather are crosslinked through the side chains of residues located in the N- and C-terminal domains. The linking sites thus generally will be between the side chains of the residues.

Many suitable methods per se are known for preparing mono- or poly-cyclized analogs/peptides as contemplated herein. Lys/Asp cyclization has been accomplished using Na-Boc-amino acids on solid-phase support with Fmoc/9-fluorenylmethyl (OFm) side-chain protection for Lys/Asp; the process is completed by piperidine treatment followed by cyclization.

Glu and Lys side chains also have been crosslinked in preparing cyclic or bicyclic analogs/peptides: the analog/peptide is synthesized by solid-phase chemistry on a p-methylbenzhydrylamine resin. The analog/peptide is cleaved from the resin and deprotected. The cyclic analog/peptide is formed using diphenylphosphorylazide in diluted methylformamide. For an alternative procedure, see Schiller et al., *Peptide Protein Res.*, 25: 171-177 (1985). See also U.S. Pat. No. 4,547,489.

Disulfide crosslinked or cyclized analogs/peptides are generated by conventional methods. The method of Pelton et al. (*J. Med. Chem.*, 29: 2370-2375 (1986)) is suitable, except that a greater proportion of cyclo-oligomers are produced by conducting the reaction in more concentrated solutions than the dilute reaction mixture described by Pelton et al., for the production of cyclo-monomers. The same chemistry is useful for synthesis of dimers or cyclo-oligomers or cyclo-monomers. Also useful are thiomethylene bridges. Lebl and Hruby, *Tetrahedron Letters*, 25: 2067-2068 (1984). See also Cody et al., *J. Med. Chem.*, 28: 583 (1985).

The desired cyclic or polymeric analogs/peptides are purified by gel filtration followed by reversed-phase high-pressure liquid chromatography or other conventional procedures. The analogs/peptides are sterile filtered and formulated into conventional pharmacologically acceptable vehicles.

The starting materials required for the processes described herein are known in the literature or can be prepared using known methods and known starting materials.

If in the analogs/peptides being created carbon atoms bonded to four nonidentical substituents are asymmetric, then the analogs/peptides may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations R) or S) and both are within the scope of the present invention.

The analogs and peptides of this invention may be contacted with the cartilage by any suitable technique, and may be combined, analog with analog, analog with peptide, or peptide with peptide. If treatment is in vivo, the analog or peptide is administered to the mammal via, e.g., oral, parenteral (e.g., intramuscular, intraperitoneal, intravenous, intra-articular, or subcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the analog or peptide, the type of analog or peptide being administered, and the particular type of disorder to be corrected. Most preferably, the administration is by continuous infusion (using, e.g., slow-release devices or minipumps such as osmotic pumps or skin patches), or by injection (using, e.g., intravenous, intra-articular or subcutaneous means). Preferably, the analog or peptide is administered locally, for example, directly to the joint where repair or prevention is needed.

The analog or peptide to be used in the therapy will be formulated and dosed in a fashion consistent with good medical practice, taking into account the clinical condition of the individual patient (especially the side effects of treatment with the analog or peptide), the type of disorder, the site of delivery, the method of administration, the scheduling of administration, and other factors known to practitioners. The effective amounts of the analog or peptide for purposes herein are thus determined by such considerations and must be amounts that result in bioavailability of the drugs to the mammal and the desired effect.

A preferred administration is a chronic administration of about two times per day for 4-8 weeks to reproduce the effects of IGF-1. As an alternative to injection, chronic infusion may be employed using an infusion device for continuous subcutaneous (SC) or intra-articular infusions. An intravenous bag solution may also be employed. The key factor in selecting an appropriate dose for the disorder in question is the result obtained, as measured by criteria for measuring treatment of the cartilage disorder as are deemed appropriate by the medical practitioner.

As a general proposition, the total pharmaceutically-effective amount of the analog or peptide administered parenterally per dose will be in a range that can be measured by a dose-response curve. For example, IGFs bound to IGFBPs or in the blood can be measured in body fluids of the mammal to be treated to determine the dosing. Alternatively, one can administer increasing amounts of the analog or peptide to the patient and check the serum levels of the patient for IGF-1 and IGF-2. The amount of analog or peptide to be employed can be calculated on a molar basis based on these serum levels of IGF-1 and IGF-2.

Specifically, one method for determining appropriate dosing of the analog or peptide entails measuring IGF levels in a biological fluid such as a body or blood fluid. Measuring such levels can be done by any means, including RIA and ELISA. After measuring IGF levels, the fluid is contacted with the analog or peptide using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, i.e., after the fluid is extracted from a mammal and the IGF levels measured, the analog or peptide herein is administered to the mammal using single or multiple doses (that is, the contacting step is achieved by administration to a mammal). Then the IGF levels are re-measured from fluid extracted from the mammal.

Another method for determining dosing is to use antibodies to the analog or peptide or another detection method for the analog or peptide in the LIFA format. This would allow detection of endogenous or exogenous IGFs bound to IGFBP and the amount of analog or peptide bound to the IGFBP.

Another method for determining dosing would be to measure the level of "free" or active IGF in blood. For some uses the level of "free" IGF would be a suitable marker of efficacy and effective doses or dosing. The amount of active IGF may also be measured in the synovial fluid.

For example, one method is described for detecting endogenous or exogenous IGF bound to an IGF binding protein or the amount of the analog or peptide herein or detecting the level of unbound IGF in a biological fluid. This method comprises:

(a) contacting the fluid with 1) a means for detecting the analog or peptide that is specific for the analog or peptide (such as a first antibody specific for epitopes on the analog or peptide) attached to a solid-phase carrier, such that in the presence of the analog or peptide the IGF binding sites remain available on the analog or peptide for binding to the IGF binding protein, thereby forming a complex between the means and the IGF binding protein; and 2) the analog or peptide for a period of time sufficient to saturate all available IGF binding sites on the IGF binding protein, thereby forming a saturated complex;

(b) contacting the saturated complex with a detectably labeled second means which is specific for the IGF binding protein (such as a second antibody specific for epitopes on the IGFBP) which are available for binding when the analog or peptide is bound to the IGF binding protein; and (c) quantitatively analyzing the amount of the labeled means bound as a measure of the IGFBP in the biological fluid, and therefore as a measure of the amount of bound analog or peptide and IGF binding protein, bound IGF and IGF binding protein, or active IGF present in the fluid.

Given the above methods for determining dosages, in general, the amount of analog or peptide that may be employed can be estimated, i.e., from about 1 µg/kg/day to 10 mg/kg/day, preferably about 10 µg/kg/day to 1 mg/kg/day, more preferably about 10-200 µg/kg/day, might be used, based on kg of patient body weight, although, as noted above, this will be subject to a great deal of therapeutic discretion.

It is noted that dosages and desired drug concentrations of pharmaceutical compositions employable with the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti and Chappell, "The use of interspecies scaling in toxicokinetics" in *Toxicokinetics and New Drug Development*, Yacobi et al., Eds., (Pergamon Press: New York, 1989), pp. 42-96.

The analog or peptide is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547-556 (1983), poly(2-hydroxyethyl methacrylate) (Langer et al., *J. Biomed. Mater. Res.*, 15: 167-277 (1981), and Langer, *Chem. Tech.*, 12: 98-105 (1982)), ethylene vinyl acetate (Langer et al., supra) or poly-D-(−)-3-hydroxybutyric acid (EP 133,988). Sustained-release compositions also include a liposomally entrapped analog or peptide. Liposomes containing the analog or peptide are prepared by methods known per se: DE 3,218,121; Epstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated analogs or peptides having a longer life can also be employed, based on, e.g., the conjugate technology described in WO 95/32003 published Nov. 30, 1995.

For parenteral administration, in one embodiment, the analog or peptide is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other peptides that are known to be deleterious to polypeptides.

Generally, the formulations are prepared by contacting the analog or peptide uniformly and intimately with liquid carriers or finely divided solid carriers or both. Then, if necessary, the product is shaped into the desired formulation. Preferably the carrier is a parenteral carrier, more preferably a solution that is isotonic with the blood or synovial fluid of the recipient. Examples of such carrier vehicles include water, saline, Ringer's solution, a buffered solution, hyaluronan, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The analog or peptide typically formulated in such vehicles at a pH of from or about 4.5 to 8. It will be understood that use of certain of the foregoing excipients, carriers, or stabilizers will result in the formation of salts of the analog or peptide. The final preparation may be a stable liquid or lyophilized solid.

Typically about 0.5 to 500 mg of the analog or peptide or mixture of analogs and/or peptides, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

The analog or peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The analog or peptide ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution of analog or peptide, and the resulting mixture is lyophilized. The infusion solution is prepared by reconstituting the lyophilized analog or peptide using bacteriostatic Water-for-Injection.

Combination therapy with the analog or peptide herein and one or more other appropriate reagents that enhance the effect of the analog or peptide is also part of this invention. These include antagonists to cytokines, NO, or IL-1ra, a cartilage catabolism antagonist, or a cartilage growth factor, such as wild-type IGF-1 and/or ALS if the active agent is an IGFBP-3 displacer peptide or an IGF-1 analog with a binding affinity preference for IGFBP-3 over IGFBP-1. In addition, the IGFBP displacer peptide may be co-administered with an IGF-1 analog herein, preferably with the analog with a binding affinity preference for IGFBP-1 over IGFBP-3.

The active agent and reagent to enhance its effect may be administered concurrently or sequentially, and the reagent may be administered at the same or lower doses than they would otherwise be administered if given alone. The displacer peptide/IGF-1 analog with binding preference for IGFBP-3 can be administered separately from the IGF-1 and/or ALS, but preferably these agents are administered together as a binary or ternary complex where such a complex can be formed. Administration as a complex of ALS, IGF-I, and IGFBP-3 displacer peptide/IGF-1 analog results in the longest half-life for the active agent.

The invention herein also contemplates using gene therapy for treating a mammal, using nucleic acid encoding the analog or peptide. Generally, gene therapy is used to increase (or overexpress) IGF levels in the mammal. Nucleic acids that encode the analog or peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the analog or peptide is required. For ex vivo treatment, the patient's cells are removed, the nucleic acid is introduced into these isolated cells and the modified cells are administered to the patient either directly or, for example, encapsulated within porous membranes which are implanted into the patient. See, e.g., U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, viral infection etc. A commonly used vector for ex vivo delivery of the gene is an adeno- or retro-virus.

The currently preferred in vivo nucleic acid transfer techniques include infection with viral vectors (such as adenovirus, Herpes simplex I virus, retrovirus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins that bind to a cell-surface membrane protein associated with endocytosis may be used for targeting and/or to facilitate uptake. Examples include capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429-4432 (1987); and Wagner et al., *Proc. Natl. Acad. Sci. USA*, 87: 3410-3414 (1990). For review of the currently known gene marking and gene therapy protocols, see Anderson et al., *Science*, 256: 808-813 (1992). See also WO 93/25673 and the references cited therein.

Kits are also contemplated for this invention. The article of manufacture comprises a container and an instruction. Suitable containers include, for example, bottles, vials, syringes, and test tubes. The containers may be formed from a variety of materials such as glass or plastic. The container holds a composition which is effective for treating the cartilage disorder, e.g., degenerative cartilagenous disorder, and may have a sterile access port (for example, the container may be an intravenous solution bag or a vial having a stopper pierceable by a hypodermic injection needle). The active agent in the composition is an IGF-1 analog or an IGFBP displacer peptide as defined herein. The composition can comprise any or multiple ingredients disclosed herein. The instruction on, or associated with, the container indicates that the composition is used for treating a cartilage disorder. For example, the instruction could indicate that the composition is effective for the treatment of osteoarthritis, rheumatoid arthritis, or any other degenerative cartilagenous disorder. The article of manufacture may further comprise a second container comprising a pharmaceutically-acceptable buffer, such as phosphate-buffered saline, Ringer's solution, or dextrose solution. Alternatively, the composition may contain any of the carriers, excipients, and/or stabilizers mentioned hereinabove. It may further include other materials desirable from a commercial and user standpoint, including other buffers, diluents, filters, needles, syringes, and package inserts with instructions for use. The kit usually includes a separate container, preferably a vial, for a co-agent to be administered along with the active agent, such as IGF-1.

The invention will be more fully understood by reference to the following examples. They should not, however, be construed as limiting the scope of the invention. All literature and patent citations mentioned herein are expressly incorporated by reference.

EXAMPLES

Examples 1-4 below are taken from WO 98/45427 as describing IGFBP-3 displacer peptides defined herein. Based upon the results of in vitro and in vivo experiments using an IGFBP-3 displacer peptide with amino acid changes at residues 24 and 31 (Y24L, Y31A), also designated (Leu$^{24}$, Ala$^{31}$) hIGF-1 or IGF-M, disclosed in WO 98/45427, it is predicted that other peptides that inhibit the interaction of an IGF with an IGFBP, and bind poorly or not at all to the IGF-1 receptor, should increase active IGF levels in a subject being treated. In addition, it is possible that another class of molecules might bind IGF-1 itself at a site remote from that involved in receptor interactions in such a way as to inhibit or prevent the interaction of IGF-1 with the IGFBPs, but not the interaction of IGF-1 with its receptor.

In the examples, common ∀-amino acids may be described by the standard one- or three-letter amino acid code when referring to intermediates and final products. By common ∀-amino acids is meant those amino acids incorporated into proteins under mRNA direction. Standard abbreviations are listed in The Merck Index, 10th Edition, pp Misc-2-Misc-3. Unless otherwise designated the common ∀-amino acids have the natural or "L"-configuration at the alpha carbon atom. If the code is preceded by a "D" this signifies the opposite enantiomer of the common ∀-amino acid. Modified or unusual ∀-amino acids such as norleucine (Nle) and ornithine (Orn) are designated as described in U.S. Patent and Trademark Office Official Gazette 1114 TMOG, May 15, 1990.

Example 1

Phage-derived Peptides to Bind IGF-1 and Binding Proteins

Introduction:

It has been shown that peptides that bind specifically and with measurable affinity to target molecules, such as proteins, can be identified from an initial library of many binding and non-binding peptides through binding selections using bacteriophage coat-protein fusions (Smith, *Science*, 228: 1315 (1985); Scott and Smith, *Science*, 249: 386 (1990); Cwirla et al., *Proc. Natl. Acad. Sci. USA*, 87: 6378-6382 (1990); Devlin et al., *Science*, 249: 404 (1990); reviewed by Wells and Lowman, *Curr. Opin. Struct. Biol.*, 2: 597 (1992); U.S. Pat. No. 5,223,409). In addition, both proteins and peptides displayed on phage can be affinity-enhanced through iterative cycles of mutations, selection, and propagation.

Libraries of peptides differing in sequence at particular residue positions can be constructed using synthetic oligodeoxynucleotides. Peptides are displayed as fusion proteins with a phage coat protein (such as g3p or g8p) on bacteriophage particles, each of which contains a single-stranded DNA genome encoding the particular peptide variant. After cycles of affinity purification, using an immobilized target molecule, individual bacteriophage clones are isolated, and the amino acid sequence of their displayed peptides is deduced from their DNA sequences.

Materials and Methods:

Construction of Peptide-phage Libraries

To identify a set of peptide molecules having the ability to bind to IGF-1 or to an IGF binding protein, such as IGFBP-1 or IGFBP-3, several diverse phage libraries of peptides, of length ranging from 18 to 20 residues, were constructed. Peptides of this size were chosen in order to favor the selection of peptides capable of maintaining well-defined structures in solution. Because natural-amino acid peptides of this size have a potential sequence diversity of $20^{18}$-$20^{20}$ (i.e., $2.6 \times 10^{23}$ to $1.0 \times 10^{26}$) variants, it is not practical to construct and test all such variants. Instead, certain residues were fixed or constant, which might be expected to allow or promote stable elements of peptide structure such as disulfide bonds or beta-turns, within each peptide.

Structural constraints or frameworks have previously been used for presentation of peptide libraries on phage and for subsequent, successive enhancement of binding affinities through mutation and selection. Such structured frameworks may favor stable binding conformations of peptide segments. By analogy, immunoglobulins provide a stable (and conserved) structural framework for presentation of a diversity of different peptide loops (CDR's, complementarity-determining regions) which can bind different antigens.

Used as a template for library constructions was a plasmid, pt4.g8 (complete DNA sequence shown in FIG. 1) expressing an antibody-recognizable (gD-tag) peptide fused to g8p of bacteriophage M13. This plasmid contains single-stranded and double-stranded origins of DNA replication. The phoA promoter and STII secretion-signal sequences are upstream of the gD peptide (underlined below), which is followed by a "linker" peptide (double underlined below), and then the g8p of bacteriophage M13:

(SEQ ID NO: 55)
SGTAMADPNRFRGKDLAGSPGGGSGGGAEGDDPAKAAFNSLQASATEYIG

YAWAMVVVIVGATIGIKLFKKFTSKAS

Several random-sequence peptide libraries (Table I) were constructed using single-stranded template-directed mutagenesis (Kunkel et al., *Methods. Enzymol.*, 204:125 (1991)), with the oligonucleotides described below.

TABLE I

Large Naive Libraries for g8 Display

| Library | Oligonucleotide no. | Peptide motif | SEQ ID NO |
|---|---|---|---|
| A | HL-300 | SGTACX$_2$GPX$_4$CSLAGSP | (SEQ ID NO: 56) |
| B | HL-301 | X$_4$CX$_2$GPX$_4$CX$_4$ | (SEQ ID NO: 57) |
| C | HL-302 | X$_{20}$ | (SEQ ID NO: 58) |
| D | HL-303 | X$_7$CX$_4$CX$_7$ | (SEQ ID NO: 59) |
| D | HL-304 | X$_7$CX$_5$CX$_6$ | (SEQ ID NO: 60) |
| D | HL-305 | X$_6$CX$_6$CX$_6$ | (SEQ ID NO: 61) |
| D | HL-306 | X$_6$CX$_7$CX$_5$ | (SEQ ID NO: 62) |
| D | HL-307 | X$_5$CX$_8$CX$_5$ | (SEQ ID NO: 63) |
| D | HL-308 | X$_5$CX$_9$CX$_4$ | (SEQ ID NO: 64) |
| D | HL-309 | X$_4$CX$_{10}$CX$_4$ | (SEQ ID NO: 65) |

A. Beta-turn Sequence Motif

An example of a peptide of known three-dimensional structure is given by Wrighton et al., who selected a peptide agonist for the erythropoietin receptor (EPO-R) by phage display (Wrighton et al., *Science*, 273: 458 (1996)). The peptide GGTYSCHFGPLTWVCKPQGG (SEQ ID NO:66) (having a disulfide bond joining the two Cys residues) forms a dimer of two beta hairpins, in the crystallized complex with EPO-R (Livnah et al., *Science*, 273: 464 (1996)). Although the structure of the unbound form of this peptide in solution has not been reported, the beta-turn structure formed by this peptide in complex with EPO-R suggested that similar structures might be formed by peptides of the form CX$_2$GPX$_4$C (SEQ ID NO:67).

As one type of structured peptide library, a portion of the gD peptide was replaced with the motif CX$_2$GPX$_4$C (SEQ ID NO:67), leaving the upstream and downstream ("flanking") residues unchanged from that of the starting plasmid. Thus, this library was designed to display on phage particles the peptide SGTACX$_2$GPX$_4$CSLAGSP (SEQ ID NO:56), where X represents any of the 20 natural L-amino acids, fused to the linker and g8p described above. This library was constructed using the oligonucleotide HL-300:

(SEQ ID NO: 68)
5'-GCC TAT GCA TCT GGT ACC GCC TGC NNS NNS GGT CCT

NNS NNS NNS NNS TGT TCT CTG GCA GGT TCA CCA G-3', where N indicates a mixture of the nucleotides A, G, C, and T, and S represents a mixture of the nucleotides G and C.

An additional library was constructed to allow for further interactions within the peptide and/or with the target proteins by randomizing the flanking sequences as well. This library was constructed with the form X$_4$CX$_2$GPX$_4$CX$_4$ (SEQ ID NO:57) by using oligonucleotide HL-301:

(SEQ ID NO: 69)
5'-GCT ACA AAT GCC TAT GCA NNS NNS NNS NNS TGC NNS

NNS GGT CCT NNS NNS NNS NNS TGT NNS NNS NNS NNS

GGT GGA GGA TCC GGA GGA G-3'.

B. Disulfide-loop Motifs

Because many additional peptide conformations might be productive for binding to a given target protein, it was desirable to test other types of peptide sequence motifs in phage-displayed libraries. For example, a single disulfide bond within a small peptide may favor stable structures that allow for relatively higher-affinity binding than in unconstrained structures (Geysen et al., *Mol. Immunol.*, 23: 709 (1986); Wood et al., *Science*, 232: 633 (1986); Oldenburg et al., *Proc. Natl. Acad. Sci. USA*, 89: 5393 (1992); O'Neil et al., *Proteins*, 14: 509 (1992); McLafferty et al., *Gene*, 128: 29 (1993); Giebel et al., *Biochem.*, 34: 15430 (1995)). Several peptide-phage libraries were therefore constructed, of the form X$_m$CX$_n$CX$_k$, where m=4, n=10, and k=4, or where m=5, n=8-9, and k=4-5, or m=6, n=6-7, and k=5-6, or m=7, n=4-5, and k=6-7 (SEQ ID NOS:59 to 65). In these peptides, a disulfide bond is predicted to form a stabilizing constraint for peptide conformation.

These peptide libraries (see Table I) were constructed as X$_7$CX$_4$CX$_7$ (SEQ ID NO:59), using oligonucleotide HL-303:

(SEQ ID NO: 70)
5'-GCT ACA AAT GCC TAT GCA NNS NNS NNS NNS NNS NNS

NNS TGC NNS NNS NNS NNS TGC NNS NNS NNS NNS NNS

NNS NNS GGT GGA GGA TCC GGA GGA G-3';

X$_7$CX$_5$CX$_6$ (SEQ ID NO:60), using oligonucleotide HL-304:

(SEQ ID NO: 71)
5'-GCT ACA AAT GCC TAT GCA NNS NNS NNS NNS NNS NNS

NNS TGC NNS NNS NNS NNS NNS TGC NNS NNS NNS NNS

NNS NNS GGT GGA GGA TCC GGA GGA G-3';

X$_6$CX$_6$CX$_6$ (SEQ ID NO:61), using oligonucleotide HL-305:

(SEQ ID NO: 72)
5'-GCT ACA AAT GCC TAT GCA NNS NNS NNS NNS NNS NNS

TGC NNS NNS NNS NNS NNS NNS TGC NNS NNS NNS NNS

NNS NNS GGT GGA GGA TCC GGA GGA G-3';

$X_6CX_7CX_5$ (SEQ ID NO:62), using oligonucleotide HL-306:

(SEQ ID NO: 73)
5'-GCT ACA AAT CCC TAT GCA NNS NNS NNS NNS NNS NNS

TGC NNS NNS NNS NNS NNS NNS NNS TGC NNS NNS NNS

NNS NNS GGT GGA GGA TCC GGA GGA G-3';

$X_5CX_8CX_5$ (SEQ ID NO:63), using oligonucleotide HL-307:

(SEQ ID NO: 74)
5'-GCT ACA AAT GCC TAT GCA NNS NNS NNS NNS NNS TGC

NNS NNS NNS NNS NNS NNS NNS NNS TGC NNS NNS NNS

NNS NNS GGT GGA GGA TCC GGA GGA G-3';

$X_5CX_9CX_4$ (SEQ ID NO:64), using oligonucleotide HL-308:

(SEQ ID NO: 75)
5'-GCT ACA AAT GCC TAT GCA NNS NNS NNS NNS NNS TGC

NNS NNS NNS NNS NNS NNS NNS NNS NNS TGC NNS NNS

NNS NNS GGT GGA GGA TCC GGA GGA G-3';
and $X_4CX_{10}CX_4$ (SEQ ID NO:65), using oligonucleotide HL-309:

(SEQ ID NO: 76)
5'-GCT ACA AAT GCC TAT GCA NNS NNS NNS NNS TGC NNS

NNS NNS NNS NNS NNS NNS NNS NNS NNS TGC NNS NNS

NNS NNS GGT GGA GGA TCC GGA GGA G-3'.

C. Unconstrained Peptides

Unconstrained libraries (i.e., having no fixed residues within the peptide) have also yielded specific binding molecules (Scott and Smith, supra; Cwirla et al., supra; Devlin et al., supra; Kay et al., *Gene,* 128: 59 (1993)). Such libraries may yield structured peptides, nevertheless, since noncovalent interactions may still induce structure in the bound and/or unbound forms. An unconstrained peptide library, of the form $X_{20}$ (SEQ ID NO:58), was constructed using oligonucleotide HL-302:

(SEQ ID NO: 77)
5'-GCT ACA AAT GCC TAT GCA NNS NNS NNS NNS NNS NNS

NNS NNS NNS NNS NNS NNS NNS NNS NNS NNS NNS NNS

NNS NNS GGT GGA GGA TCC GGA GGA G-3'.

Polyvalent (g8) Phage Binding Selections

The products of random mutagenesis reactions were transformed into XL1-BLUE™ *E. coli* cells (Stratagene) by electroporation and amplified by growing 15-16h with M13K07 (Vieira and Messing, *Methods Enzymol.,* 153: 3-11 (1987)) or VCSM13 helper phage (Stratagene Corp.). Based upon plating of the initial transformations, the number of transformants per library was approximately $1.8 \times 10^8$ for library HL-300, $7.9 \times 10^8$ for HL-301, $5.0 \times 10^8$ for HL-302, $5.3 \times 10^8$ for HL-303, $5.6 \times 10^8$ for HL-304, $5.0 \times 10^8$ for HL-305, $6.3 \times 10^8$ for HL-306, $4.5 \times 10^8$ for HL-307, $1.9 \times 10^8$ for HL-308, and $2.1 \times 10^8$ for HL-309.

IGFBP-3 and IGF-1 were biotinylated with a 1.5:1 molar ratio of a cleavable biotin reagent, EZ-LINK™ NHS-SS-Biotin (Pierce), to protein, using the manufacturer's instructions.

The initial selection of peptides for binding to IGFBP-3 or IGF-1 was carried out using phage pools of approximately $10^{10}$ phage/ml (100:1 total volume). MAXISORP™ 96-well plastic plates (Nunc) were coated with a solution of 2:g/ml of NEUTRAVIDIN™ brand avidin (Pierce) in 50 mM sodium carbonate buffer, pH 9.6, overnight at 4° C. The NEUTRAVIDIN™ solution was then removed, and the plates were incubated with a blocking solution of 5 g/l of bovine serum albumin, or 5 g/l of ovalbumin, or 5 g/l of instant milk in 50 mM sodium carbonate buffer, for 1-2 h at room temperature. The blocking solution was then removed, and a solution of biotinylated target protein was added. After 1-2 h at room temperature, the target solution was removed, and the plates were washed ten times with PBS/TWEEN™ surfactant (0.05% TWEEN-20™ (Polysorbate 20, poly(oxyethylene)-sorbitane-monolaurate) in PBS buffer).

Phage from the libraries described above were pooled as follows: pool A consisted of HL-300 phage, pool B of HL-301 phage, pool C of HL-302 phage, and pool D of phage from the HL-303, HL-304, HL-305, HL-306, HL-307, HL-308, and HL-309 libraries. Phage were added in PBS/TWEEN™/albumin/biotin (PBS/TWEEN™ buffer with 1:M biotin, 5 g/l bovine serum albumin, or ovalbumin) to wells coated with each target, and with control wells that were coated with NEUTRAVIDIN™ brand avidin or with albumin, but not biotinylated target. The phage were allowed to bind 5-15 h at room temperature. The plates were then washed ten times with PBS/TWEEN™ buffer.

Phage remaining bound to the plates were eluted by incubating with 50 mM DTT for 1-2 h at room temperature. The eluted phage were transfected into *E. coli* cells and allowed to grow overnight at 37° C. to amplify the phage.

The second and third cycles of binding selection were carried out as above, except that streptavidin (0.1 mg/ml) was included in the phage cocktails along with biotin. An aliquot was taken from each target-coated and control well incubated with each library, and serial dilutions of the diluted phage were performed to measure specific binding to target. The diluted phage were then transfected into *E. coli* cells and plated for colony counting.

The fourth round of binding selection was carried out on MAXISORP™ plates directly coated with 2:g/ml of each target protein, or with albumin only. The results of phage-binding selections in cycles 2-4 are shown in FIG. 2.

The same initial phage libraries (A, B, C, D) were also used for binding selections to directly-coated IGFBP-3. In this case, MAXISORP™ 96-well plastic plates (Nunc) were coated with a solution of 2:g/ml of IGFBP-3 in 50 mM sodium carbonate buffer, pH 9.6, overnight at 4° C. The target solution was then removed, and the plates were incubated with a blocking solution of 5 g/L of bovine serum albumin, for 1-2 h at room temperature. Phage were incubated with the plates as above, and non-binding phage washed away. The phage remaining bound were eluted by incubating with 20 mM HCl for 10 min at room temperature. Thereafter, the acid-eluted phage were neutralized with one-fifth volume of 1 M Tris-HCl, pH 8.0. Phage were transfected for colony counting as described above.

Screening of Polyvalent Phage Clones (IGF-blocking Phage Assay)

Peptide-phage clones were isolated by mixing phage pools with *E. coli* cells, and plating onto antibiotic-containing media. Colonies were isolated and grown with helper phage (as above) to obtain single-stranded DNA for sequencing. Peptide sequences selected for binding IGFBP-3 or IGF-1 were deduced from the DNA sequences of phagemid clones. A number of such clones are represented by the peptide sequences in Tables II and III, respectively.

TABLE II

Peptide sequences from g8 display, IGFBP-3 selection

| Name | Peptide sequence | |
|---|---|---|
| 4A3.1 | SGTACYGGPEWWCCSLAGSP | (SEQ ID NO: 78) |
| 4A3.3 | SGTACYGGPEWWCCSLAGSP | (SEQ ID NO: 79) |
| 4A3.4 | SGTACYGGPEWWCCSLAGSP | (SEQ ID NO: 80) |
| 4B3.1 | DLAICAEGPEIWVCEETS | (SEQ ID NO: 81) |
| 4B3.2 | DFWICLSGPGWEECLEWW | (SEQ ID NO: 82) |
| 4B3.3 | EESECFEGPGYVICGLVG | (SEQ ID NO: 83) |
| 4B3.4 | DMGVCADGPWMYVCEWTE | (SEQ ID NO: 84) |
| 4B3.5 | DMGVCADGPWMYVCEWTE | (SEQ ID NO: 85) |
| 4C3.1 | GSAGQGMTEEWAWIWEWWKE | (SEQ ID NO: 86) |
| 4C3.2 | ELDGWVCIKVGEQNLCYLAE | (SEQ ID NO: 87) |
| 4C3.4 | ELDGWVCIKVGEQNLCYLAE | (SEQ ID NO: 88) |
| 4C3.4 | ELDGWVCIKVGEQNLCYLAE | (SEQ ID NO: 88) |
| 4C3.5 | ELDGWVCIKVGEQNLCYLAE | (SEQ ID NO: 88) |
| 4D3.1 | AIGGWCFIELDSLWCEEQIG | (SEQ ID NO: 89) |
| 4D3.2 | SEDVECWQVWENLVCSVEHR | (SEQ ID NO: 90) |
| 4D3.3 | SEEVCWPVAEWYLCNMWGR | (SEQ ID NO: 91) |
| 4D3.4 | RVGAYISCSETECWVEDLLD | (SEQ ID NO: 92) |
| 4D3.5 | WFKTVCYEWEDEVQCYTLEE | (SEQ ID NO: 93) |
| 4D3.6 | SEDVECWQVWENLVCSVEHR | (SEQ ID NO: 94) |
| 4D3.7 | RLEEQCVEVNYEPSCSFTAN | (SEQ ID NO: 95) |
| 4D3.8 | SEEVCWPVAEWYLCNILGP | (SEQ ID NO: 96) |
| 4D3.9 | ETVANCDCYMDLCLCYGSDR | (SEQ ID NO: 97) |
| 4D3.10 | YHPISCMDHYYLIICDETVN | (SEQ ID NO: 98) |
| 4D3.11 | VAWEVCWDRHDQGYICTTDS | (SEQ ID NO: 99) |
| 4D3.12 | AEWAECWIAGDQLLCVGKDN | (SEQ ID NO: 100) |
| 23A3.1 | EPWLCQYYEAAMLYLCWEEG | (SEQ ID NO: 101) |
| 23A3.2 | AEEGMVWGWTGGWYNLDELC | (SEQ ID NO: 102) |
| 23A3.3 | SGGAIYWPVEQFIAFMAVGK | (SEQ ID NO: 103) |
| 23A3.4 | EPWLCQYYEAAMLYLCWEEG | (SEQ ID NO: 104) |
| 23A3.5 | SGGAIYMPVEQFIAFMAVGK | (SEQ ID NO: 105) |
| 23B3.1 | TGVDCQCGPVHCVCMDWA | (SEQ ID NO: 12) |
| 23B3.2 | EVLLCSDGPQLYLCELYA | (SEQ ID NO: 106) |
| 23B3.4 | SGVECVWGPQWGFCVEEY | (SEQ ID NO: 107) |
| 23B3.5 | DKEVCYLGPETWLCFWWP | (SEQ ID NO: 108) |

TABLE II-continued

Peptide sequences from g8 display, IGFBP-3 selection

| Name | Peptide sequence | |
|---|---|---|
| 23B3.6 | EVLLCSDGPQLYLCELYA | (SEQ ID NO: 109) |
| 23B3.7 | GDVECIEGPWGELCVWAD | (SEQ ID NO: 110) |
| 23D3.1 | FGGWSCQPTWVDVYVCNFEE | (SEQ ID NO: 111) |
| 23D3.2 | AMWVCVSDWETVEECIQYMY | (SEQ ID NO: 112) |
| 23D3.3 | AMWVCVSDWETVEECIQYMY | (SEQ ID NO: 113) |
| 23D3.4 | AMWVCVSDWETVEECIQYMY | (SEQ ID NO: 114) |
| 23D3.5 | AMWVCVSDWETVEECIQYMY | (SEQ ID NO: 115) |
| 23D3.6 | TNWFFVCESGHQDICWLAEE | (SEQ ID NO: 116) |

TABLE III

Peptide sequences from g8 display, IGF-1 selection

| Clone | Peptide sequence | Library | Frequency |
|---|---|---|---|
| HL-8 | WVMECGAGPWPEGCTFML (SEQ ID NO: 117) | B | 5/6 |
| HL-26 | RKTSQGRGQEMCWETGGCS (SEQ ID NO: 118) | C | 1/6 |
| HL-25 | SWERGELTYMKLCEYMRLQQ (SEQ ID NO: 119) | C | 4/6 |
| HL-30 | EHGRANCLITPEAGKLARVT (SEQ ID NO: 120) | C | 1/6 |

Such peptide-phage clones could represent specific target-binding peptides which either do or do not block ligand (IGF-1 to IGFBP-3) binding, or any of a number of non-binding or background members of the selected pool. To distinguish among these possibilities, phage clones were tested for the ability to bind to IGFBP-3 in the presence and absence of IGF-1. IGFBP-3 was coated directly onto MAX-ISORP™ plates as above. Phage from clonal cultures were mixed with IGF-1 (100 nM final concentration), and incubated with the immobilized IGFBP-3 for 1 hour at room temperature. The plates were then washed ten times, as above, and a solution of rabbit anti-phage antibody mixed with a goat-anti-rabbit conjugate of horseradish peroxidase was added. After an incubation of 1 hour at room temperature, the plates were developed with a chromogenic substrate, o-phenylenediamine (Sigma). The reaction was stopped with addition of ½ volume of 2.5 M $H_2SO_4$. Optical density at 490 nm was measured on a spectrophotometric plate reader.

Figure 3:
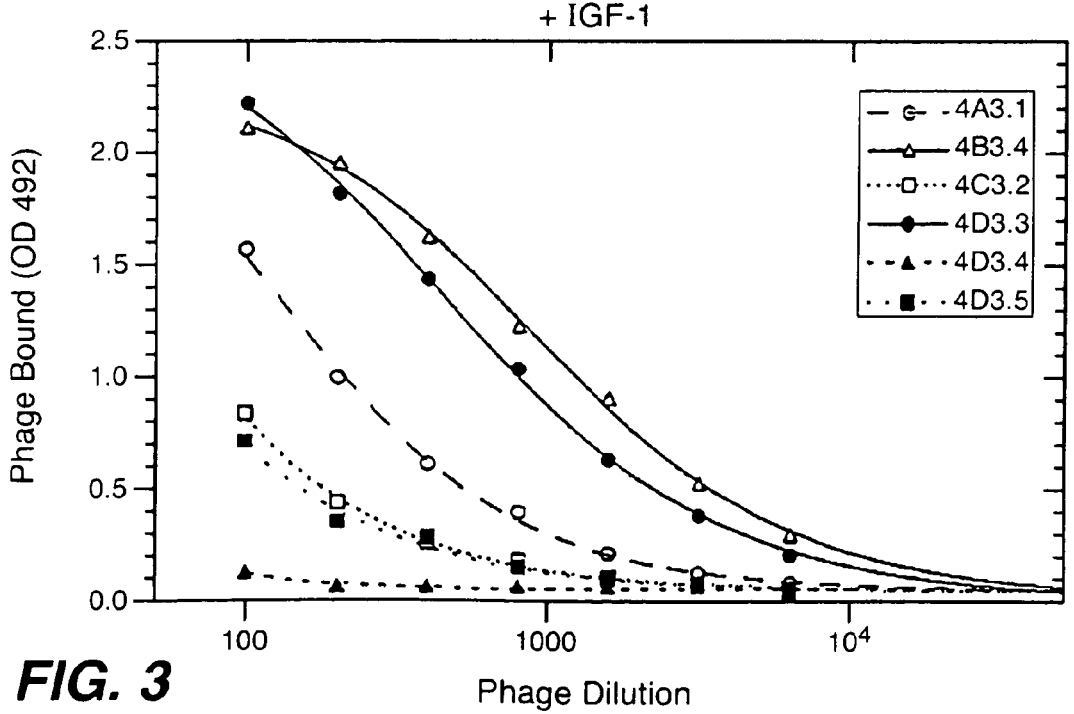
FIG. 3 shows an IGF-1 blocking assay using g8-phage peptides from IGFBP-3 selections, where the phage titration is with 100 nM IGF-1. In the Figure, the open circles are peptide 4A3.1, the open triangles are peptide 4B3.4, the open squares are peptide 4C3.2, the solid circles are peptide 4D3.3, the solid triangles are peptide 4D3.4, and the solid squares are peptide 4D3.5.
Figure 4:
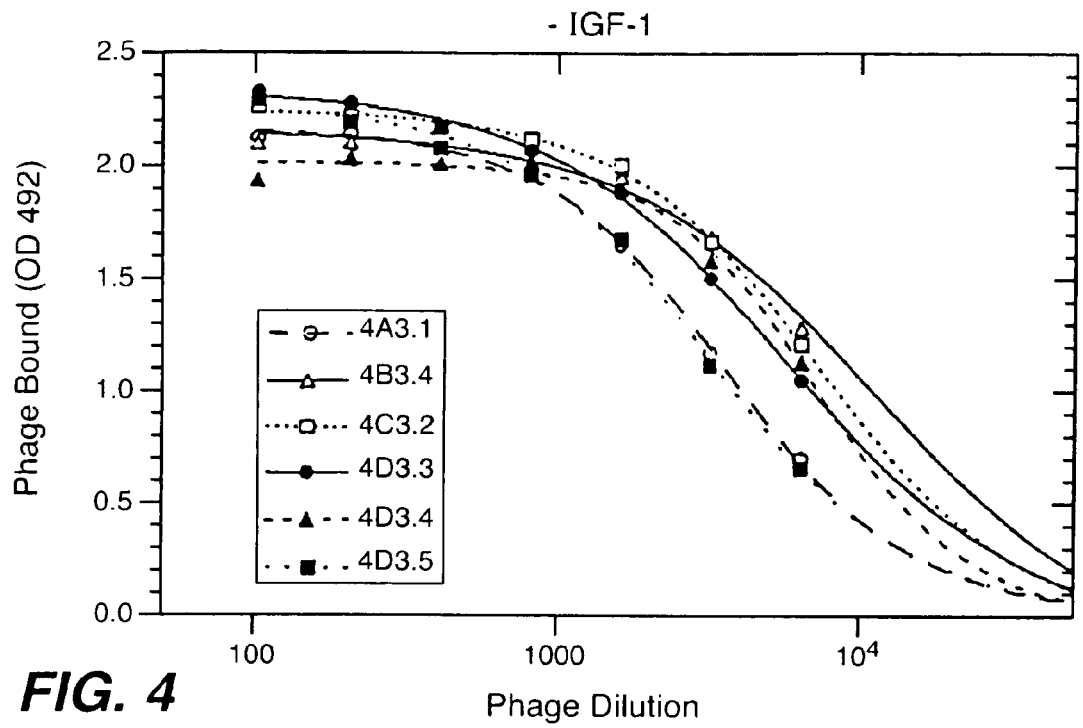
FIG. 4 shows an IGF-1 blocking assay using g8-phage peptides from IGFBP-3 selections, where the phage titration is without IGF-1. The designations for the peptides are the same as those described above for FIG. 3.

Titration of several IGFBP-3-selected peptide-phage clones showed all were inhibited by IGF-1 for binding to IGFBP-3 at some phage concentration (FIGS. 3 and 4). These peptides are thus likely to occupy an overlapping site with the IGF-binding epitope on IGFBP-3. Additional peptide-phage clones were screened similarly, at a low concentration of phage, with and without IGF-1.

Figure 5:
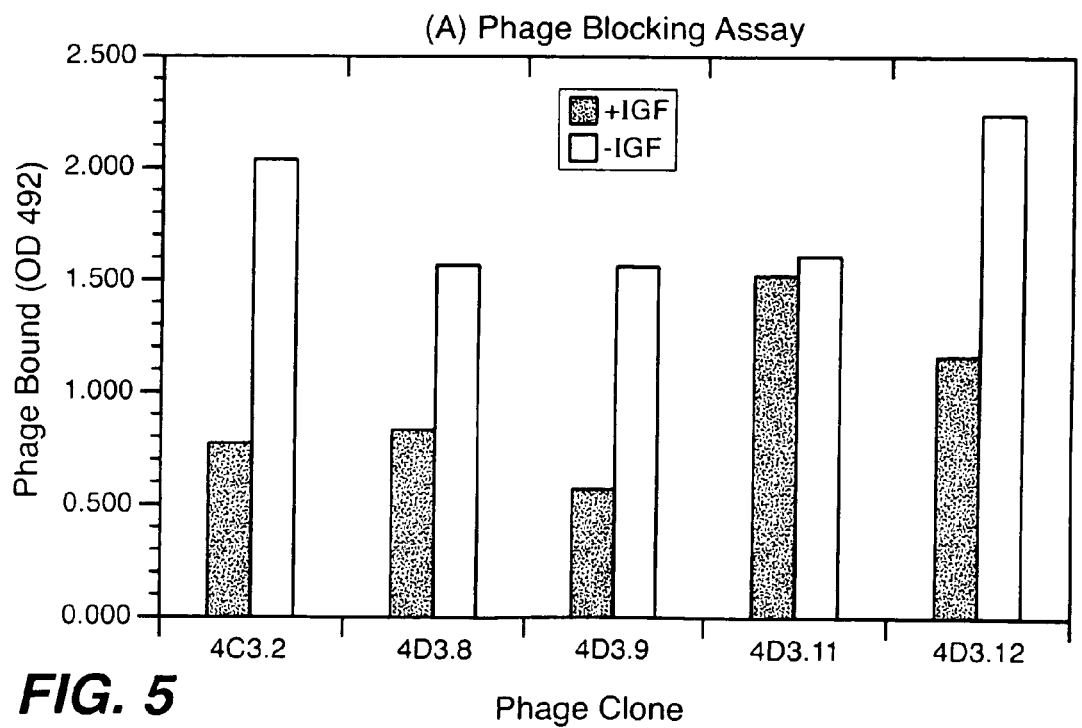
FIG. 5 shows an IGF-1 blocking assay using g8-phage peptides from IGFBP-3 selections, where the peptides (4C3.2, 4D3.8, 4D3.9, 4D3.11, and 4D3.12) are from a NEU-TRAVIDIN™ brand avidin (Pierce)/DTT selection. The solid bars are with 100:M IGF-1 and the open bars are without IGF-1.

FIG. 5 shows the results of a blocking assay of several phagemid clones derived from three rounds of DTT elution, followed by one round of HCl elution, as described above. In each case, the phagemid clone was grown from a single colony overnight at 37° C. in a culture volume of 5 ml. The phage particles were precipitated and resuspended in 0.5 ml of PBS buffer. A 50-fold dilution of each phage solution was made into PBS/TWEEN™ buffer, and the phage were incubated with or without 100 nM IGF-1 on an IGFBP-3-coated MAXISORP™ plate. As shown in FIG. 5, most clones were >40% inhibited for binding to IGFBP-3 at these phage concentrations, although clone 4D3.11 was only 5% inhibited under these conditions.

Figure 6:
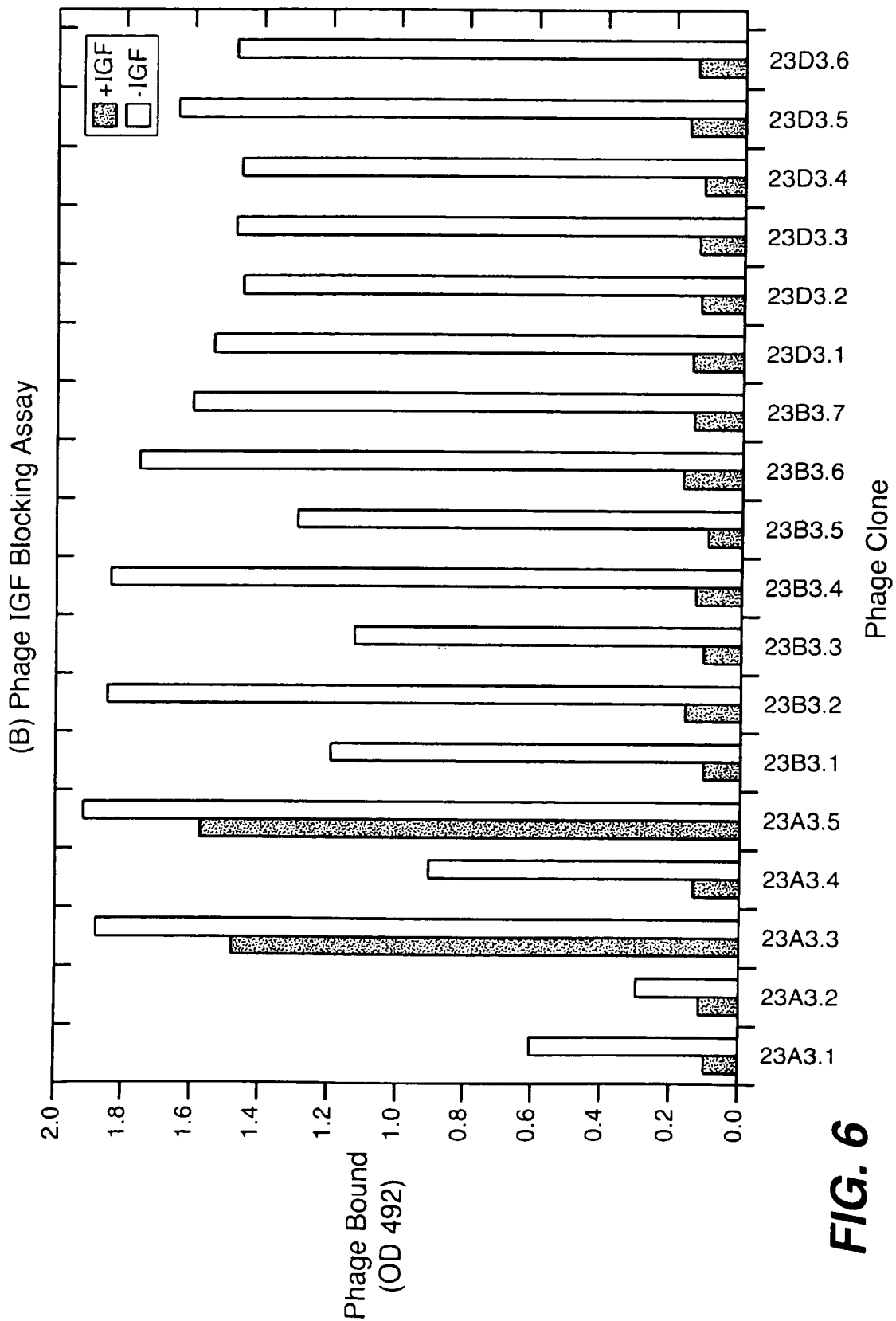
FIG. 6 shows an IGF-1 blocking assay using g8-phage peptides from IGFBP-3 selections where the peptides (indicated on the x axis) are from direct-coat/HCl selection. The solid bars are with 100:M IGF-1 and the open bars are without IGF-1.

FIG. 6 shows the results of a blocking assay of several phagemid clones derived from three rounds of HCl elution, as described above. In each case, the phagemid clone was grown from a single colony overnight at 37° C. in a culture volume of 5 ml. The phage particles were prepared as described above. In this case, as shown in FIG. 6, most clones were >80% inhibited for binding to IGFBP-3 at these phage concentrations, although clones 23A3.3 and 23A3.5 were only about 20% inhibited under these conditions.

The variation in the degree to which phage binding is blocked by a constant concentration of IGF-1, as a function of phage dilution (FIG. 3), or as a function of peptide displayed (FIGS. 5-6) is of interest because, without being limited to any one theory, it may be predictive of (1) the degree of overlap between IGF-1- and peptide-binding epitopes on the IGFBP-3 molecule, and/or (2) the relative affinity of IGF-1 versus phage-displayed peptide for binding to IGFBP-3. Since all peptide-phage clones tested here showed some degree of inhibition with IGF-1, it is likely that the epitope for peptide-binding on IGFBP-3 for each lies within an area occupied by bound IGF-1. Peptide assays (see below) support this conclusion (i.e., case 1). On the other hand, without being limited to any one theory, it is possible that some peptide epitopes could be simply within an area for which binding of the phage particle displaying such peptides is sterically excluded by bound IGF-1.

The dependence of inhibition upon phage concentration, and the differences among phage clones (FIG. 3) may reflect case 2. In particular, phage clones whose binding to an IGFBP-3 coated plate was inhibited only at low phage concentrations (e.g., 4D3.3, 4B3.4, corresponding to peptides BP3-01-ox and BP3-02-ox, respectively) appear to yield higher-affinity peptides (see below) for IGFBP-3 than do those phage clones whose binding to an IGFBP-3 coated plate was inhibited both at high and at low phage concentrations (e.g., 4C3.2, 4D3.5, corresponding to peptides BP-23 and BP-24, respectively).

Thus, this type of phage-titration blocking assay may be generally useful as a means to predict the relative affinities and inhibitory potencies of peptides derived from phage displayed libraries.

Monovalent (g3) Display of IGFBP-3-binding Peptides

Affinity maturation of a peptide or protein sequence by successive rounds of random mutagenesis, selection, and propagation can be efficiently accomplished when the copy number of displayed peptides or proteins is limited (Bass et al., *Proteins*, 8: 309-314 (1990)). Such an affinity maturation process is illustrated by the affinity maturation of hGH (U.S. Pat. No. 5,534,617). In this case, the copy number of displayed hGH was limited by fusing the displayed protein to g3, rather than to g8 of bacteriophage particles, restricting the expression level of hGH, and using a helper phage to supply wild-type g3p for phagemid packaging and propagation.

To select for higher affinity peptide variants from pools of phage displaying peptides on g8p, peptide cDNAs from two round 4 g8 library pools, 4B and 4D, were transferred to a g3 vector for monovalent phage display. Binding selections were carried out for three rounds, as described above, with acid elution of binding phage.

Peptide sequences obtained after three rounds of selections are shown in Table IV. Two clones, 4B3.3 and 4D3.11, dominated the selected pools, and were seen in the earlier, g8 phage selections. A third clone, 3Ai.2, represents a new peptide sequence that was not identified from g8 display. In phage-ELISA competition assays, the apparent affinity of the g3-4B3.3 and g3-4D3.11 clones was <100 nM; however, the corresponding peptides showed much weaker inhibition (see below).

TABLE IV

| Peptide sequences from g3 display, IGFBP-3 selection | | | |
|---|---|---|---|
| Clone | Peptide sequence | Library | Frequency |
| 3Ai.1 = 4B3.3 | EESECFEGPGYVICGLVG (SEQ ID NO: 8) | 4B | 6/10 |
| 3Ai.2 | VEDECWNGPDWAVCWTWG (SEQ ID NO: 121) | 4B | 4/10 |
| 3Bi.1 = 4D3.11 | VAWEVCWDRHDQOYICTTDS (SEQ ID NO: 6) | 4D | 10/10 |

It is anticipated that affinity improvements can be obtained by iteratively mutating, selecting, and propagating peptide-phage libraries, as described for hGH. See, e.g., U.S. Pat. No. 5,534,617.

Peptide Assays

Peptides were synthesized corresponding to a number of phage-derived sequences. In cases where two Cys residues were found in the peptide sequence, the disulfide (oxidized or "ox" suffix) monomeric form of the peptide was prepared and purified. In cases where four Cys residues were found, the {1-4, 2-3}-disulfide form was prepared and purified.

The ability of these peptides to bind IGFBP-3 and block IGF-1 binding was tested in one or more of the following assays.

BIACORE™ Competition Assay (for IGFBP-3 Binders)

IGF-1 was immobilized on a dextran chip for inhibition assays using a BIACORE™ 2000 surface-plasmon-resonance device (BIAcore, Inc., Piscataway, N.J.) to measure free binding protein. IGF-1 was biotinylated as described above, and injected over a chip to which streptavidin had been coupled (BIAcore, Inc.) to give 400 to 800 RU (response units) of immobilized IGF-1. The IGF-1 showed no detectable dissociation over the time course of each experiment. Serial dilutions of peptide were mixed with a constant concentration (40 nM) of IGFBP-3. After incubation for >1 hour at room temperature, an aliquot of 20:L was injected at a flow rate of 20:L/min over the IGF-1 chip. Following the injection, a response reading was taken to measure the relative amount of IGFBP-3 bound to the IGF-1.

Figure 7:
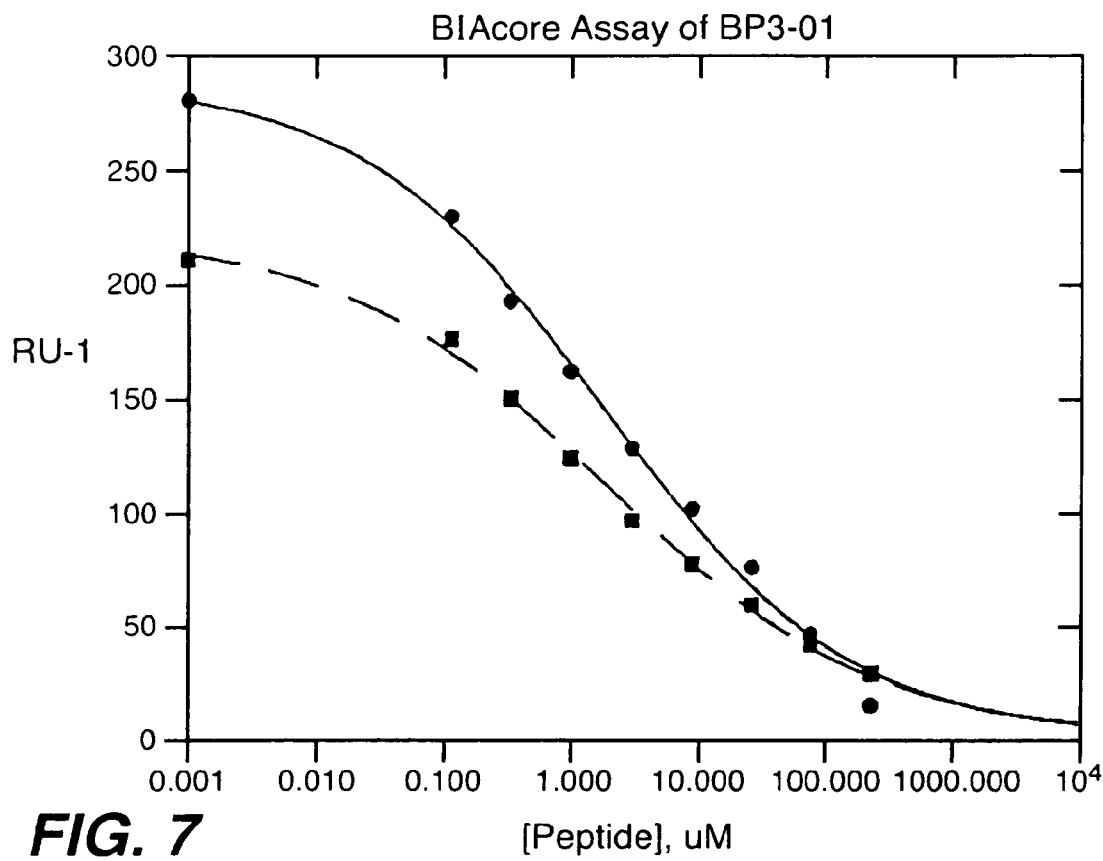
FIG. 7 depicts a competition assay of IGFBP-3 inhibition by a peptide binding to IGFBP-3 (designated BP3-01) using a BIACORE™ surface-plasmon-resonance device to measure free binding protein. The circles indicate 800 response units (RU) of IGF-1 and the squares indicate 400 RU of immobilized IGF-1.
Figure 8:
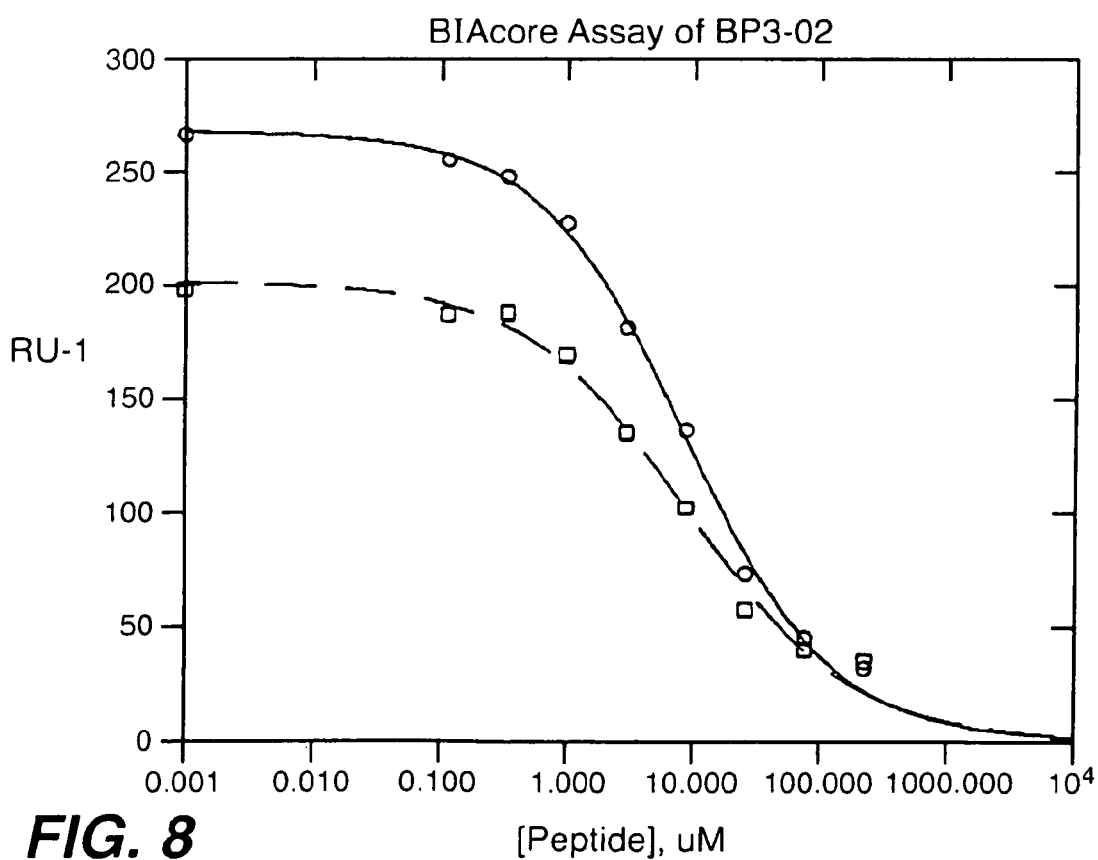
FIG. 8 depicts a competition assay of IGFBP-3 inhibition by a peptide binding to IGFBP-3 (designated BP3-02) using a BIACORE™ surface-plasmon-resonance device to measure free binding protein. The circles indicate 800 RU of IGF-1 and the squares indicate 400 RU of immobilized IGF-1.

The results (FIGS. 7-8) show a dose-response curve for each peptide's inhibition of IGFBP-3 binding to the chip. In particular, the most effective inhibitors of IGFBP-3 binding tested were peptides BP3-01-ox (corresponding to phage clone 4D3.3), and a truncated form of this peptide, BP3-15 (see Table V). In that table, a disulfide bond is formed between the two Cys residues of each 2-Cys containing peptide. For peptides containing four cysteines, the two Cys* residues form a disulfide and the remaining two form a second disulfide. These peptides showed $IC_{50}$'s of 2:M and 0.75:M, respectively. Other peptides such as BP3-4D3.11 (phage clone 4D3.11 from g8 display and 3Bi.1 from g3 display) showed inhibition with IC50's of <10:M.

IGFBP-1 did not show binding to IGF-1 immobilized in this manner.

TABLE V

Inhibition of IGF-1 binding to IGFBP-3 by synthetic peptides

| Peptide | Sequence | BIACORE ™ AssayIC50 (:M) |
|---|---|---|
| BP-23 | ELDGWVCIKVGEQNLCYLAEG-nh2 (SEQ ID NO: 122) | 220 |
| BP-24 | WFKTVCYEWEDEVQCYTLEEG-nh2 (SEQ ID NO: 123) | 100-300 |
| BP-25 | RVGAYISCSETECWVEDLLDG-nh2 (SEQ ID NO: 124) | >1000 |
| BP3-4D3.11 | VAWEVCWDRHDQGYICTTDS (SEQ ID NO: 7) | <10 |
| BP3-4D3.11 DEL | AWEVCWDRHQGYICTTDS (SEQ ID NO: 8) | 80 |
| BP3-13 | CWDRHDQGYICTTDS (SEQ ID NO: 125) | >1000 |
| BP3-4B3.3 | EESECFEGPGYVICGLVG (SEQ ID NO: 9) | 80 |
| BP3-02-OX | DMGVCADGPWMYVCEWTE (SEQ ID NO: 11) | 12 |
| BP3-01-OX | SEEVCWPVAEWYLCNMWG (SEQ ID NO: 10) | 2 |
| BP3-15 | SEEVCWPVAEWYLCN (SEQ ID NO: 14) | 0.75 |
| BP3-16 | VCWPVAEWYLCNMWG (SEQ ID NO: 15) | 30 |
| BP3-17 | VCWPVAEWYLCN (SEQ ID NO: 16) | 9 |
| BP306 | TGVDCQC*GPVHC*VCMDWA (SEQ ID NO: 12) | 5 |
| BP3-08 | TVANCDC*YMPLC*LCYDSD (SEQ ID NO: 13) | 15 | where nh2 means that the peptide has been blocked with an amide and where the C* indicates a cysteine that has been linked to another cysteine in the peptide. The remaining Cys pairs are also oxidized as disulfides in each peptide.

Radiolabeled IGF Assay (for IGFBP-3 Binders)

As an additional assay of peptide activity, several peptides were tested in an assay using $^{125}$I-labeled IGF-1 to measure inhibition of IGFBP binding, as described above (Assay 3). Serial dilutions of peptide were added to an IGFBP-1 or an IGFBP-3 plate. Thereafter, $^{125}$I-labeled IGF-1 was added and the plates were incubated for 2 hours. The plates were then washed and counted to determine the amount of bound IGF-1.

Figure 9:
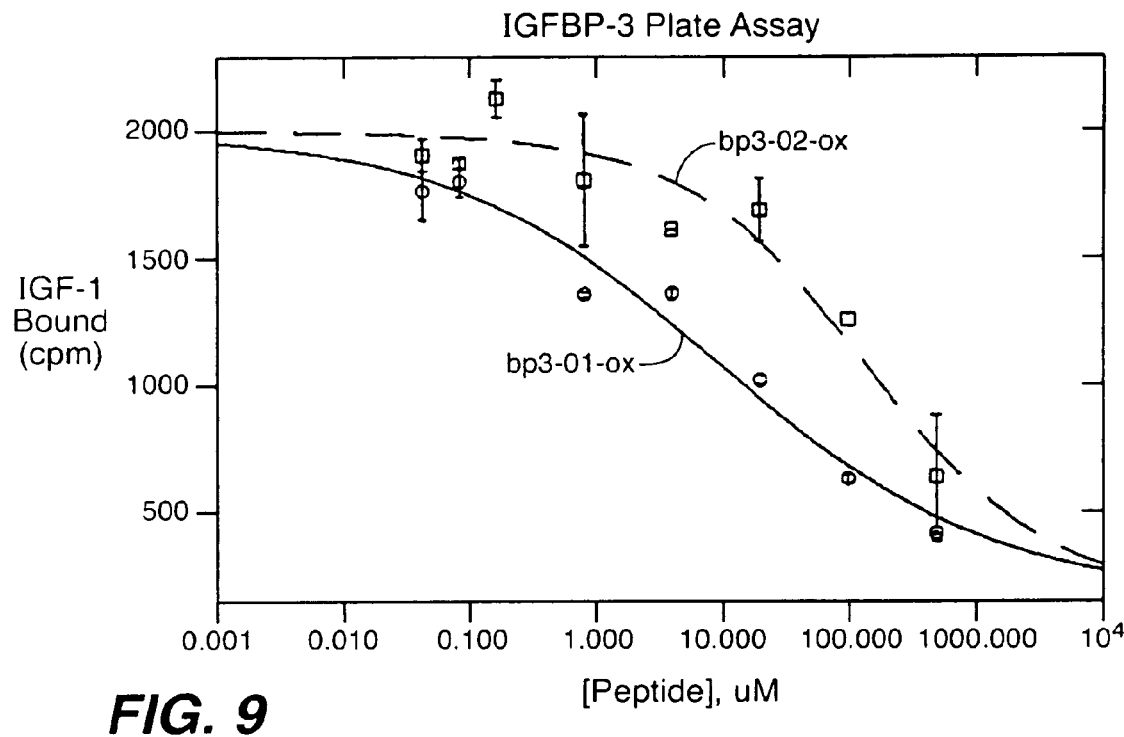
FIG. 9 shows a radiolabeled IGF-1 plate assay of the ability of two peptides that bind to IGFBP-3 but not to the Type 1 IGF receptor (BP3-01-ox: circles, and BP3-02-ox: squares) to inhibit IGFBP-3.
Figure 10:
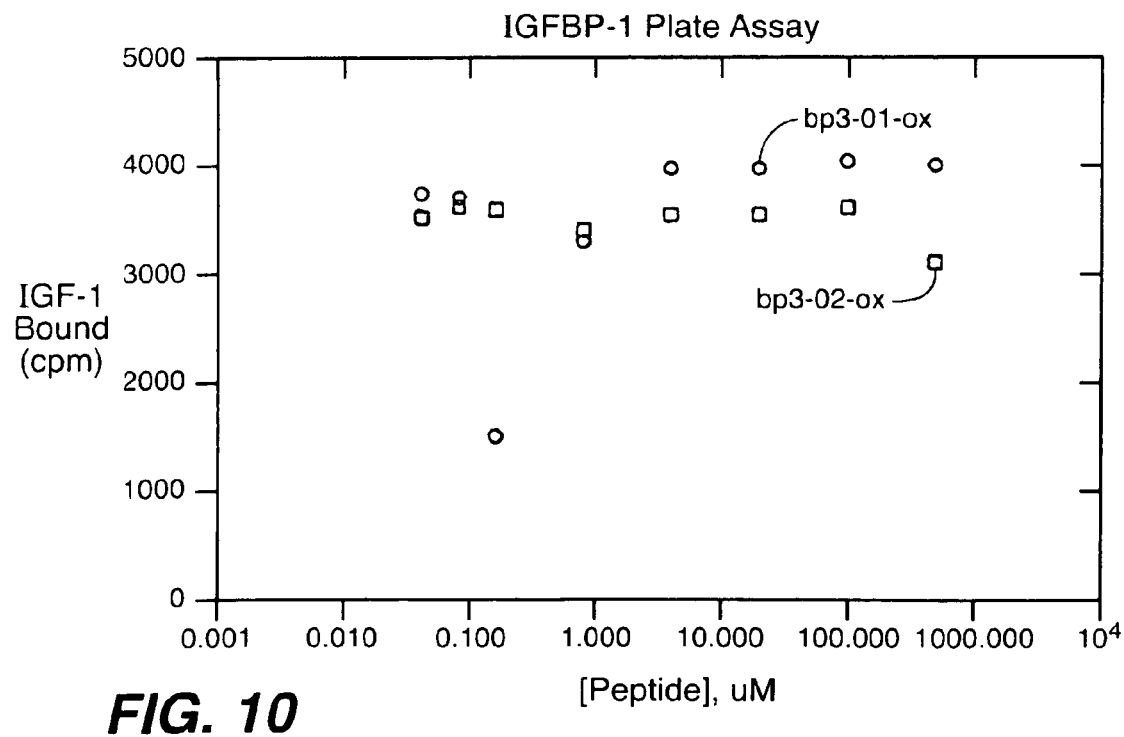
FIG. 10 shows a radiolabeled IGF-1 plate assay of the ability of the two IGFBP-3 binding peptides described for FIG. 9 to inhibit IGFBP-1 (symbols are the same).
Figure 11A:
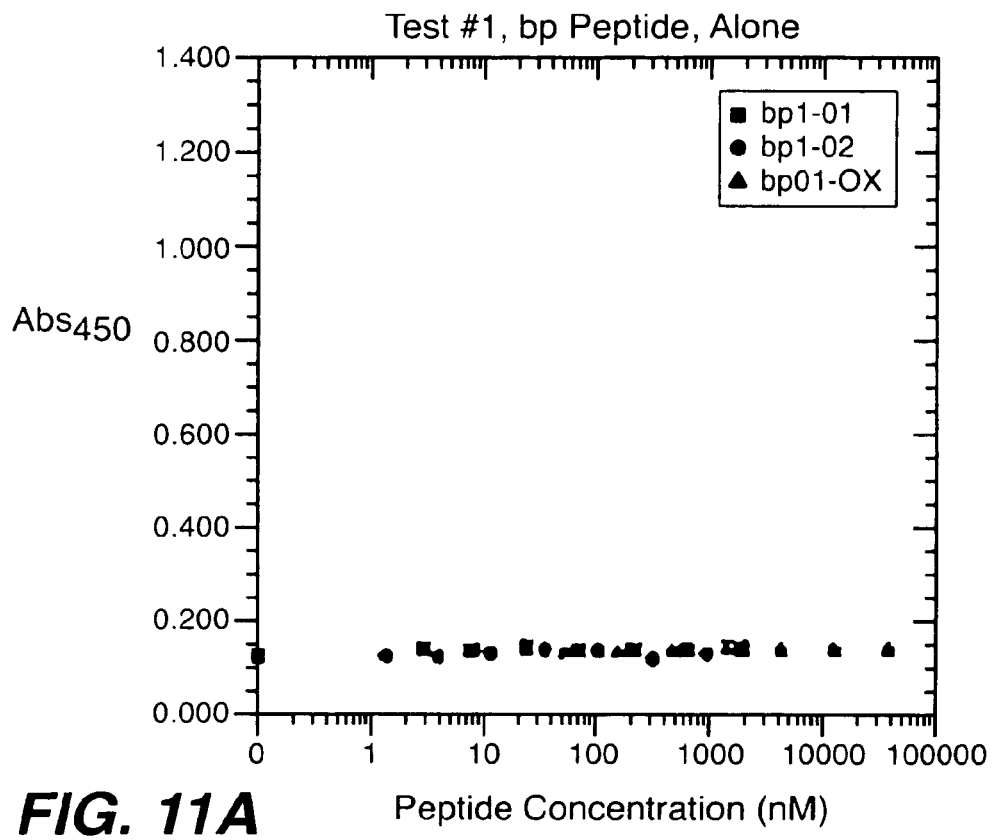
FIGS. 11A-11D depict KIRA assays of IGF-1 activity using three peptides (BP1-01: squares, BP1-02: circles, and BP03-ox: triangles).
Figure 11B:
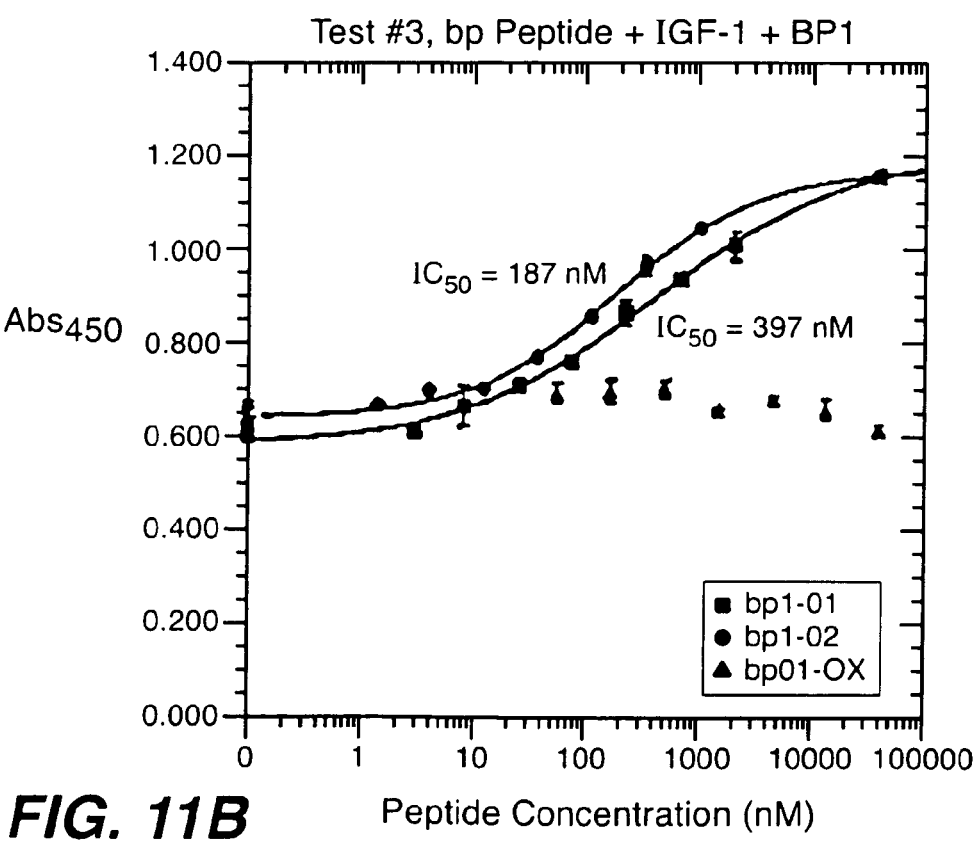
Figure 11C:
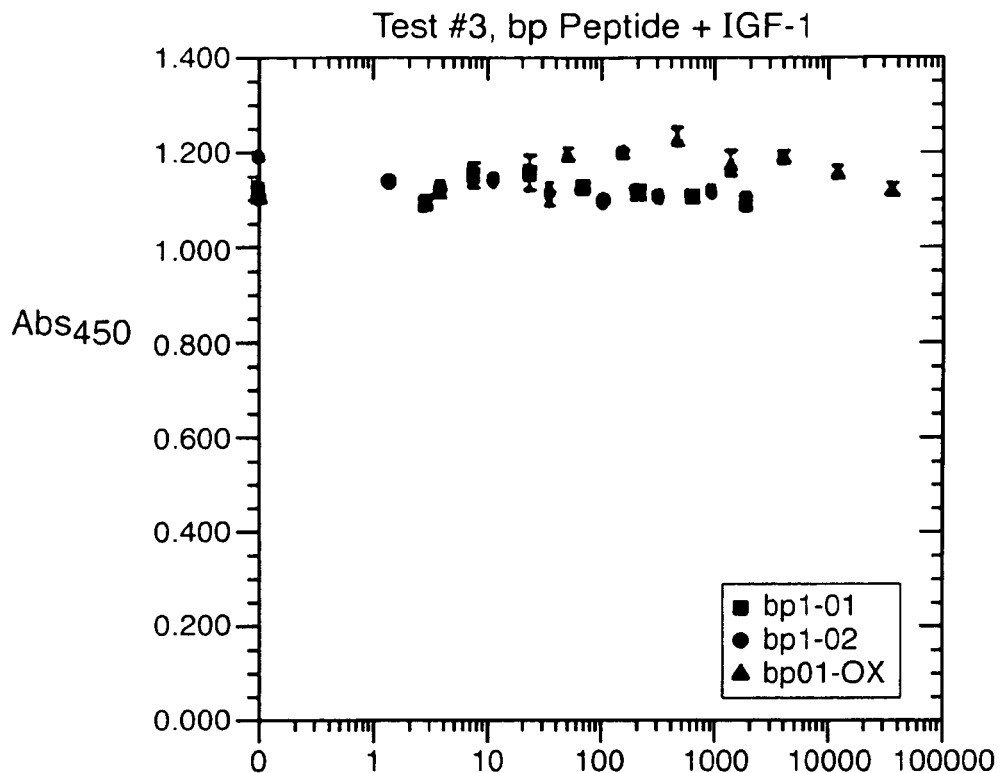
Figure 11D:
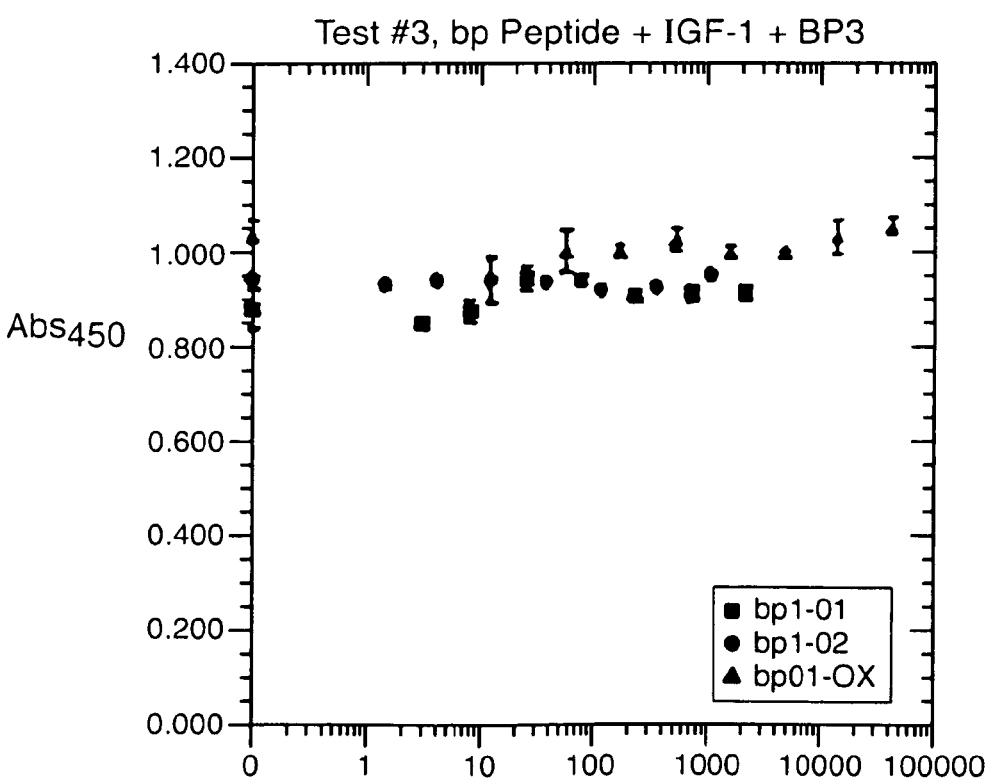

FIG. 9 shows the inhibition of two IGFBP-3-selected peptides, BP3-01-ox and BP3-02-ox, for IGF-1 binding to an IGFBP-3 plate. In contrast, these peptides did not inhibit IGF-1 binding to an IGFBP-1 coated plate (FIG. 10).

In vitro Activation (KIRA)

The ability of several synthetic peptides to block IGF-1 binding to IGFBPs and release functional IGF-1 was tested in a KIRA assay of IGF-1 activity, as described above. Cells were treated with peptide alone, peptide plus IGF-1 plus IGFBP-1, peptide plus IGF-1, and peptide plus IGF-1 plus IGFBP-3. The results are shown in FIGS. 11A-D, respectively.

While BP3-01-ox has a lower affinity for the IGFBP than the other molecules tested in this assay, the fact that BP3-01-ox inhibits binding of IGFBP-3 to IGF-1 is, in itself, useful for various purposes, including for the LIFA and other assays noted above. Further, the KIRA assay only used IGF-1; it did not employ IGF-2, and BP3-01-ox was found to inhibit binding of IGFBP-3 to IGF-2 as noted in the competition assay described below.

BIACORE™ Competition Assay (for IGFBP-3 Binders)

IGF-2 was immobilized on a dextran chip for inhibition assays using a BIACORE™ 2000 surface-plasmon-resonance device (BIAcore, Inc., Piscataway, N.J.) to measure free binding protein. IGF-2 was biotinylated as described above, and injected over a chip to which streptavidin had been coupled (BIAcore, Inc.) to give approximately 1500 RU of immobilized IGF-2. The IGF-2 showed no detectable dissociation over the time course of each experiment. Serial dilutions of peptide were mixed with a constant concentration (20 nM) of IGFBP-3. After incubation for >1 hour at room temperature, an aliquot of 20:1 was injected at a flow rate of 20:1/min over the IGF-2 chip. Following the injection, a response reading was taken to measure the relative amount of IGFBP-3 bound to the IGF-2.

The results (e.g., see FIG. 12) show a dose-response curve for each peptide's inhibition of IGFBP-3 binding to IGF-2. Peptides BP3-01-ox, BP3-14, BP3-15, and BP3-17 showed IC50's of 0.92:M, 1.0:M, 0.78:M, and 5.1:M, respectively. Thus, these peptides inhibit the binding of IGFBP-3 both to IGF-1 and to IGF-2.

Example 2

Displacement of IGF-1 from IGFBPs Using BP3-15

This Example tests an IGFBP-3-specific peptide, BP3-15, for its ability to block the binding of $^{125}$I-IGF-1 in human serum. Human serum was incubated with $^{125}$I-IGF-1 the peptide and the amount of tracer bound to IGFBPs via size-exclusion chromatography was measured. Addition of the peptide resulted in an approximate 42% decrease in $^{125}$I-IGF-1 associated with the 150-$K_D$ IGF/IGFBP-3/ALS complex and a 59% increase in the amount of free $^{125}$I-IGF-1. The peptide did not decrease $^{125}$I-IGF-1 binding to the 44-$K_D$ IGFBPs (in fact, it slightly increased it), indicating that the peptide only competes with IGF-1 for binding to IGFBP-3.

These results indicate that the analog (at 0.2 mM) can compete with IGF-1 for binding to IGFBP-3 in human serum.

Example 3

Relative Affinity of IGFBP-3 Binding Peptide Variants

The relative affinities of various BP3-01-ox variants were measured by the BIACORE™ competition assay. The results are shown in Table VI. It can be seen that 4D3.3P (SEQ ID NO:6), BP3-30 (SEQ ID NO:20), BP3-41 (SEQ ID NO:23), BP3-40 (SEQ ID NO:22), BP3-39 (SEQ ID NO:21), BP3-28 (SEQ ID NO:19), BP3-27 (SEQ ID NO:18), and BP3-25 (SEQ ID NO:17), have affinities similar to or greater than that of BP3-01-ox and are expected to increase the availability of IGF-1 in an in vitro cell culture assay. The lack of measurable activity for peptide BP3-24 (SEQ ID NO:126) indicates the critical role that the intact disulfide plays in maintaining a peptide conformation favorable for binding to IGFBP-3 for this series of peptides.

TABLE VI

Relative affinities of BP3-01-ox variants by BIACORE ™ competition assay

| Variant name | Peptide sequence | IGF-1 Inhibition IC50(:M) | IC50 (mut)/ IC50 (wt) |
|---|---|---|---|
| 4d3.3P | ASEEVCWPVAEWYLCNMWGR (SEQ ID NO: 6) | 5.6 | 2.8 |
| BP3-30 | ASEEVCWPVAEWYLCN (SEQ ID NO: 20) | 5.6 | 2.8 |
| BP3-41 | GPETCWPVAEWYLCN (SEQ ID NO: 23) | 4.0 | 2.0 |
| BP3-01-ox | SEEVCWPVAEWYLCNMWG (SEQ ID NO: 10) | 2.0 | -1- |
| BP3-40 | ac-SEEVCWPVAEWYLCN-nh2 (SEQ ID NO: 22) | 0.66 | 0.33 |
| BP3-39 | SEEVCWPVAEWYLCN-nh2 (SEQ ID NO: 21) | 0.66 | 0.33 |
| BP3-15 | SEEVCWPVAEWYLCN (SEQ ID NO: 14) | 0.72 | 0.36 |
| BP3-28 | EEVCWPVAEWYLCN (SEQ ID NO: 19) | 5.4 | 2.7 |
| BP3-27 | EVCWPVAEWYLCN (SEQ ID NO: 18) | 2.8 | 1.4 |
| BP3-25 | CWPVAEWYLCN (SEQ ID NO: 17) | 46 | 23 |
| BP3-24 | WPVAEWYLCN (SEQ ID NO: 126) | >1000 | >500 |

Example 4

Screening of Additional Libraries for Binding to IGFBP-3

Additional polyvalent (g8) peptide-phage libraries were designed and sorted that yielded two peptides that inhibited IGFBP-3 binding to IGF-1. The results, shown in Table VII, indicate that BP3-107 (SEQ ID NO:24) and BP3-108 (SEQ ID NO:25) are inhibitors and they are expected to increase the availability of IGF-1 in an in vitro cell culture assay.

TABLE VII

Peptide inhibition of IGFBP-3 binding to IGF-1 by BIACORE ™ competition

| Peptide | Phage parent | Sequence | IC50 (:M) |
|---|---|---|---|
| BP3-107 | t4H3.6 | suc-CQLVRPDLLLCQ-nh2 (SEQ ID NO: 24) | 100 |
| BP3-108 | t4H3.9 | suc-IPVSPDWFVCQ-nh2 (SEQ ID NO: 25) | 20 |

Example 5

Structure/Function of BP1-01 and Affinity Maturation

A. Kinetics of BP1-01 Binding to IGFBP-1

WO 98/45427 published Oct. 15, 1998 discloses the preparation and characterization of the IGFBP-1 displacer peptide BP1-01 (CRAGPLQWLCEKYFG) (SEQ ID NO:26). The kinetics of BP1-01 peptide variants were examined in a BIAcore™ (BIAcore, Inc., Piscataway, N.J.) assay using IGFBP-1 covalently coupled via EDC/NHS (as described by the manufacturer) to a dextran chip. Peptide BP1-01 displayed dissociation kinetics too rapid to measure. However, BP1-02, the 19-mer variant (SEVGCRAGPLQWL-CEKYFG) (SEQ ID NO:27) displayed measurable kinetics. The association rate constant was $2.30\times10^5$ $M^{-1}$ $sec^{-1}$ and the dissociation rate constant was $5.03\times10^{-2}$ $sec^{-1}$. The latter implies a half-life for peptide dissociation from IGFBP-1 of approximately 28 sec. The association rate constant is moderately fast, consistent with the notion that the peptide may not undergo significant conformation change upon binding to IGFBP-1.

B. Scanning Mutagenesis of BP1-01 Peptides

Two series of synthetic peptide variants were generated to determine which side chains of the BP1-01 peptide might contribute directly to binding IGFBP-1. In the first series an alanine-scanning approach (Cunningham and Wells, *Science*, 244: 1081-1085 (1989)) was used to remove that portion of each side chain beyond the beta carbon. The contribution of these atoms to the free energy of binding of the peptide to IGFBP-1 was then assessed by measuring the potency (IC50) of the variant for inhibiting IGFBP-1 binding to IGF-I or IGF-II in a BIAcore™ competition assay, analogous to that described for IGFBP-3. The results are shown in Table VIII.

A second series of peptides made use of non-natural amino acids to probe whether other structural features such as an added methyl group at the alpha carbon, or an isomer (D-alanine) could affect peptide binding to IGFBP-1. The potencies of these peptides were measured by biotinylated-IGFBP-1 ELISA assay, with the results shown in Table IX. These results confirm the importance of side chains L6, L9, W8, and Y13 in the binding of BP1-01 to IGFBP-1. Structural contributions are also suggested by the effects of substitutions at R2 and A3.

In contrast, some substitutions, such as aib substitutions at G4, Q7, E11, K12, and F14, had little or no effect upon binding affinity. Peptides including one or more of these substitutions may nevertheless by useful because non-natural amino acids often confer upon a peptide greater resistance to proteolysis (see Schumacher et al., *Science*, 271: 1854 (1996) and references therein). Such peptides may achieve a longer half-life in serum than those having only natural amino acids.

In view of the results shown in Table IX, it is expected that peptides with a D-alanine substituted at position 2, 3, or 6 of BP1-01 or with an alpha-aminoisobutyrate substituted at position 7, 8, 9, 11, 12, 13, or 14 will increase the availability of IGF-I in an in vitro cell culture assay.

Lastly, the relative affinities of various C-terminal BP1-01 variants were determined by ELISA, as shown in Table X. These data show that the C-terminal region of the peptide is important for binding. Only peptide BP1-18 (SEQ ID NO:37) retained measurable inhibitory activity for IGF-I:IGFBP-1 binding. It is expected that this peptide will increase the availability of IGF-I in an in vitro cell culture assay.

Taken together, the structure-function data suggest that a smaller, including a non-peptidyl, compound could be designed to mimic the action of the BP1-01 peptide by including elements of the C-terminus of this peptide in combination with the side chains L6, L9, W8, and Y13.

TABLE VIII

| Variant | IGF-I Inhibition IC50(mut)/IC50(wt) | IGF-II Inhibition IC50(mut)/IC50(wt) |
|---|---|---|
| Relative affinities of BP1-01 Ala-scan peptide variants by BIAcore ™ | | |
| C1 | n.d. | n.d. |
| R2A | 0.9 | 0.9 |
| A3 | -1- | -1- |
| G4 | n.d. | n.d. |
| P5 | n.d. | n.d. |
| L6A | 30.3 | 34.7 |
| Q7A | 0.7 | 0.6 |
| W8A | 7.4 | 6.4 |
| L9A | 33.2 | 29.7 |
| C10 | n.d. | n.d. |
| E11A | 2.9 | 2.4 |
| K12A | 7.9 | 5.3 |
| Y13A | 12.5 | 14.6 |
| F14A | 6.2 | 5.8 |
| (wt) | -1- | -1- |

TABLE IX

| Variant | IGF-I Inhibition IC50(mut)/IC50(wt) |
|---|---|
| Relative affinities of BP1-01 non-natural peptide variants by ELISA | |
| C1 | n.d. |
| R2a | 50 |
| A3a | 34 |
| G4a | 0.6 |
| P5 | n.d. |
| L6a | 400 |
| Q7aib | 1.6 |
| W8aib | 24 |
| L9aib | 400 |
| C10 | n.d. |
| E11aib | 1.0 |
| K12aib | 2.0 |
| Y13aib | 7.1 |
| F14aib | 3.0 |
| (wt) | -1- |

(a= D-alanine; aib= alpha-aminoisobutyrate)

TABLE X

| Variant name | Peptide seq. | IGF-I Inhibition IC50 (mut)/IC50 (wt) |
|---|---|---|
| Relative affinities of C-terminal BP1-01 variants by ELISA | | |
| BP1-01 | CRAGPLQWLCEKYFG (SEQ ID NO: 26) | -1- |
| BP1-04 | CRAGPLQWLCE (SEQ ID NO: 28) | >1000 |
| BP1-17 | CRAGPLQWLCEK (SEQ ID NO: 36) | >1000 |
| BP1-18 | CRAGPLQWLCEKAA (SEQ ID NO: 37) | 148 |

C. Polyvalent (g8) Selection of BP1-01 Secondary Libraries

NNS codons were used to generate diverse peptide libraries as described above. Affinity selections were performed by solution binding of phage to biotinylated IGFBP-1 (prepared as described above) in solution to minimize avidity effects. A similar strategy was used for antibody-phage selections by Hawkins et al., *J. Mol. Biol.,* 226: 889 (1992). For each round of selection, the target amount was reduced to select for enhanced affinity variants. Typically, $10^9$-$10^{10}$ purified phage were preblocked with MPBST (5% skim milk in PBS+0.05% TWEEN™ 20) for 1 hr at room temperature and screened for binding to biotinylated target. Binding conditions are described below. Phage that bound to target were captured by incubating with streptavidin-magnetic beads (Promega Corp., Madison, Wis.) for 2-5 minutes at room temperature. After binding, the beads were washed with PBS-TWEEN™/MPBST ten times before eluting with 0.1 M HCl. The eluate was immediately neutralized with ⅓ volume of 1 M TRIS, pH 8.0. The eluted phage were propagated by infecting XL1 for the next selection cycle. Rounds 1, 2, 3 were carried out with 400 nM, 200 nM, and 20 nM target, respectively, with 1-h incubations. Round 4 was carried out with 4 nM target overnight. All binding reactions were performed at room temperature.

The identified mutations are shown in Table XIII of WO 98/45427 and the relative affinities by ELISA plate assay or BIAcore™ are shown in Table XI below. It can be seen that BP1-10 (SEQ ID NO:29), BP1-11 (SEQ ID NO:30), BP1-12 (SEQ ID NO:31), BP1-13 (SEQ ID NO:32), BP1-15 (SEQ ID NO:34), BP68 (SEQ ID NO:45), BP1027 (SEQ ID NO:48), BP1028 (SEQ ID NO:49), BP1029 (SEQ ID NO:50), and BP1030 (SEQ ID NO:51) are of comparable or higher affinity than BP1-02 and BP1-01, and are thus expected to increase the availability of IGF-I in an in vitro cell culture assay.

TABLE XI

| Variant name | Peptide seq. | IGF-I Inhibition IC50 (mut)/IC50 (wt) |
|---|---|---|
| Relative affinities of g8 BP1-01 selectants by ELISA plate assay or BIAcore ™* | | |
| BP1-02 | SEVGCRAGPLQWLCEKYFG (SEQ ID NO: 27) | 0.37 |
| BP1-01 | CRAGPLQWLCEKYFG (SEQ ID NO: 26) | -1- |
| BP1-10 | CRKGPLQWLCELYF (SEQ ID NO: 29) | 1.1* |
| BP1-11 | CRKGPLQWLCEKYF (SEQ ID NO: 30) | 1.9* |
| BP1-12 | CKEGPLQWLCEKYF (SEQ ID NO: 31) | 2.9* |
| BP1-13 | CKEGPLLWLCEKYF (SEQ ID NO: 32) | 2.5* |
| BP1-14 | SEVGCREGPLQWLCEKYF (SEQ ID NO: 33) | 0.26 |
| BP1-15 | CAAGPLQWLCEKYF (SEQ ID NO: 34) | 0.68 |
| BP67 | CRAGPLQWLCERYF (SEQ ID NO: 44) | 0.34 |
| BP68 | CRAGPLQWLCEKFF (SEQ ID NO: 45) | 0.39 |
| BP1027 | CKAGPLLWLCERFF (SEQ ID NO: 48) | 8.8 |
| BP1028 | CRAGPLQWLCERFF (SEQ ID NO: 49) | 4.6 |
| BP1029 | CREGPLQWLCERFF (SEQ ID NO: 50) | 1.7 |
| BP1030 | CKEGPLLWLCERFF (SEQ ID NO: 51) | 4.3 |

D. Monovalent (g3) Selection of BP1-01 Secondary Libraries

Monovalent (g3) selections of BP1-01 secondary libraries were carried out essentially as described in part C above. Templates contained either the TAA stop codon at the targeted sites for randomization or an entirely unrelated binding sequence from BP1-01. Selection conditions were as described below with BSA replacing milk in the blocking buffer. Phage-target complexes were captured by magnetic streptavidin beads (Promega Corp., Madison, Wis.). Biotinylated target was preincubated with phage for 1-3 h at room temperature in each round, with the target concentrations being reduced from 200-500 nM in round 1, to 50-100 nM in round 2, 10-50 nM in round 3, and 1-20 mM in round 4.

The identified mutations are shown in Table XV of WO 98/45427 and the relative affinities, as determined by BIAcore™ competition assay or by ELISA plate assay (carried out as above, except that 5% acetonitrile was used for peptide solubility) of several peptides selected are shown in Table XII below. BP1-16 (SEQ ID NO:35), a 13-residue version of BP1-01 (lacking the C-terminal Gly), had similar affinity to that of BP1-01. Substitutions at the N-terminus or C-terminus yielded affinity improvements. For example, compared with BP1-16, addition of the STY sequence at the C-terminus yielded about a 3-fold affinity improvement for peptide BP1-21B. (A similar effect was seen in the context of the 18-mer: namely, a 3-fold improvement was observed between BP1-14 and BP1-21A. Substitution of the N-terminal S to G motif also improved affinity by 2- to 3-fold in peptides BP1-19 and BP1-20. All of these peptides had similar or improved apparent affinity for IGFBP-1 as compared with BP1-01 and BP1-02 and are thus expected to increase the availability of IGF-I in an in vitro cell culture assay.

TABLE XII

Relative affinities of g3 BP1-01 selectants by BIAcore™ or ELISA plate assay*

| Variant name | Peptide seq. | IGF-I Inhibition IC50 (116)/ C50 (mut) | IGF-I Inhibition IC50 (114)/ IC50 (mut) |
|---|---|---|---|
| BP1-14 | SEVGCRAGPLQWLCEKYFG-nh2 (SEQ ID NO: 33) | 4.8 | -1- |
| BP1-16 | CRAGPLQWLCEKYF-nh2 (SEQ ID NO: 35) | -1- | 0.21 |
| BP1-19 | SEMVCRAGPLQWLCEIYF-nh2* (SEQ ID NO: 38) | 9.9 | 2.1 |
| BP1-20 | EARVCRAGPLQWLCEKYF-nh2 (SEQ ID NO: 39) | 12 | 2.6 |
| BP1-21A | SEVGCRAGPLQWLCEKYFSTY-nh2 (SEQ ID NO: 40) | 15 | 3.2 |
| BP1-21B | CRAGPLQWLCEKYFSTY-nh2 (SEQ ID NO: 41) | 3.1 | 0.67 |

Example 6

Alanine-Scanning Mutagenesis of IGF-1 and Structural IGF-1 Analogs

Introduction:

An alanine-scanning mutagenesis approach (Cunningham and Wells, *Science*, 244: 1081-1085 (1989); U.S. Pat. No. 5,834,250) was used to remove that portion of each side chain of IGF-1 beyond the beta carbon. The contribution of these atoms to the free energy of binding of the IGF-1 analog to IGFBP-1 or to IGFBP-3 was then assessed by competitive phage ELISA. In this assay, IGFBP-1 or IGFBP-3 is used to inhibit IGF-phage mutants from binding to an IGFBP-1- or IGFBP-3-coated immunosorbant plate. From a titration series of binding protein, binding ($IC_{50}$) can be calculated. Some mutants were also assessed for direct binding in BIACORE™ assays.

Materials and Methods:

Construction of Phagemid Vector and Mutagenesis

The gene encoding mature human IGF-1 was amplified from pBKIGF2B (U.S. Pat. No. 5,342,763) using PCR primers 5'-AGC TGC TTT GAT ATG CAT CTC CCG AAA CTC TGT GCG GT-3' (SEQ ID NO:127) and 5'-GAG CGA TCT GGG TCT AGA CAG ATT TAG CGG GTT TCA G-3' (SEQ ID NO:128). The resulting fragment was cut with NsiI and XbaI, and ligated into pH0753 previously digested with NsiI and XbaI. pH0753 is a derivative of phGHam-g3 (Lowman et al., *Biochemistry*, 30: 10832-10838 (1991)) in which the additional XbaI site in the alkaline phosphatase promoter (PhoA) region has been deleted using the oligonucleotide 5'-AAA AGG GTA TGT AGA GGT TGA GGT-3' (SEQ ID NO:129). The ligated vector pH0753 containing the IGF-1 open reading frame was named pIGF-g3. It encodes for IGF-1 harboring the double mutation G1S-A70V fused to a fragment of the gene III protein (residues 249-406) from the *E. coli* bacteriophage M13. Binding of this IGF-1 variant to IGFBP-1 and -3 was found to be indistinguishable from wild-type IGF-1. Alanine mutagenesis was performed using single-stranded plasmid pIGF-g3 as template (Kunkel et al., *Methods Enzymol.*, 204: 125-139 (1991)). All residues of IGF-1 with the exception of cysteines and alanines were singly replaced by alanine. The resulting constructs were verified by DNA sequencing.

Binding of IGF Mutants Displayed on Phage to IGFBP-1 and -3 (Phage ELISA)

Immunosorbent plates (Nunc, MAXISORP™, 96 wells) were coated with 100 µl/well of 1 µg/ml IGFBP-1 or IGFBP-3 in PBS buffer pH 7.2 at 4° C. overnight. The plates were then blocked with 0.5% TWEEN 20%/PBS (also used as binding buffer) for 2 hours at room temperature (proteinaceous blocking agents like bovine serum albumin were avoided to prevent potential IGF or IGFBP contamination). *E. coli* cells (XL1-Blue, Stratagene) freshly transformed with phagemid vector were grown overnight in 5 mL 2YT medium (Sambrook et al., supra) in the presence of M13-VCS helper phage (Stratagene). Phage particles were harvested and resuspended in PBS buffer as described in Lowman, H. B., "Phage Display of Peptide Libraries on Protein Scaffolds," in Cabilly, S. (ed.), *Combinatorial Peptide Library Protocols* (Humana Press Inc.: Totowa, N.J., 1998), pp. 249-264. Then phage concentrations were normalized to yield a maximal ELISA signal of 0.2-0.4 for each mutant (Lowman, in Cabilly, S. (ed.), supra). Threefold serial dilutions of soluble competitor were prepared on non-absorbent microtiter plates (Nunc, F, 96 wells) with binding buffer (0.5% TWEEN 20%/PBS) containing phage at the previously determined concentrations. The dilution range of competitor protein extended over six orders of magnitude, starting at 5 µM for IGFBP-1 and 500 nM for IGFBP-3. After blocking, the plates containing immobilized target were washed with 0.05% TWEEN™/PBS buffer and subsequently incubated with 80 µl/well of the premixed phage-competitor solutions for 1 hour at room temperature. After washing, bound phage was detected with 80 µl/well of a solution containing a primary rabbit anti-phage polyclonal antibody and a secondary goat anti-rabbit monoclonal antibody-horseradish peroxidase conjugate in 0.5% TWEEN 20™/PBS. o-Phenylenediamine (Sigma) and tetramethylbenzidine (Kirkegaard and Perry) were used as chromogenic substrates, resulting in product detection at 492 and 450 nm, respectively. $IC_{50}$ values were determined by fitting the binding data to a generic saturation curve (Lowman, in Cabilly, S. (ed.), supra). At least two individual clones of each IGF-1 mutant were assayed. Numbers in Table XIII represent mean±standard deviation of individually assessed $IC_{50}$ values.

Expression and Purification of IGFBP-1 and IGFBP-3

Human IGFBP-1 was expressed in CHO cells and purified from the conditioned medium as described by Mortensen et al., *Endocrinology*, 138: 2073-2080 (1997). Recombinant human IGFBP-3 has also been cloned and expressed in mammalian cells (Wood et al., *Mol. Endocrinology*, 2: 1176-1185 (1988)). Purification from conditioned medium essentially followed the procedure described for IGFBP-1, with use of an IGF affinity column (Martin and Baxter, *J. Biol. Chem.*, 261: 8754-8760 (1986)).

Expression and Purification of Soluble IGF-1 Mutants

Plasmid pBKIGF2B (U.S. Pat. No. 5,342,763) expresses human wild-type IGF-1 fused to the leader peptide of lamB under the control of the PphoA promoter. For ease of site-directed mutagenesis the phage f1 origin of replication (f1 ori) was introduced into plasmid pBKIGF2B. For that purpose a 466-BP BamHI fragment containing the f1 ori was excised from pH0753 (Lowman et al., supra, 1991), while plasmid pBKIGF2B was linearized with EcoRI. Vector and fragment were both treated with Klenow enzyme to fill in restriction-site overhangs prior to blunt-end ligation. Correct constructs were selected for the ability to produce single-stranded phagemid DNA in the presence of M13VCS helper phage. The resulting phagemid vector was named pBKIGF2B-f1-ori and was used as template to construct the IGF-1 ala-mutants of interest (see Table XIV) using the procedure of Kunkel et al., *Methods Enzymol.*, 204: 125-139 (1991)). Every mutagenesis step was confirmed by DNA sequencing.

Expression of IGF-1 mutants was as described for the IGF-1 wild-type (Joly et al., *Proc. Natl. Acad. Sci. USA*, 95: 2773-2777 (1998)), but without transient overexpression of oxidoreductases. The purification procedure was based on a previous protocol (Chang and Swartz, "Single-Step Solubilization and Folding of IGF-1 Aggregates from *Escherichia coli*" In Cleland, J. L. (ed.), Protein Folding In Vivo and In Vitro (American Chemical Society, Washington, D.C., 1993), pp. 178-188), with minor adaptations. Typically, 6 g of wet cell paste (equivalent to 2 liters low phosphate medium grown for 24 hrs) was resuspended in 150 ml of 25 mM Tris-HCl pH 7.5 containing 5 mM EDTA. Cells were lysed in a microfluidizer (Microfluidics Corp., Newton, Mass.), and refractile particles containing accumulated IGF-1 aggregates were collected by centrifugation at 12,000×g. Refractile particles were washed twice with lysis buffer, twice with lysis buffer containing 1% N-lauroyl-sarcosine (Sigma) to extract membrane proteins, and twice with lysis buffer again. Washed refractile bodies were resuspended at approximately 2 mg/ml in 50 mM CAPS (3-(cyclohexylamino)-1-propanesulfonic acid; Sigma) buffer pH 10.4 containing 2 M urea, 100 mM NaCl, 20% MeOH, and 2 mM DTT. This procedure combines solubilization of refractile bodies and subsequent oxidative refolding of IGF-1 mutants (Chang and Swartz, supra). After 3 hrs at room temperature the refolding solutions were filtered through microconcentrator membranes (Centricon, Amicon) with a molecular weight cut off of 50 kDa. The majority of monomeric IGF-1 was recovered in the eluate, while higher molecular weight contaminants were concentrated in the retentate. At this point IGF-1 fractions were >95% pure, as judged from SDS-PAGE analysis. To separate correctly disulfide-bonded IGF-1 from IGF-swap (containing two non-native disulfides; Hober et al., *Biochemistry*, 31: 1749-1756 (1992); Miller et al., *Biochemistry*, 32: 5203-5213 (1993)), refolding solutions were acidified with 5% acetic acid and loaded on a Dynamax™ C18 semi-preparative HPLC column (Varian; 10.0 mm ID) at 4 ml/min. Buffers were $H_2O$/0.1% TFA (A) and acetonitrile/0.1% TFA (B). Separation of the disulfide isomers was achieved by applying the following gradient: 0-30% B in 20 min, 30-45% B in 60 min. The ratio of native IGF-1 to IGF-swap was usually about 2:1 for each mutant, with IGF-swap eluting earlier in the gradient than native IGF-1. The molecular mass of each mutant was verified by mass spectrometry. After HPLC purification, samples were lyophilized and reconstituted at approximately 1 mg/ml in 100 mM HEPES buffer, pH 7.4.

Biosensor Kinetic Measurements

The binding affinities of the IGF variants for IGFBP-1 and IGFBP-3 were determined using a BIACORE™-2000 real time kinetic interaction analysis system (Biacore, Inc., Piscataway, N.J.) to measure association ($k_a$) and dissociation ($k_d$) rates. Carboxymethylated dextran biosensor chips (CM5, BIAcore Inc.) were activated with EDC (N-ethyl-N'-(3-dimethylaminopropyl)-carbodiimide hydrochloride) and NHS (N-hydroxysuccinimide) according to the supplier's instructions. For immobilization, IGF mutants in 20 mM sodium acetate, pH 4.8, were injected onto the biosensor chip at a concentration of 50 µg/ml to yield approximately 450-600 RU's (resonance-response units) of covalently-coupled protein. Unreacted groups were blocked with an injection of 1 M ethanolamine. Kinetic measurements were carried out by injecting two-fold serial dilutions (starting at 1 µM) of either IGFBP-1 or IGFBP-3 in running buffer (PBS, 0.05% TWEEN 20', 0.1% ovalbumin, 0.1% sodium azide) at 25° C. using a flow rate of 20 µl/min. Association rates ($k_a$) and dissociation rates ($k_d$) were calculated separately using a 1:1 Langmuir™ association model in the BIACORE™ evaluation software v. 3.0. The equilibrium dissociation constant ($K_D$) was calculated as $k_d/k_a$.

Results:

Monovalent Phage Display of IGF-1

For a rapid and comprehensive alanine scan of the 70 amino acid residues of IGF-1 it was first determined whether the protein could be monovalently displayed on the surface of phage M13 (Bass et al., supra). Phage display technology combines the advantage of rapid single-stranded DNA mutagenesis with an easy purification of the resulting mutant protein, simply by isolation of the corresponding phage particles (e.g., Cunningham et al., *EMBO J.*, 13: 2508-2515 (1994)). A vector was constructed in which mature human IGF-1 was fused to the carboxy-terminal domain of the M13 gene III product. This construct includes the stII signal sequence which directs the fusion protein to the periplasmic space of *E. coli* and allows monovalent display of the protein (Bass et al., supra; Lowman et al., supra, 1991). For cloning purposes the first and the last amino acids of IGF-1 were changed; the resulting mutant G1S-A70V was used as the template construct for the subsequent alanine scanning mutagenesis.

Figure 13A:
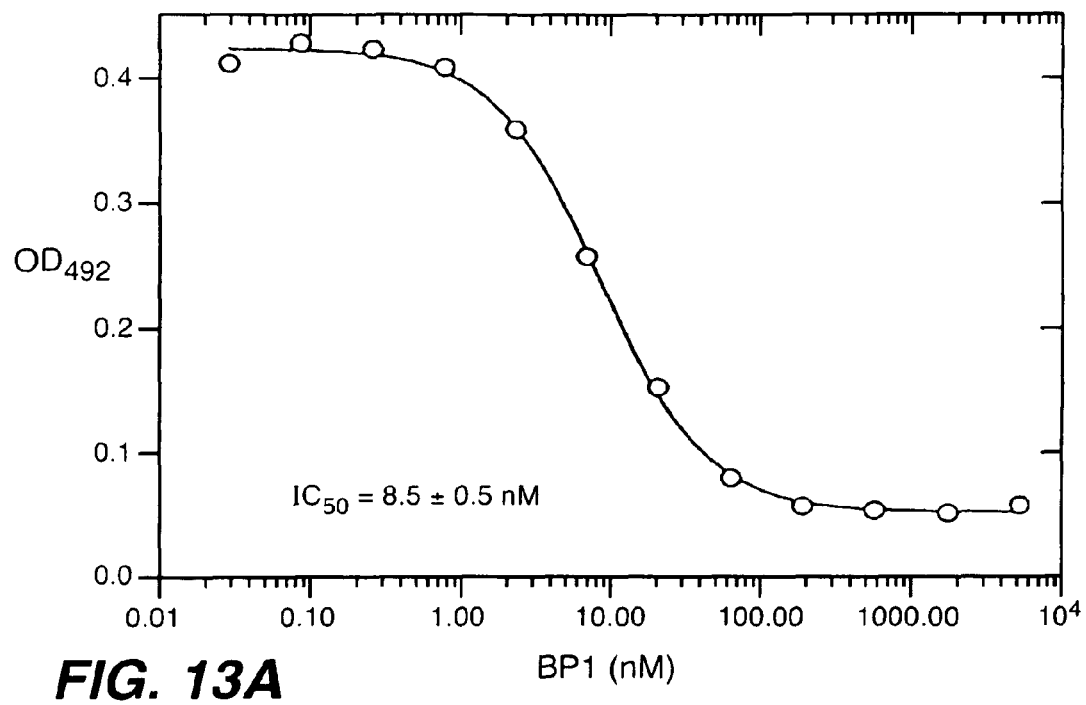
FIGS. 13A and 13B show a phage ELISA of the variant, G1S-A70V IGF-1, binding to IGFBP-1 (FIG. 13A) and IGFBP-3 (FIG. 13B). Microtiter plates coated with 1 μg/ml IGFBP-1 (FIG. 13A) or IGFBP-3 (FIG. 13B) were incubated with phage particles displaying G1S-A70V in the presence of the indicated amounts of soluble competitor protein, IGFBP-1 (FIG. 13A) or IGFBP-3 (FIG. 13B). The half-maximal inhibitory concentration ($IC_{50}$) of competitor, i.e., the inhibitory concentration of competitor that resulted in half-maximal binding of the phagemid in that particular experiment, is denoted for the respective IGFBP.
Figure 13B:
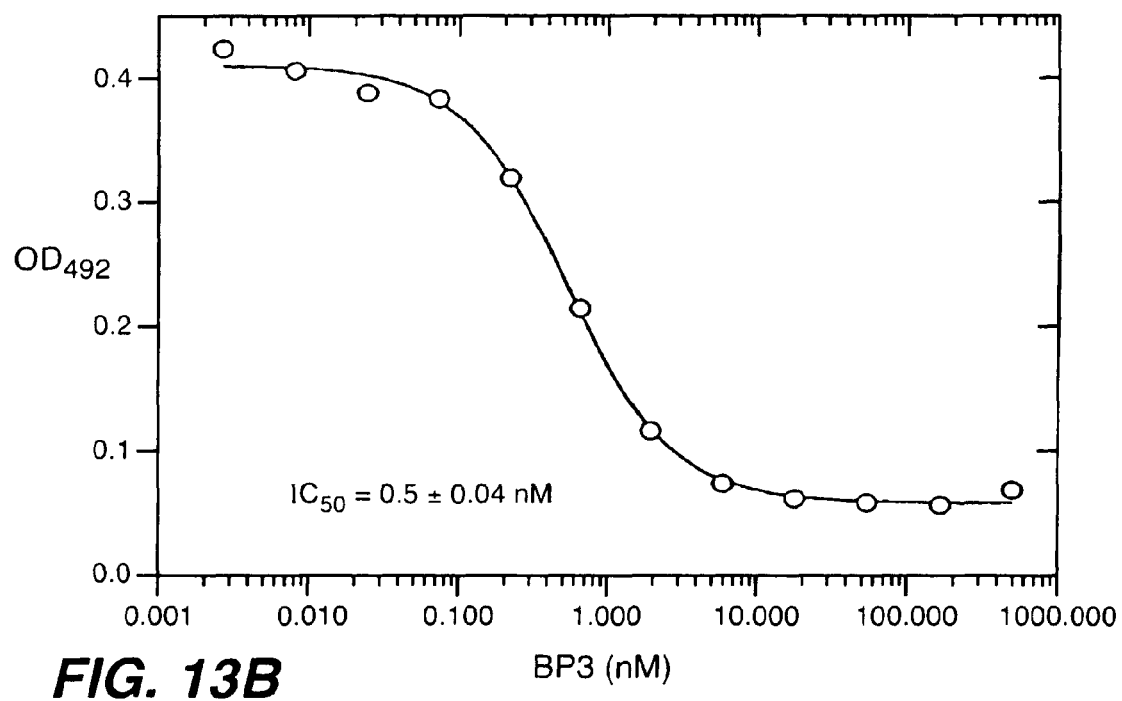

When phage particles displaying IGF-1 G1S-A70V were isolated and assayed in a binding competition phage ELISA for their affinity to IGFBP's, the $IC_{50}$ determined in that experiment were 8.5 nM for IGFBP-1 and 0.5 nM for IGFBP-3 (FIG. 13). These values are in good agreement with dissociation constants determined by BIACORE™ surface-plasmon-resonance experiments using wild-type IGF-1 (Heding et al., *J. Biol. Chem.*, 271: 13948-13952 (1996)). Wild-type IGF-1 affinities determined by radioactive immunoassays (RIA) are ~2.8 nM for IGFBP-1 and ~0.8 nM for IGFBP-3, further supporting the $IC_{50}$ values derived from phage ELISA. Additionally, phage particles displaying IGF-1 G1S-A70V were efficiently captured by 11 independent monoclonal mouse anti-IGF-1 antibodies immobilized on microtiter plates. These results together suggested that the displayed IGF-variant is folded correctly and accessible on the surface of the phage particles.

Ala-scanning Mutagenesis of IGF-1 Binding to IGFBP-1 and IGFBP-3

All residues of G1S-A70V IGF-1 with the exception of the four native alanines and six cysteines were singly substituted by alanine, using the described G1S-A70V IGF-1 gIII vector as a template. Additionally, the single mutants S1G and V70A and the double-mutation restoring wild-type IGF-1 were constructed. Each of these constructs was expressed in *E. coli* and displayed on phage. $IC_{50}$ values for binding to IGFBP-1 and IGFBP-3 were determined by competitive phage ELISA as shown in FIG. 13. At least two different clones of every mutant were tested. The resulting $IC_{50}$ values are listed in Table XIII, and the loss or gain in $IC_{50}$ for each mutant with respect to G1S-A70V is graphed in FIG. 14.

TABLE XIII

Apparent Affinities ($IC_{50}$) of IGF-1 Variants for IGFBP-1 and IGFBP-3 Determined by Phage Display[a]

| IGF-1 mutant | IGFBP-1 | | IGFBP-3 | | relative specificity |
|---|---|---|---|---|---|
| | IC50 (nM) | Relative IC50 | IC50 (nM) | relative IC50 | |
| S1A | 5.2 ± 0.9 | 0.6 | 0.91 ± 0.32 | 1.2 | 0.5 |
| P2A | 11.0 ± 3.7 | 1.3 | 0.81 ± 0.18 | 1.1 | 1.2 |
| E3A | 278 ± 86 | 33.9 | 1.05 ± 0.08 | 1.4 | 24.2 |
| T4A | 19.4 ± 6.4 | 2.4 | 0.80 ± 0.02 | 1.1 | 2.2 |
| L5A | 55.3 ± 11.6 | 6.7 | 1.53 ± 0.22 | 2.0 | 3.3 |
| G7A | >1000 | >100 | 4.58 ± 0.28 | 6.1 | >16 |
| E9A | 8.6 ± 0.6 | 1.0 | 1.32 ± 0.30 | 1.8 | 0.6 |
| L10A | 311 ± 87 | 37.9 | 3.55 ± 0.33 | 4.7 | 8.1 |
| V11A* | n.d. | — | n.d. | — | — |
| D12A | 4.3 ± 0.8 | 0.5 | 1.49 ± 0.38 | 2.0 | 0.3 |
| L14A | 36.7 ± 1.1 | 4.5 | 0.90 ± 0.04 | 1.2 | 3.7 |
| Q15A | 13.9 ± 0.9 | 1.7 | 1.26 ± 0.41 | 1.7 | 1.0 |
| F16A | 57.8 ± 20.1 | 7.0 | 1.32 ± 0.25 | 1.8 | 4.0 |
| V17A | 42.9 ± 3.2 | 5.2 | 3.67 ± 1.02 | 4.9 | 1.1 |
| G19A | 11.0 ± 2.3 | 1.3 | 0.90 ± 0.28 | 1.2 | 1.1 |
| D20A | 8.4 ± 4.1 | 1.0 | 1.11 ± 0.06 | 1.5 | 0.7 |
| R21A | 7.1 ± 1.6 | 0.9 | 0.58 ± 0.01 | 0.8 | 1.1 |
| G22A | 15.9 ± 2.8 | 1.9 | 2.07 ± 0.11 | 2.8 | 0.7 |
| F23A | 10.9 ± 1.9 | 1.3 | 2.18 ± 0.01 | 2.9 | 0.5 |
| Y24A | 13.3 ± 2.9 | 1.6 | 2.53 ± 0.76 | 3.4 | 0.5 |
| F25A | 181 ± 46 | 22.1 | 3.69 ± 0.25 | 4.9 | 4.5 |
| N26A | 9.1 ± 1.8 | 1.1 | 0.90 ± 0.07 | 1.2 | 0.9 |
| K27A | 12.8 ± 0.1 | 1.6 | 0.66 ± 0.35 | 0.9 | 1.8 |
| P28A | 9.3 ± 1.4 | 1.1 | 1.41 ± 0.05 | 1.9 | 0.6 |
| T29A | 7.3 ± 2.4 | 0.9 | 1.23 ± 0.16 | 1.6 | 0.5 |
| G30A | 7.1 ± 1.7 | 0.9 | 0.58 ± 0.11 | 0.8 | 1.1 |
| Y31A | 6.8 ± 0.5 | 0.8 | 0.73 ± 0.10 | 1.0 | 0.9 |
| G32A | 10.9 ± 1.3 | 1.3 | 0.76 ± 0.28 | 1.0 | 1.3 |
| S33A | 9.1 ± 1.0 | 1.1 | 1.01 ± 0.24 | 1.3 | 0.8 |
| S34A | 9.5 ± 0.7 | 1.2 | 1.65 ± 0.21 | 2.2 | 0.5 |
| S35A | 11.7 ± 0.6 | 1.4 | 0.47 ± 0.01 | 0.6 | 2.3 |
| R36A* | n.d. | — | n.d. | — | — |
| R37A | 12.3 ± 0.1 | 1.5 | 0.75 ± 0.08 | 1.00 | 1.5 |
| P39A* | n.d. | — | n.d. | — | — |
| Q40A | 10.2 ± 0.9 | 1.2 | 0.56 ± 0.03 | 0.7 | 1.7 |
| T41A | 13.7 ± 3.1 | 1.7 | 0.43 ± 0.06 | 0.6 | 2.9 |
| G42A | 15.7 ± 3.4 | 1.9 | 0.53 ± 0.20 | 0.7 | 2.7 |
| I43A | 31.3 ± 4.1 | 3.8 | 1.17 ± 0.07 | 1.6 | 2.4 |
| V44A | 18.8 ± 5.4 | 2.3 | 1.03 ± 0.06 | 1.4 | 1.7 |
| D45A | 4.7 ± 0.7 | 0.6 | 0.69 ± 0.21 | 0.9 | 0.6 |
| E46A | 7.9 ± 2.1 | 1.0 | 0.94 ± 0.28 | 1.3 | 0.8 |
| F49A | >1000 | >100 | 2.72 ± 1.11 | 3.6 | >28 |
| R50A | 16.2 ± 1.8 | 2.0 | 0.64 ± 0.18 | 0.9 | 2.3 |
| S51A | 13.4 ± 0.4 | 1.6 | 0.65 ± 0.35 | 0.9 | 1.9 |
| D53A | 15.3 ± 2.8 | 1.9 | 1.05 ± 0.11 | 1.2 | 1.6 |
| L54A | 23.1 ± 12.0 | 2.8 | 1.83 ± 0.91 | 2.4 | 1.2 |
| R55A | 9.0 ± 2.3 | 1.1 | 0.66 ± 0.03 | 0.9 | 1.2 |
| R56A | 13.1 ± 1.8 | 1.6 | 1.00 ± 0.19 | 1.3 | 1.2 |
| L57A | 21.8 ± 5.6 | 2.7 | 1.78 ± 0.56 | 2.4 | 1.1 |
| E58A | 11.9 ± 1.8 | 1.5 | 1.03 ± 0.47 | 1.4 | 1.1 |
| M59A | 13.1 ± 1.8 | 1.6 | 0.74 ± 0.14 | 1.0 | 1.6 |
| Y60A | 6.6 ± 1.8 | 0.8 | 0.52 ± 0.01 | 0.7 | 1.2 |
| P63A | >1000 | >100 | >100 | >100 | — |
| L64A | 12.1 ± 3.3 | 1.5 | 0.93 ± 0.03 | 1.2 | 1.2 |
| K65A | 12.4 ± 0.6 | 1.5 | 0.69 ± 0.05 | 0.9 | 1.6 |
| P66A | 9.4 ± 3.2 | 1.1 | 0.57 ± 0.12 | 0.8 | 1.5 |
| K68A | 10.5 ± 2.8 | 1.3 | 0.76 ± 0.23 | 1.0 | 1.3 |
| S69A | 12.8 ± 2.3 | 1.6 | 0.71 ± 0.62 | 1.2 | 1.3 |
| V70A | 19.1 ± 0.7 | 2.3 | 0.68 ± 0.15 | 0.9 | 2.6 |
| S1G | 11.2 ± 1.1 | 1.4 | 0.99 ± 0.42 | 1.3 | 1.0 |
| IGF-1 WT | 8.4 ± 0.8 | 1.0 | 1.01 ± 0.42 | 1.3 | 0.8 |
| G1S-A70V | 8.2 ± 1.6 | 1.0 | 0.75 ± 0.32 | 1.0 | 1.0 |
| Ala(1-3)-IGF | 90.4 ± 9.6 | 11.0 | 1.12 ± 0.04 | 1.5 | 7.3 |
| Des(1-2)-IGF | 5.0 ± 0.1 | 0.6 | 0.53 ± 0.03 | 0.7 | 0.9 |

[a]The variants noted with an asterisk were not successfully displayed on phage (n.d.), as judged by antibody experiments described in the text.
Relative $IC_{50}$ is defined as $IC_{50\,mut}/IC_{50\,G1S-A70V}$.
Relative specificity is defined as relative $IC_{50\,IGFBP-1}$/relative $IC_{50\,IGFBP-3}$ for each variant.

The majority of the alanine mutants yielded only minor changes in $IC_{50}$ values in the phage ELISA. Importantly, wild-type IGF-1 showed the same affinities for IGFBP-1 and IGFBP-3 as G1S-A70V in which background the alanine substitutions were performed (Table XIII, FIG. 14). Only a few residues caused considerable (>10-fold) losses in affinity when changed to alanine: E3, G7, L10, V11, F25, R36, P39, F49, and P63 for IGFBP-1 binding; V11, R36, P39, and P63 for IGFBP-3 binding. It has been noted that ala-substitutions of glycines and prolines can lead to structural perturbations of the protein backbone (Di Cera, *Chem. Rev.*, 98: 1563-1591 (1998)).

Only a few modest improvements in binding affinity were found by alanine replacements. S1A, D12A, and D45A showed an approximately 2-fold increase in IGFBP-1 binding, while S35A and T41A showed a similar effect for IGFBP-3. However, 2-fold changes in $IC_{50}$ values are at the limit of precision in these experiments.

IGFBP-specificity Determinants

Figure 14A:
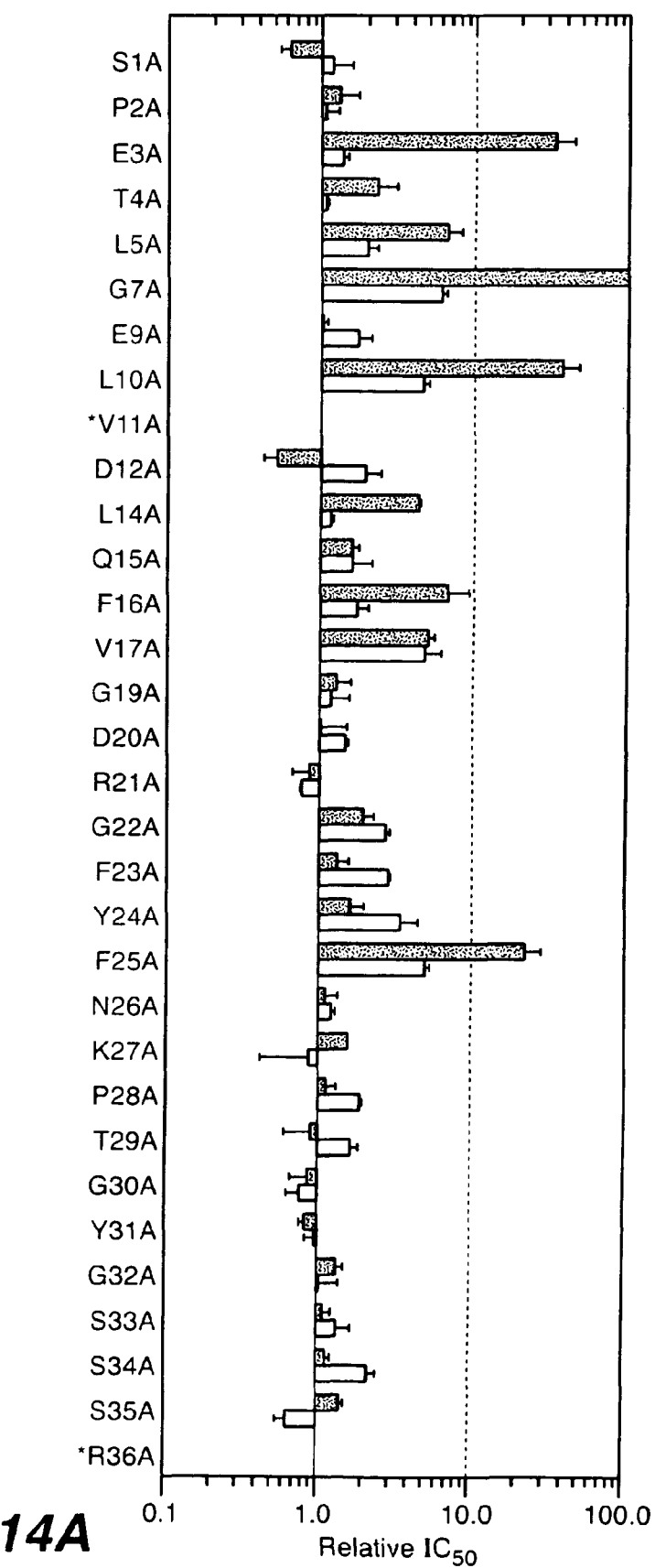
FIGS. 14A and B show the loss or gain of IGFBP affinity for the IGF-1 mutants tested by phage ELISA. Relative $IC_{50}$ values ($IC_{50}$mut/$IC_{50}$ G1S-A70V) of each IGF-1 alanine mutant (affinity changes of each mutant for the binding proteins with respect to IGF-1 G1S-A70V) are shown for IGFBP-1 (filled bars) and IGFBP-3 (open bars). Data are taken from Table I below. Relative $IC_{50}$ values <1 denote gain of affinity; values >1 denote loss of affinity. The asterisk indicates that these particular variants were not displayed on phage, as judged by antibody binding.
Figure 14B:
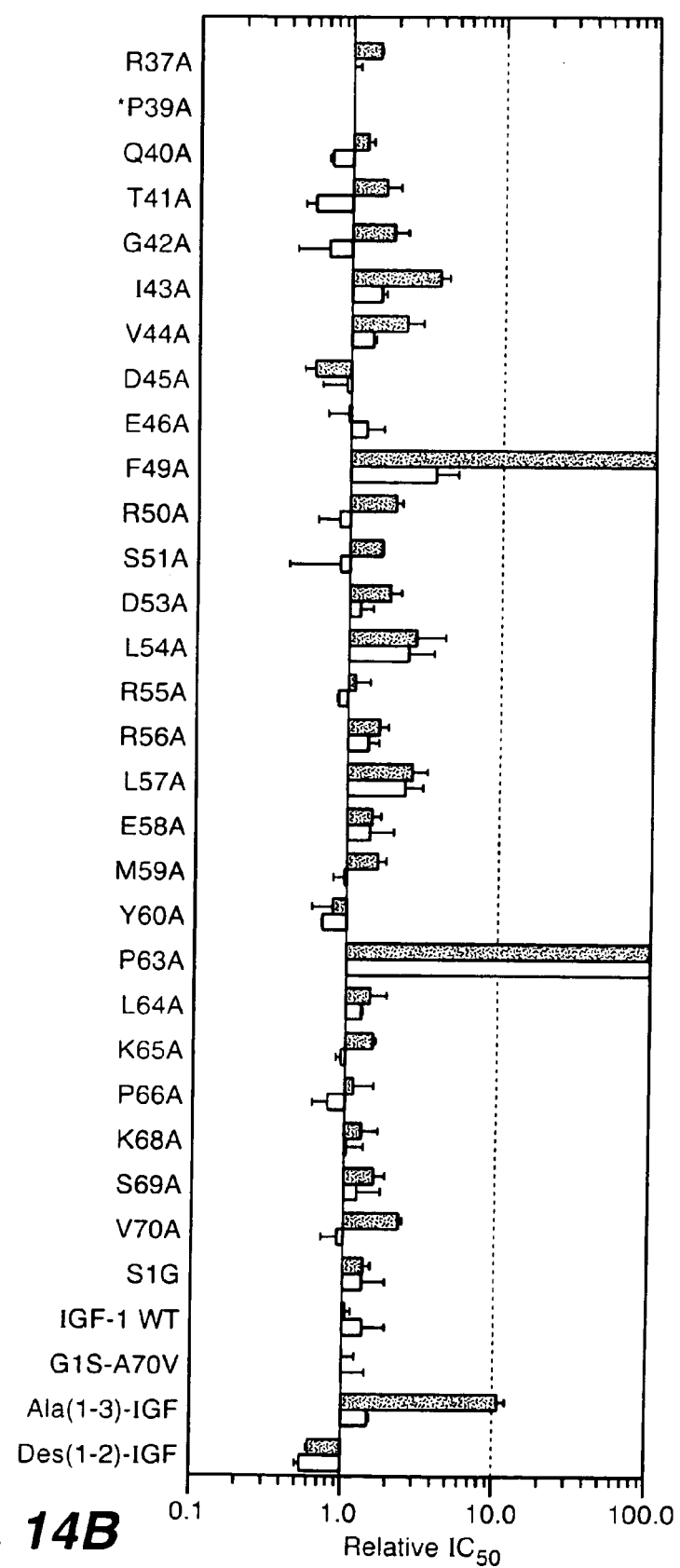
Figure 15A:
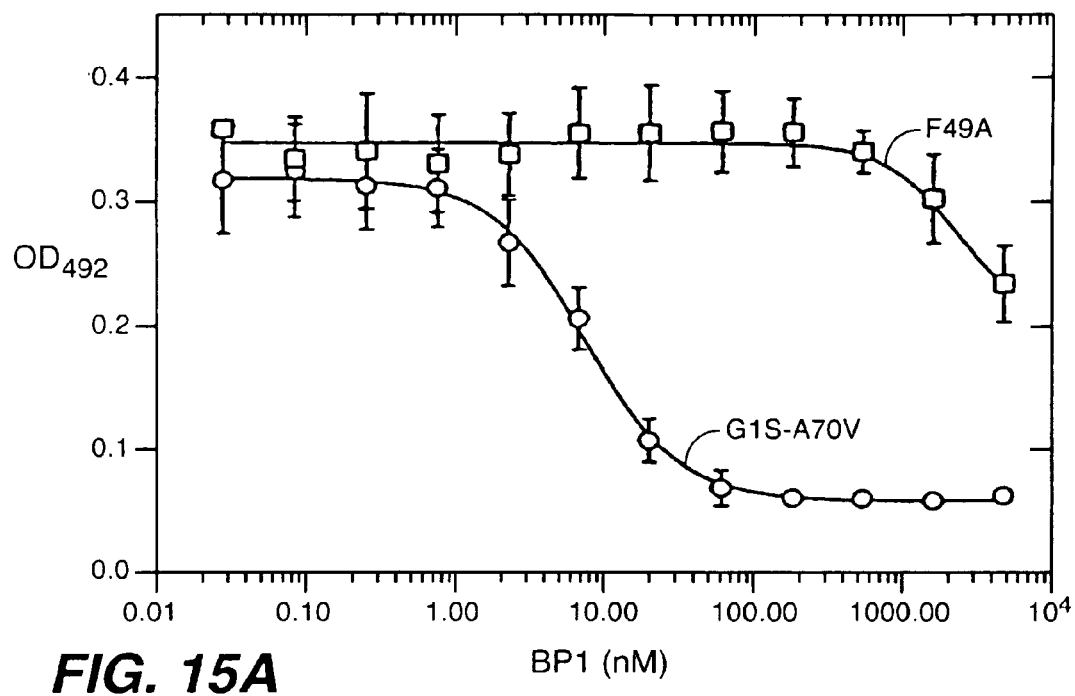
FIGS. 15A and 15B show binding specificity of the IGF-1 variant F49A displayed on phage to IGFBP-1 and -3, respectively, in competitive-phage ELISA. Phagemid particles displaying F49A (squares) were bound to plates coated with IGFBP-3 in the presence of the indicated amounts of soluble IGFBP-1 (FIG. 15A) or IGFBP-3 (FIG. 15B). The same experiment was carried out in parallel with phage displaying the wild-type-like IGF-1 variant G1S-A70V (circles). See Tables I and II below for absolute $IC_{50}$ values. Data points are mean±standard deviation, n=2. Immunosorbent plates were coated with 1 μg/ml IGFBP-3 and ELISA were carried out as described in the Examples below using wild-type IGF-1 phage (WT, circles) and IGF-F49A phage (F49A, squares) in parallel. Experiments were carried out in duplicate, and data points are shown as mean±standard deviation.
Figure 15B:
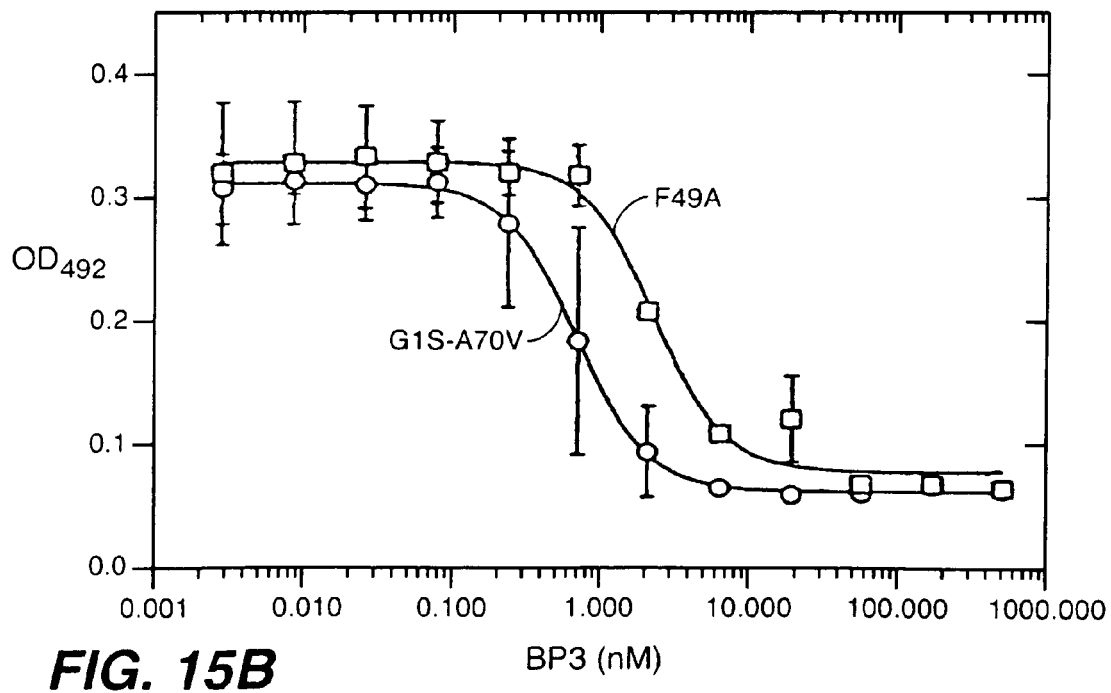

E3A, G7A, L10A, F25A, and F49A showed a differential effect in binding IGFBP-1 versus IGFBP-3. For these five IGF-1 single alanine mutants the relative $IC_{50}$ for IGFBP-1 differed by more than 4-fold from the one for IGFBP-3 (FIG. 14, Table XIII, relative specificity). E3A and F49A showed the biggest relative specificity factors in this group. Alanine substitution of E3 had virtually no effect on IGFBP-3 affinity (1.4 fold), while binding to IGFBP-1 was weakened 34-fold. Even more dramatic, the affinity of F49A was reduced more than 100-fold for IGFBP-1 but only 3.6-fold for BP-3. This result was illustrated in a direct comparison by phage ELISA. Phage particles displaying IGF-1 F49A were added to IGFBP-3 coated wells in the presence of soluble IGFBP-1 (FIG. 15A) or IGFBP-3 (FIG. 15B). Compared to control phage displaying IGF-1 G1S-A70V, the binding curve of F49A shifted by more than two orders of magnitude in the IGFBP-1 competition (FIG. 15A). In contrast, the binding curves were similar in the IGFBP-3 competition, and the $IC_{50}$ values differed by less than a factor of 4 (FIG. 15B). Thus, E3 and F49 are two major specificity determinants for IGFBP-1 binding in the IGF-1 molecule.

Residues G7, L10, and F25 appeared to be important for binding of both IGFBP's, although showing a more pronounced loss of affinity for IGFBP-1 than for IGFBP-3 when substituted by alanines. No significant specificity determinant for IGFBP-3 was identified, such as a mutant binding much tighter to IGFBP-1 than to IGFBP-3. However, mutations E9A, D12A, F23A, Y24A, T29A, S34A, and D45A had slightly larger (about 2-fold) effects on IGFBP-3 than on IGFBP-1 binding.

BIACORE™ Measurements of Purified Soluble IGF Mutants

Figure 17A:
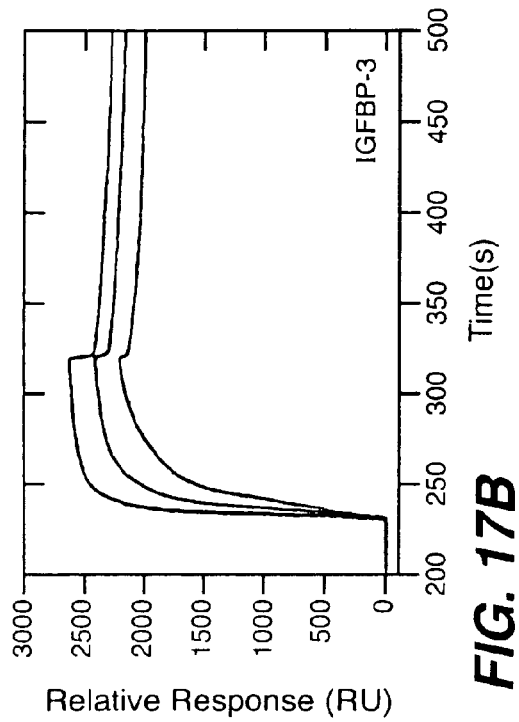
FIGS. 17A-17D show a biosensor analysis of IGFBP binding to immobilized IGF-1 variants. Sensorgrams are shown for IGFBP-1 (FIGS. 17A, 17C) or IGFBP-3 (FIGS. 17B, 17D) binding to immobilized wild-type IGF-1 (FIGS. 17A, 17B) or F49A IGF variant (FIGS. 17C, 17D). The concentrations of ligand in each experiment were 1 μM, 500 nM, and 250 nM. See Table II for kinetic parameters.
Figure 17B:
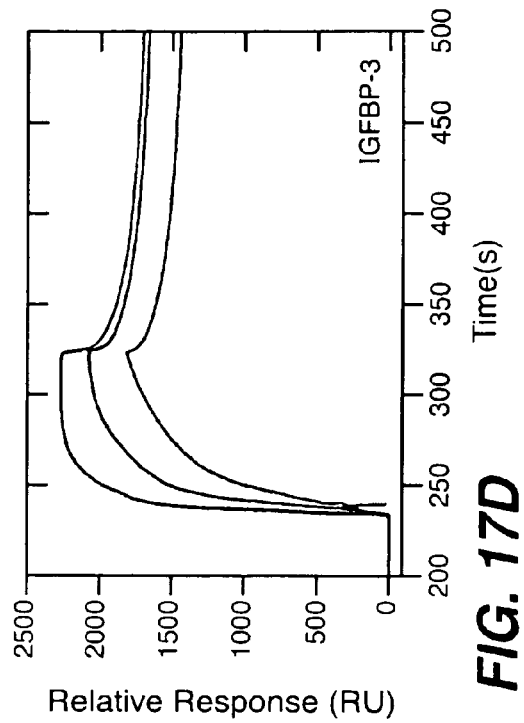

For validation of the results obtained by phage ELISA, specific alanine mutants were expressed and purified for kinetic analysis using a BIACORE™ instrument. The dissociation constant ($K_D$) of wild-type IGF-1 was determined to be 13 nM for IGFBP-1 and 1.5 nM for IGFBP-3 (FIGS. 17A and 17B; Table XIV). The difference in affinity for the IGFBP's is due to a 10-fold faster association rate ($k_a$) of IGF-1 to IGFBP-3 ($3.2 \times 10^5$ versus $3.2 \times 10^4$ $M^{-1}s^{-1}$). These results correspond well with the absolute $IC_{50}$ values determined by phage ELISA (FIGS. 13A and 13B; Table XIII). As expected, the double-mutant G1S-A70V showed kinetic parameters essentially indistinguishable from wild-type (Table XIV).

V11A, R36A, and P39A were tested because these variants had not been displayed correctly on phage, based upon the antibody recognition experiments (see above). R36A and P39A showed wild-type kinetics for both binding proteins, whereas V11A showed a 5-fold reduction in affinity for both IGFBP-1 and IGFBP-3.

Furthermore, it was decided to examine the soluble IGF variant T4A. This residue had been implicated in IGFBP binding in earlier publications (Bayne et al., *J. Biol. Chem.*, 263: 6233-6239 (1988); Clemmons et al., *J. Biol. Chem.*, 265: 12210-12216 (1990)), but had shown modest effects in the phage assays herein. The increase in the $K_D$ values of T4A relative to wild-type IGF-1 was approximately 2-3-fold higher than the $IC_{50}$ ratios determined by phage ELISA (Table XIV). A bigger discrepancy between the results obtained by phage and the biosensor analysis was seen for F16A. In this case the two methods differed by a factor of 4.

Figure 17C:
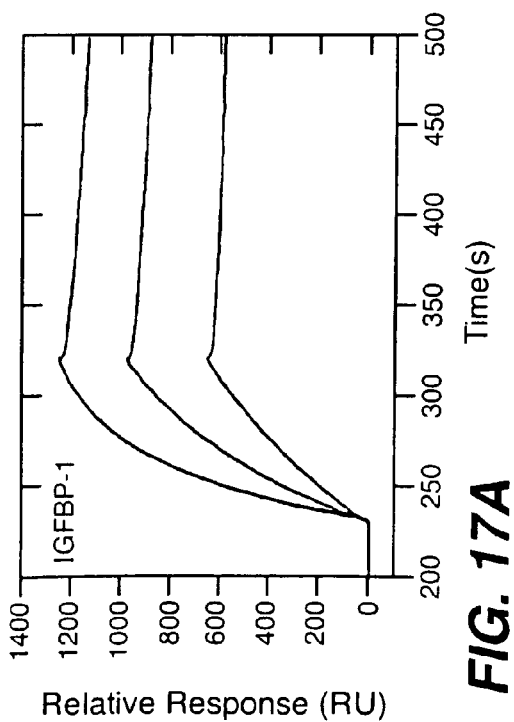
Figure 17D:
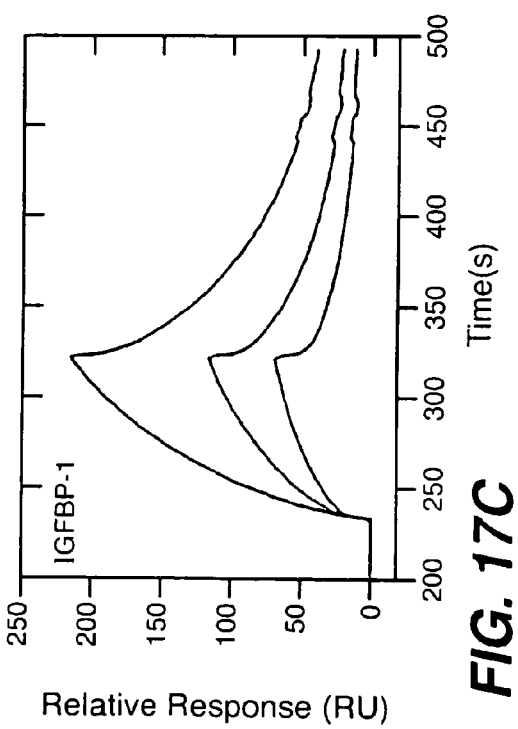

It has been shown that mutations in the first α-helical region have a destabilizing effect on the IGF-protein structure (Jansson et al., *Biochemistry*, 36: 4108-4117 (1997)). Without being limited to any one theory, it is believed that the g3 fusion protein on the surface of the phage might be more stable than the refolded, purified soluble protein. This is supported by the BIACORE™ results obtained for F25A and F49A, two residues located outside the structurally sensitive N-terminal helix. The respective changes in $K_D$ and $IC_{50}$ values are in excellent agreement for these two mutants (Table XIV). The differential effect of F49A on binding to the IGFBP's was confirmed by the BIACORE™ analysis. A 70-fold decrease in affinity was measured for IGFBP-1 binding (FIG. 17C; Table XIV), whereas IGFBP-3 binding was reduced only 4-fold (FIG. 17D; Table XIV).

TABLE XIV

Kinetic Parameters for the Interaction of Purified IGF-1 Variants with IGFBP-1 and -3 Determined by BIACORE ™ Analysis[a]

| | $k_a$ ($\times 10^4$ $M^{-1}s^{-1}$) | $k_d$ ($\times 10^4$ $s^{-1}$) | $K_D$ (nM) | relative $K_D$ | relative $IC_{50}$ |
|---|---|---|---|---|---|
| Binding to IGFBP-1 | | | | | |
| IGF-1 WT | 3.2 ± 0.2 | 4.1 ± 0.2 | 13.0 ± 1.0 | 1.0 | 1.0 |
| G1S-A70V | 3.2 ± 0.2 | 4.5 ± 0.01 | 14.0 ± 0.7 | 1.1 | 1.0 |
| T4A | 1.9 ± 0.2 | 16.7 ± 1.6 | 90.0 ± 11.0 | 6.9 | 2.4 |
| V11A | 1.9 ± 0.1 | 12.3 ± 0.6 | 66.5 ± 4.5 | 5.1 | — |
| F16A | 1.9 ± 0.6 | 60.3 ± 4.5 | 321 ± 98 | 25 | 6.0 |
| F25A | 1.5 ± 0.5 | 49.0 ± 5.7 | 323 ± 107 | 25 | 22 |
| R36A | 4.0 ± 0.2 | 5.6 ± 0.2 | 13.9 ± 0.8 | 1.1 | — |
| P39A | 3.1 ± 0.2 | 4.2 ± 0.1 | 13.6 ± 0.8 | 1.0 | — |
| F49A | 1.26 ± 0.8 | 115 ± 1.5 | 913 ± 551 | 70 | >100 |
| Binding to IGFBP-3 | | | | | |
| IGF-1 WT | 3.2 ± 0.5 | 4.7 ± 0.8 | 1.5 ± 0.3 | 1.0 | 1.4 |
| G1S-A70V | 2.9 ± 0.8 | 6.3 ± 0.5 | 2.2 ± 0.6 | 1.5 | 1.0 |
| T4A | 1.8 ± 0.6 | 5.5 ± 0.1 | 3.1 ± 1.0 | 2.1 | 1.1 |
| V11A | 3.1 ± 0.5 | 20.9 ± 2.8 | 6.7 ± 1.3 | 4.5 | — |
| F16A | 1.1 ± 0.4 | 11.4 ± 2.7 | 10.3 ± 4.7 | 6.9 | 1.8 |
| F25A | 1.5 ± 0.5 | 11.8 ± 0.1 | 7.7 ± 0.3 | 5.1 | 4.9 |
| R36A | 4.0 ± 0.1 | 4.7 ± 0.2 | 1.2 ± 0.1 | 0.8 | — |
| P39A | 2.7 ± 0.2 | 6.0 ± 0.3 | 2.2 ± 0.2 | 1.5 | — |
| F49A | 2.7 ± 0.7 | 17.1 ± 0.9 | 6.3 ± 1.7 | 4.2 | 3.6 |

[a]The relative changes in dissociation constants ($K_{D\ mut}/K_{D\ wt}$) are compared to the relative $IC_{50}$ values ($IC_{50\ mut}/IC_{50\ G1S-A70V}$) determined by phage display (Table XIII).

Role of the N-terminal IGF-1 Residues

Surprisingly, the IGFBP-3 interaction was generally much less affected by the alanine substitutions than was the interaction with IGFBP-1, despite the fact that IGFBP-3 binds IGF-1 with approximately 10-fold higher affinity. Apart from P63A, no alanine mutant exhibited a >6-fold reduction in IGFBP-3 affinity (FIG. 14; Table XIII).

It had previously been shown in biosensor experiments that des(1-3)-IGF-1 binds IGFBP-3 with 25-fold reduced affinity (Heding et al., supra). This naturally-occurring form of IGF-1 lacks the first three N-terminal residues and shows increased mitogenic potency, presumably due to its reduction in IGFBP-binding (Bagley et al., *Biochem. J.*, 259: 665-671 (1989)). Since none of the first three amino acid side chains seem to contribute any energy to the binding of IGFBP-3 (Table I) but nevertheless des(1-3)-IGF-1 is compromised in IGFBP-3 binding, without being limited to any one theory, it is hypothesized that backbone interactions might be involved.

This hypothesis was tested by displaying on phage a triple alanine mutant (Ala(1-3)-IGF-1), substituting the first three N-terminal amino acids. If the backbone in that region contributes to the interaction with IGFBP-3 this mutant should be able to bind. Binding to IGFBP-1, however, should be reduced due to the lack of the E3 side chain (Table I). As a control the des(1-2)-IGF-1 mutant was generated, testing for any potential backbone interactions with IGFBP-1 at positions 1 and 2. As expected, Ala(1-3)-IGF-1 showed a decreased IGFBP-1 affinity similar to E3A but no change in IGFBP-3 affinity (FIG. 14; Table XIII). For des(1-2)-IGF-1, no difference in affinity was observed for both binding proteins. Combined with the observations on des(1-3)-IGF-1 (Heding et al., supra), these results suggest, without limitation to any one theory, that the peptide backbone between residue 3 and 4 of IGF-1 mediates important interactions with IGFBP-3.

Figure 18A:
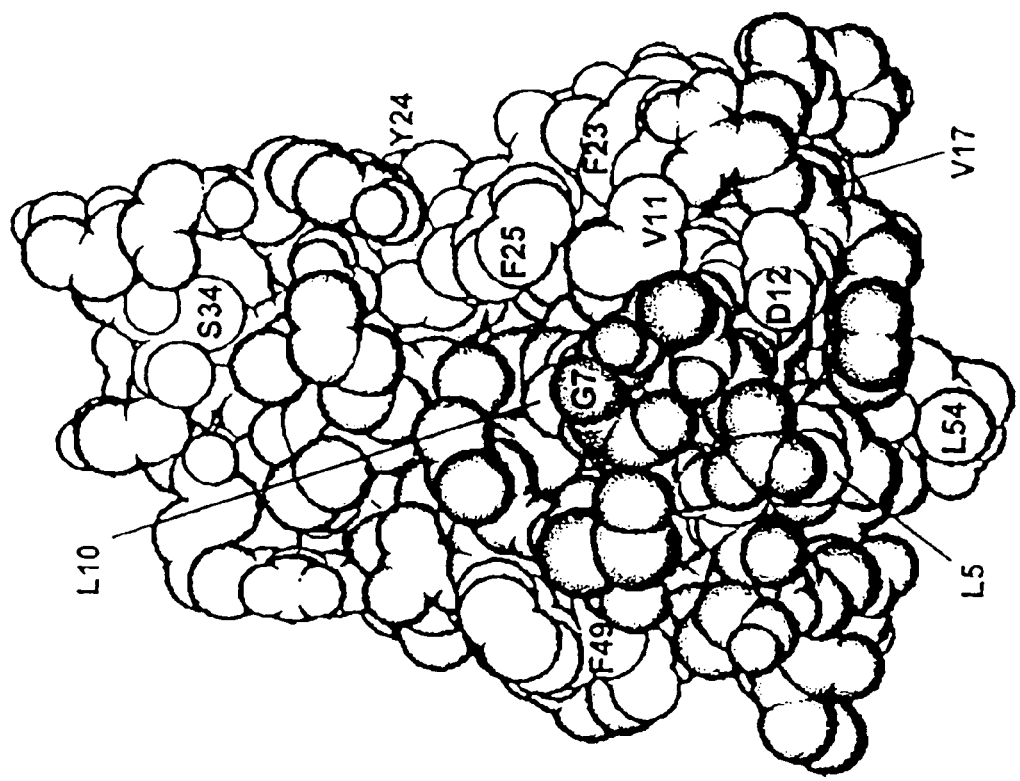
FIGS. 18A-18B show a model of the functional binding epitopes for IGFBP-1 and IGFBP-3, respectively, on the surface of IGF-1. Amino acid side chains were classified according to their relative contribution in binding energy (Table I) and colored as follows: no effect (grey); 2-5 fold loss of apparent affinity (yellow); 5-10 fold (orange); 10-100 fold (bright red); >100 fold (dark red). If available, numbers from phage ELISA experiments in Table I below were used. BIACORE™ surface-plasmon-resonance device data were used instead for V11A, R36A, and P39A variants (Table II). The NMR structure of IGF-1 (Cooke et al., *Biochemistry*, 30: 5484, (1991)) was represented using the molecular modeling program INSIGHT II™ (MSI, San Diego, Calif.). The binding epitope for IGFBP-1 (FIG. 18A) is located on the "upper" and "lower" face of the N-terminal helix (residues 8-17), connected by the energetically-important residue F49. For IGFBP-3 (FIG. 18B), individual IGF-1 side chains contribute very little binding energy. The binding epitope has shifted away from the N-terminus and newly includes G22, F23, Y24.
Figure 18B:
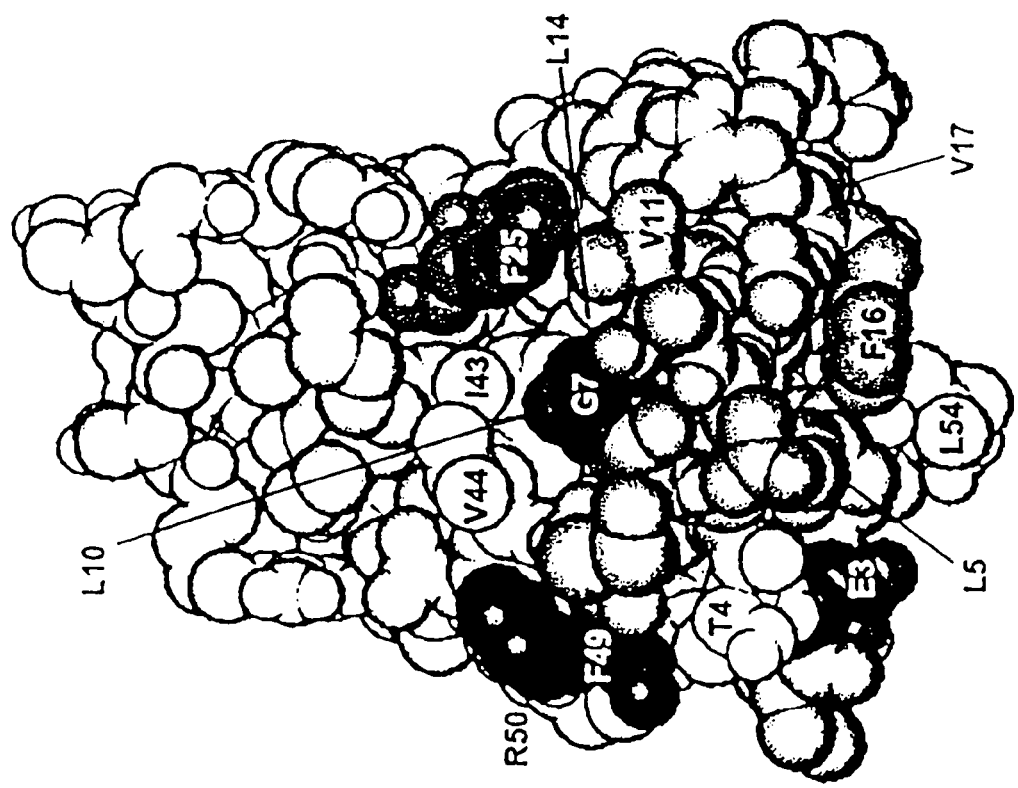

Discussion:

The functional IGFBP-1 and IGFBP-3 binding epitopes on the surface of IGF-1 have been probed by alanine-scanning mutagenesis. Both binding epitopes are illustrated in FIG. 18. Individual IGF-1 side-chain interactions play a much more important role for binding to IGFBP-1 than to IGFBP-3. Two major binding patches are found for IGFBP-1 (FIG. 18A). One is situated on the upper face of the N-terminal helix (composed of G7, L10, V11, L14, F25, I43, and V44) and one the lower face (composed of E3, T4, L5, F16, V17, and L54). These two binding patches are bridged by F49 and R50. For IGFBP-3, the binding epitope is more diffuse and has shifted to include G22, F23, and Y24 (FIG. 18B). Binding of IGFBP-3 is generally much less sensitive to alanine substitutions. In fact, the biggest reduction in affinity (apart from P63A, see below) is a 6-fold decrease seen for G7A. This result is intriguing since IGFBP-3 binds with 10-fold higher affinity to IGF-1 than does IGFBP-1. Most probably, without limitation to any one theory, interactions originating from the IGF-1 main chain backbone are contributing to the binding of IGFBP-3. This hypothesis is further substantiated by the experiments with the Ala(1-3)-IGF mutant. While the single and triple alanine substitutions have no effect on IGFBP-3 binding, deletion of the first three amino acids resulted in a 25-fold decrease in affinity (Bagley et al., supra; Clemmons et al., *Endocrinology*, 131: 890-895 (1992); Heding et al., supra). In summary, IGF-1 uses different binding modes to associate with IGFBP-1 and IGFBP-3: a few amino acid side-chain interactions are important for binding to IGFBP-1, while backbone interactions seem to play a major energetic role for binding to IGFBP-3.

A recent publication has investigated the binding epitope on IGF-1 for IGFBP-1 by heteronuclear NMR spectroscopy (Jansson et al., *J. Biol. Chem.*, 273: 24701-24707 (1998)). The authors found that the IGF-1 residues 29, 30, 36, 37, 40, 41, 63, 65, and 66 amongst others experienced chemical shift perturbations upon complexation with IGFBP-1 at 30EC. Furthermore, Jansson and co-workers identified R36, R37, and R50 to be part of the functional binding epitope and tested those alanine mutants in BIACORE™ experiments. The largest change in affinity observed by these authors was a 3-fold decrease for R50A. However, due to the structural flexibility of IGF-1 already observed in the first NMR study of the hormone (Cooke et al., supra), Jansson et al. were unable to completely assign many residues in the NMR spectrum, including F49.

In similar studies of protein-protein interfaces it was found that only a few side-chain residues contribute to the bulk of free-binding energy (Clackson and Wells, *Science*, 267: 383-386 (1995); Kelley et al., *Biochemistry*, 34: 10383-10392 (1995)). The same holds true for the IGF-1GFBP-1 interaction. However, here, as it was noticed for tissue factor binding to factor VIIa, the magnitude of the free energy of binding ())G) values derived from important side chains is smaller than in the case of growth hormone (Kelley et al., supra). The residues with predominant ))G contributions were not clustered on the IGF-1 surface like in the growth hormone-receptor interface (Clackson and Wells, supra), but still formed a continuous IGFBP-1 binding epitope (FIG. 18A). In contrast, the IGFBP-3 binding epitope on IGF-1 was discontinuous, and side chains contributed very modest individual binding energies.

Substitution of P63 by alanine in IGF-1 results in a decreased affinity for both binding proteins that cannot be measured in the concentration range used in the competition phage ELISA's. However, residue P63 is located on the opposite side of the IGF-1 molecule with respect to the main binding epitope. Furthermore, it has been noticed that alanine substitutions of glycines and prolines can lead to structural changes (Di Cera, supra). In addition, Jansson et al., 1998, supra, concluded that the C-terminal part of IGF-1 is not involved in direct IGFBP-1 contacts, but rather undergoes indirect conformational changes upon complex formation. An extensive characterization of antibody binding sites on IGF-1 has been carried out by Mafies et al., *Endocrinology*, 138: 905-915 (1997). They showed simultaneous binding of IGFBP-1 or -3 to IGF-1 in complex with antibodies recognizing the C-terminal D-domain. These results further support earlier observations that the D-domain, beginning with residue P63, is not involved in binding of IGFBP-1 or -3 (Bayne et al., supra, 1988).

The major discrepancy between an $IC_{50}$ ratio obtained by phage ELISA and a result obtained using the BIACORE™ surface-plasmon-resonance device was observed with residue F16. As already mentioned substitution of this residue by alanine induced structural changes in the IGF-1 molecule (Jansson et al., supra, 1997). The same effect was seen with the $K_D$ in the BIACORE™ surface-plasmon-resonance results, but the affinity decrease was less pronounced in the phage ELISA experiments (see Table II). Both BIACORE™ surface-plasmon-resonance measurements used IGF-F16A that had been refolded during the purification procedure (Jansson et al., supra, 1997). In phage display, however, the protein of interest is translocated naturally by the secretion machinery of *E. coli*. The low protein abundance in monovalent phage display (<1 molecule per phage particle) may disfavor aggregation and misfolding. Additionally, fusing IGF-1 to the truncated g3 phage protein might exert a stabilizing effect on the native structure of the peptide.

The levels of IGFBP-3 are positively regulated by IGF-1. The role of IGFBP-1, in contrast, is less clear. This class of binding proteins is generally less abundant than IGFBP-3, and its levels are negatively regulated by insulin (Bach and Rechler, supra; Clemmons, supra, 1997; Jones and Clemmons, supra).

Based on the results herein, IGFBP-specific variants of IGF-1 are obtained. Combination of several alanine mutations generates a variant that binds IGFBP-1 very weakly while retaining high-affinity binding of IGFBP-3. The design of IGFBP-1 specific variants that no longer bind to IGFBP-3, can involve phage display of IGF-1 and the randomization of amino acids at specific positions (Cunningham et al., 1994, supra; Lowman and Wells, *J. Mol. Biol.*, 234: 564-578 (1993)).

Conclusion:

Residues in IGF-1 important for binding to IGFBP-1 and IGFBP-3 have been identified. Several residues were found that determine the binding specificity for a particular IGFBP. Recent publications (Loddick et al., *Proc. Natl. Acad. Sci. USA*, 95: 1894-1898 (1998); Lowman et al., supra, 1998) have reported animal studies where increased pools of bioavailable "free" IGF-1 were generated by displacing endogenous IGF-1 from binding proteins. IGFBP-specific IGF-1 variants may be used diagnostically and therapeutically as described herein.

Example 7

Characterization of Certain IGF-1 Analogs

Materials and Methods:
Construction of IGF-1 Analogs

In Example 6 (and in Dubaquié and Lowman, supra) IGF-1 analogs are identified in which binding affinity to IGFBP-1, IGFBP-3, or both binding proteins, was reduced. In particular, the total alanine-scanning mutagenesis of IGF-1 identified glutamic acid 3 (E3) and phenylalanine 49 (F49), as well as phenylalanine 16 (F16) and phenylalanine 25 (F25) to some degree, as specificity determinants for binding to IGFBP-1. Phage display alanine-scanning results suggested that both of the side chains at positions 3 and 49 selectively contribute considerable binding energy for complex formation with IGFBP-1 (~30-fold loss in affinity for E3A, ~100 fold for F49A), while their contribution in binding energy for IGFBP-3 is not detectable (E3A) or minor (~4-fold for F49A) (see Example 1 and Dubaquié and Lowman, supra).

Further improved specificity for IGFBP-3 was likely to be attained by cumulative mutation of IGF-1, because the effects of point mutations are often additive with respect to their contribution to the free energy of binding (Wells, Biochemistry 29: 8509 (1990)). Therefore, a double mutant of IGF-1, E3A/F49A, was constructed by combining point mutations E3A and F49A in a single molecule. Although F16A showed a smaller IGFBP-specificity effect (Example 1 and Dubaquié and Lowman, supra), the double mutant F16A/F49A was also constructed.

Also constructed was a new point mutant of IGF-1, Y31C, containing a single putative unpaired cysteinyl thiol, to facilitate site-specific immobilization of IGF-1 for binding assays. Y31C was chosen because it is outside the binding epitopes for IGFBP-1 and IGFBP-3 (Dubaquié and Lowman, supra). This immobilization technique ensures a uniform ligand population (Cunningham and Wells, *J. Mol. Biol.*, 234: 554 (1993)) for binding by the injected analyte (i.e., IGF binding protein). The advantage of this method over the previously-employed amine coupling is that the IGF-1 N-terminus is unblocked and free of any potential amine linkages to the chip matrix. This may be especially important for binding analysis of IGFBP-1, which is believed to interact with side chains of the IGF-1 N-terminus (Dubaquié and Lowman, supra). Y31C displayed on phage showed wild-type-like affinities for both IGFBP-1 and IGFBP-3, supporting the notion that the region around residue 31 is important in receptor binding, but forms no contact with the binding proteins (Bayne et al., *J. Biol. Chem.*, 264: 11004 (1988); Bayne et al., *J. Biol. Chem.*, 265: 15648 (1990)).

Single-alanine variants of IGF-1, including F49A, as well as the E3A/F49A double mutant, were expressed, purified, and refolded to give the appropriate disulfide isomer as judged by HPLC analysis (Example 1 herein and Dubaquié and Lowman, supra). These variants were tested in assays of specific binding-protein binding and receptor activation.

Results:
IGFBP-1 and IGFBP-3 Binding Affinity

The binding affinities of these variants for IGFBP-1 and IGFBP-3 were compared to that of wild-type IGF-1 using BIACORE™ surface-plasmon-resonance analysis. Kinetic experiments with IGFBP-3 binding to immobilized IGF-1 or variants (Table III) were carried out as described in Example 1 and in Dubaquié and Lowman, supra, and compared with F49A IGF-1 and wild-type IGF-1. In this assay, the double mutant E3A/F49A was about 20-fold weaker in binding affinity to IGFBP-3 than wild-type, and the double mutant F16A/F49A was about 66-fold weaker (Table XV).

TABLE XV

Kinetics of IGFBP-3 Binding to IGF-1

| Immobilized Protein | IGFBP-3 | | |
|---|---|---|---|
| | $k_a$ ($\times 10^5$ M$^{-1}$) | $k_d$ ($\times 10^{-4}$ s$^{-1}$) | $K_D$ (nM) |
| IGF-1* | 3.2 ± 0.5 | 4.7 ± 0.8 | 1.5 ± 0.3 |
| F49A IGF-1* | 2.7 ± 0.7 | 17.1 ± 0.9 | 6.3 ± 1.7 |
| E3A/F49A IGF-1 | 0.74 ± 0.4 | 13.3 ± 0.6 | 22.2 ± 10.3 |
| F16A/F49A IGF-1 | 0.4 ± 0.1 | 38.6 ± 2.7 | 99.0 ± 26.0 |

(*data from Table II of Example 1)

For measurements of IGFBP-1 binding to IGF-1, kinetics experiments were conducted using a single-cysteine IGF-1 variant, Y31C, that was immobilized onto the sensor chip surface via a disulfide linkage (BIACORE™ System Manual Supplement, 5a-1, Pharmacia (1991)). The results are consistent (Table XVI) with the binding affinity measured using wild-type IGF-1 immobilized via nonspecific amine coupling to the biosensor chip (Example 1 and Dubaquié and Lowman, supra).

TABLE XVI

Kinetics of IGFBP-1 Binding to IGF-1

| Immobilized Protein | IGFBP-1 | | |
|---|---|---|---|
| | $k_a$ ($\times 10^4$ M$^{-1}$) | $k_d$ ($\times 10^{-4}$ s$^{-1}$) | $K_D$ (nM) |
| Y31C IGF-1 | 3.9 ± 0.4 | 3.8 ± 0.1 | 10.0 ± 1.1 |
| IGF-1* | 3.2 ± 0.2 | 4.1 ± 0.2 | 13.0 ± 1.0 |

(*data from Table XIV of Example 6)

The binding of F49A and E3A/F49A to IGFBP-1 was too weak for accurate kinetic measurements. Therefore, a competitive binding assay (WO 98/45427 published Oct. 15, 1998) was performed to estimate the corresponding affinities. The single-cysteine IGF-1 variant, Y31C, was used that was immobilized onto a BIACORE™ biosensor chip surface as described above. Competitive binding experiments yielding half-maximal inhibitory concentration values (IC$_{50}$) were conducted as follows: 50 nM IGFBP-1 was incubated with a dilution series of the desired IGF variant. These protein mixture solutions were injected at 5 µL/min over a B1 chip containing cysteine-coupled IGF-1 Y31C (200 response units). The amount of bound IGFBP-1 was determined by subtracting non-specific binding after a 20-minute injection and plotted against the IGF variant concentration (FIG. 19). The results are shown in Table XVII.

TABLE XVII

Inhibition of IGFBP-1 Binding to Immobilized Y31C IGF-1

| Immobilized Protein | Competing Protein | IGFBP-1 IC$_{50}$ (µM) |
|---|---|---|
| Y31C IGF-1 | F49A IGF-1 | 1.6 ± 0.2 |
| Y31C IGF-1 | E3A/F49A IGF-1 | 64 ± 9 |

Compared to wild-type IGF-1, F49A and E3A/F49A had severely decreased binding affinities for IGFBP-1. F49A bound to IGFBP-1 with an IC$_{50}$ of 1.6±0.2 µM (Table XVII), while preserving a high-affinity dissociation constant ($K_D$) of 6.3±1.7 nM for IGFBP-3 (Table XV). Binding of E3A/F49A to IGFBP-1 was found to be even weaker, with an estimated IC$_{50}$ of 64±9 µM (Table XVII), while having only moderately reduced affinity ($K_D$=22.2±10.3 nM) for IGFBP-3 (Table XV). These in vitro measurements suggest that neither IGF variant should stably associate with IGFBP-1 under physiological conditions.

KIRA Assays of IGF Type I Receptor Activation

The Kinase Receptor Activation Assay (KIRA) specifically and quantitatively monitors the extent of cytoplasmic IGF receptor phosphorylation upon extracellular stimulation by ligand (Sadick et al., *J. Pharm. Biomed. Analysis*, 19 (6): 883-891 (1999)). Several IGF variants, G1S/A70V, T4A, V11A, F16A, F25A, F16A/F49A, R36A, P39A, and F49A, were tested in single-concentration assays of receptor activation. The IGFBP-1 and IGFBP-3 binding affinities of these variants, except for F16A/F49A, are set forth in Table XIV and in Dubaquié and Lowman, supra. Table XVIII summarizes the relative affinities and specificities from BIA-CORE™ surface-plasmon-resonance measurements.

Figure 20A:
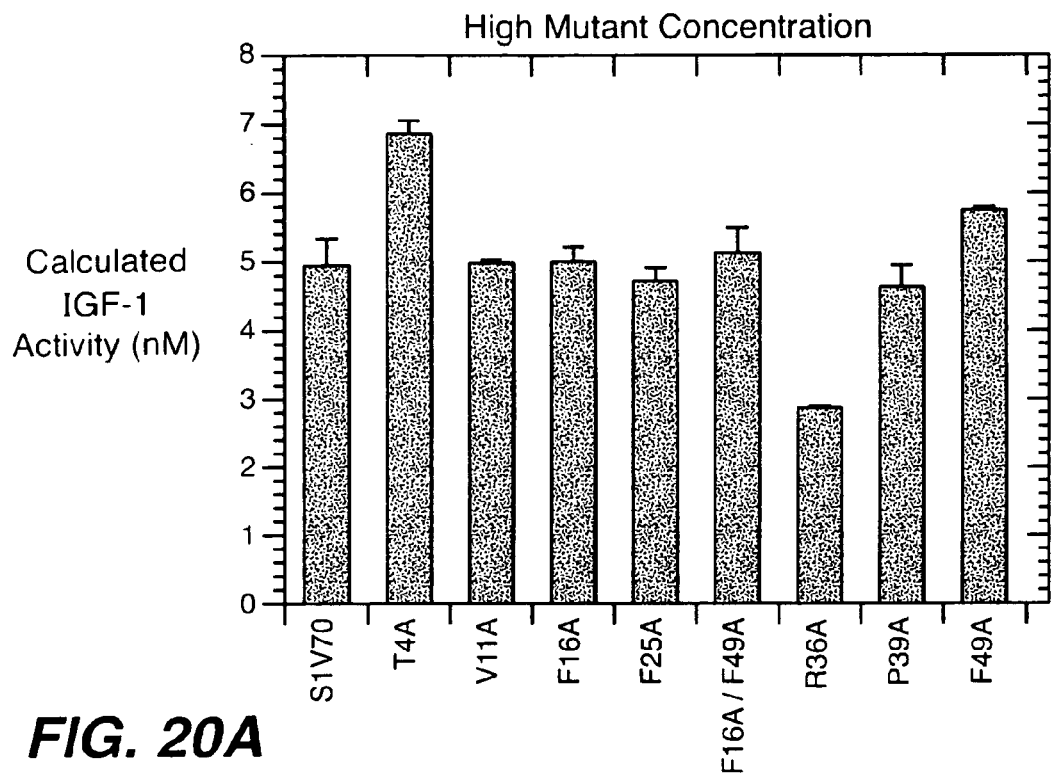
FIGS. 20A and 20B show, respectively, the calculated IGF-1 activity in nM units for several IGF-1 variants at 13 nM (high) and 1.3 nM (low) variant concentrations using IGF-1 KIRA optical density analysis. The signal obtained for each IGF variant was compared to that of a standard-dilution series of wild-type IGF-1, and reported in terms of an apparent IGF-1 concentration corresponding to the observed activity.
Figure 20B:
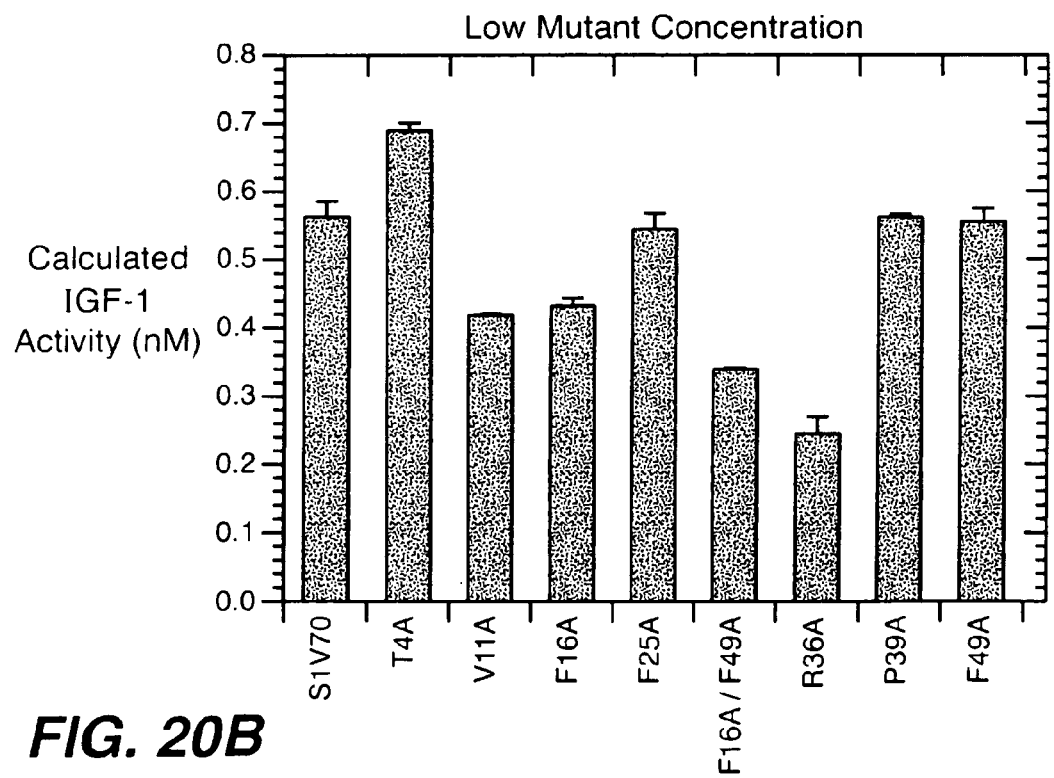

For the KIRA assay, variant concentrations were roughly estimated at 13 nM ("high concentration") or 1.3 nM ("low concentration"), based on optical density measurements. The signal obtained for each IGF variant was compared to that of a standard-dilution series of wild-type IGF-1, and reported in terms of an apparent IGF-1 concentration corresponding to the observed activity in the KIRA assay (FIGS. 20A and 20B). Although exact relative potencies were not measured, these results show that all tested mutants maintain the ability to activate the IGF type I receptor.

TABLE XVIII

Relative IGFBP-1 and IGFBP-3 Affinities of IGF-1 Variants.

| IGF-1 Variant | IGFBP-1 $K_D$(mutant)/ $K_D$(IGF-1)) | IGFBP-3 $K_D$(mutant)/ $K_D$(IGF-1)) | Specificity Relative BP-1/ Relative BP-3 |
|---|---|---|---|
| G1S/A70V* | 1.1 | 1.5 | 0.7 |
| T4A* | 6.9 | 2.1 | 3.3 |
| V11A* | 5.1 | 4.5 | 1.1 |
| F16A* | 25 | 6.9 | 3.6 |
| F25A* | 25 | 5.1 | 4.9 |
| R36A* | 1.1 | 0.8 | 1.4 |
| P39A* | 1.0 | 1.5 | 0.7 |
| F49A* | 70 | 4.2 | 16.7 |
| F16A/F49A | ND | 65.6 | ND |

NDB, no detectable binding;
ND, not determined;
*data from Table XIV of Example 6)

Table XVIII shows that, in addition to F49A, F16A and F25A are both substantially reduced in affinity for IGFBP-1, but less so for IGFBP-3. Both still retain biological activity based on KIRA assays (FIG. 20).

Figure 21A:
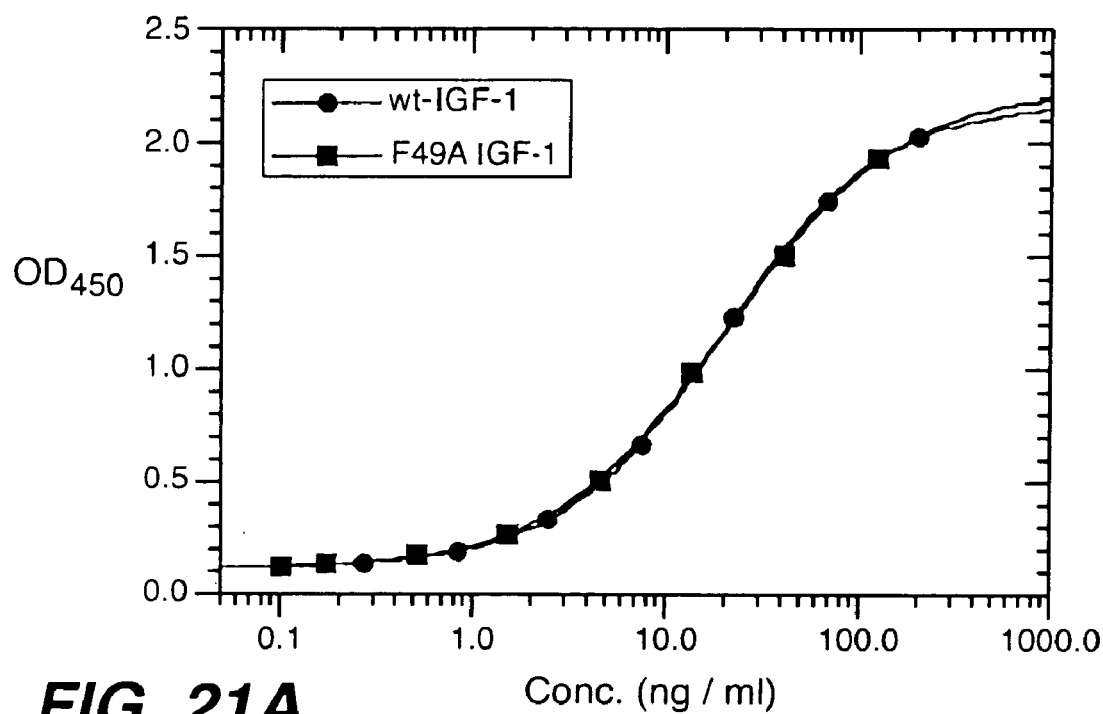
FIGS. 21A and 21B show IGF receptor activation curves for F49A IGF-1 (FIG. 21A) and E3A/F49A (FIG. 21B) as well as for wild-type IGF-1, as measured using serial dilutions in KIRA assays. The variants are represented by squares and the wild-type IGF-1 is represented by circles.
Figure 21B:
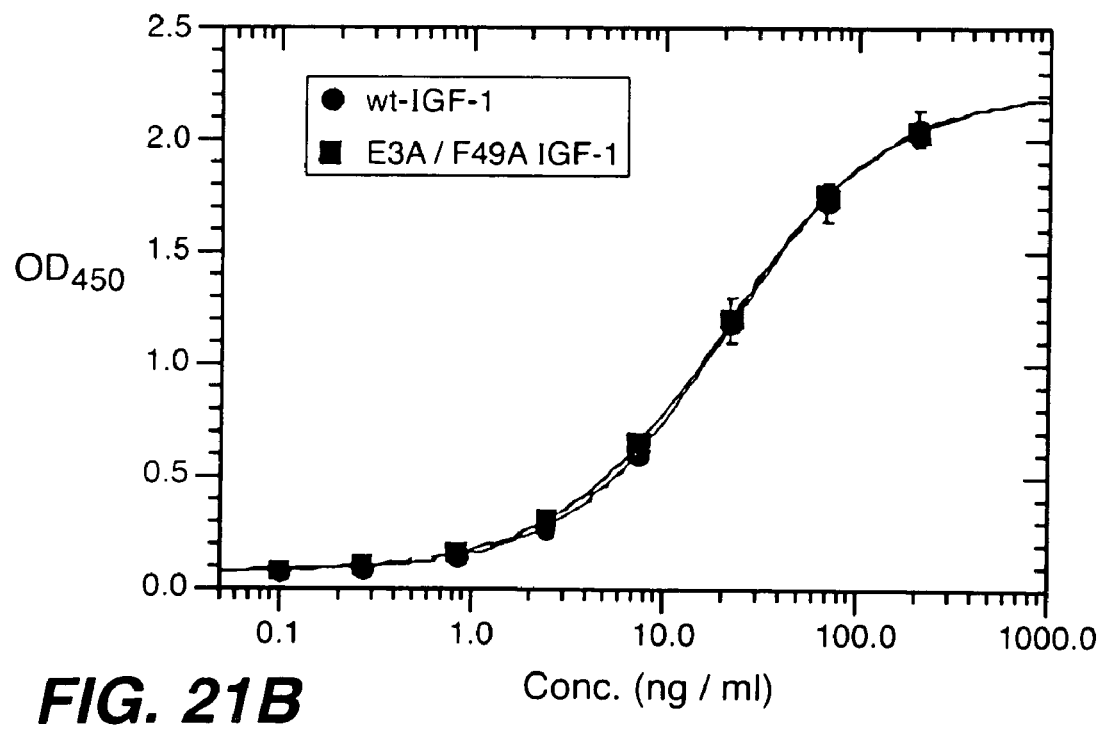

For determining relative potency of F49A and E3A/F49A, their ability to activate the type I IGF receptor was measured using serial dilutions in KIRA assays. As shown in FIGS. 21A-21B, both F49A and E3A/F49A display IGF receptor activation curves that are indistinguishable from wild-type IGF-1. The half-maximal effective concentrations ($EC_{50}$) were 20.0±1.3 ng/ml for F49A, 19.8±0.5 ng/ml for E3A/F49A, and 18.9±0.2 ng/ml and 19.8±0.6 ng/ml for wild-type IGF-1. These results strongly suggest that both IGF mutants are fully biologically active.

Blood Clearance and Renal Accumulation of IGF-1 Variants in Rats

Figure 22A:
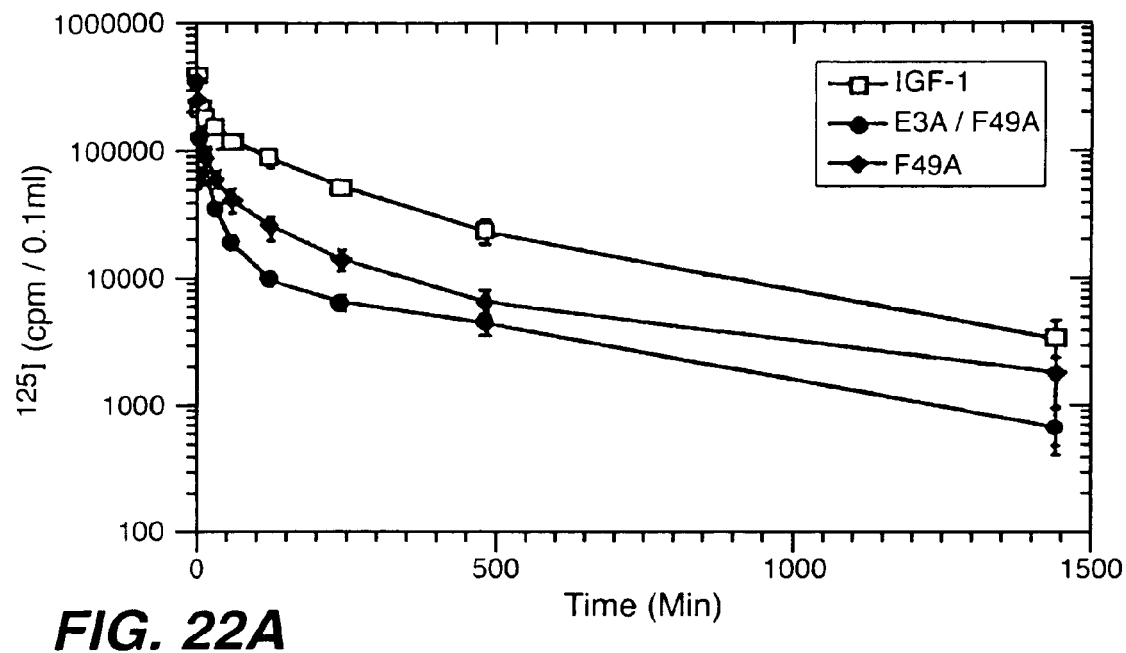
FIGS. 22A and 22B show an assessment of preliminary pharmacological properties of F49A and E3A/F49A IGF-1, radiolabeled and administered intravenously to rats.
Figure 22B:
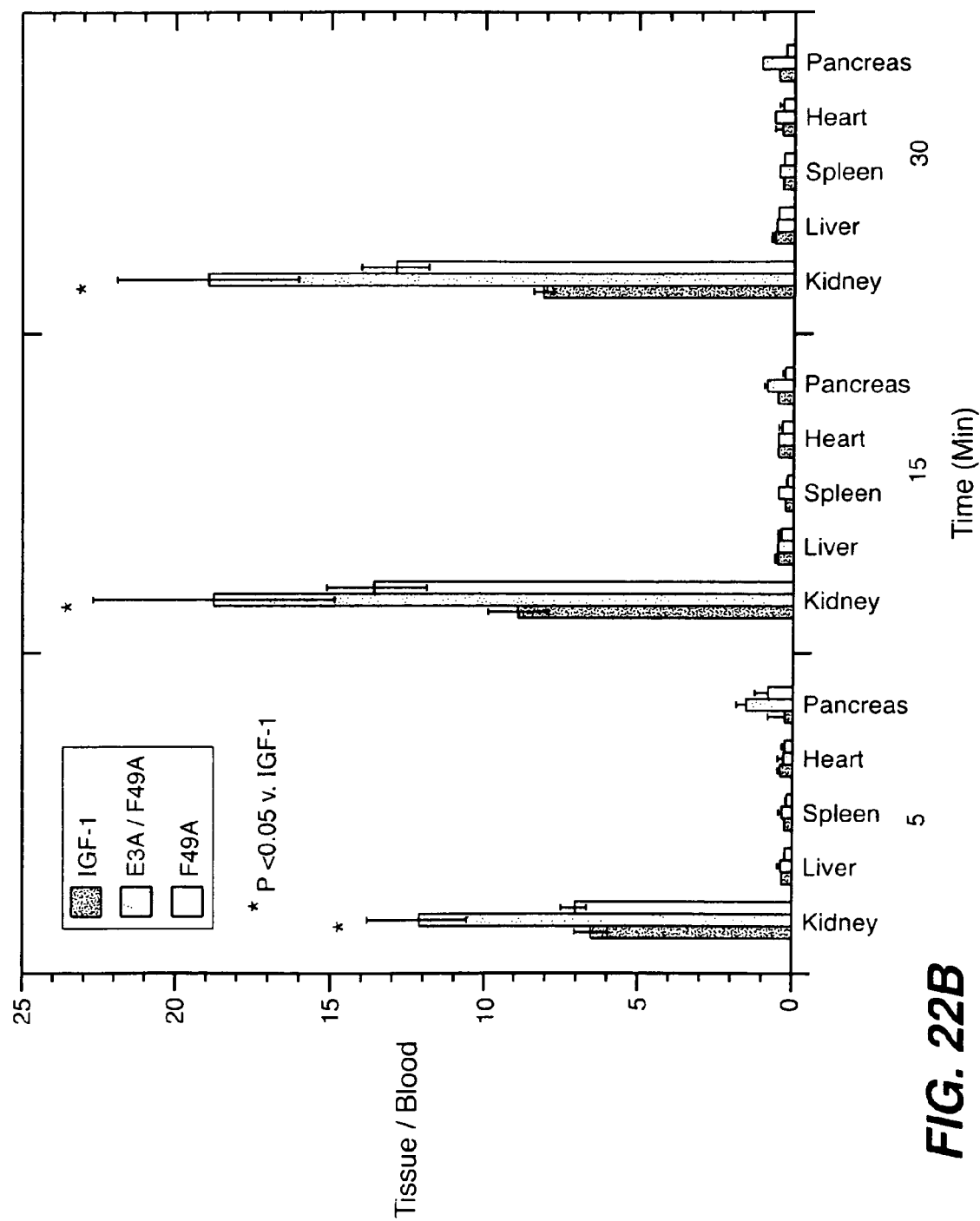
Figure 24:
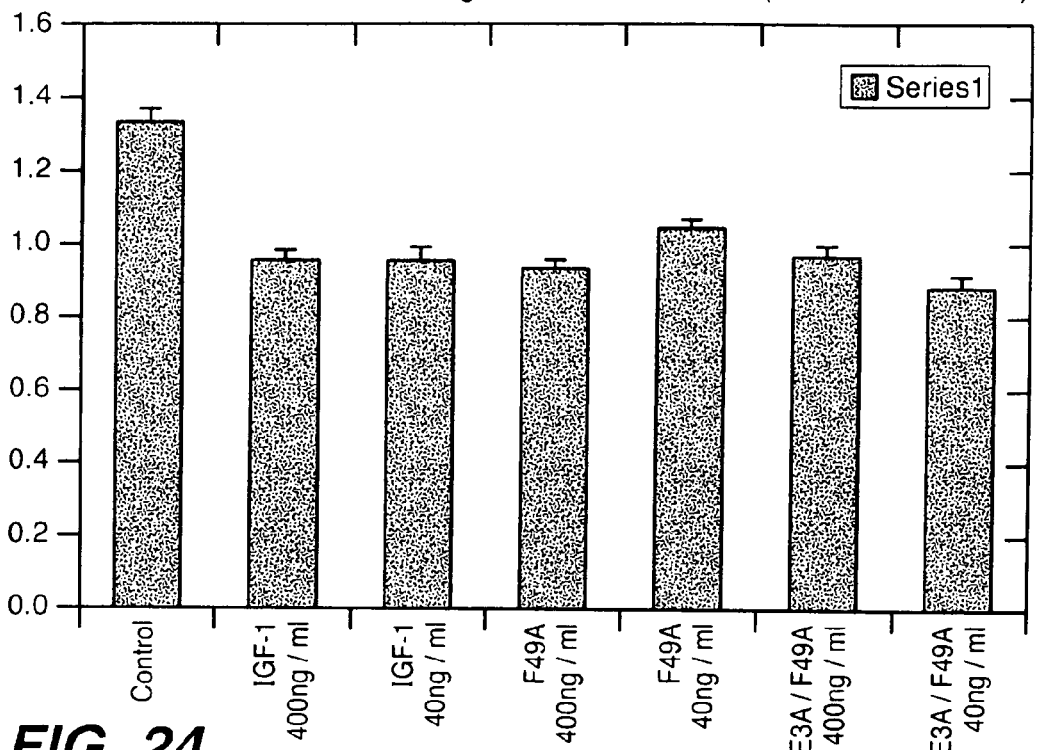
FIG. 24 is a bar graph showing the effect of control, wild-type IGF-1, F49A, and E3A/F49A (at a concentration of 40 or 400 ng/ml) on cartilage matrix breakdown (proteoglycan release at 72 hours).
Figure 25:
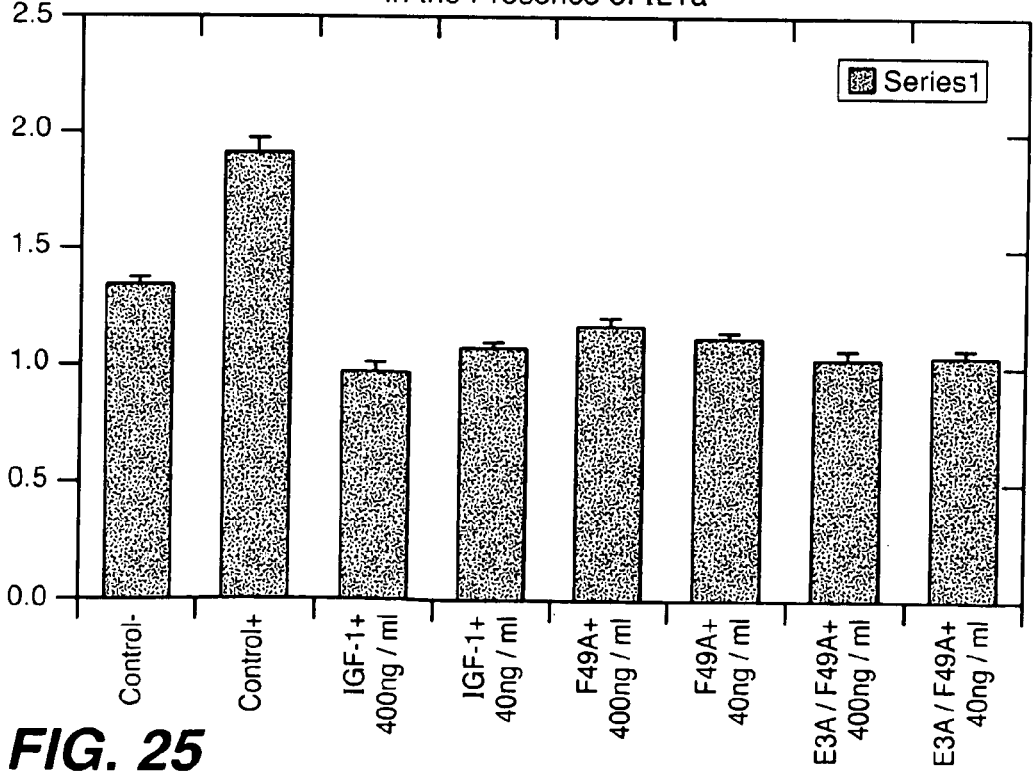
FIG. 25 is a bar graph showing the effect of wild-type IGF-1, F49A, and E3A/F49A (at a concentration of 40 or 400 ng/ml) on IL1α-induced cartilage breakdown at 72 hours.
Figure 26:
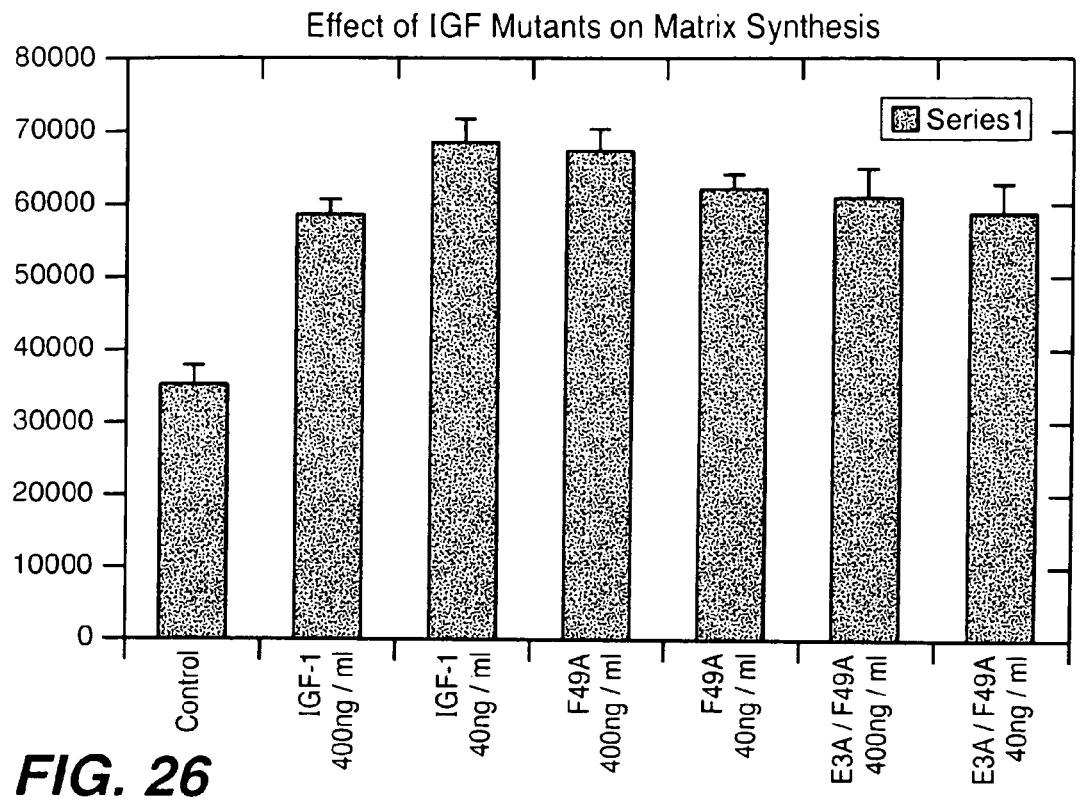
FIG. 26 is a bar graph showing the effect of control, wild-type IGF-1, F49A, E3A/F49A (at a concentration of 40 or 400 ng/ml) on matrix synthesis.
Figure 27:
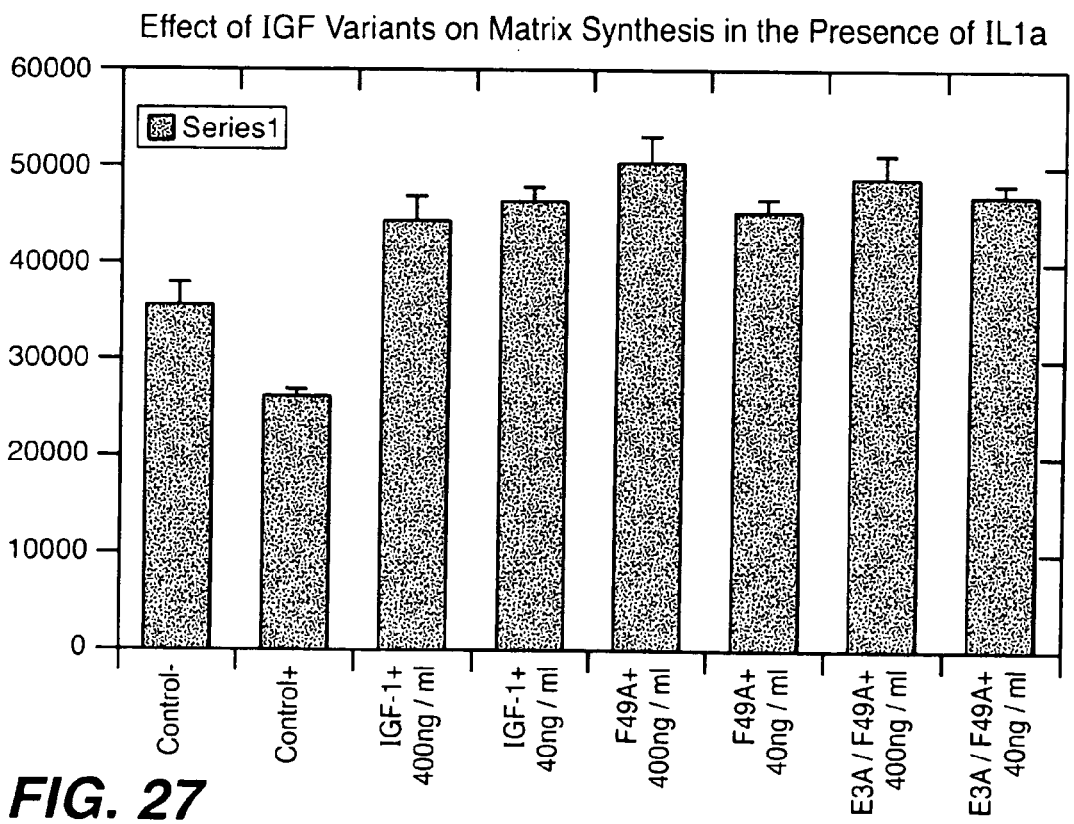
FIG. 27 is a bar graph showing the effect of wild-type IGF-1, F49A, and E3A/F49A (at a concentration of 40 or 400 ng/ml) on IL1α-induced inhibition of matrix synthesis.

To assess preliminary pharmacological properties of F49A and E3A/F49A IGF-1, both proteins were radiolabeled and administered intravenously to rats. FIG. 22A shows a time course of the rate at which both molecules are cleared from the blood of the animals. As expected due to their decreased IGFBP affinities, both variants were cleared at a faster rate compared to wild-type human IGF-1. Interestingly, the double mutant (E3A/F49A) was cleared faster than the single mutant (F49A), correlating well with the respective affinities for the major binding protein in the serum, IGFBP-3 (Table XV). FIG. 22B shows the tissue-to-blood ratio for the IGF variants in different organs. The majority of the radioactively-labeled IGF molecules were detected in the kidney, whereas radioactivity levels in the liver, spleen, heart, and pancreas were much lower. It is evident that the variants F49A and E3A/F49A accumulate at statistically significant higher levels in the kidney compared to wild-type IGF-1.

Circular Dichroism Analysis of IGF-1 Variants

Figure 23:
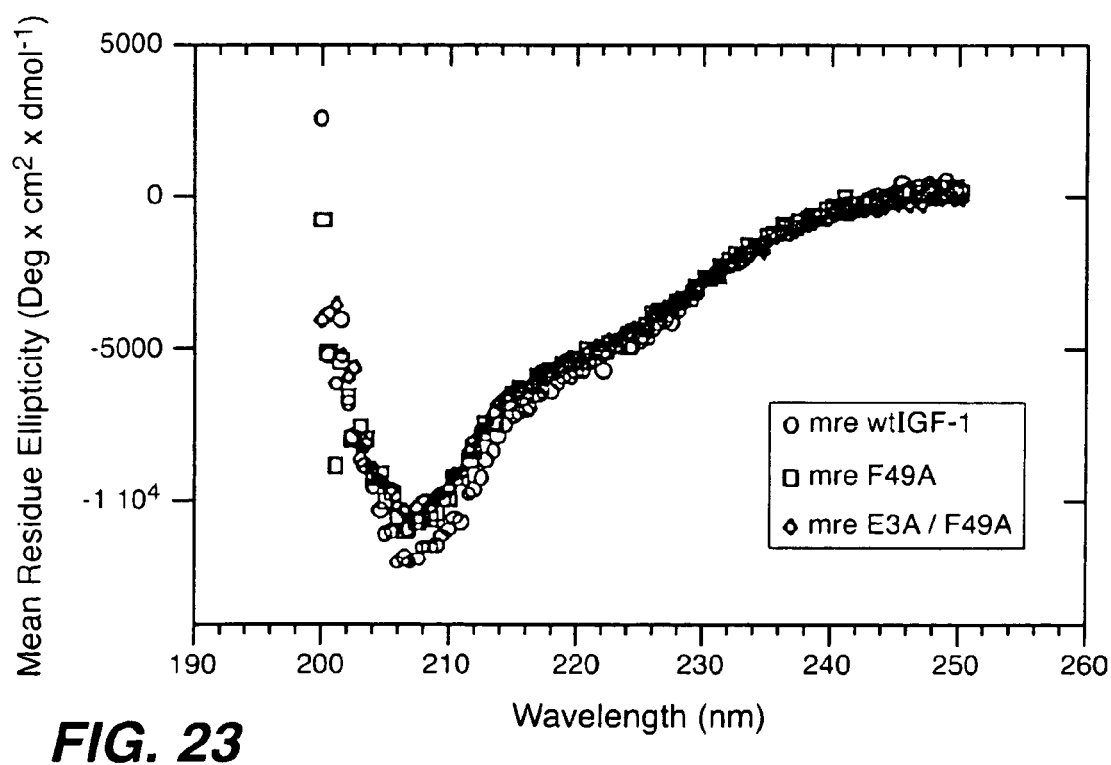
FIG. 23 shows circular dichroism spectra of wild-type IGF-1 (circles), F49A IGF-1 (squares), and E3A/F49A IGF-1 (diamonds).

The circular dichroism spectra of F49A and E3A/F49A IGF-1 were analyzed to test whether the introduced mutations cause major changes to the protein structure. Structural destabilization could lead to increased proteolytic susceptibility, providing an alternative explanation for the faster blood clearance rates of the IGF variants. As shown in FIG. 23, however, both mutants have virtually identical spectra to the one recorded for wild-type IGF-1. The CD spectra reveal elements of both V-helix and random coil, as expected from NMR spectroscopy of IGF-1 (Cooke et al., supra). The thermal stability of IGF-1 could not be determined accurately by circular dichroism, presumably due to the relatively high content (~30%) of random coil (Jansson et al., supra, 1997) already present at room temperature. The fact that the CD spectra of both variants showed no significant deviation from wild-type IGF-1 is an indication that the introduced mutations do not alter the overall structure of IGF-1.

Conclusion:

From the evidence presented above, it would be expected that the single and double mutants F16A, F16G, F16S, F25A, F25G, F25S, F49A, F49G, F49S, E3A/F49A, E3A/F49G, E3G/F49A, E3G/F49G, E3A/F49S, E3S/F49A, E3S/F49S, E3G/F49S, and E3S/F49G IGF-1 would be effective in treating cartilage disorders, since the alanine-substituted mutants exhibit a reduced affinity for IGFBP-1 without substantial loss of ability to bind to IGFBP-3 and are biologically active based on many tests. Further, such mutants are expected to be efficacious in treating cartilage disorders, since the alanine-substituted mutants only weakly bind to IGFBP-1 and there is disregulation in IGFBP-3 present in arthritic disorders (Martel-Pelletier et al., supra). It would also be expected that BP3-01 and BP3-15 would also be efficacious for this purpose in view of their role in displacing IGFBP-3 (Lowman et al., supra, 1998; WO 98/45427).

Example 8

Articular Cartilage Explant Assay of IGF-1 Analogs with Selectively Reduced Affinity for IGFBP-1 versus IGFBP-3

Introduction:

The experiments of this example examine both the synthetic and prophylactic potential of the IGF-1 analogs E3A/F49A and F49A on the cartilage matrix.

Materials and Methods:

Articular Cartilage Explants

The metacarpophalangeal joint of 18-24 month old cows was aseptically dissected, and articular cartilage was removed by free-hand slicing, taking care so as to avoid the underlying bone. The cartilage was minced, washed, and cultured in bulk for at least 24 hours in a humidified atmosphere of 95% air and 5% $CO_2$ in serum-free (SF) LG DMEM/F12 medium with 0.1% BSA, 100 U/ml penicillin/streptomycin (Gibco), 2 mM L-Glutamine, 0.1 mM MEM sodium pyruvate (Gibco), 20:g/ml gentamicin (Gibco) antibiotic, and 1.25 mg/L amphotericin B (Sigma) antibiotic. Articular cartilage was aliquoted into MICRONICS™ tubes (approximately 55 mg per tube) and incubated for at least 24 hours in the above media. Control (media alone), wild-type IGF-1, E3A/F49A, or F49A was then added to each tube (to a final concentration of 40 or 400 ng/ml as indicated). The media was harvested and changed at various time points (0, 24, 48 and 72 hours).

Proteoglycan Release

Medium harvested at various time points was assayed for proteoglycan content using the 1,9-dimethylmethylene blue (DMMB) colorimetric assay of Farndale and Buttle, Bio-

*chem. Bhiophys. Acta,* 883: 173-177 (1986). A standard curve was prepared of chondroitin sulfate ranging from 0.0 to 5.0:g.

Proteoglycan Synthesis

After the media change at 48 hours, $^{35}$S-sulfate (to a final concentration of 10:Ci/ml) was added to the cartilage explant cultures. After an additional 17 hours of incubation at 37° C., the amount of proteoglycans in the media was measured using the DMMB assay. The cartilage pieces themselves were washed twice with explant media and digested overnight at 50° C. in a 900:L reaction volume of 10 mM EDTA, 0.1 M sodium phosphate, and 1 mg/ml proteinase K (Gibco BRL). 600:1 of the digestion reaction was mixed (2:1) with 10% w/v cetylpyridinium chloride (Sigma) and centrifuged at 1000×g for 15 minutes. The supernatant was removed and formic acid (500:1, Sigma) was added to dissolve the pellets. The samples were then transferred to scintillation vials containing 10 ml scintillation fluid (ICN) and read in a scintillation counter.

Remaining Proteoglycan in Cartilage Tissues

After 72 hours, the remaining articular cartilage explants were digested as described above under Proteoglycan synthesis and assayed for proteoglycan content using the DMMB colorimetric assay (referenced above under Proteoglycan release).

Nitric Oxide Assay

Articular cartilage media, saved from the cartilage explants at various times (24, 48, and 72 hours), was mixed with 10:l 0.05 mg/ml 2,3-diaminonapthalene (DAN) in 0.62M HCl and incubated at room temperature for 10-20 minutes in the dark. The reaction was terminated with 5:l of 2.8N NaOH. The amount of fluorescence of 2,3-diamionaphthotriazole was measured with a CYTOFLOR™ fluorescent plate reader at 365-nm excitation at 409-nm emission.

Results:

The data presented in FIGS. 24-27 show that the two IGF-1 analogs tested decrease cartilage matrix breakdown (as measured by proteoglycan release), block the induction of cartilage matrix breakdown by IL-1∀, induce cartilage matrix synthesis (as measured by proteoglycan synthesis), and prevent inhibition of matrix synthesis by IL-1∀.

These effects are similar to those of wild-type IGF-1. However, since human IGF-1 is employed with bovine tissue, the species differences may mask an inhibitory effect of endogenous binding proteins on wild-type IGF-1 activity.

Figure 28:
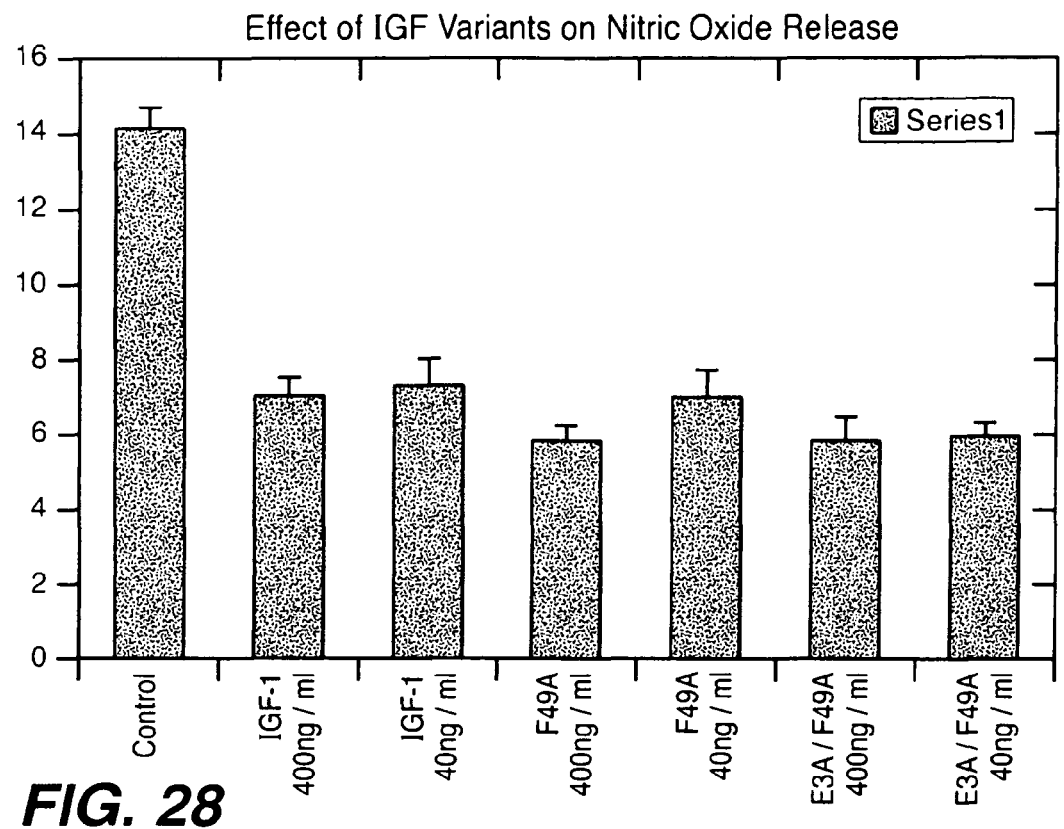
FIG. 28 is a bar graph showing the effect of control, wild-type IGF-1, F49A and E3A/F49A (at a concentration of 40 or 400 ng/ml) on nitric oxide release.
Figure 29:
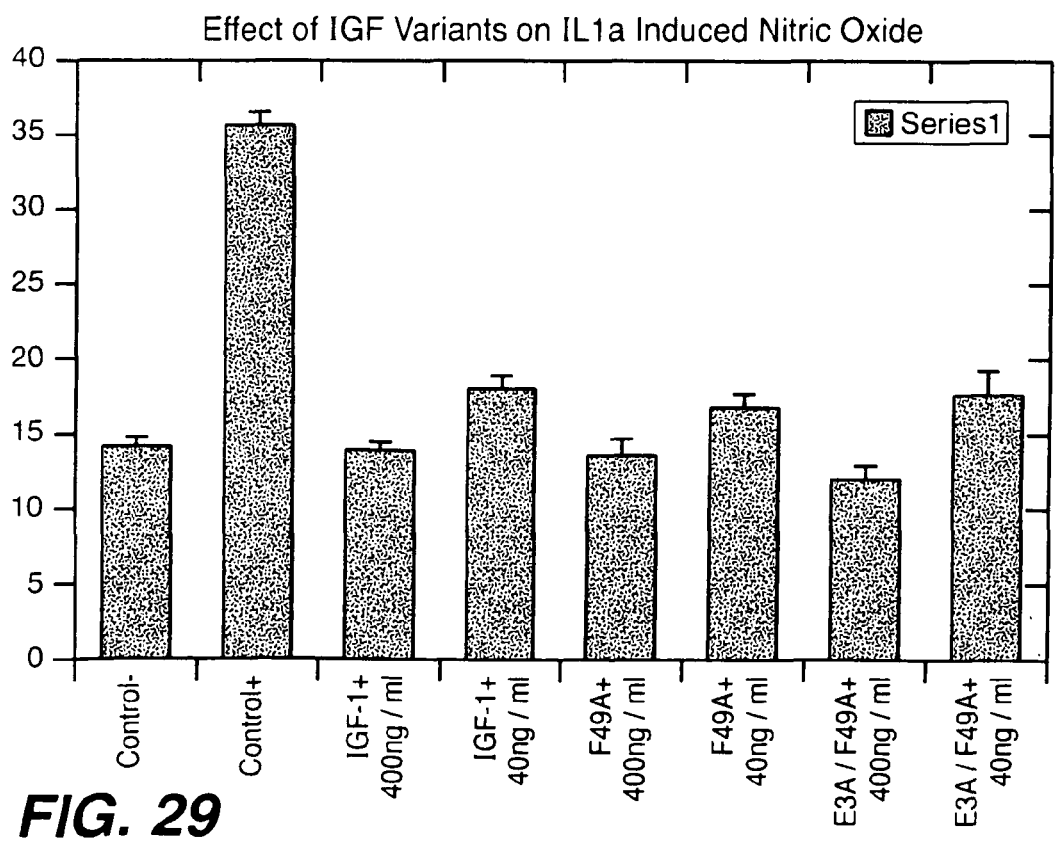
FIG. 29 is a bar graph showing the effect of wild-type IGF-1, F49A, and E3A/F49A (at a concentration of 40 or 400 ng/ml) on IL1α-induced nitric oxide production.

The IGF-1 analogs significantly decreased nitric oxide release (FIG. 28). In addition, the IGF-1 analogs blocked induction of nitric oxide by IL-1∀ (FIG. 29).

Discussion:

It is shown herein that IGF-1 analogs are capable of inhibiting matrix breakdown, stimulating new matrix synthesis, and inhibiting nitric oxide release. In addition, these IGF-1 analogs inhibit the detrimental effects of interleukin 1, which is elevated in diseased joints.

The role of nitric oxide in breakdown of articular cartilage, especially the destruction associated with osteoarthritis has been described in Amin et al., *Curr. Opin. Rheum.*, 10: 263-268 (1998). Since nitric oxide also has effects on other cells, the presence of nitric oxide within the joint could increase vasodilation and permeability, potentiate cytokine release by leukocytes, and stimulate angiogenic activity by monocyte-macrophages. Normal cartilage does not produce nitric oxide unless stimulated with cytokines such as IL-1, while osteoarthritic cartilage explants continue to release nitric oxide for over 3 days in culture despite the absence of added stimuli. Thus, production of nitric oxide by cartilage correlates with a diseased state, and since nitric oxide appears to play a role in both the erosive and the inflammatory components of joint diseases, a protein or peptide that decreases nitric oxide production would likely be beneficial for the treatment of degenerative cartilagenous disorders. In fact, in vivo animal models suggest that inhibition of nitric oxide production reduces progression of arthritis (Pelletier et al., *Arthritis Rheum.,* 41(7): 1275-1286 (1998); van de Loo et al., *Arthritis Rheum.,* 41: 634-646 (1998); Stichtenoth and Frolich, *Br. J. Rheumatol.,* 37: 246-257 (1998)).

The assay described herein is based on the principle that 2,3-diaminonapthalene (DAN) reacts with nitrite under acidic conditions to form 1-(H)-naphthotriazole, a fluorescent product. As nitric oxide is quickly metabolized into nitrite ($NO_2^{-1}$) and nitrate ($NO_3^{-1}$), detection of nitrite is one means of detecting (albeit undercounting) the actual nitric oxide produced in cartilagenous tissue.

As described above, nitric oxide has detrimental effects on chondrocytes as well as other cell types within the joint. Since inhibition of nitric oxide has been shown to inhibit progression of arthritis in animals, the effect of the IGF analogs on nitric oxide further suggests that the tested IGF analogs would be protective for joint tissues in vivo. Finally, these analogs or the IGFBP displacer peptides are expected to have anabolic effects on tissues, such as arthritic cartilage, which are otherwise IGF-1 resistant.

In summary, two IGFBP-selective variants (F49A and E3AF49A) demonstrated a 700-fold and 80,000-fold apparent reduction in affinity for IGFBP-1, while preserving low nanomolar affinity for IGFBP-3, the major carrier of IGF-1 in plasma. Both variants displayed wild-type-like potency in cellular receptor kinase assays, stimulated human cartilage matrix synthesis, and retained their ability to associate with ALS in complex with IGFBP-3. Hence, the half-life of these variants is still determined by IGFBP-3, but their activity is no longer regulated by IGFBP-1. Furthermore, pharmacokinetic parameters and tissue distribution of these two IGF-1 variants in rats differed from wild-type IGF-1 as a function of their IGFBP affinities.

Example 9

Generation of IGF-1 Analogs with Selectively Reduced Affinity for IGFBP-3 Versus IGFBP-1 and Articular Cartilage Explant Assay therefor Introduction:

The IGFBPs are generally thought to inhibit the biological activity of IGF-1 by sequestering the growth factor into high-affinity complexes and thereby preventing its receptor association (Jones and Clemmons, *Endocr. Rev.* 16: 3-34 (1995)). The levels of IGFBP-3 (and IGFBP-4) were found to be increased in human inflammatory synovial fluid (Kanety et al., *J. Rheumatol.* 23: 815-818 (1996)). This change in IGFBP homeostasis is thought to contribute to the pathological condition by depriving cells from the IGF-1 survival signal. In this example IGF-1 molecules were generated with selectively reduced affinity for IGFBP-3, without altering activity on the IGF type I receptor. Such molecules would be predicted to be more biologically potent than wild-type IGF-1 in the presence of elevated pathophysiological IGFBP-3 levels. Furthermore, since IGFBP-3 is the major carrier of IGF-1 in serum, the half-life and biological distribution of such IGF-1 variants would presumably be drastically altered.

The binding epitopes of IGFBP-1 and IGFBP-3 have been mapped by alanine-scanning on the surface of IGF-1 (Dubaquié and Lowman, *Biochemistry,* 38: 6386-6396 (1999)). Each individual IGF-1 side-chain contributes only modest amounts of binding energy for IGFBP-3. Based on this observation it seems impossible to substantially decrease IGFBP-3 affinity by introducing only a few specific alanine mutations into IGF-1. A different strategy to disrupt protein-protein interactions involves the introduction of a charged residue into the binding interface, leading to electrostatic repulsion of the binding partners. It has been noted by Jansson et al. (*Biochemistry*, 36: 4108-4117 (1997)) that IGF-1 is an electrostatically polarized protein with a continuous negatively-charged patch at the N-terminus (including the B-region helix), while the C-region is mainly positively charged. Based on these observations residue D12 was selected, since it does not contribute any binding energy for IGFBP-1 and seems to be part of the structural IGFBP-3 binding epitope (Dubaquié and Lowman, supra). It was reasoned that replacing residue 12 with a positive charge would disrupt the continuous negatively-charged patch that might possibly be involved in the IGFBP-3 interaction.

Materials and Methods:

Generation of Analogs

Phage particles displaying IGF-1 variants in which the aspartate residue at position 12 was mutated to lysine (D12K) or arginine (D12R) were constructed as described in Dubaquié and Lowman, supra. Furthermore, these protein variants were expressed in *E. coli* and purified as described in Dubaquié and Lowman, supra.

Articular Cartilage Explants

The metacarpophalangeal joint of a six-month old pig was cultured as described above for bovine articular cartilage in Example 8. This explant was cultured in media alone or in media with D12K, D12R, or wild-type IGF-1 (at 10 nM) alone or in the presence of IL-1∀ at 1 ng/ml, as described above. Human explants were from patients undergoing joint replacement surgery. Articular cartilage was harvested, aliquoted (40-45 mg/tube) and cultured as above. Twenty-four hours later, explants were treated with 40 ng/ml IGF-1, F16A/F49A, E3A/F49A, or F49A, every day for five days. Fresh media was added on days 0, 1, 2, and 3. Matrix breakdown was determined by measuring the amount of proteoglycans in the media using the DMMB assay as set forth above. Matrix (proteoglycan) synthesis was determined by measuring $^{35}$S-sulfate uptake as set forth above.

Further, for comparison purposes, F49A, E3A/F49A, F16A/F49A, D12K, D12R, or wild-type IGF-1 (at 40 ng/ml) were tested for cartilage matrix synthesis in human tissue as described above. Human articular cartilage from diseased joints was cultured in media alone or with F49A, E3A/F49A, F16A/F49A, D12K, D12R or wild-type IGF-1 (at 40 ng/ml) and matrix synthesis was determined by measuring $^{35}$S-sulfate uptake as described above.

Figure 30A:
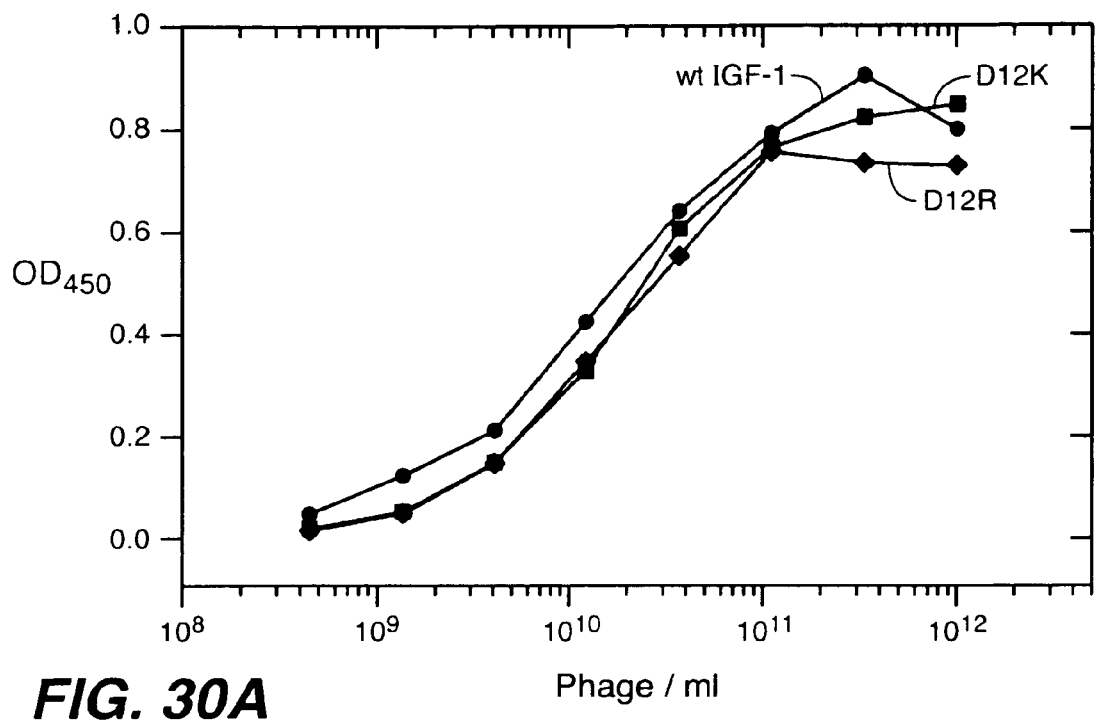
FIGS. 30A and 30B show the binding curves for phage particles displaying either wild-type IGF-1 (circles), D12K (squares), or D12R (diamonds) bound to immobilized IGFBP-1 (FIG. 30A) or IGFBP-3 (FIG. 30B).
Figure 30B:
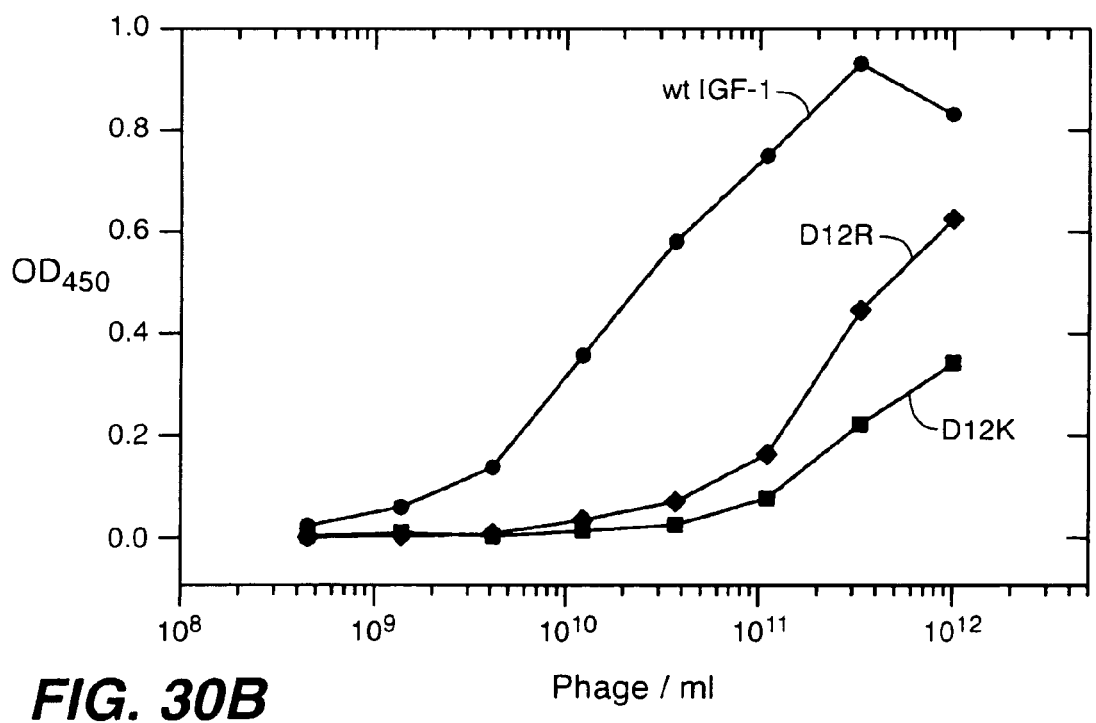

Results:

FIG. 30 shows the binding curves of phage particles displaying either wild-type IGF-1, D12K, or D12R bound to immobilized IGFBP-1 (FIG. 30A) or IGFBP-3 (FIG. 30B). The wild-type IGF-1 phage particles bound to IGFBP-1 or IGFBP-3 generated similar detection signal intensities. D12K and D12R, however, displayed lower signal intensities when binding to IGFBP-3 compared to IGFBP-1. This result suggests that these variants have a selectively-reduced affinity for IGFBP-3 compared to wild-type IGF-1.

Figure 31A:
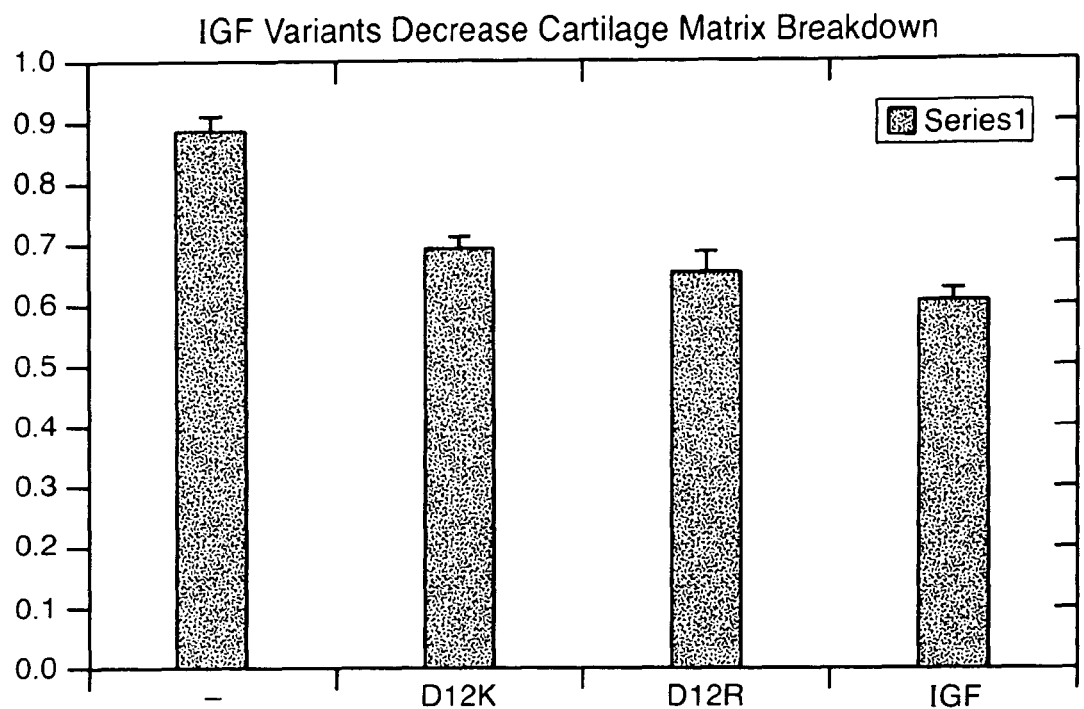
FIGS. 31A-31D show the effects on porcine articular cartilage explants cultured in media (−) or media with D12K, D12R, or wild-type IGF-1 (at 10 nM) alone (FIGS. 31A, 31C) or in the presence of IL-1∀ (+a) at 1 ng/ml (FIGS. 31B, 31D).
Figure 31B:
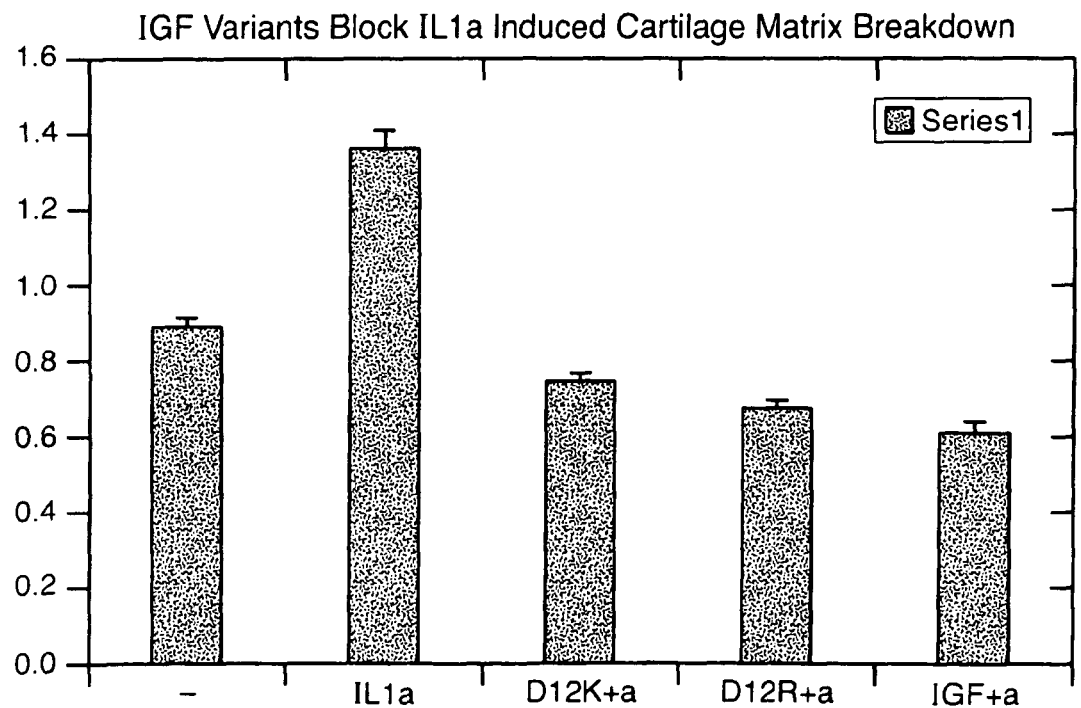
Figure 31C:
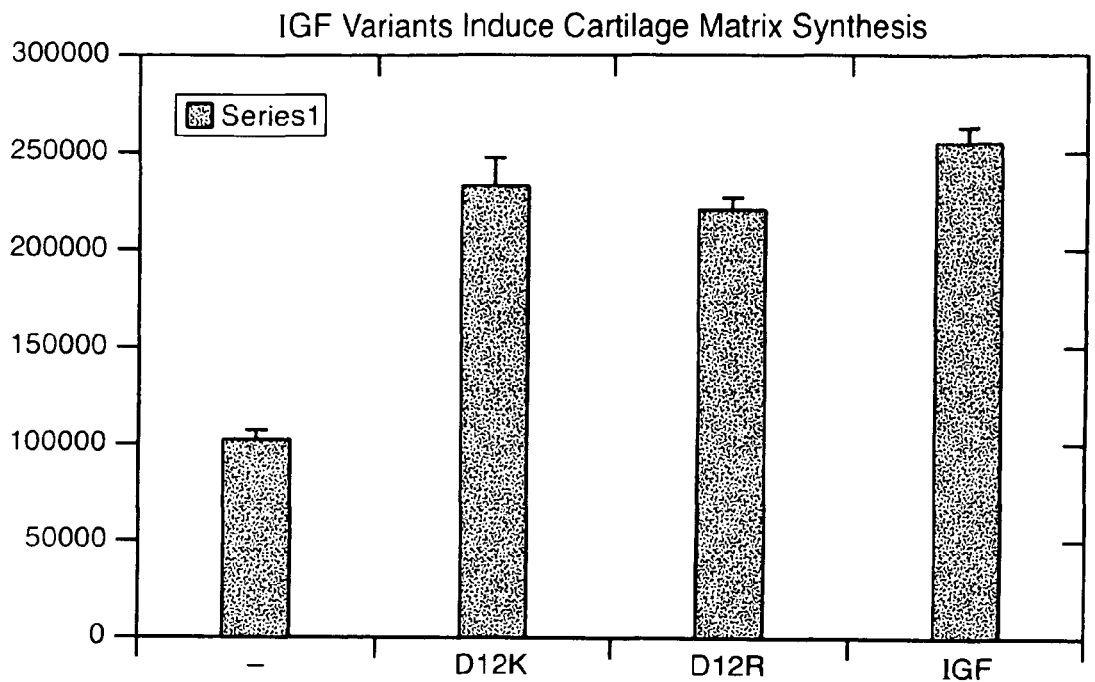
Figure 31D:
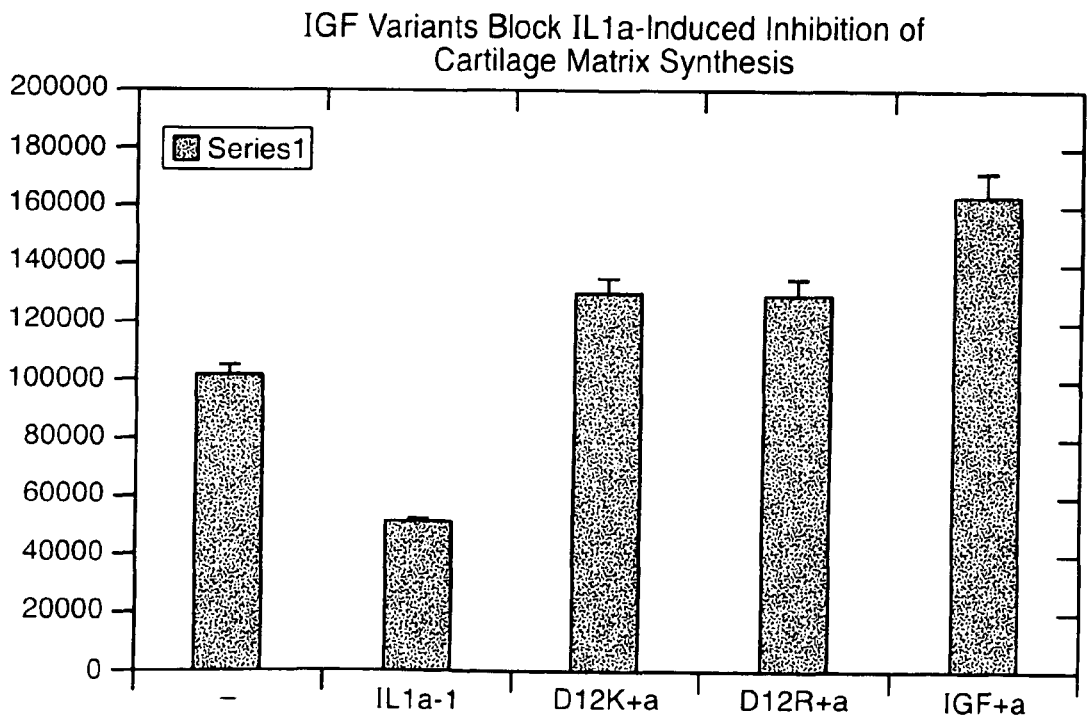

Like IGF-1, D12K and D12R inhibited cartilage matrix breakdown (FIG. 31A) and increased matrix synthesis (FIG. 31C). In addition, like IGF-1, D12K or D12R inhibited the catabolic effects of IL-1∀ (FIG. 31B) and prevented IL-1∀-induced inhibition of proteoglycan synthesis (FIG. 31D). Thus, these mutants retain full activity, and are expected to be good therapeutic agents for cartilage disorders such as arthritis, which are characterized by increased matrix breakdown and decreased matrix synthesis. In addition, since high levels of IL-1 are found in diseased joints, the ability of these mutants to inhibit the detrimental effects of IL-1∀ on cartilage further suggest utility of these IGF variants as treatments for arthritis.

Figure 32:
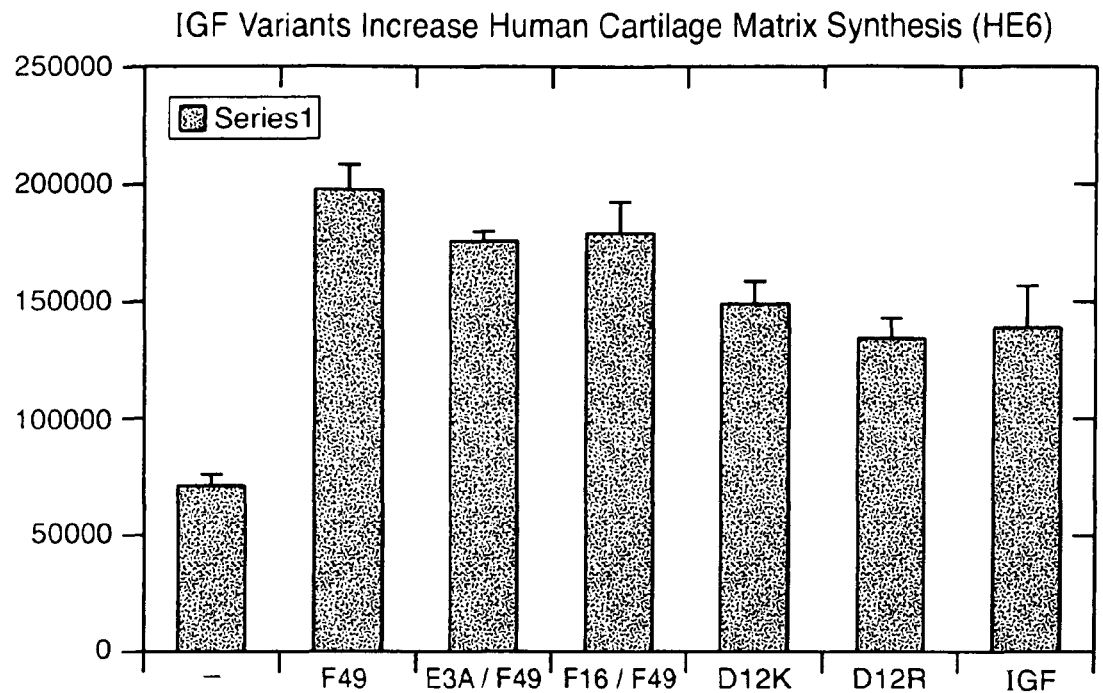
FIG. 32 shows the effect on articular cartilage matrix synthesis in human tissue from diseased joints cultured in media alone (−) or with F49, E3A/F49, F16/F49, D12K, D12R or wild-type IGF-1 (at 40 ng/ml).

Importantly, the IGF-1 variants have activity on human cartilage obtained from patients undergoing joint replacement, i.e., with arthritis. As shown in FIG. 32, all five IGF variants tested with selective preferences for IGFBP-3 over IGFBP-1 or vice-versa (F49A, E3AF49A, F16A/F49A, D12K, and D12R) stimulated matrix synthesis in diseased human articular cartilage, and the activity of the variants was as good as, or better than, that of wild-type IGF-1. Unlike previous studies showing IGF-1 resistance in articular cartilage from osteoarthritic joints, cartilage from these particular patients remained responsive to IGF-1.

Discussion:

The protein interface between IGF-1 and IGFBP-3 seems to be sensitive to mutations changing the charge distribution. Introducing positive charges into the N-terminal region of IGF-1 is expected to selectively reduce IGFBP-3 affinity.

The IGF-1 variants D12K and D12R are biologically active, as shown in the articular matrix synthesis stimulation experiments herein.

IGF-1 is a key regulator of matrix homeostasis in articular cartilage. The metabolic imbalance in osteoarthritis that favors matrix breakdown over new matrix synthesis may be due, at least in part, to insensitivity of chondrocytes to IGF-1 stimulation. While the mechanism underlying this IGF-1 resistance is not known, without being limited to any one theory, it is believed that IGFBPs, which are elevated in many arthritic patients, play a role. In these patients, IGF-1 analogs that do not bind to, and are thus not inhibited by, IGFBPs would likely stimulate cartilage repair in tissue that is otherwise IGF-1 resistant. Alternatively, peptides that block IGF-1 binding to inhibitory binding proteins may thus free IGF-1 to act on resident chondrocytes. Furthermore, based on the possible role of IGFBPs (especially IGFBP-1) in modifying the activity of IGF-1, the IGF-1 analogs described herein may have better clearance from, and/or transport through tissues within, human joints relative to that of wild-type IGF-1.

Since loss of cartilage matrix proteins is an early and continuous part of joint damage leading to joint failure, the ability of these IGF-1 analogs to inhibit cartilage catabolism and stimulate new matrix synthesis strongly suggests that these IGF analogs will have beneficial effects on diseased or damaged joints.

Il-1∀ has catabolic effects on cartilage, including the generation of synovial inflammation, up-regulation of matrix metalloproteinases, stimulation of matrix breakdown, and inhibition of proteoglycan and collagen synthesis. Furthermore, IL-1 protein is found in diseased, but not normal joints. Thus, the ability of the tested analogs to have positive effects on cartilage, as well as to counteract the deleterious effects of IL-1∀, strongly suggests that such molecules would have a protective effect on cartilage disorders, including damaged and/or diseased cartilage. In addition, such an activity predicts that the test IGF-1 analogs and peptides would inhibit the degradation that occurs in arthritic conditions, since antagonism of IL-1∀ function has been shown to reduce the progression of osteoarthritis (Arend et al., *Ann. Rev. Immunol.*, 16: 27-55 (1998)).

Example 10

Articular Cartilage Explant Assay of BP3-15 and BP3-40 Analogs

Materials and Methods:

Human articular cartilage explants were cultured in media or treated with IGF-1 by itself or in combination with either BP3-40 or BP3-15 at 0.1 mg/ml as set forth above. Matrix breakdown was determined by measuring the release of proteoglycans into media as described above. Matrix synthesis was determined by counting the amount of $^{35}$S-sulfate incorporated into the cartilage tissue as described above.

Figure 33A:
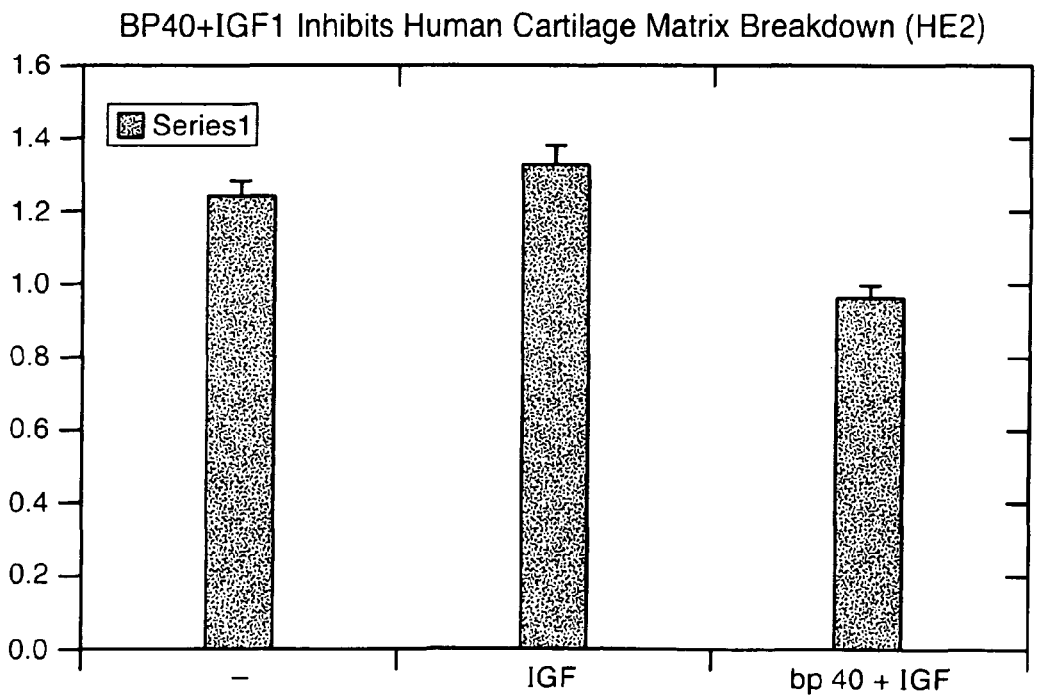
FIGS. 33A-33D show the effect on human articular cartilage explants cultured in media (−) or treated with wild-type IGF-1 by itself or in combination with either BP3-40 (FIGS. 33A, 33B) or BP3-15 (FIGS. 33C, 33D) (at 0.1 mg/ml).
Figure 33B:
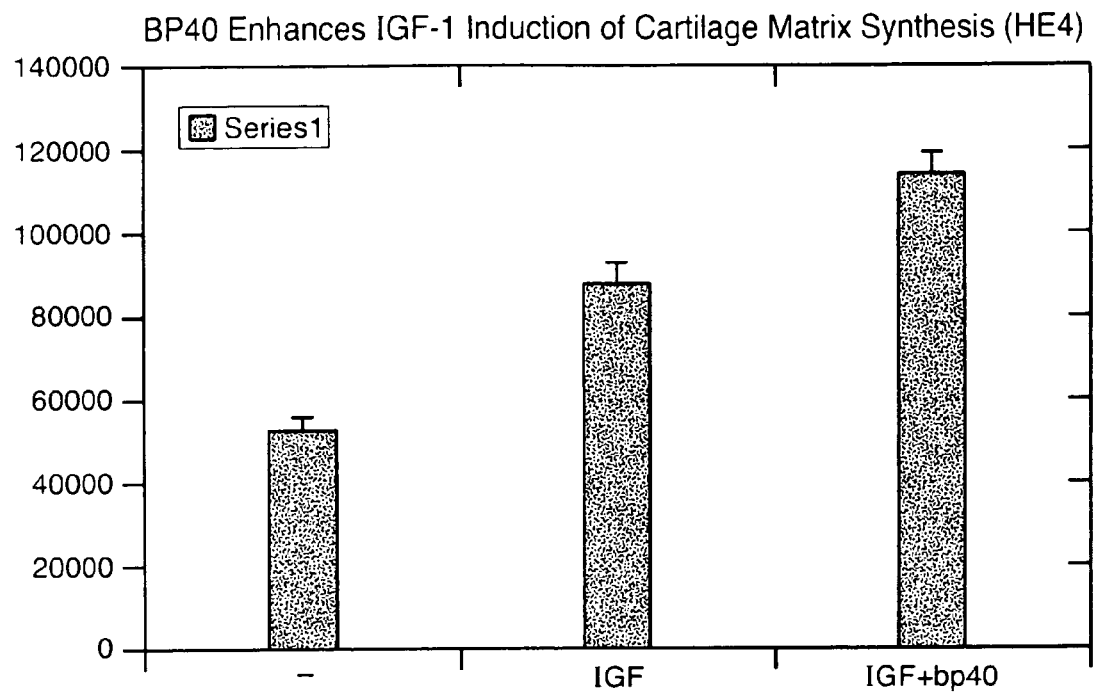
Figure 33C:
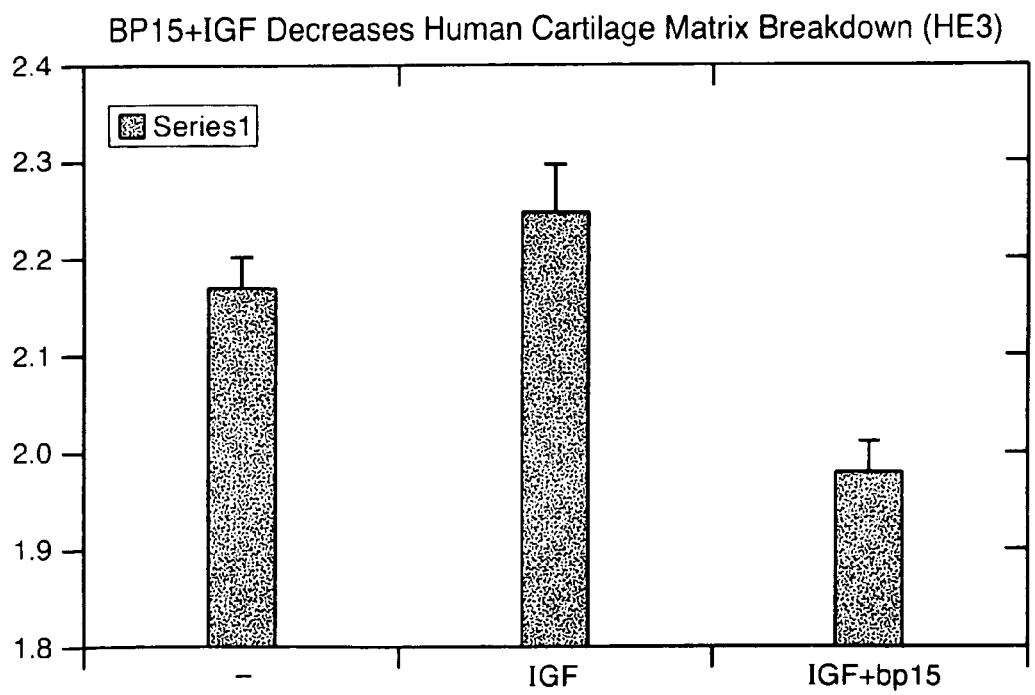
Figure 33D:
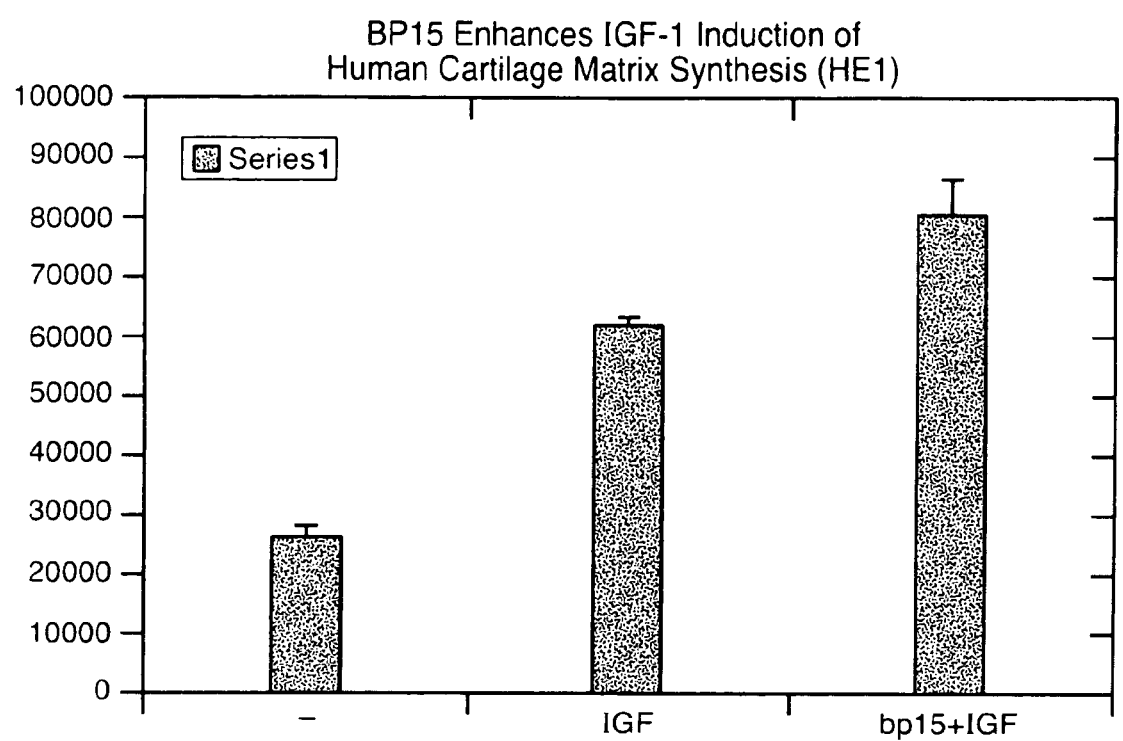

Results and Discussion:

Since high levels of IGFBPs have been found in diseased cartilage, and these IGFBPs may inhibit IGF-1 activity, the effect of two IGFBP-3 displacer peptides on IGF-1 activity was tested. Human articular cartilage explants from arthritic patients were treated with IGF-1 alone or in combination with an IGFBP displacer peptide (BP3-15 or BP3-40). These displacer peptides appeared to enhance the ability of IGF-1 to decrease matrix breakdown (FIG. 33A, 33C) and to stimulate matrix synthesis (FIG. 33B, 33D). Thus, these peptides are expected to be useful for conditions, such as arthritis, where high levels of inhibitory binding proteins are present. In such conditions, treatment with a displacer peptide alone, or in combination with IGF-1, is expected to enhance the anabolic effects of endogenous or exogenous IGF-1 and to be useful in treating arthritis.

Example 11

Complex Formation with ALS

Materials and Methods:

Human ALS was expressed in CHO cells (Leong et al., *Mol. Endocrinol.*, 6: 870-876 (1992)). The secreted ALS was enriched on DEAE-Sepharose, followed by affinity purification on an IGF-1/IGFBP-3 column, as described in Baxter et al., *J. Biol. Chem.*, 264: 11843-11848 (1989).

To monitor trimeric complex formation, 300 RU's of biotinylated IGFBP-3 (Sulfo-NHS-LC-LC-biotin; Pierce, Rockford, Ill.) were immobilized on a streptavidin-coupled chip (SA; Biacore, Inc., Piscataway, N.J.) in PBS, 0.05% TWEEN™-20, and 0.01% sodium azide. The biosensor chip was primed with running buffer containing 1:M of the respective IGF-1 analog (F49A or E3A/F49A). ALS was injected in amounts of 98, 148, and 333 nM at 50:L/min. for 2 minutes, followed by a 2-minute dissociation period. The chip was regenerated with 10:L of 2M KSCN (in 50 mM HEPES pH 7.2) at a flow rate of 20:L/min., followed by a 3-minute buffer flow for baseline stabilization.

Results:

F49A and E3A/F49A form Ternary Complexes with IGFBP-3 and ALS

Figure 34A:
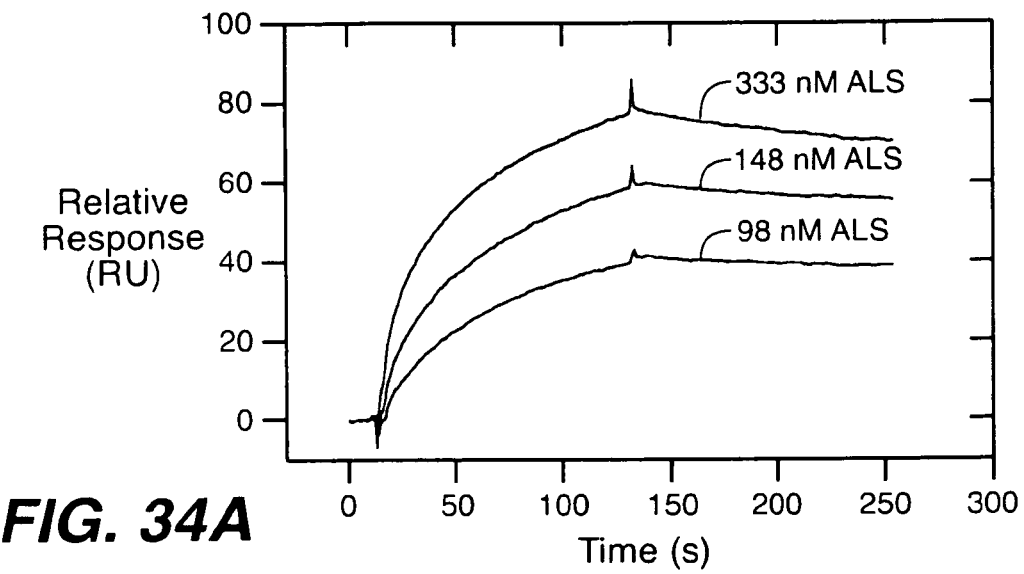
FIGS. 34A-34C show the trimeric complex formation of F49A or E3A/F49A with IGFBP-3 and ALS. IGFBP-3 immobilized on a biosensor chip was saturated by including 1:M wild-type IGF-1 (FIG. 34A), F49A (FIG. 34B), or E3A/F49A (FIG. 34C) in the running buffer. ALS was injected at 98 nM, 148 nM, and 33 nm, monitoring real-time association and dissociation to the preformed binary complex.
Figure 34B:
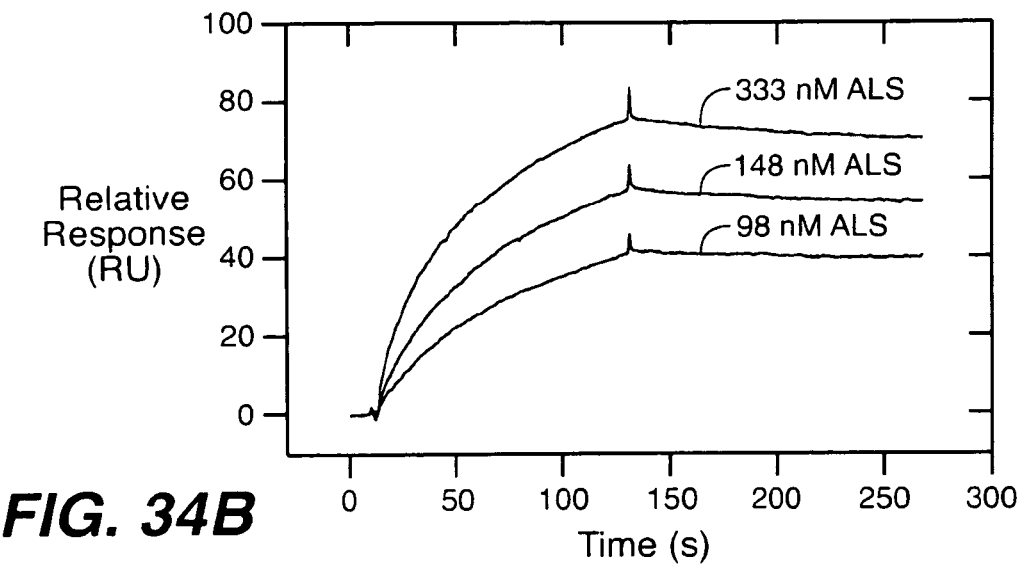
Figure 34C:
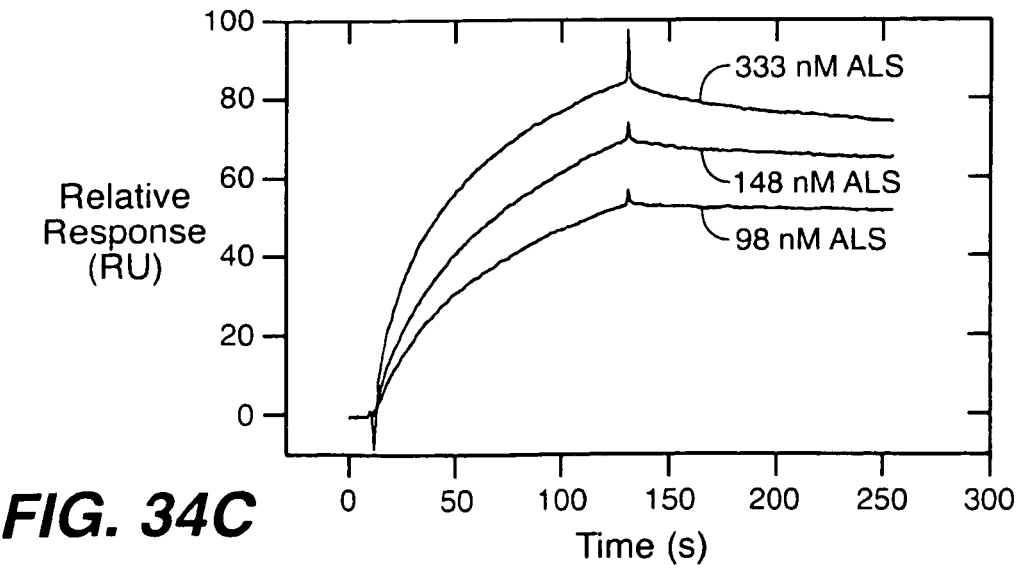
Figure 35:
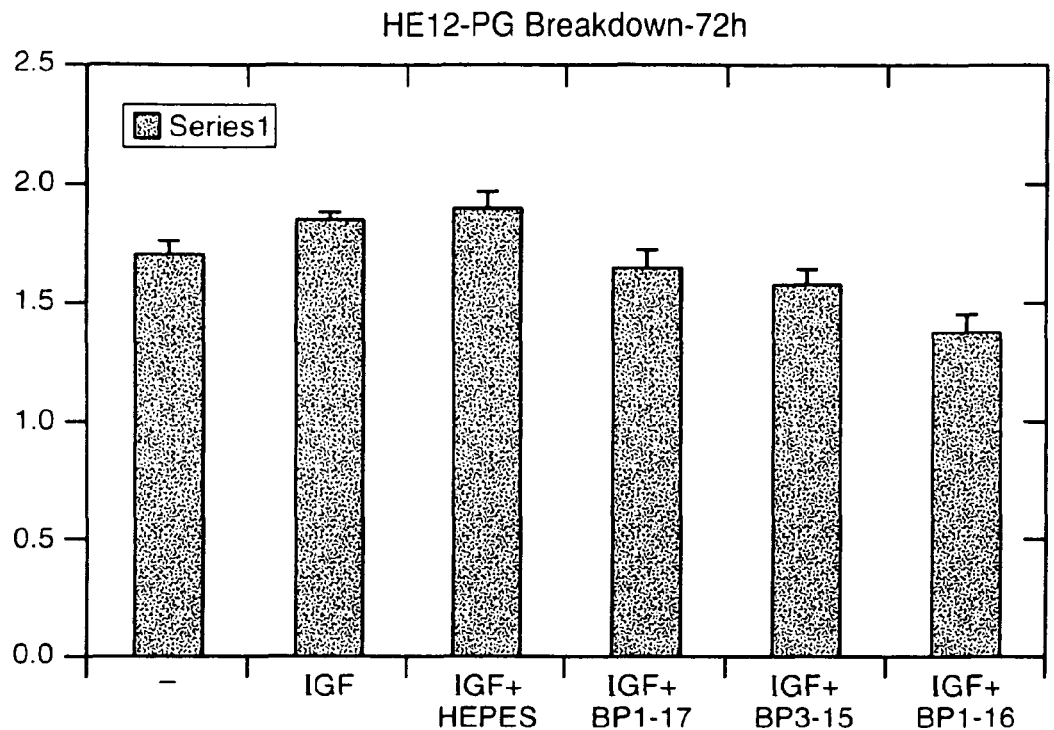
FIG. 35 shows a BIACORE™ surface-plasmon-resonance device inhibition assay of IGF-I activity using seven different peptides (BP1-16: filled circles, (i+7)A: open circles, (i+7)B: open diamonds, (i+7)C: open triangles, (i+7)D: open squares, (i+8)B: filled squares, (i+8)C: filled triangles).

The majority of IGF-1 in serum is found in a 150-kDa ternary complex composed of IGFBP-3 and a glycoprotein termed ALS. The half-life of this ternary complex is an order of magnitude longer than that of free IGF-1 (Ferry et al., *Horm. Metab. Res.*, 31: 192-202 (1999)). Hence, ternary complex formation is a major determinant for IGF-1 biodistribution. To test whether the engineered IGF-1 variants were still able to form trimeric complexes with ALS, a biosensor binding experiment was performed. Biotinylated IGFBP-3 was immobilized on a biosensor chip, and ALS was injected having either wild-type IGF-1 (FIG. 34A), F49A (FIG. 34B), or E3A/F49A (FIG. 34C) included in the running buffer at a concentration of 1:M. As shown in FIG. 34, the ALS binding curves were essentially identical for the wild-type IGF-1 and the two IGF-1 variants. The dissociation rate for wild-type IGF-1 and each IGF-1 variant is listed in Table XIX, ranging from $4.0\times10^{-4} s^{-1}$ to $6.3\times10^{-4} s^{-1}$. In the absence of any IGF-1 in the running buffer, ALS did not associate with IGFBP-3 on the chip. This experiment indicates that the IGF-1 variants retain the ability to form ternary complexes, and that their terminal half-life in serum therefore should not be drastically shorter than for wild-type IGF-1.

TABLE XIX

ALS Dissociation Rates from IGFBP-3/IGF-1 complexes determined by Biosensor Experiments

| Material | Dissociation Rate kd ($\times 10^{-4} s^{-1}$) |
|---|---|
| wt IGF-1 | 6.3 ± 1.7 |
| F49A IGF-1 | 4.2 ± 0.9 |
| E3A/F49A IGF-1 | 4.0 ± 2.2 |

Clearance and Distribution of F49A and E3A/F49A in Rats.

Human wild-type IGF-1, F49A, and E3A/F49A were radiolabeled and administered intravenously to rats to assess their pharmacokinetic properties. Both IGF-1 variants cleared significantly faster when compared to wild-type human IGF-1 (Table XX). E3A/F49A cleared at the fastest rate (1107±45 ml/hr/kg), followed by F49A (427±125 ml/hr/kg) and wt IGF-1 (151±24.7 ml/hr/kg). A similar trend was observed for the intermediate half-life $t_{1/2}^\beta$: E3A/F49A had the shortest, F49A intermediate, and wt IGF-1 the longest $t_{1/2}^\beta$ (Table XX). These findings correlate well with the corresponding in vitro affinities for the major binding protein in the serum, IGFBP-3. Interestingly, the steady-state distribution volumes were much greater for the IGF-1 variants, indicating that they are less confined to the plasma compartment than is wild-type IGF-1 (Table XX). The greatest tissue-to-blood ratios for the IGF-1 molecules were detected in the kidney, whereas ratios in the liver, spleen, heart, and pancreas were much lower. It is evident from this experiment that F49A and E3A/F49A accumulate at statistically significant higher ratios in the kidney compared to wild-type IGF-1.

TABLE XX

Pharmacokinetic parameters following a single IV dose in rats.

| Group | Half-life (hr) | | | clearance | steady-state distribution volume |
|---|---|---|---|---|---|
| | $t_{1/2}^\forall$ | $t_{1/2}^\exists$ | $t_{1/2}^\subset$ | (ml/hr/kg) | (ml/kg) |
| $^{125}$I-wt IGF-1 | 0.033 ± 0.004 | 1.22 ± 0.237 | 5.88 ± 0.374 | 151 ± 24.7 | 936 ± 94.8 |
| $^{125}$I-F49A | 0.064 ± 0.052 | 0.971 ± 0.336[+] | 8.97 ± 4.50 | 427 ± 125[*+] | 3201 ± 488[*+] |
| $^{125}$I-E3A/F49A | 0.032 ± 0.005 | 0.321 ± 0.091[*] | 6.23 ± 1.47 | 1107 ± 45.0[*] | 6520 ± 874[*] |

*P < 0.05 compared to $^{125}$I-wt IGF-1
+P < 0.05 compared to $^{125}$I-E3A/F49A Discussion:

The ability of the analogs F49A and E3A/F49A to form ternary complexes with ALS and IGFBP-3 has important consequences for the serum half-life of these variants. How ALS interacts with the IGF-1/IGFBP-3 complex is unknown due to a lack of structural information on IGFBP-3 and ALS. A recent model of ALS postulates a donut-shaped structure whose internal cavity is lined with negative charges; these regions could potentially interact with positive charges on IGFBP-3 and IGFBP-5 (Janosi et al., *J. Biol. Chem.*, 274: 5292-5298 (1999)). The affinity of ALS for a crosslinked IGF-1/IGFBP-3 complex is on the order of 0.1 to 0.3 nM, depending on the carbohydrate content of ALS (Janosi et al., supra). In the biosensor measurements that analyzed ALS binding to a non-covalent IGF-1/IGFBP-3 complex (by including saturating amounts of IGF-1 in the running buffer), the dissociation rates of the wild-type IGF-1, F49A, and E3A/F49A remained constant between $4.0 \times 10^{-4} s^{-1}$ to $6.3 \times 10^{-4} s^{-1}$ (Table XIX). The experiment confirms that both IGF-1 variants tested form ternary complexes with ALS.

The pharmacokinetics of the IGF-1 variants in rats showed different characteristics from wild-type IGF-1 (Table XX). It appears that the majority of differences are observed in the first 60-100 minutes of the experiment. In the pharmacokinetic analysis model, this phase is characterized by the initial and intermediate half-lives $t_{1/2}{}^{\forall}$ and $t_{1/2}{}^{\exists}$, which likely describe the distribution of free and total radiolabeled molecules to extravascular tissues and their clearance (Table XX). Following this initial phase, all three IGF-1 molecules are cleared at comparable rates, as suggested by their similar terminal half-life values $t_{1/2}{}^{(}$, which likely reflect the elimination of $^{125}$-I from the rat (Table XX). The trends in $t_{1/2}{}^{\forall}$ and $t_{1/2}{}^{\exists}$ observed across the three molecules are generally consistent with a more rapid rate of distribution and clearance for the IGF-1 variants that are less bound to IGFBPs. Furthermore, the calculated steady-state distribution volumes and clearance rates also support the interpretation that IGFBP association plays a major role in the distribution and clearance of the IGF-1 variants. Therefore, without being limited to any one theory, this suggests that the initial differences in the pharmacokinetic profile reflect the IGF-1/IGFBP-3 binding equilibrium, since they correlate well with the corresponding affinities of the IGF-1 variants for IGFBP-3 in vitro.

Because IGFBP-3 in the blood seems to be saturated under normal conditions (Jones and Clemmons, *Endocr. Rev.*, 16: 3-34 (1995)), it is believed, without limitation to any one theory, that the injected IGF-1 variants have to compete with endogenous IGF-1 for IGFBP-3 binding. The IGF-1 molecules that are unable to associate with IGFBP-3 could diffuse out of the vasculature, and either associate with other binding proteins or be cleared at a rapid rate ($t_{1/2}$ for free IGF-1=10-15 min[11]). Those molecules that achieve ternary complex formation with IGFBP-3 and ALS, however, experience a more prolonged serum half-life and become "trapped" in the vasculature. Ternary complex formation of the IGF-1 variants occurs with the same efficiency as wild-type IGF-1 in vitro (FIG. 33, Table XIX), and this property appears to be reflected in the later phase (>100 minutes) of the pharmacokinetic profile. The fact that both human IGF-1 variants and wild-type human IGF-1 display terminal half-lives in the order of 6-9 hours strongly suggests that complex formation with rat IGFBP-3 and ALS occurs in vivo. This is important, since all in vitro experiments were done exclusively with human IGFBP-3 and ALS, whereas the in vivo experiments rely on preservation of the engineered specificities for the homologous rat binding proteins.

Example 12

Substitutions in BP1-16

Several single-residue substitutions in BP1-16 were tested for their effect on IGFBP-1 binding affinity by synthesizing peptides and measuring inhibition of IGFBP-1 binding to IGF-I. Sites for substitution were chosen based upon the known effect of an alanine or other substituted residue at the site.

G4 was previously found to be substitutable by D-alanine. Because the conformational effects of D-alanine are different from those of L-alanine, L-alanine was substituted for G4 in peptide BP1-29. Inhibition assays showed a 50-fold loss in binding affinity with this substitution (Table XXI).

P5 was previously found to be highly conserved in phage-displayed peptide libraries; however, some substitutions were observed. For example, three different peptide-phage clones were found with arginine at this position. Therefore, the L-alanine substitution for proline was tested, as well as several alternative substitutions (BP1-30, BP1-31, BP1-34). The results (Table XXI) show that P5A, P5N, and P5R are well tolerated.

L6 and L9 were completely conserved in 40 of 40 sequenced clones and 61 of 61 sequenced clones, respectively, from two different IGFBP-1 selected peptide-phage libraries. In addition, substitution of either of these residues with L-alanine or aib (alpha-aminoisobutyrate) side-chains resulted in a significant loss in IGFBP-1 binding affinity. Two further substitutions were tested at each position: norleucine (Nle), an isomer of leucine, or arginine (the aliphatic portion of the side-chain of which might still be able to pack into the peptide structure). While the Arg substitutions resulted in peptides having undetectable IGFBP-1 affinity (BP1-32 and BP1-26), the Nle substitutions were well-tolerated (BP1-36 and BP1-37). The non-natural substitutions L6(Nle) and L9(Nle) are therefore the only substitutions at these positions known to preserve moderate-affinity binding to IGFBP-1.

W8 was also completely conserved in IGFBP-1 selected peptide-phage libraries, although the alanine substitution had a smaller effect on binding than in the case of L6 or L9. Therefore, several large side-chain substitutions were tested at this position. Interestingly, arginine, 1-naphthylalanine (Nal(1)), or histidine substitutions (BP1-22, BP1-23, and BP1-24, respectively) each had modest (<10-fold) effects on IGFBP-1 binding affinity (Table XXI). From these experiments, a new consensus sequence for IGFBP-1 binding may be formulated as follows:

CysXaa$_{(6)}$Xaa$_{(7)}$GlyXaa$_{(9)}$LeuXaa$_{(11)}$TrpLeuCysXaa$_{(15)}$ Xaa$_{(16)}$Xaa$_{(17)}$Xaa$_{(18)}$ (SEQ ID NO:130), where Xaa$_{(6)}$, Xaa$_{(7)}$, Xaa$_{(9)}$, Xaa$_{(11)}$, Xaa$_{(15)}$, and Xaa$_{(16)}$ are independently any amino acid, and Xaa$_{(12)}$, Xaa$_{(17)}$, and Xaa$_{(18)}$ are independently Nal(1), His, Phe, Trp, Tyr, Pro, Gln, or Met.

TABLE XXI

Relative affinities of BP1-16 variants measured by ELISA or BIAcore ™ (*) inhibition assays

| BP1-16 Variant | Peptide Sequence | Fold potency reduction IC$_{50}$ (mut)/ IC$_{50}$ (BP1-16) |
|---|---|---|
| BP1-16 | CRAGPLQWLCEKYF (SEQ ID NO: 35) | -1- |
| BP1-29 | CRA<u>A</u>PLQWLCEKYF (SEQ ID NO: 131) | 50 |
| BP1-30 | CRAG<u>A</u>LQWLCEKYF (SEQ ID NO: 132) | 1.5 |
| BP1-31 | CRAG<u>R</u>LQWLCEKYF (SEQ ID NO: 133) | 2.0 |
| BP1-34 | CRAG<u>N</u>LQWLCEKYF (SEQ ID NO: 134) | 3.1 |

TABLE XXI-continued

Relative affinities of BP1-16 variants measured by ELISA or BIAcore ™ (*) inhibition assays

| BP1-16 Variant | Peptide Sequence | Fold potency reduction $IC_{50}$ (mut)/ $IC_{50}$ (BP1-16) |
|---|---|---|
| BP1-32 | CRAGPRQWLCEKYF (SEQ ID NO: 135) | >1000 |
| BP1-36 | CRAGPLQWLCEKYF, (SEQ ID NO: 136) where the underlined L is Nle | 6.9 |
| BP1-26 | CRAGPLQWRCEKYF (SEQ ID NO: 137) | >570 |
| BP1-37 | CRAGPLQWLCEKYF, (SEQ ID NO: 138) where the underlined L is Nle | 1.7 |
| BP1-22 | CRAGPLQRLCEKYF (SEQ ID NO: 139) | 3.3* |
| BP1-23 | CRAGPLQALCEKYF, (SEQ ID NO: 140) where the underlined A is Nal (1) | 4.8* |
| BP1-24 | CRAGPLQHLCEKYF (SEQ ID NO: 141) | 7.5 |

Example 13

Minimization of the BP1-01 Peptide Via "Locked Helix"

It was previously shown that removal of the disulfide bond in BP1-01 is destabilizing to both structure and function of the peptide. The possibility has been investigated of replacing the disulfide bond of BP1-01 with a chemically distinct structural constraint, while maintaining moderate binding affinity to IGFBP-1. These constraints were designed to link side-chain positions separated by 7 (from position i to position i+7) or 8 (from i to i+8) residues in the BP1-01 peptide.

The i+7 locked helix strategy, one of the approaches used herein, has been described by Phelan et al., *J. Am. Chem. Soc.*, 119: 455-460 (1997); WO 98/20036 published May 14, 1998, as have other i+7, i+3, and i+4 linkages (reviewed in Phelan et al., supra). In addition, other side-chain substitutions, allowing for ionic or hydrophobic interactions or metal chelation, have been used for the purpose of stabilizing a helical structure (reviewed by Phelan et al., supra). Herein is described a novel i+8 locked helix strategy, which is particularly useful for stabilization of the helical structure found in the BP1-01 peptide family.

Mutagenesis studies indicated that major determinants for IGFBP-1 binding reside primarily in the helical segment of BP1-01. These important binding determinants segregate mainly to one face of the helix, and include Leu6 and Leu9, and the aromatic residues Trp8, Tyr13, and Phe14. Without being limited to any one theory, the remainder of the peptide might act primarily to stabilize the helix and to ensure appropriate presentation of the major side-chain binding determinants. Therefore, other methods for constraining the binding segment of the peptide to a helical conformation might yield potent BP1-binding peptides. Side-chain-side-chain crosslinks on the opposite helical face from the major BP1-binding determinants were chosen for use. This method has been described in WO 98/20036, supra. In the present case, the i+7 crosslinking connects residues replacing Gln7 to Phe14, which replaces one of the hydrophobic IGFBP-1 binding determinants. The i+8 crosslinking connects residues replacing Gln7 to Gly15.

The crosslinking chemistry involves replacement of the appropriate two residues with glutamic acid residues (the first and last Glu (E) residues shown in Table XXII), where the two Glu residues are joined by forming amides with 1,5-diaminopentane. This cross-linking method has been described in WO 98/20036, supra.

To develop active peptides shorter than BP1-01, it was also decided to delete the disulfide (Cys1-Cys10) and truncate the N-terminal loop region in constrained helical peptides. The Cys10 was changed to Ala and Cys1 replaced with an acetyl group (ac in Table XXII). Several shorter variants lacked one or more of the other loop residues. Thus, these peptides were cyclized only through the 1,5-diaminopentane linkage. Such peptides, lacking disulfide bonds, may be more stable to degradation in vitro and in vivo. They may also be reduced in immunogenicity compared to disulfide-containing analogs.

Functional Analysis of Locked Helices

Peptides were assayed in a BIAcore™ assay as described in WO 98/45427, supra. These inhibition assays (FIG. 35) compared the relative potency of these peptides for blocking the interaction of IGFBP-1 with IGF-1. Adding the "i+7 helical lock" to a variant of BP1-01 reduced relative potency (Table XXII) by 6-fold (peptide (i+8)C) to 8-fold (peptide (i+7)D or (i+8)B) in the best locked-helix variants. These peptides demonstrate that a disulfide bond is not necessary to obtain structured, functional peptides of the BP1-01 family.

In contrast to the locked helix variants described above, a locked helix variant in which two of the key IGFBP-1 binding determinants were lost ((i+7)A; Table XXII) exhibited significant loss in binding activity relative to BP1-01. In this peptide, W8 is replaced with the first cross-linking residue and Gly15 is replaced with the second cross-linking residue; F14 is replaced by alanine in this peptide. The disulfide bond is still present in this peptide.

Certain additions to the N-terminus and C-terminus of these peptides (see Example 3) are predicted to improve their binding affinity and potency, as in the case of disulfide-constrained peptide variants discussed below.

Hence, a consensus sequence can be formulated as follows: $Xaa_{(1-4)}Xaa_{(5)}Xaa_{(6-7)}$ProLeuGlu$Xaa_{(11)}$LeuAla$Xaa_{(14)}$ $Xaa_{(15)}Xaa_{(16)}Xaa_{(17)}$Glu$Xaa_{(19)}$ (SEQ ID NO:142), wherein $Xaa_{(1-4)}$ is absent or is between 1 and 4 amino acids of any kind; $Xaa_{(5)}$ is any amino acid, $Xaa_{(6-7)}$ is absent or is between 1 and 2 amino acids, $Xaa_{(14)}$ and $Xaa_{(15)}$ are independently any amino acid, $Xaa_{(11)}$ and $Xaa_{(16)}$ are independently NaI (1), His, Phe, Trp, Tyr, Pro, Gln, or Met, $Xaa_{(17)}$ is absent or is 1-napthyl-Ala, His, Phe, Trp, Tyr, Pro, Gln, or Met, and $Xaa_{(19)}$ is absent or is Gly.

NMR Analysis of Locked Helices $^{1}$H NMR spectroscopy was used to ascertain that the locked helix variants of BP1-01 did have the desired three-dimensional helical structure. 1-dimensional spectra and 2-dimensional COSY, TOCSY, and ROESY spectra were acquired for peptides (i+7)A, (i+7)B, (i+7)C, (i+7)D and (i+8)C; experimental details were similar to those described for BP1-01 in Lowman et al., supra, 1998. Preliminary analysis of backbone $^{3}$JHN-Ha scalar coupling constants (derived from 2D COSY spectra) and short Ha(i)-$H^{N}$(i+3) distances (derived from ROESY spectra), indicated that for (i+7)A, (i+7)C, (i+7)D, and (i+8)C, the designed helix was present. In the case of (i+7)B, the NMR data were not consistent with a helical structure. The lack of a well-folded structure presumably explains the low affinity of this peptide for IGFBP-1 (>360 fold weaker than BP1-01)

The scalar coupling and ROESY data for (i+7)A, (i+7)D, and (i+8)C were analyzed in more detail to generate input restraints for the calculation of three-dimensional structures as described previously for BP1-01 (Lowman et al., supra, 1998). Comparison of the minimized mean structures of the locked helix variants to that of BP1-01 yielded RMSDs (N, Ca, C atoms of Leu6-Phe14) of 1.02 Å and 0.22 Å for (i+7)D and (i+8)C, respectively. Further, the packing of hydrophobic side-chains Leu6, Trp8, Leu9, and Tyr13 in these two locked helix variants was also very similar to the packing in BP1-01. Thus, the (i,i+7) and (i,i+8) locked helix scaffolds have successfully maintained many aspects of the BP1-01 structure without the need for a disulfide bond. Although the covalent tethers in (i+7)A did produce the desired two turns of helix (the N, Ca, C RMSD between minimized means of BP1-01 and (i+7)A is 1.06 Å), some side-chain rotamers differed significantly from those of BP1-01.

The structural analyses described above suggest that covalent tethers (other than the disulfide bond observed in BP1-01) may be used to control peptide structure. The use of i,i+7 or i,i+8 tethers produced peptides (i+7)D and (i+8)C that retained high affinity towards IGFBP-1 in the absence of a disulfide bond. Presumably, the affinity derives from stabilization of a structure that maintains both the backbone helical fold and the side-chain packing arrangement of the key binding determinants observed in BP1-01. Although the peptide (i+7)A maintains the backbone fold, two of the key determinants (Trp8 and Phe14) are missing, and the orientation of others (e.g. Tyr13) is perturbed; as a result, this peptide has reduced affinity. The peptide (i+7)B fails to adopt the desired fold, and hence has no measurable affinity for IGFBP-1.

TABLE XXII

Locked-helix variants of BP1-01
(The first and last Glus (Es) are sites of cyclizing "lock")

| BP1-16 Variant | Peptide Sequence | Fold potency reduction $IC_{50}$ (BP1-01)/$IC_{50}$ (mut) |
|---|---|---|
| BP1-01 | CRAGPLQWLCEKYFG (SEQ ID NO: 26) | -1- |
| (i + 7) A | acCRAGPLQELCEKYAE (SEQ ID NO: 143) | 40 |
| (i + 7) B | acLEWLAEKYEG (SEQ ID NO: 144) | >360 |
| (i + 7) C | acPLEWLAEKYEG (SEQ ID NO: 145) | 20 |
| (i + 7) D | acRAGPLEWLAEKYEG (SEQ ID NO: 52) | 7.7 |
| (i + 8) A | acLEWLAEKYFE (SEQ ID NO: 146) | >200 |
| (i + 8) B | acRPLEWLAEKYFE (SEQ ID NO: 53) | 7.7 |
| (i + 8) C | acRAGPLEWLAEKYFE (SEQ ID NO: 54) | 5.9 |

Example 14

N-terminal Variants of BP1-16

Previous affinity-maturation experiments led to a peptide addition to the C-terminus of BP1-02, including a number of peptide-phage clones (Table XXIII), and the synthetic peptide BP1-21A, the sequence of which is shown in Table XXIII. Table XXIII illustrates the C-terminal substitutions in the background of BP1-02.

TABLE XXIII

C-terminal substitutions derived from round 3 of monovalent phage selections in the BP1-02 peptide background

| BP1-02 Variant | Peptide Sequence | SEQ ID NO: | Number of clones sequenced |
|---|---|---|---|
| Y135C (BP1-21A) | SEVGCRAGPLQWLCEKYFSTY | 13 | 2 |
| Y135D | SEVGCRAGPLQWLCEKYFATY | 14 | 3 |
| Y135F | SEVGCRAGPLQWLCEKYFQTY | 15 | 1 |
| Y135B | SEVGCRAGPLQWLCEKYFQTYT | 16 | 1 |
| Y135A | SEVGCRAGPLQWLCEKYFDTY | 17 | 1 |
| Y135E | SEVGCRAGPLQWLCEKYFETY | 18 | 1 |
| Y135K | SEVGCRAGPLQWLCEKYFKTY | 19 | 1 |

It is sought herein to improve affinity further by two methods: substitution of the first four N-terminal amino acid residues from BP1-20 into BP1-21A, and re-randomization of the N-terminal amino acid residues of BP1-21A (in the context of the previously improved C-terminus).

Peptide BP1-25 (Table XXV) was synthesized to test the additivity (Wells, Biochemistry, 29: 8509-8517 (1990)) for the N-terminal and C-terminal maximally-preferred substitutions. Compared with BP1-16 in inhibition assays, BP1-25 showed about a 20-fold affinity improvement. However, the affinity of BP1-25 was not significantly improved over BP1-21A. This affinity improvement was confirmed in other assays described below.

In the second approach, a monovalent-display peptide-phage library, presenting BP1-21A as a fusion to g3p, was randomized (Lowman, Methods Mol. Biol., 87: 249-264 (1998)) at the N-terminal four residues. Binding selection to IGFBP-1 was carried out by first allowing library phage to bind to solution biotinylated IGFBP-1, with an initial concentration of 50 nM, followed by 28 nM for the subsequent four rounds of selection. Peptide-phage capable of binding IGFBP-1 were captured by incubating with streptavidin magnetic beads (Promega) for 10 minutes at room temperature. For each round of selection, the washing was gradually modified to be more stringent. Off-rate selection was performed by adding 2.5-5 ΦM IGF in solution to prevent rebinding of phage with faster off-rates. It is of interest to note that for the last round of selection (round 5), with an overnight incubation at 4° C. in the presence of 2.5 ΦM IGF, there were still phage remaining bound to the beads ($2.2 \times 10^4$ total phage were eluted). Subsequent sequencing data revealed that 14 out of 20 selected clones had converged to a single DNA sequence (clone Y0791A; Table XXIV). A peptide corresponding to this sequence, BP1-40, was synthetically produced for analysis.

TABLE XXIV

N-terminal substitutions derived from round 5 of monovalent phage selections in the BP1-21A peptide background

| BP1-16 Variant | Peptide Sequence | SEQ ID NO: | Number of clones sequenced |
|---|---|---|---|
| Y0791A (BP1-40) | GQQSCRAGPLQWLCEKYFSTY | 21 | 14 |
| Y0791D | ASSMCRAGPLQWLCEKYFSTY | 22 | 1 |
| Y0791H | QGPDCRAGPLQWLCEKYFSTY | 23 | 1 |
| Y0791K | QASECRAGPLQWLCEKYFSTY | 24 | 1 |
| Y0791L | AETLCRAGPLQWLCEKYFSTY | 25 | 1 |
| Y0791S | NSLLCRAGPLQWLCEKYFSTY | 26 | 1 |
| Y0791T | AQWVCRAGPLQWLCEKYFSTY | 27 | 1 |

Inhibition assays for measuring relative potencies of peptides for inhibiting IGFBP-1 binding to IGF-I have been described (e.g., WO 98/45427, supra). Peptides described herein were of sufficient binding affinity to allow for direct measurement of binding affinities by surface plasmon resonance (SPR) using a BIACORE™-system. The direct binding kinetics of IGFBP-1 peptides were measured by injecting a series of 2-fold diluted peptides in running buffer (0.05% TWEEN 20™ in PBS) over a carboxy-methyl (CM) biosensor chip coupled with about 590-1000 RU of IGFBP-1 at a flow rate of 50 µl/min on a BIACORE-2000™ or BIACORE-3000™ surface-plasmon-resonance instrument. The immobilization of IGFBP-1 was performed through EDC/NHS chemistry as described by the manufacturer. Peptides were also injected through a flow cell containing IGFBP-3 as background control. Since the off-rate for most of the peptides is relatively fast (in the range of $2 \times 10^{-2}$ s$^{-1}$), off-rate measurement was set for 30 minutes. This allowed for regeneration of IGFBP-1 on the chip by simple dissociation, rather than by addition of eluent. For each dilution of peptides, a global fit of the sensorgram data was performed using a 1:1 Langmuir binding model. On-rates ranged from $4 \times 10^5$ to $1.9 \times 10^6$ M$^{-1}$s$^{-1}$. The binding affinities, $K_D$, calculated as $k_{off}/k_{on}$ are summarized in Table XXV. Peptides BP1-20, BP1-21A, BP1-25, and BP1-40 were all found to have similar binding affinities ($K_D$) of about 20 nM to 40 nM.

The conclusion from these experiments is that N-terminal extensions to the BP1-01 peptide can improve binding affinity (as in BP1-02, BP1-20, BP1-21A, BP1-25, BP1-40, and other variants identified in Table XXIV). Some substitutions may alter expression levels in *E. coli*, since GQQS (SEQ ID NO:147) was clearly selected from phage-displayed peptide libraries. However, peptides having the sequences SEVG (SEQ ID NO:148), SEMV (SEQ ID NO:149), EARV (SEQ ID NO:150), or GQQS (SEQ ID NO:151) at their N-termini all had similar binding affinities. Therefore, the nature of added side-chains at the N-terminus appears to have little effect upon peptide binding affinity. This suggests that main-chain interaction of the peptide in this region may contribute to binding affinity for IGFBP-1.

An improved consensus sequence for IGFBP-1 binding peptides is expected therefore to be:

Xaa$_{(1-4)}$CysXaa$_{(6)}$Xaa$_{(7)}$GlyXaa$_{(9)}$LeuXaa$_{(11)}$Xaa$_{(12)}$LeuCysXaa$_{(15)}$Xaa$_{(16)}$Xaa$_{(17)}$Xaa$_{(18)}$ (SEQ ID NO:152), wherein Xaa$_{(1-4)}$ is absent or is between 1 and 4 amino acids of any kind, Xaa$_{(6)}$, Xaa$_{(7)}$, Xaa$_{(9)}$, Xaa$_{(11)}$, Xaa$_{(15)}$, and Xaa$_{(16)}$ are independently any amino acid, and Xaa$_{(12)}$, Xaa$_{(17)}$, and Xaa$_{(18)}$ are independently NaI(1), His, Phe, Trp, Tyr, Pro, Gln, or Met. As noted in Example 1, truncation of the amino-terminal 4 residues (Xaa$_{(1-4)}$) has only a small effect on activity, giving a shorter consensus that still retains binding:

CysXaa$_{(6)}$Xaa$_{(7)}$GlyXaa$_{(9)}$LeuXaa$_{(11)}$TrpLeuCysXaa$_{(15)}$Xaa$_{(16)}$Xaa$_{(17)}$Xaa$_{(18)}$ (SEQ ID NO:130).

TABLE XXV

Peptide affinity determinations by BIAcore™ kinetics

| BP1-16 Variant | Peptide Sequence | $K_D \pm$ (SD or SE) (nM) |
|---|---|---|
| BP1-02 | SEVGCRAGPLQWLCEKYFG (SEQ ID NO: 50) | 210 ± 46 |
| BP1-20 | EARVCRAGPLQWLCEKYF (SEQ ID NO: 39) | 33 ± 15 |
| BP1-21A | SEVGCRAGPLQWLCEKYFSTY (SEQ ID NO: 40) | 41 ± 17 |
| BP1-25 | EARVCRAGPLQWLCEKYFSTY (SEQ ID NO: 42) | 42 ± 11 |
| BP1-40 | GQQSCRAGPLQWLCEKYFSTY (SEQ ID NO: 43) | 27 ± 21 |

Example 15

Cell-based Assay of Peptide Activity

A cell-based (KIRA) assay was previously described for measuring the amount of IGF-like activity displaced by peptides from mixtures of IGF-I and binding proteins (Lowman et al., supra, 1998; WO 98/45427, supra). The KIRA assay was used to compare in vitro bioactivity of BP1-16, BP1-02, BP1-25, and BP1-40. In this example, very low concentrations of IGF-I and IGFBP-1 were used, i.e., below the $K_D$ of the peptide: 2 nM [IGF-I] and 1.5 nM [IGFBP-1], with a titration series of [peptide]=0.1 to 200 nM. IGF-I and peptide were mixed and added to cells expressing IGF receptor for 30 min, then IGFBP-1 was added for an additional 1 h.

Figure 36:
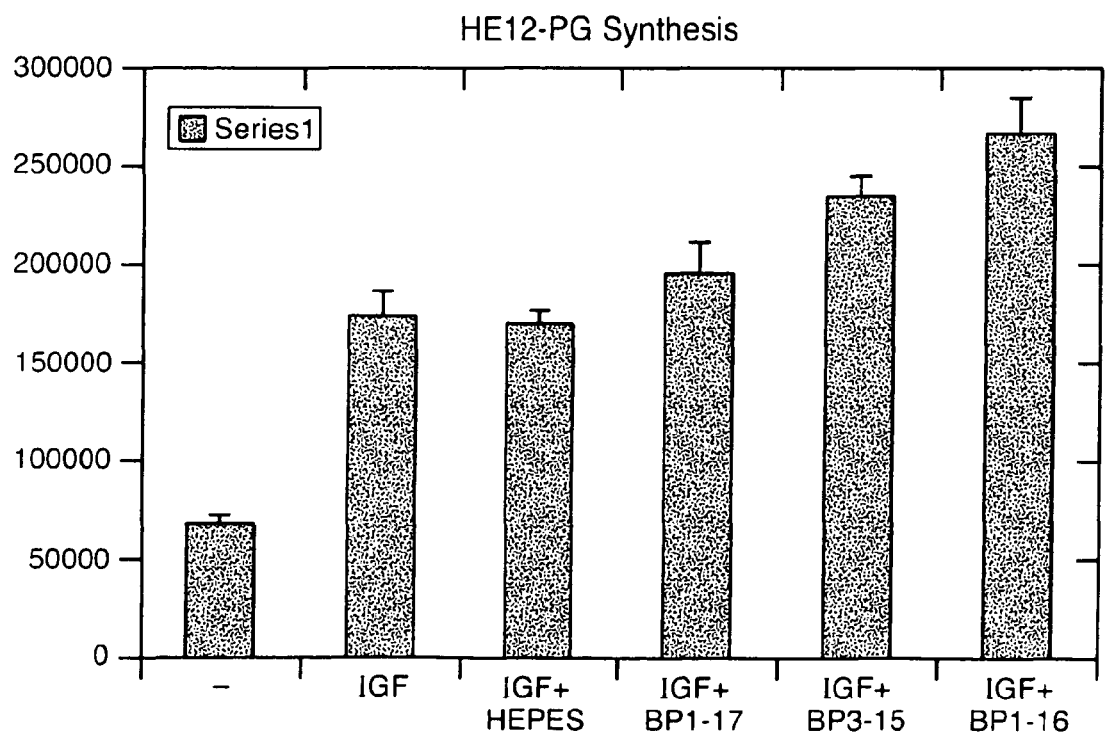
FIG. 36 shows a KIRA assay of peptide activity using four different peptides (BP1-16: circles, BP1-02: squares, BP1-25: triangles, and BP1-40: diamonds).

Increased potency was observed for both peptides BP1-25 and BP1-40 over peptides BP1-16 and BP1-02 (FIG. 36). However, under these conditions, BP1-02 was not significantly more active than BP1-16; and BP1-40 was not significantly more active than BP1-25. The EC$_{20}$ (concentration at which 20% of maximal IGF-I activity is observed) values were 10-20 nM for BP1-25 and BP1-40, and 150-200 nM for BP1-16 and BP1-02.

Example 16

Biosynthesis of a BP1-01 Peptide Variant

An additional variant of BP1-21A was designed for peptide biosynthesis in *E. coli*. For this approach, a DNA sequence encoding the peptide was fused by site-directed mutagenesis to the gene for a consensus domain of protein-A known as Z-domain (Nilsson et al., *Protein Engineering*, 1(2):107-113 (1987). After expression and secretion from *E. coli*, the fusion protein was enzymatically cleaved with trypsin to yield free peptide, which can be purified from the enzymatic reaction mix (see, e.g., Varadarajan et al., *PNAS*, 82:5681-5684 (1985); Castellanos-Serra et al., *FEBS*, 378:171-176 (1996); Nilsson et al., *J. Biotechnology*, 48:241-250 (1996).

A detailed procedure for trypsin digestions has been described in Smith, *Methods in Mol. Biol.*, 32:289-296 (1994). Because this protease is highly specific for Arg and Lys residues, the BP1-40 peptide was modified by mutation of these residues for construction of the fusion. From previous mutagenesis and phage-library results, it was known that Arg and Lys residues of BP1-01 could be substituted without significant loss of binding affinity. Therefore, a fusion protein was designed with substitutions R2A and K12H (numbering is according to the BP1-01 sequence). Furthermore, BP1-01, having a Gly residue following the C-terminal F14 of BP1-16, was known to have no significant effect on binding affinity. Therefore, a Gly-Arg sequence was added at the end of the peptide to allow for trypsin cleavage. The sequences of the BP1-625-Z fusion protein and the BP1-625 peptide (as cleaved by trypsin) are given in Table XXVI.

TABLE XXVI

Peptide sequences for *E. coli* biosynthesis

| Construct | Peptide sequence |
| --- | --- |
| BP1-625-Z | GQQSCAAGPLQWLCEHYFSTYGRGGGSGGAQHDEAVDNKFN KEQQNAFYEILHLPNLNEEQRNAFIQSLKDDPSQSANLLAE AKKLNDAQAPNVDMN (SEQ ID NO: 47) |
| BP1-625 | GQQSCAAGPLQWLCEHYFSTYGR (SEQ ID NO: 46) |

Figure 37:
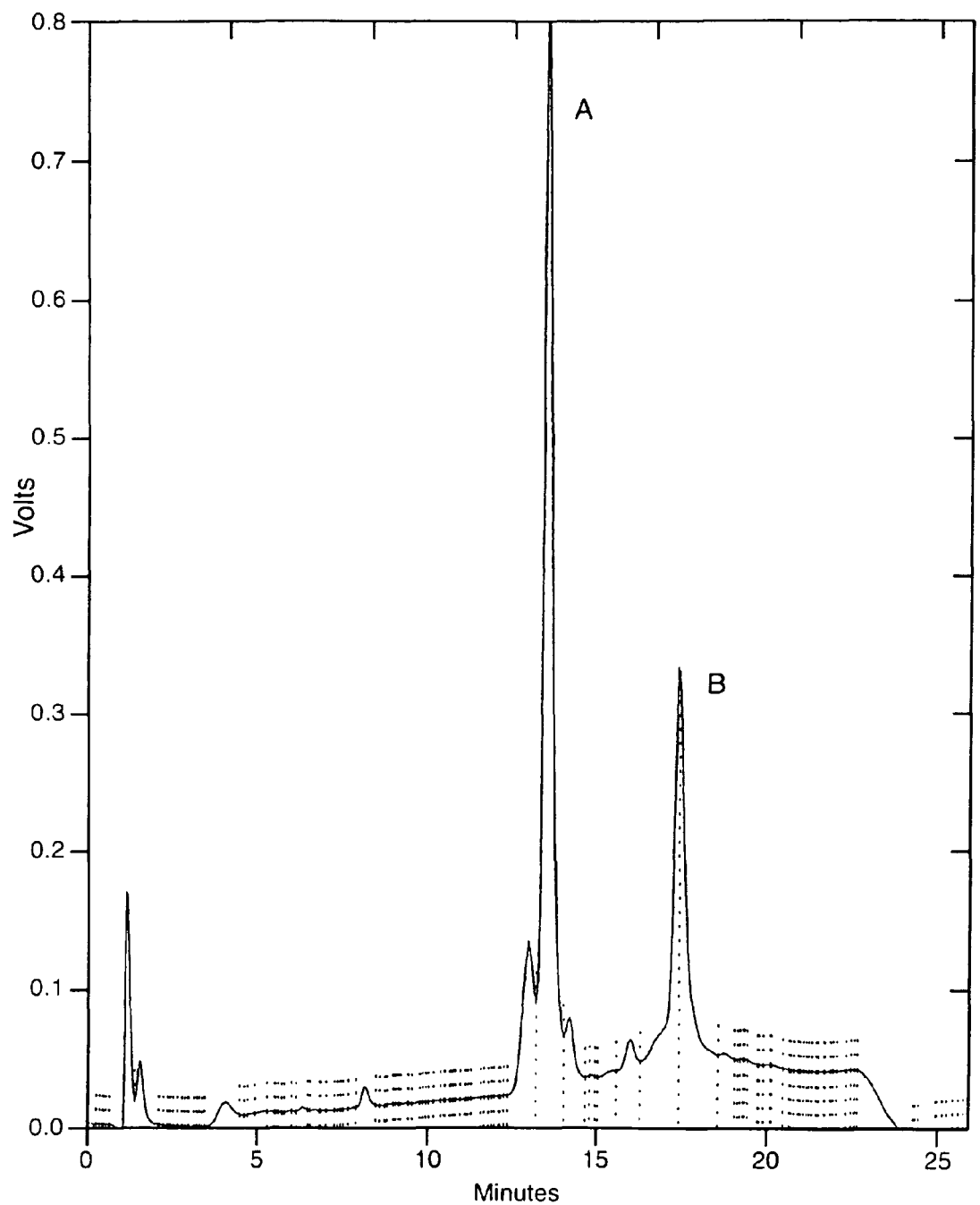
FIG. 37 shows an analytical HPLC run of the trypsin-cleaved BP1-625-Z fusion. The major peaks were identified by mass spectrometry as (A) Z-domain fragment and (B) BP1-625 peptide.

The fusion protein BP1-625-Z was produced from *E. coli* shake-flask cultures. Culture supernatants were sterile-filtered, then applied to an IgG-Sepharose™ column (Pharmacia). The bound fraction was eluted with 1M acetic acid, then lyophilized and resuspended in trypsin-digest buffer: 10 mM Tris (pH 8.0), 100 mM NaCl, 1 mM $CaCl_2$. TPCK-treated trypsin (Sigma) was added at a weight/weight ratio of 1:100 to 1:200 (trypsin to substrate) and digestion was carried out at 25° C. for 1-2 hours. Thereafter, PMSF was added to 1 mM to stop the reaction. Samples were adjusted to 1 mM TFA and run on an analytical HPLC column with a 0-60% acetonitrile gradient in 0.1% TFA. The two predominant peaks were collected (FIG. 37) and shown by mass spectrometry to correspond to a Z-domain fragment, and the peptide BP1-625.

Figure 38:
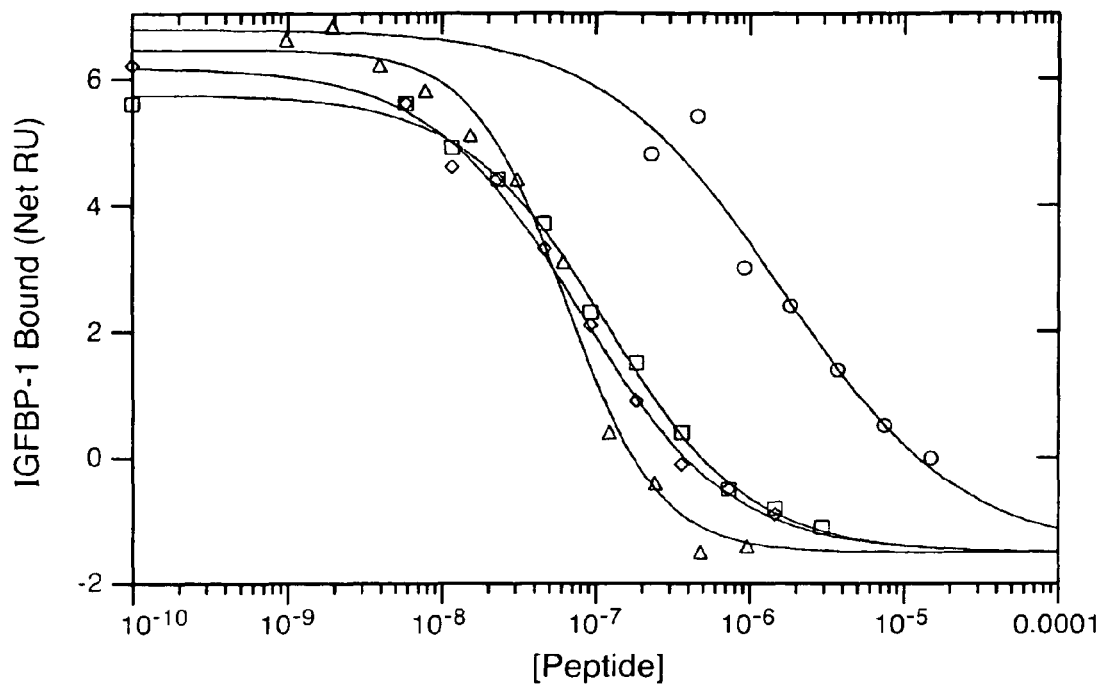
FIG. 38 shows a BIACORE™ surface-plasmon-resonance device inhibition assay of IGF-I activity using four different peptides (BP1-01: circles, BP1-625: squares, BP1-21A: triangles, and BP1-25: diamonds).

The peptide BP1-625 fraction was lyophilized and resuspended in 100 mM HEPES buffer, pH 7.2. Inhibition experiments were carried out in a BIAcore™ assay as previously described, except that limiting amounts (9-10 nM IGFBP-1) were used to make the assay sensitive with respect to affinities in the $10^{-8}$ M range. These assays showed that the BP1-625 peptide blocked IGFBP-1 binding to immobilized IGF-1 and was similar in activity to BP1-25, having about 20-fold improved potency over BP1-01 (FIG. 38).

It may be predicted that BP1-625 will block IGF-I binding to IGFBP-1 and produce IGF-like activity on cells, with similar potency to BP1-21A, BP1-25, or BP1-40. It would also be expected that a peptide, BP1-625T, comprising the sequence: GlyGlnGlnSerCysAlaAlaGlyPro-LeuGlnTrpLeuCysGluHisTyrPheSerThrTyr (SEQ ID NO:153) would act similarly to BP1-625.

The BP1-625-Z fusion is useful for producing IGFBP-binding peptides from *E. coli*, and the Z part of the fusion can be advantageously attached to other peptides herein than just BP1-625.

Example 17

Articular Cartilage Explants from Human Joints

Materials and Methods:

The same Material and Methods (for human tissue) were used as described above, using articular cartilage explants from human joints removed from patients undergoing joint replacement. These explants were cultured with IGF-1 alone at 40 ng/ml, or IGF-1 with BP1-17, BP3-15, or BP1-16 (0.1 mg/ml), or IGF-1 with buffer (HEPES).

Proteoglycan breakdown and synthesis were measured as described above.

Results and Discussion:

The role of specific IGFBPs in IGF-1 activity was tested by treating articular cartilage explants from patients undergoing joint replacement with IGF-1 in the presence of peptides that inhibit IGF-1 binding to particular IGFBPs. In particular, BP1-16 inhibits IGF-1 binding to IGFBP-1, and BP3-15 inhibits IGF-1 binding to IGFBP-3. BP1-17 binds with much lower affinity to IGFBP-1. In addition, buffer alone (100 mM HEPES) was included as a negative control.

Figure 39:
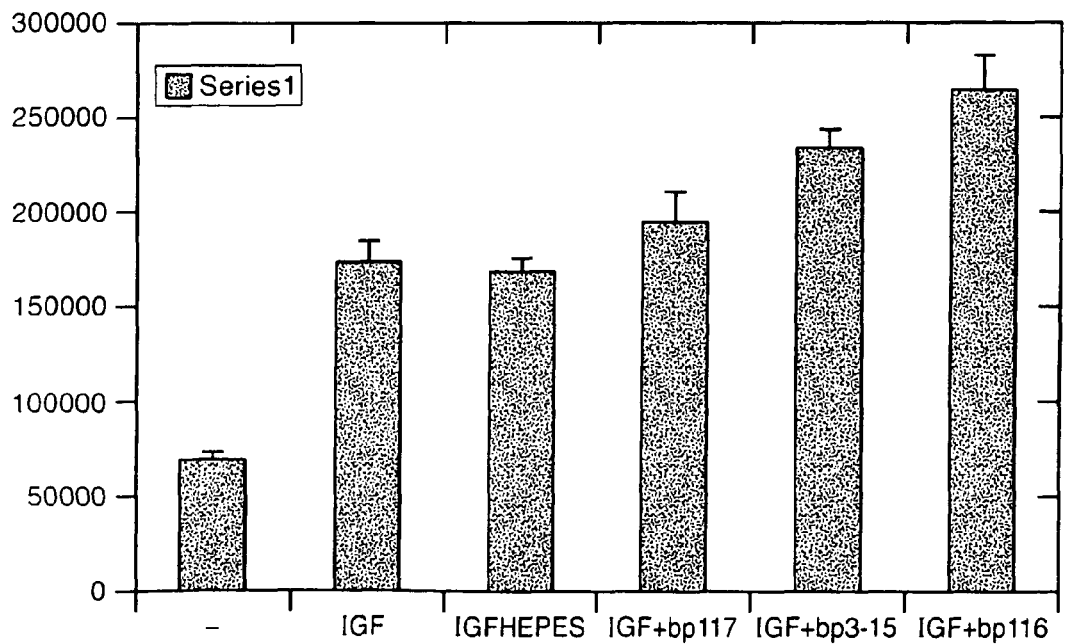
FIG. 39 shows the effect on proteoglycan synthesis of articular cartilage explants from human joints removed from patients undergoing joint replacement cultured with IGF-1 alone (IGF) at 40 ng/ml, or IGF-1 with BP1-17, BP3-15, or BP1-16 (0.1 mg/ml), or IGF-1 with buffer (HEPES).

As shown in FIG. 39, both BP3-15 and BP1-16, and also BP1-17 to a lesser extent, enhance the protective effect of IGF-1. Namely, BP3-15 and BP1-16, and to some extent BP1-17, enhance anabolism, as shown by the increase in matrix synthesis. Thus, these three peptides, and especially BP3-15 and BP1-16, are expected to be useful therapeutics for the treatment of arthritis.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. An article of manufacture comprising a container holding
an insulin-like growth factor-1 (IGF-1) analog with a binding affinity preference for insulin-like growth factor protein-3 (IGFBP-3) over insulin-like growth factor binding protein-1 (IGFBP-1) which analog comprises a substitution at a position selected from the group consisting of amino acid residues 3, 7, 10, 16, 25 and 49 in the sequence of IGFBP-1 (SEQ ID NO: 3),
in a pharmaceutically acceptable carrier with instructions for treating a cartilage disorder.

2. The article of manufacture of claim 1, wherein the container is selected from the group consisting of a bottle, a vial, a syringe, a test tube, an intravenous solution bag.

3. The article of manufacture of claim 1, wherein the cartilage disorder is a degenerative cartilaginous disorder.

4. The article of manufacture of claim 1, wherein the cartilage disorder is osteoarthritis or rheumatoid arthritis.

5. The article of manufacture of claim 1, further comprising a second container comprising a pharmaceutically acceptable buffer.

6. The article of manufacture of claim 1, further comprising one or more of a diluent, a filter, a needle, a syringe, and a package insert.

7. The article of manufacture of claim 1, wherein the IGF-1 analog with a binding affinity preference for IGFBP-3 over IGFBP-1 is selected from the group consisting of F49A, F49G, F49S, E3A, E3G, E3S, E3AF49A, E3AF49G, E3AF49S, E3GF49A, E3GF49G, E3GF49S, E3SF49A, E3SF49G, E3SF49S, F16A, F16G, F16S, F16AF49A, F16GF49A, F16SF49A, F16AF49G, F16SF49S, F16SF49G, F16GF49S, and F16GF49G.

* * * * *

SEQUENCE LISTING

<160> NUMBER OF SEQ ID NOS: 153

<210> SEQ ID NO 1
<211> LENGTH: 5140
<212> TYPE: DNA
<213> ORGANISM: Artificial sequence
<220> FEATURE:
<223> OTHER INFORMATION: Sequence is synthesized

<400> SEQUENCE: 1

```
gaattcaact tctccatact ttggataagg aaatacagac atgaaaaatc         50
tcattgctga gttgttattt aagcttgccc aaaaagaaga agagtcgaat        100
gaactgtgtg cgcaggtaga agctttggag attatcgtca ctgcaatgct        150
```

```
tcgcaatatg gcgcaaaatg accaacagcg gttgattgat caggtagagg      200
gggcgctgta cgaggtaaag cccgatgcca gcattcctga cgacgatacg      250
gagctgctgc gcgattacgt aaagaagtta ttgaagcatc ctcgtcagta      300
aaaagttaat cttttcaaca gctgtcataa agttgtcacg gccgagactt      350
atagtcgctt tgttttattt ttttaatgta tttgtaacta gtacgcaagt      400
tcacgtaaaa agggtatcta gaggttgagg tgatttatg aaaaagaata       450 tcgcatttct tcttgcatct atgttcgttt tttctattgc tacaaatgcc      500
tatgcatctg gtaccgccat ggctgatccg aaccgtttcc gcggtaaaga      550
tctggcaggt tcaccaggtg gaggatccgg aggaggcgcc gagggtgacg      600
atcccgcaaa agcggccttt aactccctgc aagcctcagc gaccgaatat      650
atcggttatg cgtgggcgat ggttgttgtc attgtcggcg caactatcgg      700
tatcaagctg tttaagaaat tcacctcgaa agcaagctga taaaccgata      750
caattaaagg ctccttttgg agccttttt tttggagatt ttcaacgtga       800
aaaaattatt attcgcaatt cctttagttg ttccttct a ttctcactcc      850 gctgaaactg ttgaaagttg tttagcaaaa ccccatacag aaaattcatt      900
tactaacgtc tggaaagacg acaaaacttt agatcgttac gctaactatg      950
agggttgtct gtggaatgct acaggcgttg tagtttgtac tggtgacgaa      1000
actcagtgtc tagctagagt ggcggtggct ctggttccgg tgattttgat      1050
tatgaaaaga tggcaaacgc taataagggg gctatgaccg aaaatgccga      1100
tgaaaacgcg ctacagtctg acgctaaagg caaacttgat tctgtcgcta      1150
ctgattacgg tgctgctatc gatggtttca ttggtgacgt ttccggcctt      1200
gctaatggta atggtgctac tggtgatttt gctggctcta attcccaaat      1250
ggctcaagtc ggtgacggtg ataattcacc tttaatgaat aatttccgtc      1300
aatatttacc ttccctccct caatcggttg aatgtcgccc ttttgtcttt      1350
agcgctggta accatatga attttctatt gattgtgaca aaataaactt       1400
attccgtggt gtcttgcgt ttcttttata tgttgccacc tttatgtatg       1450
tattttctac gtttgctaac atactgcgta ataaggagtc ttaatcatgc      1500
cagttctttt ggctagcgcc gccctatacc ttgtctgcct ccccgcgttg      1550
cgtcgcggtg catggagccg ggccacctcg acctgaatgg aagccggcgg      1600
cacctcgcta acggattcac cactccaaga attggagcca atcaattctt      1650
gcggagaact gtgaatgcgc aaaccaaccc ttggcagaac atatccatcg      1700
cgtccgccat ctccagcagc cgcacgcggc gcatctcggg cagcgttggg      1750
tcctggccac gggtgcgcat gatcgtgctc ctgtcgttga ggacccggct      1800
aggctggcgg ggttgcctta ctggttagca gaatgaatca ccgatacgcg      1850
agcgaacgtg aagcgactgc tgctgcaaaa cgtctgcgac ctgagcaaca      1900
acatgaatgg tcttcggttt ccgtgtttcg taaagtctgg aaacgcggaa      1950
gtcagcgccc tgcaccatta tgttccggat ctgcatcgca ggatgctgct      2000
ggctaccctg tggaacacct acatctgtat taacgaagcg ctggcattga      2050
ccctgagtga ttttttctctg gtcccgccgc atccataccg ccagttgttt     2100
accctcacaa cgttccagta accgggcatg ttcatcatca gtaacccgta      2150
```

```
tcgtgagcat cctctctcgt ttcatcggta tcattacccc catgaacaga        2200 aattcccect tacacggagg catcaagtga ccaaacagga aaaaaccgcc        2250
cttaacatgg cccgctttat cagaagccag acattaacgc ttctggagaa        2300
actcaacgag ctggacgcgg atgaacaggc agacatctgt gaatcgcttc        2350
acgaccacgc tgatgagctt taccgcagga tccggaaatt gtaaacgtta        2400
atattttgtt aaaattcgcg ttaaattttt gttaaatcag ctcatttttt        2450
aaccaatagg ccgaaatcgg caaaatccct tataaatcaa agaatagac         2500 cgagataggg ttgagtgttg ttccagtttg gaacaagagt ccactattaa        2550
agaacgtgga ctccaacgtc aaagggcgaa aaaccgtcta tcagggctat        2600
ggcccactac gtgaaccatc accctaatca agttttttgg ggtcgaggtg        2650
ccgtaaagca ctaaatcgga accctaaagg gagcccccga tttagagctt        2700
gacggggaaa gccggcgaac gtggcgagaa aggaagggaa gaaagcgaaa        2750
ggagcgggcg ctagggcgct ggcaagtgta gcggtcacgc tgcgcgtaac        2800
caccacaccc gccgcgctta atgcgccgct acagggcgcg tccggatcct        2850
gcctcgcgcg tttcggtgat gacggtgaaa acctctgaca catgcagctc        2900
ccggagacgt tcacagcttg tctgtaagcg gatgccggga gcagacaagc        2950
ccgtcagggc gcgtcagcgg gtgttggcgg gtgtcggggc gcagccatga        3000
cccagtcacg tagcgatagc ggagtgtata ctggcttaac tatgcggcat        3050
cagagcagat tgtactgaga gtgcaccata tgcggtgtga ataccgcac         3100 agatgcgtaa ggagaaaata ccgcatcagg cgctcttccg cttcctcgct        3150
cactgactcg ctgcgctcgg tcgttcggct gcggcgagcg gtatcagctc        3200
actcaaaggc ggtaatacgg ttatccacag aatcagggga taacgcagga        3250
aagaacatgt gagcaaaagg ccagcaaaag gccaggaacc gtaaaaggc         3300 cgcgttgctg gcgtttttcc ataggctccg ccccctgac gagcatcaca         3350 aaaatcgacg ctcaagtcag aggtggcgaa acccgacagg actataaaga        3400
taccaggcgt ttccccctgg aagctccctc gtgcgctctc ctgttccgac        3450
cctgccgctt accggatacc tgtccgcctt tctcccttcg ggaagcgtgg        3500
cgctttctca tagctcacgc tgtaggtatc tcagttcggt gtaggtcgtt        3550
cgctccaagc tgggctgtgt gcacgaaccc cccgttcagc ccgaccgctg        3600
cgccttatcc ggtaactatc gtcttgagtc aacccggta  agacacgact        3650 tatcgccact ggcagcagcc actggtaaca ggattagcag agcgaggtat        3700
gtaggcggtg ctacagagtt cttgaagtgg tggcctaact acggctacac        3750
tagaaggaca gtatttggta tctgcgctct gctgaagcca gttaccttcg        3800
gaaaaagagt tggtagctct tgatccggca acaaaccac cgctggtagc         3850 ggtggttttt ttgtttgcaa gcagcagatt acgcgcagaa aaaaggatc         3900 tcaagaagat cctttgatct tttctacggg gtctgacgct cagtggaacg        3950
aaaactcacg ttaagggatt ttggtcatga gattatcaaa aaggatcttc        4000
acctagatcc ttttaaatta aaatgaagt ttttaaatcaa tctaaagtat        4050 atatgagtaa acttggtctg acagttacca atgcttaatc agtgaggcac        4100
ctatctcagc gatctgtcta tttcgttcat ccatagttgc ctgactcccc        4150
```

```
gtcgtgtaga taactacgat acgggagggc ttaccatctg gccccagtgc         4200
tgcaatgata ccgcgagacc cacgctcacc ggctccagat ttatcagcaa         4250
taaaccagcc agccggaagg gccgagcgca gaagtggtcc tgcaacttta         4300
tccgcctcca tccagtctat taattgttgc cgggaagcta gagtaagtag         4350
ttcgccagtt aatagtttgc gcaacgttgt tgccattgct gcaggcatcg         4400
tggtgtcacg ctcgtcgttt ggtatggctt cattcagctc cggttcccaa         4450
cgatcaaggc gagttacatg atcccccatg ttgtgcaaaa aagcggttag         4500
ctccttcggt cctccgatcg ttgtcagaag taagttggcc gcagtgttat         4550
cactcatggt tatggcagca ctgcataatt ctcttactgt catgccatcc         4600
gtaagatgct tttctgtgac tggtgagtac tcaaccaagt cattctgaga         4650
atagtgtatg cggcgaccga gttgctcttg cccggcgtca acacgggata         4700
ataccgcgcc acatagcaga actttaaaag tgctcatcat tggaaaacgt         4750 tcttcgggc gaaaactctc aaggatctta ccgctgttga gatccagttc          4800
gatgtaaccc actcgtgcac ccaactgatc ttcagcatct tttactttca         4850
ccagcgtttc tgggtgagca aaaacaggaa ggcaaaatgc cgcaaaaaag         4900
ggaataaggg cgacacggaa atgttgaata ctcatactct ccttttttca         4950
atattattga agcatttatc agggttattg tctcatgagc ggatacatat         5000
ttgaatgtat ttagaaaaat aaacaaatag gggttccgcg cacatttccc         5050
cgaaaagtgc cacctgacgt ctaagaaacc attattatca tgacattaac         5100
ctataaaaat aggcgtatca cgaggccctt tcgtcttcaa                    5140
```

<210> SEQ ID NO 2
<211> LENGTH: 77
<212> TYPE: PRT
<213> ORGANISM: Artificial sequence
<220> FEATURE:
<223> OTHER INFORMATION: Sequence is synthesized

<400> SEQUENCE: 2

Ser Gly Thr Ala Met Ala Asp Pro Asn Arg Phe Arg Gly Lys Asp
1               5                   10                  15

Leu Ala Gly Ser Pro Gly Gly Gly Ser Gly Gly Gly Ala Glu Gly
                20                  25                  30

Asp Asp Pro Ala Lys Ala Ala Phe Asn Ser Leu Gln Ala Ser Ala
                35                  40                  45

Thr Glu Tyr Ile Gly Tyr Ala Trp Ala Met Val Val Ile Val
                50                  55                  60

Gly Ala Thr Ile Gly Ile Lys Leu Phe Lys Lys Phe Thr Ser Lys
                65                  70                  75

Ala Ser

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly
                20                  25                  30

```
Tyr Gly Ser Ser Arg Arg Ala Pro Gln Thr Gly Ile Val Asp
            35                  40                  45

Glu Cys Cys Phe Arg Ser Cys Asp Leu Arg Arg Leu Glu Met Tyr
            50                  55                  60

Cys Ala Pro Leu Lys Pro Ala Lys Ser Ala
            65                  70

<210> SEQ ID NO 4
<211> LENGTH: 86
<212> TYPE: PRT
<213> ORGANISM: Homo sapiens

<400> SEQUENCE: 4

Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                20                  25                  30

Arg Arg Glu Ala Glu Asp Leu Gln Val Gly Gln Val Glu Leu Gly
            35                  40                  45

Gly Gly Pro Gly Ala Gly Ser Leu Gln Pro Leu Ala Leu Glu Gly
            50                  55                  60

Ser Leu Gln Lys Arg Gly Ile Val Glu Gln Cys Cys Thr Ser Ile
            65                  70                  75

Cys Ser Leu Tyr Gln Leu Glu Asn Tyr Cys Asn
            80                  85

<210> SEQ ID NO 5
<211> LENGTH: 51
<212> TYPE: PRT
<213> ORGANISM: Homo sapiens

<400> SEQUENCE: 5

Phe Val Asn Gln His Leu Cys Gly Ser His Leu Val Glu Ala Leu
 1               5                  10                  15

Tyr Leu Val Cys Gly Glu Arg Gly Phe Phe Tyr Thr Pro Lys Thr
                20                  25                  30

Gly Ile Val Glu Gln Cys Cys Thr Ser Ile Cys Ser Leu Tyr Gln
            35                  40                  45

Leu Glu Asn Tyr Cys Asn
            50

<210> SEQ ID NO 6
<211> LENGTH: 20
<212> TYPE: PRT
<213> ORGANISM: Artificial sequence
<220> FEATURE:
<223> OTHER INFORMATION: Sequence is synthesized

<400> SEQUENCE: 6

Ala Ser Glu Glu Val Cys Trp Pro Val Ala Glu Trp Tyr Leu Cys
 1               5                  10                  15

Asn Met Trp Gly Arg
                20

<210> SEQ ID NO 7
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 7

Val Ala Trp Glu Val Cys Trp Asp Arg His Asp Gln Gly Tyr Ile
 1               5                  10                  15
Cys Thr Thr Asp Ser
                20

<210> SEQ ID NO 8
<211> LENGTH: 18
<212> TYPE: PRT
<213> ORGANISM: Artificial sequence
<220> FEATURE:
<223> OTHER INFORMATION: Sequence is synthesized

<400> SEQUENCE: 8

Ala Trp Glu Val Cys Trp Asp Arg His Gln Gly Tyr Ile Cys Thr
 1               5                  10                  15
Thr Asp Ser

<210> SEQ ID NO 9
<211> LENGTH: 18
<212> TYPE: PRT
<213> ORGANISM: Artificial sequence
<220> FEATURE:
<223> OTHER INFORMATION: Sequence is synthesized

<400> SEQUENCE: 9

Glu Glu Ser Glu Cys Phe Glu Gly Pro Gly Tyr Val Ile Cys Gly
 1               5                  10                  15
Leu Val Gly

<210> SEQ ID NO 10
<211> LENGTH: 18
<212> TYPE: PRT
<213> ORGANISM: Artificial sequence
<220> FEATURE:
<223> OTHER INFORMATION: Sequence is synthesized

<400> SEQUENCE: 10

Ser Glu Glu Val Cys Trp Pro Val Ala Glu Trp Tyr Leu Cys Asn
 1               5                  10                  15
Met Trp Gly

<210> SEQ ID NO 11
<211> LENGTH: 18
<212> TYPE: PRT
<213> ORGANISM: Artificial sequence
<220> FEATURE:
<223> OTHER INFORMATION: Sequence is synthesized

<400> SEQUENCE: 11

Asp Met Gly Val Cys Ala Asp Gly Pro Trp Met Tyr Val Cys Glu
 1               5                  10                  15
Trp Thr Glu

<210> SEQ ID NO 12
<211> LENGTH: 18
<212> TYPE: PRT
<213> ORGANISM: Artificial sequence
<220> FEATURE:
<223> OTHER INFORMATION: Sequence is synthesized
```

```
<400> SEQUENCE: 12

Thr Gly Val Asp Cys Gln Cys Gly Pro Val His Cys Val Cys Met
 1               5                  10                  15

Asp Trp Ala

<210> SEQ ID NO 13
<211> LENGTH: 18
<212> TYPE: PRT
<213> ORGANISM: Artificial sequence
<220> FEATURE:
<223> OTHER INFORMATION: Sequence is synthesized

<400> SEQUENCE: 13

Thr Val Ala Asn Cys Asp Cys Tyr Met Pro Leu Cys Leu Cys Tyr
 1               5                  10                  15

Asp Ser Asp

<210> SEQ ID NO 14
<211> LENGTH: 15
<212> TYPE: PRT
<213> ORGANISM: Artificial sequence
<220> FEATURE:
<223> OTHER INFORMATION: Sequence is synthesized

<400> SEQUENCE: 14

Ser Glu Glu Val Cys Trp Pro Val Ala Glu Trp Tyr Leu Cys Asn
 1               5                  10                  15

<210> SEQ ID NO 15
<211> LENGTH: 15
<212> TYPE: PRT
<213> ORGANISM: Artificial sequence
<220> FEATURE:
<223> OTHER INFORMATION: Sequence is synthesized

<400> SEQUENCE: 15

Val Cys Trp Pro Val Ala Glu Trp Tyr Leu Cys Asn Met Trp Gly
 1               5                  10                  15

<210> SEQ ID NO 16
<211> LENGTH: 12
<212> TYPE: PRT
<213> ORGANISM: Artificial sequence
<220> FEATURE:
<223> OTHER INFORMATION: Sequence is synthesized

<400> SEQUENCE: 16

Val Cys Trp Pro Val Ala Glu Trp Tyr Leu Cys Asn
 1               5                  10

<210> SEQ ID NO 17
<211> LENGTH: 11
<212> TYPE: PRT
<213> ORGANISM: Artificial sequence
<220> FEATURE:
<223> OTHER INFORMATION: Sequence is synthesized

<400> SEQUENCE: 17

Cys Trp Pro Val Ala Glu Trp Tyr Leu Cys Asn
 1               5                  10

<210> SEQ ID NO 18
<211> LENGTH: 13
<212> TYPE: PRT
<213> ORGANISM: Artificial sequence
```

```
<220> FEATURE:
<223> OTHER INFORMATION: Sequence is synthesized

<400> SEQUENCE: 18

Glu Val Cys Trp Pro Val Ala Glu Trp Tyr Leu Cys Asn
 1               5                  10

<210> SEQ ID NO 19
<211> LENGTH: 14
<212> TYPE: PRT
<213> ORGANISM: Artificial sequence
<220> FEATURE:
<223> OTHER INFORMATION: Sequence is synthesized

<400> SEQUENCE: 19

Glu Glu Val Cys Trp Pro Val Ala Glu Trp Tyr Leu Cys Asn
 1               5                  10

<210> SEQ ID NO 20
<211> LENGTH: 16
<212> TYPE: PRT
<213> ORGANISM: Artificial sequence
<220> FEATURE:
<223> OTHER INFORMATION: Sequence is synthesized

<400> SEQUENCE: 20

Ala Ser Glu Glu Val Cys Trp Pro Val Ala Glu Trp Tyr Leu Cys
 1               5                  10                  15

Asn

<210> SEQ ID NO 21
<211> LENGTH: 15
<212> TYPE: PRT
<213> ORGANISM: Artificial sequence
<220> FEATURE:
<223> OTHER INFORMATION: Sequence is synthesized

<400> SEQUENCE: 21

Ser Glu Glu Val Cys Trp Pro Val Ala Glu Trp Tyr Leu Cys Asn
 1               5                  10                  15

<210> SEQ ID NO 22
<211> LENGTH: 15
<212> TYPE: PRT
<213> ORGANISM: Artificial sequence
<220> FEATURE:
<223> OTHER INFORMATION: Sequence is synthesized

<400> SEQUENCE: 22

Ser Glu Glu Val Cys Trp Pro Val Ala Glu Trp Tyr Leu Cys Asn
 1               5                  10                  15

<210> SEQ ID NO 23
<211> LENGTH: 15
<212> TYPE: PRT
<213> ORGANISM: Artificial sequence
<220> FEATURE:
<223> OTHER INFORMATION: Sequence is synthesized

<400> SEQUENCE: 23

Gly Pro Glu Thr Cys Trp Pro Val Ala Glu Trp Tyr Leu Cys Asn
 1               5                  10                  15

<210> SEQ ID NO 24
<211> LENGTH: 12
<212> TYPE: PRT
<213> ORGANISM: Artificial sequence
```

```
<220> FEATURE:
<223> OTHER INFORMATION: Sequence is synthesized

<400> SEQUENCE: 24

Cys Gln Leu Val Arg Pro Asp Leu Leu Leu Cys Gln
  1               5                  10

<210> SEQ ID NO 25
<211> LENGTH: 11
<212> TYPE: PRT
<213> ORGANISM: Artificial sequence
<220> FEATURE:
<223> OTHER INFORMATION: Sequence is synthesized

<400> SEQUENCE: 25

Ile Pro Val Ser Pro Asp Trp Phe Val Cys Gln
  1               5                  10

<210> SEQ ID NO 26
<211> LENGTH: 15
<212> TYPE: PRT
<213> ORGANISM: Artificial sequence
<220> FEATURE:
<223> OTHER INFORMATION: Sequence is synthesized

<400> SEQUENCE: 26

Cys Arg Ala Gly Pro Leu Gln Trp Leu Cys Glu Lys Tyr Phe Gly
  1               5                  10                  15

<210> SEQ ID NO 27
<211> LENGTH: 19
<212> TYPE: PRT
<213> ORGANISM: Artificial sequence
<220> FEATURE:
<223> OTHER INFORMATION: Sequence is synthesized

<400> SEQUENCE: 27

Ser Glu Val Gly Cys Arg Ala Gly Pro Leu Gln Trp Leu Cys Glu
  1               5                  10                  15

Lys Tyr Phe Gly

<210> SEQ ID NO 28
<211> LENGTH: 11
<212> TYPE: PRT
<213> ORGANISM: Artificial sequence
<220> FEATURE:
<223> OTHER INFORMATION: Sequence is synthesized

<400> SEQUENCE: 28

Cys Arg Ala Gly Pro Leu Gln Trp Leu Cys Glu
  1               5                  10

<210> SEQ ID NO 29
<211> LENGTH: 14
<212> TYPE: PRT
<213> ORGANISM: Artificial sequence
<220> FEATURE:
<223> OTHER INFORMATION: Sequence is synthesized

<400> SEQUENCE: 29

Cys Arg Lys Gly Pro Leu Gln Trp Leu Cys Glu Leu Tyr Phe
  1               5                  10

<210> SEQ ID NO 30
<211> LENGTH: 14
<212> TYPE: PRT
<213> ORGANISM: Artificial sequence
```

```
<220> FEATURE:
<223> OTHER INFORMATION: Sequence is synthesized

<400> SEQUENCE: 30

Cys Arg Lys Gly Pro Leu Gln Trp Leu Cys Glu Lys Tyr Phe
 1               5                  10

<210> SEQ ID NO 31
<211> LENGTH: 14
<212> TYPE: PRT
<213> ORGANISM: Artificial sequence
<220> FEATURE:
<223> OTHER INFORMATION: Sequence is synthesized

<400> SEQUENCE: 31

Cys Lys Glu Gly Pro Leu Gln Trp Leu Cys Glu Lys Tyr Phe
 1               5                  10

<210> SEQ ID NO 32
<211> LENGTH: 14
<212> TYPE: PRT
<213> ORGANISM: Artificial sequence
<220> FEATURE:
<223> OTHER INFORMATION: Sequence is synthesized

<400> SEQUENCE: 32

Cys Lys Glu Gly Pro Leu Leu Trp Leu Cys Glu Lys Tyr Phe
 1               5                  10

<210> SEQ ID NO 33
<211> LENGTH: 19
<212> TYPE: PRT
<213> ORGANISM: Artificial sequence
<220> FEATURE:
<223> OTHER INFORMATION: Sequence is synthesized

<400> SEQUENCE: 33

Ser Glu Val Gly Cys Arg Ala Gly Pro Leu Gln Trp Leu Cys Glu
 1               5                  10                  15

Lys Tyr Phe Gly

<210> SEQ ID NO 34
<211> LENGTH: 14
<212> TYPE: PRT
<213> ORGANISM: Artificial sequence
<220> FEATURE:
<223> OTHER INFORMATION: Sequence is synthesized

<400> SEQUENCE: 34

Cys Ala Ala Gly Pro Leu Gln Trp Leu Cys Glu Lys Tyr Phe
 1               5                  10

<210> SEQ ID NO 35
<211> LENGTH: 14
<212> TYPE: PRT
<213> ORGANISM: Artificial sequence
<220> FEATURE:
<223> OTHER INFORMATION: Sequence is synthesized

<400> SEQUENCE: 35

Cys Arg Ala Gly Pro Leu Gln Trp Leu Cys Glu Lys Tyr Phe
 1               5                  10

<210> SEQ ID NO 36
<211> LENGTH: 12
<212> TYPE: PRT
<213> ORGANISM: Artificial sequence
```

```
<220> FEATURE:
<223> OTHER INFORMATION: Sequence is synthesized

<400> SEQUENCE: 36

Cys Arg Ala Gly Pro Leu Gln Trp Leu Cys Glu Lys
 1               5                  10

<210> SEQ ID NO 37
<211> LENGTH: 14
<212> TYPE: PRT
<213> ORGANISM: Artificial sequence
<220> FEATURE:
<223> OTHER INFORMATION: Sequence is synthesized

<400> SEQUENCE: 37

Cys Arg Ala Gly Pro Leu Gln Trp Leu Cys Glu Lys Ala Ala
 1               5                  10

<210> SEQ ID NO 38
<211> LENGTH: 18
<212> TYPE: PRT
<213> ORGANISM: Artificial sequence
<220> FEATURE:
<223> OTHER INFORMATION: Sequence is synthesized

<400> SEQUENCE: 38

Ser Glu Met Val Cys Arg Ala Gly Pro Leu Gln Trp Leu Cys Glu
 1               5                  10                  15

Ile Tyr Phe

<210> SEQ ID NO 39
<211> LENGTH: 18
<212> TYPE: PRT
<213> ORGANISM: Artificial sequence
<220> FEATURE:
<223> OTHER INFORMATION: Sequence is synthesized

<400> SEQUENCE: 39

Glu Ala Arg Val Cys Arg Ala Gly Pro Leu Gln Trp Leu Cys Glu
 1               5                  10                  15

Lys Tyr Phe

<210> SEQ ID NO 40
<211> LENGTH: 21
<212> TYPE: PRT
<213> ORGANISM: Artificial sequence
<220> FEATURE:
<223> OTHER INFORMATION: Sequence is synthesized

<400> SEQUENCE: 40

Ser Glu Val Gly Cys Arg Ala Gly Pro Leu Gln Trp Leu Cys Glu
 1               5                  10                  15

Lys Tyr Phe Ser Thr Tyr
                 20

<210> SEQ ID NO 41
<211> LENGTH: 17
<212> TYPE: PRT
<213> ORGANISM: Artificial sequence
<220> FEATURE:
<223> OTHER INFORMATION: Sequence is synthesized
```

-continued

```
<400> SEQUENCE: 41

Cys Arg Ala Gly Pro Leu Gln Trp Leu Cys Glu Lys Tyr Phe Ser
 1               5                  10                  15

Thr Tyr

<210> SEQ ID NO 42
<211> LENGTH: 21
<212> TYPE: PRT
<213> ORGANISM: Artificial sequence
<220> FEATURE:
<223> OTHER INFORMATION: Sequence is synthesized

<400> SEQUENCE: 42

Glu Ala Arg Val Cys Arg Ala Gly Pro Leu Gln Trp Leu Cys Glu
 1               5                  10                  15

Lys Tyr Phe Ser Thr Tyr
                 20

<210> SEQ ID NO 43
<211> LENGTH: 21
<212> TYPE: PRT
<213> ORGANISM: Artificial sequence
<220> FEATURE:
<223> OTHER INFORMATION: Sequence is synthesized

<400> SEQUENCE: 43

Gly Gln Gln Ser Cys Arg Ala Gly Pro Leu Gln Trp Leu Cys Glu
 1               5                  10                  15

Lys Tyr Phe Ser Thr Tyr
                 20

<210> SEQ ID NO 44
<211> LENGTH: 14
<212> TYPE: PRT
<213> ORGANISM: Artificial sequence
<220> FEATURE:
<223> OTHER INFORMATION: Sequence is synthesized

<400> SEQUENCE: 44

Cys Arg Ala Gly Pro Leu Gln Trp Leu Cys Glu Arg Tyr Phe
 1               5                  10

<210> SEQ ID NO 45
<211> LENGTH: 14
<212> TYPE: PRT
<213> ORGANISM: Artificial sequence
<220> FEATURE:
<223> OTHER INFORMATION: Sequence is synthesized

<400> SEQUENCE: 45

Cys Arg Ala Gly Pro Leu Gln Trp Leu Cys Glu Lys Phe Phe
 1               5                  10

<210> SEQ ID NO 46
<211> LENGTH: 23
<212> TYPE: PRT
<213> ORGANISM: Artificial sequence
<220> FEATURE:
<223> OTHER INFORMATION: Sequence is synthesized

<400> SEQUENCE: 46

Gly Gln Gln Ser Cys Ala Ala Gly Pro Leu Gln Trp Leu Cys Glu
 1               5                  10                  15

His Tyr Phe Ser Thr Tyr Gly Arg
                 20
```

```
<210> SEQ ID NO 47
<211> LENGTH: 97
<212> TYPE: PRT
<213> ORGANISM: Artificial sequence
<220> FEATURE:
<223> OTHER INFORMATION: Sequence is synthesized

<400> SEQUENCE: 47

Gly Gln Gln Ser Cys Ala Ala Gly Pro Leu Gln Trp Leu Cys Glu
 1               5                  10                  15

His Tyr Phe Ser Thr Tyr Gly Arg Gly Gly Ser Gly Gly Ala
            20                  25                  30

Gln His Asp Glu Ala Val Asp Asn Lys Phe Asn Lys Glu Gln Gln
        35                  40                  45

Asn Ala Phe Tyr Glu Ile Leu His Leu Pro Asn Leu Asn Glu Glu
            50                  55                  60

Gln Arg Asn Ala Phe Ile Gln Ser Leu Lys Asp Asp Pro Ser Gln
 65                  70                  75

Ser Ala Asn Leu Leu Ala Glu Ala Lys Lys Leu Asn Asp Ala Gln
                80                  85                  90

Ala Pro Asn Val Asp Met Asn
                95

<210> SEQ ID NO 48
<211> LENGTH: 14
<212> TYPE: PRT
<213> ORGANISM: Artificial sequence
<220> FEATURE:
<223> OTHER INFORMATION: Sequence is synthesized

<400> SEQUENCE: 48

Cys Lys Ala Gly Pro Leu Leu Trp Leu Cys Glu Arg Phe Phe
 1               5                  10

<210> SEQ ID NO 49
<211> LENGTH: 14
<212> TYPE: PRT
<213> ORGANISM: Artificial sequence
<220> FEATURE:
<223> OTHER INFORMATION: Sequence is synthesized

<400> SEQUENCE: 49

Cys Arg Ala Gly Pro Leu Gln Trp Leu Cys Glu Arg Phe Phe
 1               5                  10

<210> SEQ ID NO 50
<211> LENGTH: 14
<212> TYPE: PRT
<213> ORGANISM: Artificial sequence
<220> FEATURE:
<223> OTHER INFORMATION: Sequence is synthesized

<400> SEQUENCE: 50

Cys Arg Glu Gly Pro Leu Gln Trp Leu Cys Glu Arg Phe Phe
 1               5                  10

<210> SEQ ID NO 51
<211> LENGTH: 14
<212> TYPE: PRT
<213> ORGANISM: Artificial sequence
<220> FEATURE:
<223> OTHER INFORMATION: Sequence is synthesized
```

```
<400> SEQUENCE: 51

Cys Lys Glu Gly Pro Leu Leu Trp Leu Cys Glu Arg Phe Phe
 1               5                  10

<210> SEQ ID NO 52
<211> LENGTH: 14
<212> TYPE: PRT
<213> ORGANISM: Artificial sequence
<220> FEATURE:
<223> OTHER INFORMATION: Sequence is synthesized

<400> SEQUENCE: 52

Arg Ala Gly Pro Leu Glu Trp Leu Ala Glu Lys Tyr Glu Gly
 1               5                  10

<210> SEQ ID NO 53
<211> LENGTH: 12
<212> TYPE: PRT
<213> ORGANISM: Artificial sequence
<220> FEATURE:
<223> OTHER INFORMATION: Sequence is synthesized

<400> SEQUENCE: 53

Arg Pro Leu Glu Trp Leu Ala Glu Lys Tyr Phe Glu
 1               5                  10

<210> SEQ ID NO 54
<211> LENGTH: 14
<212> TYPE: PRT
<213> ORGANISM: Artificial sequence
<220> FEATURE:
<223> OTHER INFORMATION: Sequence is synthesized

<400> SEQUENCE: 54

Arg Ala Gly Pro Leu Glu Trp Leu Ala Glu Lys Tyr Phe Glu
 1               5                  10

<210> SEQ ID NO 55
<211> LENGTH: 77
<212> TYPE: PRT
<213> ORGANISM: Artificial sequence
<220> FEATURE:
<223> OTHER INFORMATION: Sequence is synthesized

<400> SEQUENCE: 55

Ser Gly Thr Ala Met Ala Asp Pro Asn Arg Phe Arg Gly Lys Asp
 1               5                  10                  15

Leu Ala Gly Ser Pro Gly Gly Ser Gly Gly Gly Ala Glu Gly
                20                  25                  30

Asp Asp Pro Ala Lys Ala Ala Phe Asn Ser Leu Gln Ala Ser Ala
                    35                  40                  45

Thr Glu Tyr Ile Gly Tyr Ala Trp Ala Met Val Val Ile Val
                    50                  55                  60

Gly Ala Thr Ile Gly Ile Lys Leu Phe Lys Lys Phe Thr Ser Lys
                    65                  70                  75

Ala Ser

<210> SEQ ID NO 56
<211> LENGTH: 16
<212> TYPE: PRT
<213> ORGANISM: Artificial sequence
<220> FEATURE:
<223> OTHER INFORMATION: Sequence is synthesized
```

```
<220> FEATURE:
<221> NAME/KEY: Xaa
<222> LOCATION: 6, 9
<223> OTHER INFORMATION: unknown amino acid

<400> SEQUENCE: 56

Ser Gly Thr Ala Cys Xaa Gly Pro Xaa Cys Ser Leu Ala Gly Ser
 1               5                  10                  15

Pro

<210> SEQ ID NO 57
<211> LENGTH: 18
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-4, 6, 7, 10-13, 15-18
<223> OTHER INFORMATION: Unknown amino acid

<400> SEQUENCE: 57

Xaa Xaa Xaa Xaa Cys Xaa Xaa Gly Pro Xaa Xaa Xaa Xaa Cys Xaa
 1               5                  10                  15

Xaa Xaa Xaa

<210> SEQ ID NO 58
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-20
<223> OTHER INFORMATION: Unknown amino acid

<400> SEQUENCE: 58

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
                20

<210> SEQ ID NO 59
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-7, 9-12, 14-20
<223> OTHER INFORMATION: Unknown amino acid

<400> SEQUENCE: 59

Xaa Xaa Xaa Xaa Xaa Xaa Xaa Cys Xaa Xaa Xaa Xaa Cys Xaa Xaa
 1               5                  10                  15

Xaa Xaa Xaa Xaa Xaa
                20

<210> SEQ ID NO 60
<211> LENGTH: 20
<212> TYPE: PRT
<213> ORGANISM: Artificial sequence
<220> FEATURE:
<223> OTHER INFORMATION: Sequence is synthesized
```

```
<220> FEATURE:
<221> NAME/KEY: Xaa
<222> LOCATION: 1-7, 9-13, 15-20
<223> OTHER INFORMATION: Unknown amino acid

<400> SEQUENCE: 60

Xaa Xaa Xaa Xaa Xaa Xaa Xaa Cys Xaa Xaa Xaa Xaa Xaa Cys Xaa
 1               5                  10                  15

Xaa Xaa Xaa Xaa Xaa
                20

<210> SEQ ID NO 61
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-6, 8-13, 15-20
<223> OTHER INFORMATION: Unknown amino acid

<400> SEQUENCE: 61

Xaa Xaa Xaa Xaa Xaa Xaa Cys Xaa Xaa Xaa Xaa Xaa Xaa Cys Xaa
 1               5                  10                  15

Xaa Xaa Xaa Xaa Xaa
                20

<210> SEQ ID NO 62
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-6, 8-14, 16-20
<223> OTHER INFORMATION: Unknown amino acid

<400> SEQUENCE: 62

Xaa Xaa Xaa Xaa Xaa Xaa Cys Xaa Xaa Xaa Xaa Xaa Xaa Xaa Cys
 1               5                  10                  15

Xaa Xaa Xaa Xaa Xaa
                20

<210> SEQ ID NO 63
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-5, 7-14, 16-20
<223> OTHER INFORMATION: Unknown amino acid

<400> SEQUENCE: 63

Xaa Xaa Xaa Xaa Xaa Cys Xaa Xaa Xaa Xaa Xaa Xaa Xaa Xaa Cys
 1               5                  10                  15

Xaa Xaa Xaa Xaa Xaa
                20

<210> SEQ ID NO 64
<211> LENGTH: 20
<212> TYPE: PRT
<213> ORGANISM: Artificial sequence
```

```
<220> FEATURE:
<223> OTHER INFORMATION: Sequence is synthesized
<220> FEATURE:
<221> NAME/KEY: Xaa
<222> LOCATION: 1-5, 7-15, 17-20
<223> OTHER INFORMATION: Unknown amino acid

<400> SEQUENCE: 64

Xaa Xaa Xaa Xaa Xaa Cys Xaa Xaa Xaa Xaa Xaa Xaa Xaa Xaa Xaa
  1               5                  10                  15

Cys Xaa Xaa Xaa Xaa
             20

<210> SEQ ID NO 65
<211> LENGTH: 20
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-4, 6-15, 17-20
<223> OTHER INFORMATION: Unknown amino acid

<400> SEQUENCE: 65

Xaa Xaa Xaa Xaa Cys Xaa Xaa Xaa Xaa Xaa Xaa Xaa Xaa Xaa Xaa
  1               5                  10                  15

Cys Xaa Xaa Xaa Xaa
             20

<210> SEQ ID NO 66
<211> LENGTH: 20
<212> TYPE: PRT
<213> ORGANISM: Artificial sequence
<220> FEATURE:
<223> OTHER INFORMATION: Sequence is synthesized

<400> SEQUENCE: 66

Gly Gly Thr Tyr Ser Cys His Phe Gly Pro Leu Thr Trp Val Cys
  1               5                  10                  15

Lys Pro Gln Gly Gly
             20

<210> SEQ ID NO 67
<211> LENGTH: 10
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 2-3, 6-9
<223> OTHER INFORMATION: Unknown amino acid

<400> SEQUENCE: 67

Cys Xaa Xaa Gly Pro Xaa Xaa Xaa Xaa Cys
  1               5                  10

<210> SEQ ID NO 68
<211> LENGTH: 70
<212> TYPE: PRT
<213> ORGANISM: Artificial sequence
<220> FEATURE:
<223> OTHER INFORMATION: Sequence is synthesized
```

-continued

<400> SEQUENCE: 68

Gly Cys Cys Thr Ala Thr Gly Cys Ala Thr Cys Thr Gly Gly Thr
1               5                   10                  15

Ala Cys Cys Gly Cys Cys Thr Gly Cys Asn Asn Ser Asn Asn Ser
                20                  25                  30

Gly Gly Thr Cys Cys Thr Asn Asn Ser Asn Asn Ser Asn Asn Ser
            35                  40                  45

Asn Asn Ser Thr Gly Thr Thr Cys Thr Cys Thr Gly Gly Cys Ala
        50                  55                  60

Gly Gly Thr Thr Cys Ala Cys Cys Ala Gly
            65                  70

<210> SEQ ID NO 69
<211> LENGTH: 91
<212> TYPE: PRT
<213> ORGANISM: Artificial sequence
<220> FEATURE:
<223> OTHER INFORMATION: Sequence is synthesized

<400> SEQUENCE: 69

Gly Cys Thr Ala Cys Ala Ala Thr Gly Cys Cys Thr Ala Thr
1               5                   10                  15

Gly Cys Ala Asn Asn Ser Asn Asn Ser Asn Asn Ser Asn Asn Ser
                20                  25                  30

Thr Gly Cys Asn Asn Ser Asn Asn Ser Gly Gly Thr Cys Cys Thr
            35                  40                  45

Asn Asn Ser Asn Asn Ser Asn Asn Ser Asn Asn Ser Thr Gly Thr
        50                  55                  60

Asn Asn Ser Asn Asn Ser Asn Asn Ser Asn Asn Ser Gly Gly Thr
            65                  70                  75

Gly Gly Ala Gly Gly Ala Thr Cys Cys Gly Gly Ala Gly Gly Ala
            80                  85                  90

Gly

<210> SEQ ID NO 70
<211> LENGTH: 97
<212> TYPE: PRT
<213> ORGANISM: Artificial sequence
<220> FEATURE:
<223> OTHER INFORMATION: Sequence is synthesized

<400> SEQUENCE: 70

Gly Cys Thr Ala Cys Ala Ala Thr Gly Cys Cys Thr Ala Thr
1               5                   10                  15

Gly Cys Ala Asn Asn Ser Asn Asn Ser Asn Asn Ser Asn Asn Ser
                20                  25                  30

Asn Asn Ser Asn Asn Ser Asn Asn Ser Thr Gly Cys Asn Asn Ser
            35                  40                  45

Asn Asn Ser Asn Asn Ser Asn Asn Ser Thr Gly Cys Asn Asn Ser
        50                  55                  60

Asn Asn Ser Asn Asn Ser Asn Asn Ser Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
                95

<210> SEQ ID NO 71
<211> LENGTH: 97
<212> TYPE: PRT
<213> ORGANISM: Artificial sequence
<220> FEATURE:
<223> OTHER INFORMATION: Sequence is synthesized

<400> SEQUENCE: 71

Gly Cys Thr Ala Cys Ala Ala Ala Thr Gly Cys Cys Thr Ala Thr
 1               5                  10                  15

Gly Cys Ala Asn Asn Ser Asn Asn Ser Asn Asn Ser Asn Asn Ser
                20                  25                  30

Asn Asn Ser Asn Asn Ser Asn Asn Ser Thr Gly Cys Asn Asn Ser
                35                  40                  45

Asn Asn Ser Asn Asn Ser Asn Asn Ser Asn Asn Ser Thr Gly Cys
                50                  55                  60

Asn Asn Ser Asn Asn Ser Asn Asn Ser Asn Asn Ser Asn Asn Ser
                65                  70                  75

Asn Asn Ser Gly Gly Thr Gly Gly Ala Gly Gly Ala Thr Cys Cys
                80                  85                  90

Gly Gly Ala Gly Gly Ala Gly
                95

<210> SEQ ID NO 72
<211> LENGTH: 97
<212> TYPE: PRT
<213> ORGANISM: Artificial sequence
<220> FEATURE:
<223> OTHER INFORMATION: Sequence is synthesized

<400> SEQUENCE: 72

Gly Cys Thr Ala Cys Ala Ala Ala Thr Gly Cys Cys Thr Ala Thr
 1               5                  10                  15

Gly Cys Ala Asn Asn Ser Asn Asn Ser Asn Asn Ser Asn Asn Ser
                20                  25                  30

Asn Asn Ser Asn Asn Ser Thr Gly Cys Asn Asn Ser Asn Asn Ser
                35                  40                  45

Asn Asn Ser Asn Asn Ser Asn Asn Ser Asn Asn Ser Thr Gly Cys
                50                  55                  60

Asn Asn Ser Asn Asn Ser Asn Asn Ser Asn Asn Ser Asn Asn Ser
                65                  70                  75

Asn Asn Ser Gly Gly Thr Gly Gly Ala Gly Gly Ala Thr Cys Cys
                80                  85                  90

Gly Gly Ala Gly Gly Ala Gly
                95

<210> SEQ ID NO 73
<211> LENGTH: 97
<212> TYPE: PRT
<213> ORGANISM: Artificial sequence
<220> FEATURE:
<223> OTHER INFORMATION: Sequence is synthesized

<400> SEQUENCE: 73

Gly Cys Thr Ala Cys Ala Ala Ala Thr Gly Cys Cys Thr Ala Thr
 1               5                  10                  15

Gly Cys Ala Asn Asn Ser Asn Asn Ser Asn Asn Ser Asn Asn Ser
                20                  25                  30

Asn Asn Ser Asn Asn Ser Thr Gly Cys Asn Asn Ser Asn Asn Ser
                35                  40                  45

Asn Asn Ser Asn Asn Ser Asn Asn Ser Asn Asn Ser
            50                  55                  60

Thr Gly Cys Asn Asn Ser Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
            95

<210> SEQ ID NO 74
<211> LENGTH: 97
<212> TYPE: PRT
<213> ORGANISM: Artificial sequence
<220> FEATURE:
<223> OTHER INFORMATION: Sequence is synthesized

<400> SEQUENCE: 74

Gly Cys Thr Ala Cys Ala Ala Ala Thr Gly Cys Cys Thr Ala Thr
1               5                   10                  15

Gly Cys Ala Asn Asn Ser Asn Asn Ser Asn Asn Ser Asn Asn Ser
                20                  25                  30

Asn Asn Ser Thr Gly Cys Asn Asn Ser Asn Asn Ser Asn Asn Ser
            35                  40                  45

Asn Asn Ser Asn Asn Ser Asn Asn Ser Asn Asn Ser
            50                  55                  60

Thr Gly Cys Asn Asn Ser Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
            95

<210> SEQ ID NO 75
<211> LENGTH: 97
<212> TYPE: PRT
<213> ORGANISM: Artificial sequence
<220> FEATURE:
<223> OTHER INFORMATION: Sequence is synthesized

<400> SEQUENCE: 75

Gly Cys Thr Ala Cys Ala Ala Ala Thr Gly Cys Cys Thr Ala Thr
1               5                   10                  15

Gly Cys Ala Asn Asn Ser Asn Asn Ser Asn Asn Ser Asn Asn Ser
                20                  25                  30

Asn Asn Ser Thr Gly Cys Asn Asn Ser Asn Asn Ser Asn Asn Ser
            35                  40                  45

Asn Asn Ser Asn Asn Ser Asn Asn Ser Asn Asn Ser
            50                  55                  60

Asn Asn Ser Thr Gly Cys Asn Asn Ser Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
            95

<210> SEQ ID NO 76
<211> LENGTH: 97
<212> TYPE: PRT
<213> ORGANISM: Artificial sequence
<220> FEATURE:
<223> OTHER INFORMATION: Sequence is synthesized

<400> SEQUENCE: 76

Gly Cys Thr Ala Cys Ala Ala Ala Thr Gly Cys Cys Thr Ala Thr
1               5                   10                  15

Gly Cys Ala Asn Asn Ser Asn Asn Ser Asn Asn Ser Asn Asn Ser
            20                  25                  30

Thr Gly Cys Asn Asn Ser Asn Asn Ser Asn Asn Ser Asn Asn Ser
            35                  40                  45

Asn Asn Ser Asn Asn Ser Asn Asn Ser Asn Asn Ser
            50                  55                  60

Asn Asn Ser Thr Gly Cys Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
                95

<210> SEQ ID NO 77
<211> LENGTH: 97
<212> TYPE: PRT
<213> ORGANISM: Artificial sequence
<220> FEATURE:
<223> OTHER INFORMATION: Sequence is synthesized

<400> SEQUENCE: 77

Gly Cys Thr Ala Cys Ala Ala Ala Thr Gly Cys Cys Thr Ala Thr
1               5                   10                  15

Gly Cys Ala Asn Asn Ser Asn Asn Ser Asn Asn Ser Asn Asn Ser
            20                  25                  30

Asn Asn Ser Asn Asn Ser Asn Asn Ser Asn Asn Ser
            35                  40                  45

Asn Asn Ser Asn Asn Ser Asn Asn Ser Asn Asn Ser
            50                  55                  60

Asn Asn Ser Asn Asn Ser Asn Asn Ser Asn Asn Ser
            65                  70                  75

Asn Asn Ser Gly Gly Thr Gly Gly Ala Gly Gly Ala Thr Cys Cys
            80                  85                  90

Gly Gly Ala Gly Gly Ala Gly
                95

<210> SEQ ID NO 78
<211> LENGTH: 20
<212> TYPE: PRT
<213> ORGANISM: Artificial sequence
<220> FEATURE:
<223> OTHER INFORMATION: Sequence is synthesized

<400> SEQUENCE: 78

Ser Gly Thr Ala Cys Tyr Gly Gly Pro Glu Trp Trp Cys Cys Ser
1               5                   10                  15

Leu Ala Gly Ser Pro
                20

<210> SEQ ID NO 79
<211> LENGTH: 20
<212> TYPE: PRT
<213> ORGANISM: Artificial sequence
<220> FEATURE:
<223> OTHER INFORMATION: Sequence is synthesized -continued

```
<400> SEQUENCE: 79

Ser Gly Thr Ala Cys Tyr Gly Gly Pro Glu Trp Trp Cys Cys Ser
1               5                   10                  15

Leu Ala Gly Ser Pro
            20

<210> SEQ ID NO 80
<211> LENGTH: 20
<212> TYPE: PRT
<213> ORGANISM: Artificial sequence
<220> FEATURE:
<223> OTHER INFORMATION: Sequence is synthesized

<400> SEQUENCE: 80

Ser Gly Thr Ala Cys Tyr Gly Gly Pro Glu Trp Trp Cys Cys Ser
1               5                   10                  15

Leu Ala Gly Ser Pro
            20

<210> SEQ ID NO 81
<211> LENGTH: 18
<212> TYPE: PRT
<213> ORGANISM: Artificial sequence
<220> FEATURE:
<223> OTHER INFORMATION: Sequence is synthesized

<400> SEQUENCE: 81

Asp Leu Ala Ile Cys Ala Glu Gly Pro Glu Ile Trp Val Cys Glu
1               5                   10                  15

Glu Thr Ser

<210> SEQ ID NO 82
<211> LENGTH: 18
<212> TYPE: PRT
<213> ORGANISM: Artificial sequence
<220> FEATURE:
<223> OTHER INFORMATION: Sequence is synthesized

<400> SEQUENCE: 82

Asp Phe Trp Ile Cys Leu Ser Gly Pro Gly Trp Glu Glu Cys Leu
1               5                   10                  15

Glu Trp Trp

<210> SEQ ID NO 83
<211> LENGTH: 18
<212> TYPE: PRT
<213> ORGANISM: Artificial sequence
<220> FEATURE:
<223> OTHER INFORMATION: Sequence is synthesized

<400> SEQUENCE: 83

Glu Glu Ser Glu Cys Phe Glu Gly Pro Gly Tyr Val Ile Cys Gly
1               5                   10                  15

Leu Val Gly

<210> SEQ ID NO 84
<211> LENGTH: 18
<212> TYPE: PRT
<213> ORGANISM: Artificial sequence
<220> FEATURE:
<223> OTHER INFORMATION: Sequence is synthesized
```

-continued

```
<400> SEQUENCE: 84

Asp Met Gly Val Cys Ala Asp Gly Pro Trp Met Tyr Val Cys Glu
1               5                   10                  15

Trp Thr Glu

<210> SEQ ID NO 85
<211> LENGTH: 18
<212> TYPE: PRT
<213> ORGANISM: Artificial sequence
<220> FEATURE:
<223> OTHER INFORMATION: Sequence is synthesized

<400> SEQUENCE: 85

Asp Met Gly Val Cys Ala Asp Gly Pro Trp Met Tyr Val Cys Glu
1               5                   10                  15

Trp Thr Glu

<210> SEQ ID NO 86
<211> LENGTH: 20
<212> TYPE: PRT
<213> ORGANISM: Artificial sequence
<220> FEATURE:
<223> OTHER INFORMATION: Sequence is synthesized

<400> SEQUENCE: 86

Gly Ser Ala Gly Gln Gly Met Thr Glu Glu Trp Ala Trp Ile Trp
1               5                   10                  15

Glu Trp Trp Lys Glu
                20

<210> SEQ ID NO 87
<211> LENGTH: 20
<212> TYPE: PRT
<213> ORGANISM: Artificial sequence
<220> FEATURE:
<223> OTHER INFORMATION: Sequence is synthesized

<400> SEQUENCE: 87

Glu Leu Asp Gly Trp Val Cys Ile Lys Val Gly Glu Gln Asn Leu
1               5                   10                  15

Cys Tyr Leu Ala Glu
                20

<210> SEQ ID NO 88
<211> LENGTH: 20
<212> TYPE: PRT
<213> ORGANISM: Artificial sequence
<220> FEATURE:
<223> OTHER INFORMATION: Sequence is synthesized

<400> SEQUENCE: 88

Glu Leu Asp Gly Trp Val Cys Ile Lys Val Gly Glu Gln Asn Leu
1               5                   10                  15

Cys Tyr Leu Ala Glu
                20

<210> SEQ ID NO 89
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 89

Ala Ile Gly Gly Trp Cys Phe Ile Glu Leu Asp Ser Leu Trp Cys
 1               5                  10                  15

Glu Glu Gln Ile Gly
                20

<210> SEQ ID NO 90
<211> LENGTH: 20
<212> TYPE: PRT
<213> ORGANISM: Artificial sequence
<220> FEATURE:
<223> OTHER INFORMATION: Sequence is synthesized

<400> SEQUENCE: 90

Ser Glu Asp Val Glu Cys Trp Gln Val Trp Glu Asn Leu Val Cys
 1               5                  10                  15

Ser Val Glu His Arg
                20

<210> SEQ ID NO 91
<211> LENGTH: 19
<212> TYPE: PRT
<213> ORGANISM: Artificial sequence
<220> FEATURE:
<223> OTHER INFORMATION: Sequence is synthesized

<400> SEQUENCE: 91

Ser Glu Glu Val Cys Trp Pro Val Ala Glu Trp Tyr Leu Cys Asn
 1               5                  10                  15

Met Trp Gly Arg

<210> SEQ ID NO 92
<211> LENGTH: 20
<212> TYPE: PRT
<213> ORGANISM: Artificial sequence
<220> FEATURE:
<223> OTHER INFORMATION: Sequence is synthesized

<400> SEQUENCE: 92

Arg Val Gly Ala Tyr Ile Ser Cys Ser Glu Thr Glu Cys Trp Val
 1               5                  10                  15

Glu Asp Leu Leu Asp
                20

<210> SEQ ID NO 93
<211> LENGTH: 20
<212> TYPE: PRT
<213> ORGANISM: Artificial sequence
<220> FEATURE:
<223> OTHER INFORMATION: Sequence is synthesized

<400> SEQUENCE: 93

Trp Phe Lys Thr Val Cys Tyr Glu Trp Glu Asp Glu Val Gln Cys
 1               5                  10                  15

Tyr Thr Leu Glu Glu
                20

<210> SEQ ID NO 94
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 94

Ser Glu Asp Val Glu Cys Trp Gln Val Trp Glu Asn Leu Val Cys
 1               5                  10                  15

Ser Val Glu His Arg
                20

<210> SEQ ID NO 95
<211> LENGTH: 20
<212> TYPE: PRT
<213> ORGANISM: Artificial sequence
<220> FEATURE:
<223> OTHER INFORMATION: Sequence is synthesized

<400> SEQUENCE: 95

Arg Leu Glu Glu Gln Cys Val Glu Val Asn Tyr Glu Pro Ser Cys
 1               5                  10                  15

Ser Phe Thr Ala Asn
                20

<210> SEQ ID NO 96
<211> LENGTH: 19
<212> TYPE: PRT
<213> ORGANISM: Artificial sequence
<220> FEATURE:
<223> OTHER INFORMATION: Sequence is synthesized

<400> SEQUENCE: 96

Ser Glu Glu Val Cys Trp Pro Val Ala Glu Trp Tyr Leu Cys Asn
 1               5                  10                  15

Ile Leu Gly Pro

<210> SEQ ID NO 97
<211> LENGTH: 20
<212> TYPE: PRT
<213> ORGANISM: Artificial sequence
<220> FEATURE:
<223> OTHER INFORMATION: Sequence is synthesized

<400> SEQUENCE: 97

Glu Thr Val Ala Asn Cys Asp Cys Tyr Met Asp Leu Cys Leu Cys
 1               5                  10                  15

Tyr Gly Ser Asp Arg
                20

<210> SEQ ID NO 98
<211> LENGTH: 20
<212> TYPE: PRT
<213> ORGANISM: Artificial sequence
<220> FEATURE:
<223> OTHER INFORMATION: Sequence is synthesized

<400> SEQUENCE: 98

Tyr His Pro Ile Ser Cys Met Asp His Tyr Tyr Leu Ile Ile Cys
 1               5                  10                  15

Asp Glu Thr Val Asn
                20

<210> SEQ ID NO 99
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 99

Val Ala Trp Glu Val Cys Trp Asp Arg His Asp Gln Gly Tyr Ile
 1               5                  10                  15
Cys Thr Thr Asp Ser
            20

<210> SEQ ID NO 100
<211> LENGTH: 20
<212> TYPE: PRT
<213> ORGANISM: Artificial sequence
<220> FEATURE:
<223> OTHER INFORMATION: Sequence is synthesized

<400> SEQUENCE: 100

Ala Glu Trp Ala Glu Cys Trp Ile Ala Gly Asp Gln Leu Leu Cys
 1               5                  10                  15
Val Gly Lys Asp Asn
            20

<210> SEQ ID NO 101
<211> LENGTH: 20
<212> TYPE: PRT
<213> ORGANISM: Artificial sequence
<220> FEATURE:
<223> OTHER INFORMATION: Sequence is synthesized

<400> SEQUENCE: 101

Glu Pro Trp Leu Cys Gln Tyr Tyr Glu Ala Ala Met Leu Tyr Leu
 1               5                  10                  15
Cys Trp Glu Glu Gly
            20

<210> SEQ ID NO 102
<211> LENGTH: 20
<212> TYPE: PRT
<213> ORGANISM: Artificial sequence
<220> FEATURE:
<223> OTHER INFORMATION: Sequence is synthesized

<400> SEQUENCE: 102

Ala Glu Glu Gly Met Val Trp Gly Trp Thr Gly Gly Trp Tyr Asn
 1               5                  10                  15
Leu Asp Glu Leu Cys
            20

<210> SEQ ID NO 103
<211> LENGTH: 20
<212> TYPE: PRT
<213> ORGANISM: Artificial sequence
<220> FEATURE:
<223> OTHER INFORMATION: Sequence is synthesized

<400> SEQUENCE: 103

Ser Gly Gly Ala Ile Tyr Trp Pro Val Glu Gln Phe Ile Ala Phe
 1               5                  10                  15
Met Ala Val Gly Lys
            20

<210> SEQ ID NO 104
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 104

Glu Pro Trp Leu Cys Gln Tyr Tyr Glu Ala Ala Met Leu Tyr Leu
 1               5                  10                  15

Cys Trp Glu Glu Gly
                20

<210> SEQ ID NO 105
<211> LENGTH: 20
<212> TYPE: PRT
<213> ORGANISM: Artificial sequence
<220> FEATURE:
<223> OTHER INFORMATION: Sequence is synthesized

<400> SEQUENCE: 105

Ser Gly Gly Ala Ile Tyr Met Pro Val Glu Gln Phe Ile Ala Phe
 1               5                  10                  15

Met Ala Val Gly Lys
                20

<210> SEQ ID NO 106
<211> LENGTH: 18
<212> TYPE: PRT
<213> ORGANISM: Artificial sequence
<220> FEATURE:
<223> OTHER INFORMATION: Sequence is synthesized

<400> SEQUENCE: 106

Glu Val Leu Leu Cys Ser Asp Gly Pro Gln Leu Tyr Leu Cys Glu
 1               5                  10                  15

Leu Tyr Ala

<210> SEQ ID NO 107
<211> LENGTH: 18
<212> TYPE: PRT
<213> ORGANISM: Artificial sequence
<220> FEATURE:
<223> OTHER INFORMATION: Sequence is synthesized

<400> SEQUENCE: 107

Ser Gly Val Glu Cys Val Trp Gly Pro Gln Trp Gly Phe Cys Val
 1               5                  10                  15

Glu Glu Tyr

<210> SEQ ID NO 108
<211> LENGTH: 18
<212> TYPE: PRT
<213> ORGANISM: Artificial sequence
<220> FEATURE:
<223> OTHER INFORMATION: Sequence is synthesized

<400> SEQUENCE: 108

Asp Lys Glu Val Cys Tyr Leu Gly Pro Glu Thr Trp Leu Cys Phe
 1               5                  10                  15

Trp Trp Pro

<210> SEQ ID NO 109
<211> LENGTH: 18
<212> TYPE: PRT
<213> ORGANISM: Artificial sequence
<220> FEATURE:
<223> OTHER INFORMATION: Sequence is synthesized
```

```
<400> SEQUENCE: 109

Glu Val Leu Leu Cys Ser Asp Gly Pro Gln Leu Tyr Leu Cys Glu
 1               5                  10                  15

Leu Tyr Ala

<210> SEQ ID NO 110
<211> LENGTH: 18
<212> TYPE: PRT
<213> ORGANISM: Artificial sequence
<220> FEATURE:
<223> OTHER INFORMATION: Sequence is synthesized

<400> SEQUENCE: 110

Gly Asp Val Glu Cys Ile Glu Gly Pro Trp Gly Glu Leu Cys Val
 1               5                  10                  15

Trp Ala Asp

<210> SEQ ID NO 111
<211> LENGTH: 20
<212> TYPE: PRT
<213> ORGANISM: Artificial sequence
<220> FEATURE:
<223> OTHER INFORMATION: Sequence is synthesized

<400> SEQUENCE: 111

Phe Gly Gly Trp Ser Cys Gln Pro Thr Trp Val Asp Val Tyr Val
 1               5                  10                  15

Cys Asn Phe Glu Glu
             20

<210> SEQ ID NO 112
<211> LENGTH: 20
<212> TYPE: PRT
<213> ORGANISM: Artificial sequence
<220> FEATURE:
<223> OTHER INFORMATION: Sequence is synthesized

<400> SEQUENCE: 112

Ala Met Trp Val Cys Val Ser Asp Trp Glu Thr Val Glu Glu Cys
 1               5                  10                  15

Ile Gln Tyr Met Tyr
             20

<210> SEQ ID NO 113
<211> LENGTH: 20
<212> TYPE: PRT
<213> ORGANISM: Artificial sequence
<220> FEATURE:
<223> OTHER INFORMATION: Sequence is synthesized

<400> SEQUENCE: 113

Ala Met Trp Val Cys Val Ser Asp Trp Glu Thr Val Glu Glu Cys
 1               5                  10                  15

Ile Gln Tyr Met Tyr
             20

<210> SEQ ID NO 114
<211> LENGTH: 20
<212> TYPE: PRT
<213> ORGANISM: Artificial sequence
<220> FEATURE:
<223> OTHER INFORMATION: Sequence is synthesized
```

-continued

```
<400> SEQUENCE: 114

Ala Met Trp Val Cys Val Ser Asp Trp Glu Thr Val Glu Glu Cys
1               5                   10                  15

Ile Gln Tyr Met Tyr
                20

<210> SEQ ID NO 115
<211> LENGTH: 20
<212> TYPE: PRT
<213> ORGANISM: Artificial sequence
<220> FEATURE:
<223> OTHER INFORMATION: Sequence is synthesized

<400> SEQUENCE: 115

Ala Met Trp Val Cys Val Ser Asp Trp Glu Thr Val Glu Glu Cys
1               5                   10                  15

Ile Gln Tyr Met Tyr
                20

<210> SEQ ID NO 116
<211> LENGTH: 20
<212> TYPE: PRT
<213> ORGANISM: Artificial sequence
<220> FEATURE:
<223> OTHER INFORMATION: Sequence is synthesized

<400> SEQUENCE: 116

Thr Asn Trp Phe Phe Val Cys Glu Ser Gly His Gln Asp Ile Cys
1               5                   10                  15

Trp Leu Ala Glu Glu
                20

<210> SEQ ID NO 117
<211> LENGTH: 18
<212> TYPE: PRT
<213> ORGANISM: Artificial sequence
<220> FEATURE:
<223> OTHER INFORMATION: Sequence is synthesized

<400> SEQUENCE: 117

Trp Val Met Glu Cys Gly Ala Gly Pro Trp Pro Glu Gly Cys Thr
1               5                   10                  15

Phe Met Leu

<210> SEQ ID NO 118
<211> LENGTH: 19
<212> TYPE: PRT
<213> ORGANISM: Artificial sequence
<220> FEATURE:
<223> OTHER INFORMATION: Sequence is synthesized

<400> SEQUENCE: 118

Arg Lys Thr Ser Gln Gly Arg Gly Gln Glu Met Cys Trp Glu Thr
1               5                   10                  15

Gly Gly Cys Ser

<210> SEQ ID NO 119
<211> LENGTH: 20
<212> TYPE: PRT
<213> ORGANISM: Artificial sequence
<220> FEATURE:
<223> OTHER INFORMATION: Sequence is synthesized
```

```
<400> SEQUENCE: 119

Ser Trp Glu Arg Gly Glu Leu Thr Tyr Met Lys Leu Cys Glu Tyr
 1               5                  10                  15

Met Arg Leu Gln Gln
            20

<210> SEQ ID NO 120
<211> LENGTH: 20
<212> TYPE: PRT
<213> ORGANISM: Artificial sequence
<220> FEATURE:
<223> OTHER INFORMATION: Sequence is synthesized

<400> SEQUENCE: 120

Glu His Gly Arg Ala Asn Cys Leu Ile Thr Pro Glu Ala Gly Lys
 1               5                  10                  15

Leu Ala Arg Val Thr
            20

<210> SEQ ID NO 121
<211> LENGTH: 18
<212> TYPE: PRT
<213> ORGANISM: Artificial sequence
<220> FEATURE:
<223> OTHER INFORMATION: Sequence is synthesized

<400> SEQUENCE: 121

Val Glu Asp Glu Cys Trp Met Gly Pro Asp Trp Ala Val Cys Trp
 1               5                  10                  15

Thr Trp Gly

<210> SEQ ID NO 122
<211> LENGTH: 21
<212> TYPE: PRT
<213> ORGANISM: Artificial sequence
<220> FEATURE:
<223> OTHER INFORMATION: Sequence is synthesized

<400> SEQUENCE: 122

Glu Leu Asp Gly Trp Val Cys Ile Lys Val Gly Glu Gln Asn Leu
 1               5                  10                  15

Cys Tyr Leu Ala Glu Gly
            20

<210> SEQ ID NO 123
<211> LENGTH: 21
<212> TYPE: PRT
<213> ORGANISM: Artificial sequence
<220> FEATURE:
<223> OTHER INFORMATION: Sequence is synthesized

<400> SEQUENCE: 123

Trp Phe Lys Thr Val Cys Tyr Glu Trp Glu Asp Glu Val Gln Cys
 1               5                  10                  15

Tyr Thr Leu Glu Glu Gly
            20

<210> SEQ ID NO 124
<211> LENGTH: 21
<212> TYPE: PRT
<213> ORGANISM: Artificial sequence
<220> FEATURE:
<223> OTHER INFORMATION: Sequence is synthesized
```

```
<400> SEQUENCE: 124

Arg Val Gly Ala Tyr Ile Ser Cys Ser Glu Thr Glu Cys Trp Val
 1               5                  10                  15

Glu Asp Leu Leu Asp Gly
             20

<210> SEQ ID NO 125
<211> LENGTH: 15
<212> TYPE: PRT
<213> ORGANISM: Artificial sequence
<220> FEATURE:
<223> OTHER INFORMATION: Sequence is synthesized

<400> SEQUENCE: 125

Cys Trp Asp Arg His Asp Gln Gly Tyr Ile Cys Thr Thr Asp Ser
 1               5                  10                  15

<210> SEQ ID NO 126
<211> LENGTH: 10
<212> TYPE: PRT
<213> ORGANISM: Artificial sequence
<220> FEATURE:
<223> OTHER INFORMATION: Sequence is synthesized

<400> SEQUENCE: 126

Trp Pro Val Ala Glu Trp Tyr Leu Cys Asn
 1               5                  10

<210> SEQ ID NO 127
<211> LENGTH: 38
<212> TYPE: DNA
<213> ORGANISM: Artificial sequence
<220> FEATURE:
<223> OTHER INFORMATION: Sequence is synthesized

<400> SEQUENCE: 127
agctgctttg atatgcatct cccgaaactc tgtgcggt                              38

<210> SEQ ID NO 128
<211> LENGTH: 37
<212> TYPE: DNA
<213> ORGANISM: Artificial sequence
<220> FEATURE:
<223> OTHER INFORMATION: Sequence is synthesized

<400> SEQUENCE: 128
gagcgatctg ggtctagaca gatttagcgg gtttcag                               37

<210> SEQ ID NO 129
<211> LENGTH: 24
<212> TYPE: DNA
<213> ORGANISM: Artificial sequence
<220> FEATURE:
<223> OTHER INFORMATION: Sequence is synthesized

<400> SEQUENCE: 129
aaaagggtat gtagaggttg aggt                                             24

<210> SEQ ID NO 130
<211> LENGTH: 14
<212> TYPE: PRT
<213> ORGANISM: Artificial sequence
<220> FEATURE:
<223> OTHER INFORMATION: Sequence is synthesized
```

```
<220> FEATURE:
<221> NAME/KEY: Xaa
<222> LOCATION: 2, 3, 5, 7, 11-14
<223> OTHER INFORMATION: Unknown amino acid

<400> SEQUENCE: 130

Cys Xaa Xaa Gly Xaa Leu Xaa Trp Leu Cys Xaa Xaa Xaa Xaa
 1               5                  10

<210> SEQ ID NO 131
<211> LENGTH: 14
<212> TYPE: PRT
<213> ORGANISM: Artificial sequence
<220> FEATURE:
<223> OTHER INFORMATION: Sequence is synthsized

<400> SEQUENCE: 131

Cys Arg Ala Ala Pro Leu Gln Trp Leu Cys Glu Lys Tyr Phe
 1               5                  10

<210> SEQ ID NO 132
<211> LENGTH: 14
<212> TYPE: PRT
<213> ORGANISM: Artificial sequence
<220> FEATURE:
<223> OTHER INFORMATION: Sequence is synthesized

<400> SEQUENCE: 132

Cys Arg Ala Gly Ala Leu Gln Trp Leu Cys Glu Lys Tyr Phe
 1               5                  10

<210> SEQ ID NO 133
<211> LENGTH: 14
<212> TYPE: PRT
<213> ORGANISM: Artificial sequence
<220> FEATURE:
<223> OTHER INFORMATION: Sequence is synthesized

<400> SEQUENCE: 133

Cys Arg Ala Gly Arg Leu Gln Trp Leu Cys Glu Lys Tyr Phe
 1               5                  10

<210> SEQ ID NO 134
<211> LENGTH: 14
<212> TYPE: PRT
<213> ORGANISM: Artificial sequence
<220> FEATURE:
<223> OTHER INFORMATION: Sequence is synthesized

<400> SEQUENCE: 134

Cys Arg Ala Gly Asn Leu Gln Trp Leu Cys Glu Lys Tyr Phe
 1               5                  10

<210> SEQ ID NO 135
<211> LENGTH: 14
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 6
<223> OTHER INFORMATION: Xaa represents Nle

<400> SEQUENCE: 135

Cys Arg Ala Gly Pro Xaa Gln Trp Leu Cys Glu Lys Tyr Phe
 1               5                  10
```

```
<210> SEQ ID NO 136
<211> LENGTH: 14
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 6
<223> OTHER INFORMATION: Xaa represents Nle

<400> SEQUENCE: 136

Cys Arg Ala Gly Pro Xaa Gln Trp Leu Cys Glu Lys Tyr Phe
 1               5                  10

<210> SEQ ID NO 137
<211> LENGTH: 14
<212> TYPE: PRT
<213> ORGANISM: Artificial sequence
<220> FEATURE:
<223> OTHER INFORMATION: Sequence is synthesized

<400> SEQUENCE: 137

Cys Arg Ala Gly Pro Leu Gln Trp Arg Cys Glu Lys Tyr Phe
 1               5                  10

<210> SEQ ID NO 138
<211> LENGTH: 14
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 9
<223> OTHER INFORMATION: Xaa represents Nle

<400> SEQUENCE: 138

Cys Arg Ala Gly Pro Leu Gln Trp Xaa Cys Glu Lys Tyr Phe
 1               5                  10

<210> SEQ ID NO 139
<211> LENGTH: 14
<212> TYPE: PRT
<213> ORGANISM: Artificial sequence
<220> FEATURE:
<223> OTHER INFORMATION: Sequence is synthesized

<400> SEQUENCE: 139

Cys Arg Ala Gly Pro Leu Gln Arg Leu Cys Glu Lys Tyr Phe
 1               5                  10

<210> SEQ ID NO 140
<211> LENGTH: 14
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 8
<223> OTHER INFORMATION: Xaa represents Nal(1)

<400> SEQUENCE: 140

Cys Arg Ala Gly Pro Leu Gln Xaa Leu Cys Glu Lys Tyr Phe
 1               5                  10
```

```
<210> SEQ ID NO 141
<211> LENGTH: 14
<212> TYPE: PRT
<213> ORGANISM: Artificial sequence
<220> FEATURE:
<223> OTHER INFORMATION: Sequence is synthesized

<400> SEQUENCE: 141

Cys Arg Ala Gly Pro Leu Gln His Leu Cys Glu Lys Tyr Phe
 1               5                  10

<210> SEQ ID NO 142
<211> LENGTH: 19
<212> TYPE: PRT
<213> ORGANISM: Artificial sequence
<220> FEATURE:
<223> OTHER INFORMATION: Sequence is synthesized
<220> FEATURE:
<221> NAME/KEY: Xaa
<222> LOCATION: 1-7, 11, 14, 15-17, 19
<223> OTHER INFORMATION: Unknown amino acid

<400> SEQUENCE: 142

Xaa Xaa Xaa Xaa Xaa Xaa Xaa Pro Leu Glu Xaa Leu Ala Xaa Xaa
 1               5                  10                  15

Xaa Xaa Glu Xaa

<210> SEQ ID NO 143
<211> LENGTH: 15
<212> TYPE: PRT
<213> ORGANISM: Artificial sequence
<220> FEATURE:
<223> OTHER INFORMATION: Sequence is synthesized

<400> SEQUENCE: 143

Cys Arg Ala Gly Pro Leu Gln Glu Leu Cys Glu Lys Tyr Ala Glu
 1               5                  10                  15

<210> SEQ ID NO 144
<211> LENGTH: 10
<212> TYPE: PRT
<213> ORGANISM: Artificial sequence
<220> FEATURE:
<223> OTHER INFORMATION: Sequence is synthesized

<400> SEQUENCE: 144

Leu Glu Trp Leu Ala Glu Lys Tyr Glu Gly
 1               5                  10

<210> SEQ ID NO 145
<211> LENGTH: 11
<212> TYPE: PRT
<213> ORGANISM: Artificial sequence
<220> FEATURE:
<223> OTHER INFORMATION: Sequence is synthesized

<400> SEQUENCE: 145

Pro Leu Glu Trp Leu Ala Glu Lys Tyr Glu Gly
 1               5                  10

<210> SEQ ID NO 146
<211> LENGTH: 10
<212> TYPE: PRT
<213> ORGANISM: Artificial sequence
<220> FEATURE:
<223> OTHER INFORMATION: Sequence is synthesized
```

```
<400> SEQUENCE: 146

Leu Glu Trp Leu Ala Glu Lys Tyr Phe Glu
 1               5                  10

<210> SEQ ID NO 147
<211> LENGTH: 4
<212> TYPE: PRT
<213> ORGANISM: Artificial sequence
<220> FEATURE:
<223> OTHER INFORMATION: Sequence is synthesized

<400> SEQUENCE: 147

Gly Gln Gln Ser
 1

<210> SEQ ID NO 148
<211> LENGTH: 4
<212> TYPE: PRT
<213> ORGANISM: Artificial sequence
<220> FEATURE:
<223> OTHER INFORMATION: Sequence is synthesized

<400> SEQUENCE: 148

Ser Glu Val Gly
 1

<210> SEQ ID NO 149
<211> LENGTH: 4
<212> TYPE: PRT
<213> ORGANISM: Artificial sequence
<220> FEATURE:
<223> OTHER INFORMATION: Sequence is synthesized

<400> SEQUENCE: 149

Ser Glu Met Val
 1

<210> SEQ ID NO 150
<211> LENGTH: 4
<212> TYPE: PRT
<213> ORGANISM: Artificial sequence
<220> FEATURE:
<223> OTHER INFORMATION: Sequence is synthesized

<400> SEQUENCE: 150

Glu Ala Arg Val
 1

<210> SEQ ID NO 151
<211> LENGTH: 4
<212> TYPE: PRT
<213> ORGANISM: Artificial sequence
<220> FEATURE:
<223> OTHER INFORMATION: Sequence is synthesized

<400> SEQUENCE: 151

Gly Gln Gln Ser
 1

<210> SEQ ID NO 152
<211> LENGTH: 18
<212> TYPE: PRT
<213> ORGANISM: Artificial sequence
<220> FEATURE:
<223> OTHER INFORMATION: Sequence is synthesized
```

```
<220> FEATURE:
<221> NAME/KEY: Xaa
<222> LOCATION: 1-4, 6-7, 9, 11-12, 15-18
<223> OTHER INFORMATION: Unknown amino acid

<400> SEQUENCE: 152

Xaa Xaa Xaa Xaa Cys Xaa Xaa Gly Xaa Leu Xaa Xaa Leu Cys Xaa
 1               5                  10                  15

Xaa Xaa Xaa

<210> SEQ ID NO 153
<211> LENGTH: 21
<212> TYPE: PRT
<213> ORGANISM: Artificial sequence
<220> FEATURE:
<223> OTHER INFORMATION: Sequence is synthesized

<400> SEQUENCE: 153

Gly Gln Gln Ser Cys Ala Ala Gly Pro Leu Gln Trp Leu Cys Glu
 1               5                  10                  15

His Tyr Phe Ser Thr Tyr
                20
```